US012583849B2

(12) United States Patent
Griffin et al.

(10) Patent No.: US 12,583,849 B2
(45) Date of Patent: Mar. 24, 2026

(54) KCNT1 INHIBITORS AND METHODS OF USE

(71) Applicant: Praxis Precision Medicines, Inc., Boston, MA (US)

(72) Inventors: Andrew Mark Griffin, L'lle Bizard (CA); Gabriel Martinez Botella, Wayland, MA (US); Brian Edward Marron, Ada, MI (US); Paul S. Charifson, Framingham, MA (US)

(73) Assignee: PRAXIS PRECISION MEDICINES, INC., Cambridge, MA (US)

( * ) Notice: Subject to any disclaimer, the term of this patent is extended or adjusted under 35 U.S.C. 154(b) by 529 days.

(21) Appl. No.: 17/904,963

(22) PCT Filed: Feb. 26, 2021

(86) PCT No.: PCT/US2021/019814
§ 371 (c)(1),
(2) Date: Aug. 25, 2022

(87) PCT Pub. No.: WO2021/173930
PCT Pub. Date: Sep. 2, 2021

(65) Prior Publication Data

US 2023/0167102 A1 Jun. 1, 2023

Related U.S. Application Data

(60) Provisional application No. 62/982,838, filed on Feb. 28, 2020, provisional application No. 62/982,804, filed on Feb. 28, 2020, provisional application No. 62/982,830, filed on Feb. 28, 2020.

(51) Int. Cl.

| | |
|---|---|
| ***C07D 413/14*** | (2006.01) |
| ***C07D 413/04*** | (2006.01) |
| ***C07D 413/12*** | (2006.01) |
| ***C07D 417/12*** | (2006.01) |
| ***C07D 417/14*** | (2006.01) |
| ***C07D 471/04*** | (2006.01) |

(52) U.S. Cl.
CPC ......... *C07D 413/14* (2013.01); *C07D 413/04* (2013.01); *C07D 413/12* (2013.01); *C07D 417/12* (2013.01); *C07D 417/14* (2013.01); *C07D 471/04* (2013.01)

(58) Field of Classification Search
CPC ................ C07D 417/12; C07D 413/14; C07D 413/04; C07D 471/04
See application file for complete search history.

(56) References Cited

U.S. PATENT DOCUMENTS

| | | | |
|---|---|---|---|
| 3,845,770 | A | 11/1974 | Theeuwes et al. |
| 4,326,525 | A | 4/1982 | Swanson et al. |
| 4,902,514 | A | 2/1990 | Barclay et al. |
| 4,992,445 | A | 2/1991 | Lawter et al. |
| 5,001,139 | A | 3/1991 | Lawter et al. |
| 5,023,252 | A | 6/1991 | Hseih |
| 5,616,345 | A | 4/1997 | Geoghegan et al. |
| 6,221,866 | B1 | 4/2001 | Brendel et al. |
| 9,321,727 | B2 | 4/2016 | Bissantz et al. |
| 11,773,088 | B2 | 10/2023 | Martinez Botella et al. |
| 2003/0055093 | A1 | 3/2003 | Strobel et al. |
| 2004/0266823 | A1 | 12/2004 | Cumming et al. |
| 2008/0021217 | A1 | 1/2008 | Borchardt et al. |
| 2008/0045571 | A1 | 2/2008 | Edwards et al. |
| 2008/0269241 | A1 | 10/2008 | Allen et al. |
| 2015/0105386 | A1 | 4/2015 | Mack et al. |
| 2018/0036295 | A1 | 2/2018 | Cheng et al. |
| 2018/0051015 | A1 | 2/2018 | Caferro et al. |
| 2018/0072708 | A1 | 3/2018 | Yanagisawa et al. |
| 2019/0022039 | A1 | 1/2019 | Fujii et al. |
| 2022/0135553 | A1 | 5/2022 | Martinez Botella et al. |
| 2022/0259193 | A1 | 8/2022 | Martinez Botella et al. |
| 2024/0043415 | A1 | 2/2024 | Griffin et al. |
| 2024/0368142 | A1 | 11/2024 | Griffin et al. |

FOREIGN PATENT DOCUMENTS

| | | | |
|---|---|---|---|
| CL | 202102876 | A1 | 8/2022 |
| CL | 202102878 | A1 | 10/2022 |
| CN | 101096368 | A | 1/2008 |
| CN | 101790527 | A | 7/2010 |
| CN | 105263929 | A | 1/2016 |
| JP | 2005060255 | A | 3/2005 |
| KR | 1020160140892 | A | 12/2016 |
| WO | 03059269 | A2 | 7/2003 |

(Continued)

OTHER PUBLICATIONS

STN Registry Database CAS No. 2193413-67-9, "1H-Pyrazole-5-carboxamide, 3-(difluoromethyl)-1-methyl-N-[1-[3-(4-pyridinyl)-1,2,4-oxadiazol-5-yl]ethyl]-," Mar. 18, 2018, 13 pages.
STN Registry No. 1823229-23-7, "Carbamic acid, N-[1-[3-(3-methoxyphenyl)-1,2,4-oxadiazol-5-yl]ethyl]-, 1,1-dimethylethyl ester," Dec. 6, 2015, 1 page.
STN Registry No. 1824064-84-7, "Carbamic acid, N-[1-[3-(3-fluorophenyl)-1,2,4-oxadiazol-5-yl]ethyl]-, 1,1-dimethylethyl ester," Dec. 7, 2015, 1 page.
STN Registry No. 1338698-26-2, "Carbamic acid, N-[1-[3-(3-methoxyphenyl)-1,2,4-oxadiazol-5-yl]ethyl]-, 1,1-dimethylethyl ester," Dec. 6, 2015, 1 page.
Albrecht et al., "Discovery and optimization of substituted piperidines as potent, selective, CNS-penetrant α4β2 nicotinic acetylcholine receptor potentiators", Bioorganic & Medicinal Chemistry Letters, vol. 18, 2008 (Available online Aug. 28, 2008), pp. 5209-5212.

(Continued)

*Primary Examiner* — Kamal A Saeed
(74) *Attorney, Agent, or Firm* — MH2 Technology Law Group, LLP

(57) ABSTRACT

The present invention is directed to, in part, compounds and compositions useful for preventing and/or treating a neurological disease or disorder, a disease or condition relating to excessive neuronal excitability, and/or a gain-of-function mutation in a gene (e.g., KCNT1). Methods of treating a neurological disease or disorder, a disease or condition relating to excessive neuronal excitability, and/or a gain-of-function mutation in a gene such as KCNT1 are also provided herein.

14 Claims, No Drawings

(56) References Cited

FOREIGN PATENT DOCUMENTS

| | | | |
|---|---|---|---|
| WO | 2006014185 | A1 | 2/2006 |
| WO | 2014141104 | A1 | 9/2014 |
| WO | 2015150097 | A1 | 10/2015 |
| WO | 2018187480 | A1 | 10/2018 |
| WO | 2020225147 | A1 | 11/2020 |
| WO | 2020227097 | A1 | 11/2020 |
| WO | 2020227101 | A1 | 11/2020 |
| WO | 2021195066 | A2 | 9/2021 |
| WO | 2022010880 | A1 | 1/2022 |
| WO | 2023239839 | | 12/2023 |

OTHER PUBLICATIONS

Al-Harbi, Examination Report for Saudi Arabian Patent Application No. 521430751 dated Feb. 27, 2023, with English language translation, 10 pages.

Barcia et al., "De novo gain of function KCNT1 channel mutations cause malignant migrating partial seizures of infancy," Nat. Genet., vol. 44, No. 11, Nov. 2012, pp. 1255-1259 (14 pages provided).

Baumer et al. "Quinidine-associated skin discoloration in KCNT1-associated pediatric epilepsy," Neurology, vol. 89, 2017, p. 2212 (3 pages provided).

Berge et al., "Pharmaceutical Salts," Journal of Pharmaceutical Sciences, vol. 66, No. 1, Jan. 1977, pp. 1-19.

Borlot, F. et al., "KCNT1-related epilepsy: An international multicenter cohort of 27 pediatric cases," Epilepsia, vol. 61, No. 4, Apr. 2020 (First published Mar. 13, 2020), pp. 679-692.

Braga, A. et al., "'One-Pot' Synthesis of Chiral N-Protected α-Amino Acid-Derived 1,2,4-Oxadiazoles," Synthesis, No. 10, Jan. 9, 2004, pp. 1589-1594, XP002541366.

Braga, V. et al., "Synthesis of New 1,2,4-0xadiazoles Carrying (1'S,2'S)-t-Butyloxycarbonyl-1-amino-2-methyl-1-butyl and (1'S)-t-Butyloxycarbonyl-1'-amino-1'-ethyl Groups at C-5," J. Braz. Chem. Soc., vol. 15, No. 4, 2004 (Published on the web May 17, 2004), pp. 603-607, XP093021400.

Copenheaver, Blaine R. (PCT Authorized Officer), International Search Report and Written Opinion of the International Searching Authority for International Patent Application No. PCT/US2020/031039 dated Sep. 11, 2020, 14 pages.

Copenheaver, Blaine R. (PCT Authorized Officer), International Search Report and Written Opinion of the International Searching Authority for International Patent Application No. PCT/US2020/031046 dated Sep. 4, 2020, 13 pages.

Pubchem, "N-(3,4-dimethylphenyl)-2-(3-(4-fluorophenyl)-7-oxoisothiazolo[4,5-d]pyrimidin-6(7H)-yl]acetamide: CID 53124354," 2011 (Create Jun. 21, 2011), Available online at <https://pubchem.ncbi.nlm.nih .gov/compound/53124354)>, 7 pages.

Pubchem, "N,3-Dimethyl-N-[(pyridin-2-yl)methyl]-5-sulfamoylthiophene-2-carboxamide: CID 51106824," 2011 (Create Date: May 3, 2011), Available online at <https://pubchem.ncbi.nlm.nih.gov/compound/511 06824>, 7 pages.

Pubchem, "N-[[3-(dimethylamino)phenyl]methyl]-N-methyl-5-methylsulfonylthiophene-2-carboxamide: CID 136548438," 2019 (Create Date: Jan. 24, 2019), Available online at <https://pubchem.ncbi.nlm.nih.gov/compound/136548438>, 6 pages.

Pubchem, "N-Benzyl-5-sulfamoylthiophene-2-carboxamide: CID 22901904," 2007 (Create Date: Dec. 5, 2007), Available online at <https://pubchem.ncbi.nlm.nih.gov/compound/22901904>, 7 pages.

Pubchem, "N-methyl-N-[(3-methylphenyl)methyl]-5-methylsulfonylthiophene-2-carboxamide: CID 136548429," 2019 (Create Date: Jan. 24, 2019), Available online at <https://pubchem.ncbi.nlm.nih.gov/compound/136548429>,7 pages.

Pubchem, "Substance Record: SID 299402484," 2016 (Available/Deposit Dates: Jan. 28, 2016), Available online at <https://pubchem.ncbi.nlm.nih.gov/substance/299402484>, 4 pages.

Rizzo et al., "Characterization of two de novo KCNT1 mutations in children with malignant migrating partial seizures in infancy," Molecular and Cellular Neuroscience, vol. 72, 2016 (Available online Jan. 16, 2016), pp. 54-63.

Rodriquez, Kari (PCT Authorized Officer), International Search Report and Written Opinion of the International Searching Authority for International Patent Application No. PCT/US2021/023653 dated Sep. 14, 2021, 10 pages.

Rodriquez, Kari (PCT Authorized Officer), International Search Report and Written Opinion of the International Searching Authority for International Patent Application No. PCT/US2021/040486 dated Oct. 20, 2021, 9 pages.

Extended European Search Report for European Application No. 21760026.1 dated Jan. 30, 2024, 5 pages.

Wilen et al., "Strategies in Optical Resolutions," Tetrahedron, vol. 33, Report No. 38, 1977, pp. 2725-2736.

Zhang et al., "Gene mutation analysis of 175 Chinese patients with early-onset epileptic encephalopathy," Clinical Genetics, vol. 91, No. 5, 2017, pp. 717-724.

Zhou et al., "Novel mutations and phenotypes of epilepsy-associated genes in epileptic encephalopathies," Genes, Brain and Behavior, vol. 17, e12456, 2018, 11 pages.

Griffin, A. et al., "Discovery of the First Orally Available, Selective KNa 1.1 Inhibitor: In Vitro and In Vivo Activity of an Oxadiazole Series," ACS Medicinal Chemistry Letters, vol. 12, No. 4, Mar. 9, 2021, pp. 593-602, XP093003438.

Ishii, A. et al., "A recurrent KCNT1 mutation in two sporadic cases with malignant migrating partial seizures in infancy," Gene, vol. 531, No. 2, Dec. 1, 2013 (Available online Sep. 10, 2013), pp. 467-471.

Extended European Search Report for European Patent Application No. 20801870.5 dated Feb. 16, 2023, 15 pages.

McTague, A et al., "Clinical and molecular characterization of KCNT1-related severe early-onset epilepsy," Neurology, vol. 90, No. 1, Jan. 2, 2018 (Published online Dec. 1, 2017), pp. e55-e66.

Poulain, R. et al., "Parallel synthesis of 1,2,4-oxadiazoles from carboxylic acids using an improved, uronium-based, activation," Tetrahedron Letters, vol. 42, No. 8, Feb. 19, 2001, pp. 1495-1498, XP002427070.

Thomas, Shane (PCT Authorized Officer), International Search Report and Written Opinion of the International Searching Authority for International Application No. PCT/US2023/024794 dated Sep. 27, 2023, 9 pages.

Dilena et al., "Early Treatment with Quinidine in 2 Patients with Epilepsy of Infancy with Migrating Focal Seizures (EIMFS) Due to Gain-of-Function KCNT1 Mutations: Functional Studies, Clinical Responses, and Critical Issues for Personalized Therapy," Neurotherapeutics, vol. 15, 2018 (Published online Aug. 15, 2018), pp. 1112-1126.

Epi4K Consortium & Epilepsy Phenome/Genome Project, "De novo mutations in the classic epileptic encephalopathies," Nature, vol. 501, No. 7466, Sep. 12, 2013, pp. 217-221 (16 pages provided).

Fukuoka et al., "Quinidine therapy for West syndrome with KCNTI mutation: A case report," Brain & Development, vol. 39, 2017, pp. 80-83.

Gould, "Salt selection for basic drugs," International Journal of Pharmaceutics, vol. 33, 1986, pp. 201-217.

Heron et al., "Missense mutations in the sodium-gated potassium channel gene KCNT1 cause severe autosomal dominant nocturnal frontal lobe epilepsy," Nature Genetics, vol. 44, No. 11, Nov. 2012 (Published online Oct. 21, 2012), pp. 1188-1190.

Kawasaki et al., "Three Cases of KCNT1 Mutations: Malignant Migrating Partial Seizures in Infancy with Massive Systemic to Pulmonary Collateral Arteries," The Journal of Pediatrics, vol. 191, Oct. 5, 2017, pp. 270-274.

Kim et al., "Human Slack Potassium Channel Mutations Increase Positive Cooperativity between Individual Channels," Cell Reports, vol. 9, Dec. 11, 2014, pp. 1661-1672.

Lim et al., "KCNT1 mutations in seizure disorders: the phenotypic spectrum and functional effects," J. Med. Genet., vol. 53, 2016 (Published online first Jan. 6, 2016), pp. 217-225.

Madaan et al., "A quinidine non responsive novel KCNT1 mutation in an Indian infant with epilepsy of infancy with migrating focal seizures," Brain & Development, vol. 40, No. 3, 2017, pp. 229-232.

McTague et al., "Migrating partial seizures of infancy: expansion of the electroclinical, radiological and pathological disease spectrum," Brain, vol. 136, 2013, pp. 1578-1591.

(56) References Cited

OTHER PUBLICATIONS

Mikati et al., "Quinidine in the Treatment of KCNT1-Positive Epilepsies," Annals of Neurology, vol. 78, No. 6, Mar. 2015, pp. 995-999.
Milligan et al., "KCNT1 Gain of Function in 2 Epilepsy Phenotypes Is Reversed by Quinidine," Annals of Neurology, vol. 75, No. 4, Mar. 2014, pp. 581-590.
Møller et al., "Mutations in KCNT1 cause a spectrum of focal epilepsies," Epilepsia, vol. 56, No. 9, 2015 (Early View publication Jun. 30, 2015), pp. e114-e120.
Numis et al., "Lack of response to quinidine in KCNT1-related neonatal epilepsy," Epilepsia, vol. 59, Issue 10, Oct. 2018 (First published Sep. 4, 2018), pp. 1889-1898.
Ohba et al., "De novo KCNT1 mutations in early-onset epileptic encephalopathy," Epilepsia, vol. 56, No. 9, 2015 (Early View publication Jul. 3, 2015), pp. e121-e128.
STN Registry, "3-Furancarboxamide, N-[1-[3-[2-(trifluorornethyl)-4-pyridinyl]-1,2,4-oxadiazol-5-yl]ethyl]," May 2, 2017, 3 pages.
Purushotham, N. et al., "An Expeditious Synthesis of Chiral 1,2,4-Oxadiazole Peptidomimetics from Heteroaroyl Monopeptides," Organic and Supramolecular Chemistry, vol. 3, Oct. 22, 2018, pp. 10996-10998.
Pubchem, "N-{1-[3-(3-Chlorophenyl)-1,2,4-oxadiazol-5-YL]ethyl}benzamide," 2010 (Available/Deposit Date: Jun. 22, 2010), available online at <https://pubchem.ncbi.nlm.nih.gov/compound/46128945>, 4 pages.
Pubchem, "N-[(1R)-1-[3-(3-chlorophenyl)-1,2,4-oxadiazol-5-yl]ethyl]benzamide," 2015 (Available/Deposit Date: Dec. 10, 2015), available online at <https://pubchem.ncbi.nlm.nih.gov/compound/93117409>, 8 pages.
STN Search Report for Registry Library Compounds (Year: 2025).
Young, Lee (Authorized Officer), International Search Report and Written Opinion issued Jul. 1, 2021 in corresponding International Application No. PCT/US2021/019814, 12 pages.
PUBCHEM-SID:260692697 Deposit Date: Dec. 10, 2015 (Dec. 10, 2015) pp. 1-6, p. 2.
PUBCHEM-SID:165919505 Deposit Date: Nov. 30, 2013 (Nov. 30, 2013) pp. 1-7, p. 2.
Camci et al., "Bioisosterism: 1,2,4-Oxadiazole Rings," ChemMedChem, vol. 18, Issue 9, First Published Feb. 11, 2023 (14 pages).
Patani et al., "Bioisosterism: A Rational Approach in Drug Design," Chemical Review, vol. 96 , No. 8, pp. 3147-3176, 1996.
CAS Registry No. 2395549-12-7, "1-Ethyl-N-[1-[3-(3-fluorophenyl)-1,2,4-oxadiazol-5-yl]ethyl]-5-methyl-1H-pyrazole-3-carboxamide" [1], entered Dec. 20, 2019, 1 page.
CAS Registry No. 1832156-07-6, "N-[1-[3-(3-fluorophenyl)-1,2,4-oxadiazol-5-yl]ethyl]-4,5,6,7-tetrahydro- 2H-Pyrazolo[4,3-c]pyridine-3-carboxamide," entered Dec. 18, 2015, 1 page.
STN Registry Database No. 1783147-39-6 "1H-Pyrazole-5-carboxamide, 1-(2-ethoxyethyl)-3-methyl-N-[1-[3-(4-pyridinyl)-1,2,4-oxadiazol-5-yl]ethyl]-," Entered Jun. 18, 2015, 1 page.
STN Registry Database No. 1625535-70-7, "1H-Pyrazole-4-carboxamide, 1-(2,4-difluorophenyl)-N,3,5-trimethyl-N-[[3-(3-pyridinyl)-1,2,4-oxadiazol-5-yl)methyl]-," Entered Sep. 24, 2014, 1 page.
STN Registry Database No. 1422830-47-4, "1H-Pyrazole-4-carboxamide, N, 1,3-trimethyl-N-[3-(4-pyridinyl)-1,2,4-oxadiazol-5-yl]methyl]-" Entered Mar. 11, 2013, 1 page.
STN Registry Database No. 1322538-98-6, "1H-Pyrazole-4-carboxamide, 5-methyl-N- [2-methyl-1-[3-(3-pyrdinyl)-1,2,4-oxadiazol-5-yl]propyl]-1-(2-pyridinyl)-" entered Aug. 24, 2011, 1 page.

KCNT1 INHIBITORS AND METHODS OF USE

CROSS-REFERENCE TO RELATED APPLICATIONS

This application is a U.S. National Stage Application of PCT/US2021/019814, filed Feb. 26, 2021, which claims priority to and the benefit of U.S. Provisional Patent Application No. 62/982,838 filed Feb. 28, 2020, U.S. Provisional Patent Application No. 62/982,830 filed Feb. 28, 2020, and U.S. Provisional Patent Application No. 63/982,804 filed Feb. 28, 2020, the contents of each of which are incorporated herein by reference in their entirety.

BACKGROUND

KCNT1 encodes sodium-activated potassium channels known as Slack (Sequence like a calcium-activated $K^+$ channel). These channels are found in neurons throughout the brain and can mediate a sodium-activated potassium current $I_{KNa}$. This delayed outward current can regulate neuronal excitability and the rate of adaption in response to maintained stimulation. Abnormal Slack activity have been associated with development of early onset epilepsies and intellectual impairment. Accordingly, pharmaceutical compounds that selectively regulate sodium-activated potassium channels, e.g., abnormal KCNT1, abnormal $I_{KNa}$, are useful in treating a neurological disease or disorder or a disease or condition related to excessive neuronal excitability and/or KCNT1 gain-of-function mutations.

SUMMARY OF THE INVENTION

Described herein are compounds and compositions useful for preventing and/or treating a disease, disorder, or condition, e.g., a neurological disease or disorder, a disease, disorder, or condition associated with excessive neuronal excitability and/or a gain-of-function mutation in a gene, for example, KCNT1.

In one aspect, the present disclosure features a pharmaceutical composition comprising a compound of Formula I-I:

(I-I)

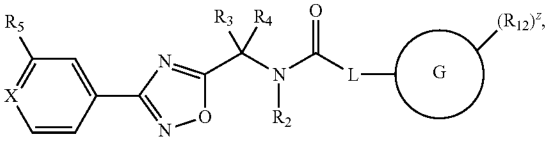

or a pharmaceutically acceptable salt thereof, wherein

- L is a bond or $C_{1-6}$alkyl;
- X is CH or N, wherein, if X is CH, the hydrogen of CH may be substituted by $R_5$;
- G is selected from the group consisting of phenyl, $C_{3-10}$cycloalkyl, 5-10 membered heterocyclyl, and 5-10 membered heteroaryl;
- $R_2$ is hydrogen;
- $R_3$ is $C_{1-6}$alkyl optionally substituted with $C_{1-6}$alkoxy;
- $R_4$ is hydrogen;
- $R_5$ is each independently selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;
- $R_6$ is each independently selected from hydrogen or $C_{1-6}$alkyl;
- $R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and
- z is 0, 1, 2, 3, or 4;

and a pharmaceutically acceptable excipient.

In another aspect, provided herein is a pharmaceutical composition comprising a compound of Formula I-I-I:

(I-I-I)

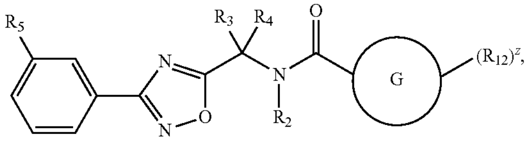

or a pharmaceutically acceptable salt thereof, wherein

- G is selected from the group consisting of phenyl, 5-10 membered heterocyclyl comprising at least one unsaturated bond in the heterocyclyl ring, and 5-10 membered heteroaryl;
- $R_2$ is hydrogen;
- $R_3$ is $C_{1-6}$alkyl optionally substituted with $C_{1-6}$alkoxy;
- $R_4$ is hydrogen;
- $R_5$ is selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;
- $R_6$ is each independently selected from hydrogen or $C_{1-6}$alkyl;
- $R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and
- z is 0, 1, 2, 3, or 4;

and a pharmaceutically acceptable excipient.

In some embodiments, the compound of Formula I-I-I is a compound of Formula I-I-Ia or Formula I-I-Ib:

(I-I-Ia)

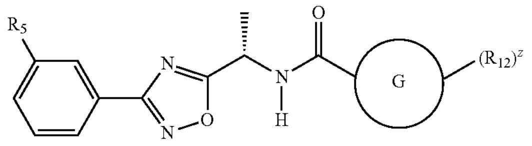

(I-I-Ib)

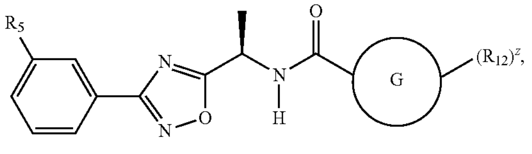

or a pharmaceutically acceptable salt thereof.

In another aspect, provided herein is a pharmaceutical composition comprising a compound of Formula I-I-II:

(I-I-II)

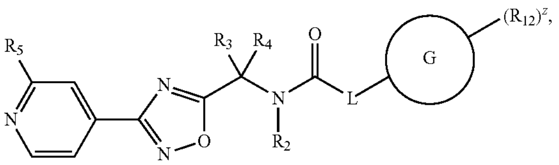

or a pharmaceutically acceptable salt thereof, wherein

L is bond or $C_{1-6}$alkyl;

G is selected from the group consisting of phenyl, $C_{3-10}$cycloalkyl, 5-10 membered heterocyclyl, and 5-10 membered heteroaryl;

$R_2$ is hydrogen;

$R_3$ is $C_{1-6}$alkyl optionally substituted with $C_{1-6}$alkoxy;

$R_4$ is hydrogen;

$R_5$ is selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4;

and a pharmaceutically acceptable excipient.

In some embodiments, the compound is a compound of Formula I-I-IIa:

(I-I-IIa)

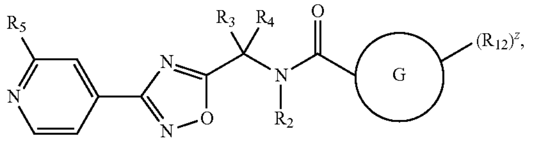

or a pharmaceutically acceptable salt thereof.

In some embodiments, the compound is a compound of Formula I-I-IIb or Formula I-I-IIc:

(I-I-IIb)

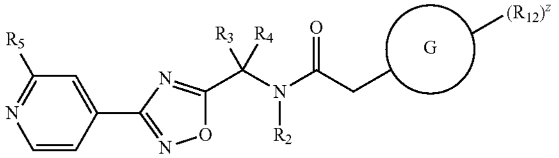

(I-I-IIc)

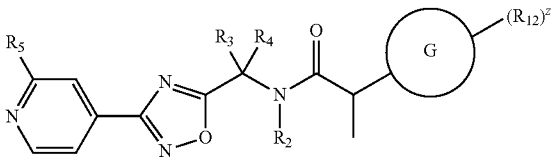

or a pharmaceutically acceptable salt thereof.

In some embodiments, the compound is a compound of Formula I-I-IId:

(I-I-IId)

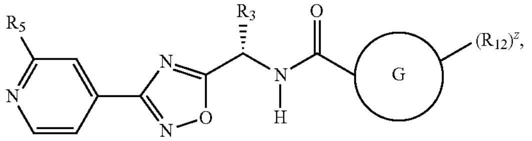

or a pharmaceutically acceptable salt thereof.

In some embodiments, the compound is a compound of Formula I-I-IIe or Formula I-I-IIf:

(I-I-IIe)

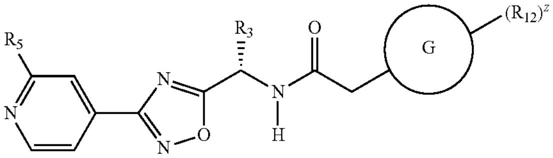

(I-I-IIf)

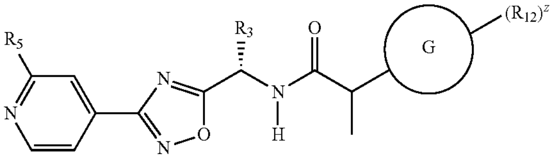

or a pharmaceutically acceptable salt thereof.

In another aspect, the present disclosure features a pharmaceutical composition comprising a compound of Formula II-I:

(II-I)

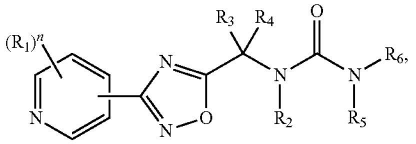

or a pharmaceutically acceptable salt thereof, wherein $R_1$ is each independently halogen, —CN, —OH, $C_{1-6}$alkyl, $C_{1-6}$haloalkyl, $C_{1-6}$alkoxy, $C_{1-6}$haloalkoxy, $C_{3-10}$cycloalkyl, phenyl, 3-10 membered heteroaryl, or 3-10 membered heterocyclyl;

$R_2$ is hydrogen or $C_{1-4}$alkyl;

$R_3$ is $C_{1-6}$alkyl optionally substituted with $C_{1-6}$alkoxy;

$R_4$ is hydrogen or $C_{1-6}$alkyl optionally substituted with $C_{1-6}$alkoxy;

$R_5$ and $R_6$ is each independently hydrogen, $C_{1-6}$alkyl, $C_{3-10}$cycloalkyl, phenyl, 3-10 membered heteroaryl, or 3-10 membered heterocyclyl, wherein the $C_{1-6}$alkyl, $C_{3-10}$cycloalkyl, phenyl, 3-10 membered heteroaryl, or 3-10 membered heterocyclyl may be optionally substituted with one or more of halogen, —CN, —OH, $C_{1-6}$alkyl, $C_{1-6}$haloalkyl, $C_{1-6}$alkoxy, aryl, $C_{3-10}$cycloalkyl, 3-10 membered heteroaryl, or 3-10 membered heterocyclyl; wherein $R_5$ and $R_6$ are not both hydrogen; or $R_5$ and $R_6$ can be taken together with the nitrogen attached to $R_5$ and $R_6$ to form a 3-10 membered heterocyclyl ring optionally substituted with one or more of halogen, —CN, —OH, $C_{1-6}$alkyl, $C_{1-6}$haloalkyl, aryl, $C_{3-10}$cycloalkyl, or 3-10 membered heterocyclyl; and n is 1 or 2;

and a pharmaceutically acceptable excipient.

In some embodiments, the compound of Formula II-I is a compound of Formula II-I-a:

(II-I-a)

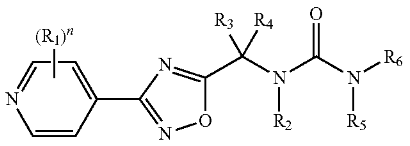

or a pharmaceutically acceptable salt thereof.

In some embodiments, the compound of Formula II-I is a compound of Formula II-I-b:

(II-I-b)

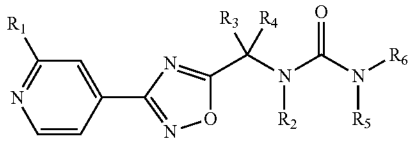

or a pharmaceutically acceptable salt thereof.

In some embodiments, the compound of Formula II-I is a compound of Formula II-I-c:

(II-I-c)

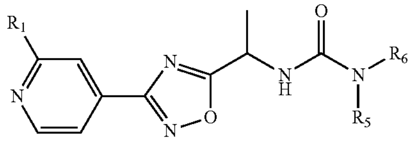

or a pharmaceutically acceptable salt thereof.

In some embodiments, the compound of Formula II-I is a compound of Formula II-I-d:

(II-I-d)

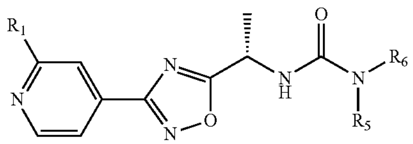

or a pharmaceutically acceptable salt thereof.

In another aspect, the present disclosure features a compound of Formula III-I:

(III-I)

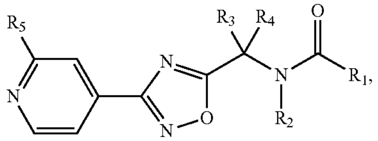

or a pharmaceutically acceptable salt thereof, wherein

- $R_1$ is $C_{1-6}$alkyl optionally substituted with one or more halogen, cyano, $C_{1-6}$haloalkyl, $C_{1-6}$alkoxy, $C_{1-6}$haloalkoxy, or $N(R^a)(R^b)$;
- $R_2$ is hydrogen;
- $R_3$ is $C_{1-6}$alkyl optionally substituted with $C_{1-6}$alkoxy;
- $R_4$ is hydrogen;
- $R_5$ is selected from the group consisting of halogen, $C_{1-6}$alkyl, $C_{1-6}$haloalkyl, $C_{1-6}$ alkoxy, $C_{1-6}$haloalkoxy, $N(R^c)(R^d)$, and $C_{3-10}$cycloalkyl; and $R^a$ and $R^b$ are each independently selected from the group consisting of $C_{1-6}$alkyl, $C_{1-6}$haloalkyl, and phenyl;

- $R^c$ and $R^d$ are each independently selected from the group consisting of hydrogen, $C_{1-6}$alkyl, $C_{1-6}$haloalkyl, $C_{3-10}$cycloalkyl, and phenyl;
- wherein, when $R_5$ is methoxy, $R_3$ is $C_{1-3}$alkyl.

In some embodiments of Formula III-I, the compound of Formula III-I is a compound of Formula III-Ia:

(III-Ia)

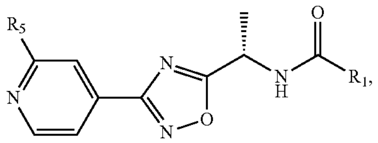

or a pharmaceutically acceptable salt thereof.

In another aspect, the present disclosure provides a pharmaceutical composition comprising a compound of Formula III-I (e.g., Formula III-Ia) or a pharmaceutically acceptable salt thereof, and an pharmaceutically acceptable excipient.

In one aspect, the present disclosure provides a method of treating neurological disease or disorder, wherein the method comprises administering to a subject in need thereof a compound disclosed herein (e.g., compound of Formula (I-I), (I-I-2), (I-I-I), (I-I-I2), (I-I-I3), (I-I-II), (I-I-II2), (II-I), or (III-I) or a pharmaceutical composition disclosed herein (e.g., a pharmaceutical composition comprising a compound of Formula (I-I), (I-I-2), (I-I-I), (I-I-I2), (I-I-I3), (I-I-II), (I-I-II2), (II-I), or (III-I), or a pharmaceutically acceptable salt thereof, and a pharmaceutically acceptable excipient).

In another aspect, the present disclosure provides a method of treating a disease or condition associated with excessive neuronal excitability, wherein the method comprises administering to a subject in need thereof a compound disclosed herein (e.g., compound of Formula (I-I), (I-I-I2), (I-I-I), (I-I-I2), (I-I-I3), (I-I-II), (I-I-II2), (II-I), or (III-I) or a pharmaceutical composition disclosed herein (e.g., a pharmaceutical composition comprising a compound of Formula (I-I), (I-I-2), (I-I-I), (I-I-I2), (I-I-I3), (I-I-II), (I-I-II2), (II-I), or (III-I), or a pharmaceutically acceptable salt thereof, and a pharmaceutically acceptable excipient).

In another aspect, the present disclosure provides a method of treating a disease or condition associated with a gain-of-function mutation of a gene (e.g. KCNT1), wherein the method comprises administering to a subject in need thereof a compound disclosed herein (e.g., a compound of Formula (I-I), (I-I-2), (I-I-I), (I-I-I2), (I-I-I3), (I-I-II), (I-I-II2), (II-I), or (III-I) or a pharmaceutical composition disclosed herein (e.g., a pharmaceutical composition comprising a compound of Formula (I-I), (I-I-2), (I-I-I), (I-I-I2), (I-I-I3), (I-I-II), (I-I-II2), (II-I), or (III-I), or a pharmaceutically acceptable salt thereof, and a pharmaceutically acceptable excipient).

In some embodiments, the neurological disease or disorder, the disease or condition associated with excessive neuronal excitability, or the disease or condition associated with a gain-of-function mutation of a gene (e.g., KCNT1) is epilepsy, an epilepsy syndrome, or an encephalopathy.

In some embodiments, the neurological disease or disorder, the disease or condition associated with excessive neuronal excitability, or the disease or condition associated with a gain-of-function mutation of a gene (e.g., KCNT1) is a genetic or pediatric epilepsy or a genetic or pediatric epilepsy syndrome.

In some embodiments, the neurological disease or disorder, the disease or condition associated with excessive neuronal excitability, or the disease or condition associated with a gain-of-function mutation of a gene (e.g., KCNT1) is a cardiac dysfunction.

In some embodiments, the neurological disease or disorder, the disease or condition associated with excessive neuronal excitability, or the disease or condition associated with a gain-of-function mutation of a gene (e.g., KCNT1) is selected from epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures (e.g., Generalized tonic clonic seizures, Asymmetric Tonic Seizures), leukodystrophy, leukoencephalopathy, intellectual disability, Multifocal Epilepsy, Drug resistant epilepsy, Temporal lobe epilepsy, cerebellar ataxia).

In some embodiments, the neurological disease or disorder, the disease or condition associated with excessive neuronal excitability, or the disease or condition associated with a gain-of-function mutation of a gene (e.g., KCNT1) is selected from the group consisting of cardiac arrhythmia, sudden unexpected death in epilepsy, Brugada syndrome, and myocardial infarction.

In some embodiments, the neurological disease or disorder, the disease or condition associated with excessive neuronal excitability, or the disease or condition associated with a gain-of-function mutation of a gene (e.g., KCNT1) is selected from pain and related conditions (e.g. neuropathic pain, acute/chronic pain, migraine, etc).

In some embodiments, the neurological disease or disorder, the disease or condition associated with excessive neuronal excitability, or the disease or condition associated with a gain-of-function mutation of a gene (e.g., KCNT1) is a muscle disorder (e.g. myotonia, neuromyotonia, cramp muscle spasms, spasticity).

In some embodiments, the neurological disease or disorder, the disease or condition associated with excessive neuronal excitability, or the disease or condition associated with a gain-of-function mutation of a gene (e.g., KCNT1) is selected from itch and pruritis, ataxia and cerebellar ataxias.

In some embodiments, the neurological disease or disorder, the disease or condition associated with excessive neuronal excitability, or the disease or condition associated with a gain-of-function mutation of a gene (e.g., KCNT1) is selected from psychiatric disorders (e.g. major depression, anxiety, bipolar disorder, schizophrenia).

In some embodiments, the neurological disease or disorder or the disease or condition associated with excessive neuronal excitability and/or a gain-of-function mutation in a gene (e.g., KCNT1) is selected from the group consisting of learning disorders, Fragile X, neuronal plasticity, and autism spectrum disorders.

In some embodiments, the neurological disease or disorder, the disease or condition associated with excessive neuronal excitability, or the disease or condition associated with a gain-of-function mutation of a gene (e.g., KCNT1) is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

Other objects and advantages will become apparent to those skilled in the art from a consideration of the ensuing Detailed Description, Examples, and Claims.

DETAILED DESCRIPTION OF THE INVENTION

As generally described herein, the present invention provides compounds and compositions useful for preventing and/or treating a disease, disorder, or condition described herein, e.g., a disease, disorder, or condition associated with excessive neuronal excitability, and/or a disease, disorder, or condition associated with gain-of-function mutations in KCNT1. Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures, leukodystrophy, leukoencephalopathy, Intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, and psychiatric disorders (e.g. major depression, anxiety, bipolar disorder, schizophrenia).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, IN 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

Compound described herein may also comprise one or more isotopic substitutions. For example, H may be in any isotopic form, including $^{1}H$, $^{2}H$ (D or deuterium), and $^{3}H$ (T or tritium); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

The term "heteroalkyl" as used herein refers to an "alkyl" group in which at least one carbon atom has been replaced with an O or S atom. The heteroalkyl may be, for example, an —O—$C_1$-$C_{10}$alkyl group, an —$C_1$-$C_6$alkylene-O—$C_1$-$C_6$alkyl group, or a $C_1$-$C_6$ alkylene-OH group. In certain embodiments, the "heteroalkyl" may be 2-8 membered heteroalkyl, indicating that the heteroalkyl contains from 2 to 8 atoms selected from the group consisting of carbon, oxygen, nitrogen, and sulfur. In yet other embodiments, the heteroalkyl may be a 2-6 membered, 4-8 membered, or a 5-8 membered heteroalkyl group (which may contain for example 1 or 2 heteroatoms selected from the group oxygen and nitrogen). In certain embodiments, the heteroalkyl is an "alkyl" group in which 1-3 carbon atoms have been replaced with oxygen atoms. One type of heteroalkyl group is an "alkoxy" group.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl").

In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

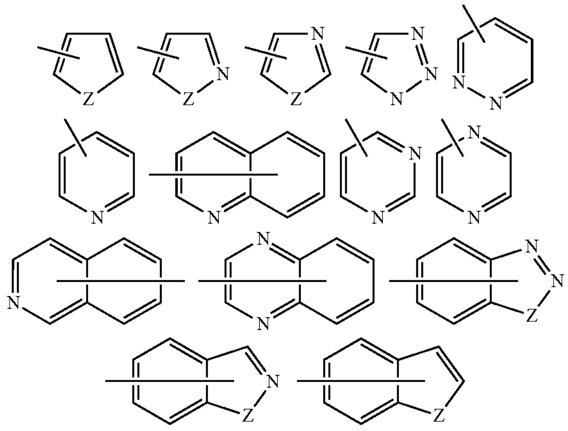

wherein each Z is selected from carbonyl, N, $NR^{65}$, O, and S; and $R^{65}$ is independently hydrogen, $C_1$-$C_8$ alkyl, $C_3$-$C_{10}$ carbocyclyl, 4-10 membered heterocyclyl, $C_6$-$C_{10}$ aryl, and 5-10 membered heteroaryl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like.

Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. Cycloalkyl groups can be fused to other cycloalkyl, aryl, or heterocyclyl groups. In certain embodiments, the cycloalkyl group is not substituted, i.e., it is unsubstituted.

As used herein, "heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like.

Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g,. heteroaryl; and the like having from 1 to 5, and particularly from 1 to 3 heteroatoms.

As used herein, "cyano" refers to —CN.

As used herein, "halo" or "halogen" refers to fluoro (F), chloro (Cl), bromo (Br) and iodo (I). In certain embodiments, the halo group is either fluoro or chloro.

As used herein, "haloalkyl" refers to an alkyl group substituted with one or more halogen atoms.

As used herein, "nitro" refers to $—NO_2$.

As used herein, "oxo" refers to —C═O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{bb})R^{aa}$, $—C(═NR^{cc})OR^{aa}$, $—C(═NRC)N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)_2R^{aa}$, $—P(═O)(R^{aa})_2$, $—P(═O)_2N(R^{cc})_2$, $—P(═O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition (also "therapeutic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, weight, health, and condition of the subject.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

In an alternate embodiment, the present invention contemplates administration of the compounds of the present invention or a pharmaceutically acceptable salt or a pharmaceutically acceptable composition thereof, as a prophylactic before a subject begins to suffer from the specified disease, disorder or condition. As used herein, "prophylactic treatment" contemplates an action that occurs before a subject begins to suffer from the specified disease, disorder or condition. As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein, a "disease or condition associated with a gain-of-function mutation in KCNT1" refers to a disease or condition that is associated with, is partially or completely caused by, or has one or more symptoms that are partially or completely caused by, a mutation in KCNT1 that results in a gain-of-function phenotype, i.e. an increase in activity of the potassium channel encoded by KCNT1 resulting in an increase in whole cell current.

As used herein, a "gain-of-function mutation" is a mutation in KCNT1 that results in an increase in activity of the potassium channel encoded by KCNT1. Activity can be assessed by, for example, ion flux assay or electrophysiology (e.g. using the whole cell patch clamp technique). Typically, a gain-of-function mutation results in an increase of at least or about 20%, 30%0, 40%, 50%, 60%, 70%, 80%, 90%, 100%, 125%, 150%, 175%, 200%, 225%, 250%, 275%, 300%, 325%, 350%, 375%, 400% or more compared to the activity of a potassium channel encoded by a wild-type KCNT1.

Compounds and Compositions

In one aspect, the present invention features a compound of Formula (I-I):

(I-I)

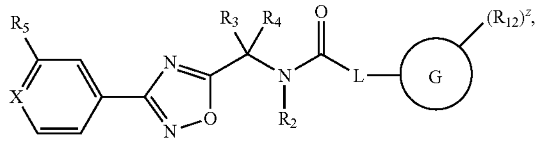

or a pharmaceutically acceptable salt thereof, wherein

L is a bond or $C_{1-6}$alkyl;

X is CH or N, wherein, if X is CH, the hydrogen of CH may be substituted by $R_5$;

G is selected from the group consisting of phenyl, $C_{3-10}$cycloalkyl, 5-10 membered heterocyclyl, and 5-10 membered heteroaryl;

$R_2$ is hydrogen;

$R_3$ is $C_{1-6}$alkyl optionally substituted with $C_{1-6}$alkoxy;

$R_4$ is hydrogen;

$R_5$ is each independently selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}alkyl)$, —$S(O)_2(C_{3-6}cycloalkyl)$, —$C(O)C_{1-6}alkyl$, —C(O)N($R_6$)$_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In another aspect, the present invention features a compound of Formula (I-I-2):

(I-I-2)

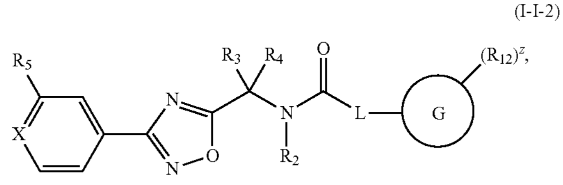

or a pharmaceutically acceptable salt thereof, wherein

L is a bond or $C_{1-6}$alkyl;

X is CH or N, wherein, if X is CH, the hydrogen of CH may be substituted by $R_5$;

G is selected from the group consisting of phenyl, $C_{3-10}$cycloalkyl, 5-10 membered heterocyclyl, and 5-10 membered heteroaryl; provided that G is not pyrazolyl;

$R_2$ is hydrogen;

$R_3$ is $C_{1-6}$alkyl optionally substituted with $C_{1-6}$alkoxy;

$R_4$ is hydrogen;

$R_5$ is each independently selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —S(O)$_2$($C_{1-6}$ alkyl), —S(O)$_2$($C_{3-6}$cycloalkyl), —C(O)$C_{1-6}$alkyl, —C(O)N($R_6$)$_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In some embodiments of Formula (I-I) or (I-I-2), $R_5$ is selected from the group consisting of halogen, $C_{1-6}$haloalkyl, $C_{1-6}$alkoxy, and $C_{3-10}$cycloalkyl. For example, $R_5$ is —F, —$CF_3$, cyclopropyl, —$OCH_2CH_3$, or —OCH($CH_3$)$_3$. In some embodiments of Formula (I-I) or (I-I-2), $R_5$ is —F. In some embodiments of Formula (I-I) or (I-I-2), $R_5$ is —$CF_3$. In some embodiments of Formula (I-I) or (I-I-2), $R_5$ is cyclopropyl.

In some embodiments of Formula (I-I) or (I-I-2), $R_3$ is methyl or ethyl. In some embodiments of Formula (I-I) or (I-I-2), $R_3$ is methyl. In some embodiments of Formula (I-I) or (I-I-2), $R_3$ is ethyl.

In some embodiments of Formula (I-I) or (I-I-2), G is selected from the group consisting of phenyl, cyclopropyl, cyclobutyl, cyclopentyl, cyclohexyl, imidazolyl, thiazolyl, pyridyl, tetrahydropyranyl, thiophenyl, isoxazolyl, isothiazolyl, pyridazinyl, piperidinyl, pyrrolidinyl, triazolyl, benzothiophenyl, pyrimidinyl, bicyclo[2.2.2]octanyl, bicyclo [1.1.1]pentanyl, spiro[2.4]heptanyl, spiro[3.3]heptanyl,

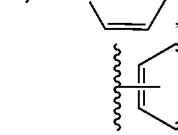,
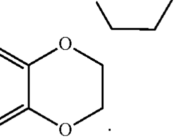, and
.

In some embodiments of Formula (I-I) or (I-I-2), z is 0, 1, or 2. For example, z is 0. In another example, z is 1 or 2.

In some embodiments of Formula (I-I) or (I-I-2), $R_{12}$ is each independently selected from the group consisting of halogen, cyano, hydroxyl, oxo, —S(O)$_2CH_3$, —S(O)$_2$ $CH_2CH_3$, —S(O)$_2$(cyclopropyl), —C(O)$CH_3$, —C(O)$NH_2$, —C(O)N($CH_3$)$_2$, methyl, ethyl, propyl, butyl, isopropyl, isobutyl, —$CF_3$, —$OCF_3$, —$OCH_3$, cyclopropyl, cyclobutyl, and phenyl. In some embodiments of Formula (I-I) or (I-I-2), $R_{12}$ is each independently selected from the group consisting of —F, —Cl, —Br, —$CF_3$, cyano, oxo, methyl, and ethyl. In some embodiments of Formula (I-I) or (I-I-2), $R_{12}$ is each independently selected from the group consisting of methyl, ethyl, phenyl, and —$CF_3$.

In another aspect, the present invention features a compound of Formula I-I-I.

(I-I-I)

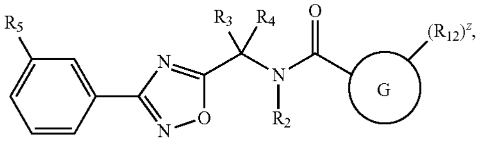

or a pharmaceutically acceptable salt thereof, wherein

G is selected from the group consisting of phenyl, 5-10 membered heterocyclyl comprising at least one unsaturated bond in the heterocyclyl ring, and 5-10 membered heteroaryl;

$R_2$ is hydrogen;

$R_3$ is $C_{1-6}$alkyl optionally substituted with $C_{1-6}$alkoxy;

$R_4$ is hydrogen;

$R_5$ is selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —S(O)$_2$($C_{1-6}$ alkyl), —S(O)$_2$($C_{3-6}$cycloalkyl), —C(O)$C_{1-6}$alkyl, —C(O)N($R_6$)$_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In another aspect, the present invention features a compound of Formula I-I-I2:

(I-I-12)

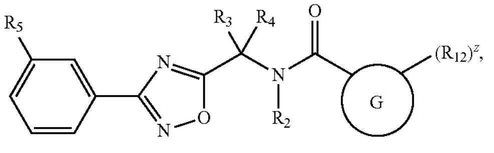

or a pharmaceutically acceptable salt thereof, wherein

G is selected from the group consisting of phenyl, 5-10 membered heterocyclyl comprising at least one unsaturated bond in the heterocyclyl ring, and 5-10 membered heteroaryl;

$R_2$ is hydrogen;

$R_3$ is $C_{1-6}$alkyl optionally substituted with $C_{1-6}$alkoxy;

$R_4$ is hydrogen;

$R_5$ is halogen;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In another aspect, the present invention features a compound of Formula I-I-I3:

(I-I-13)

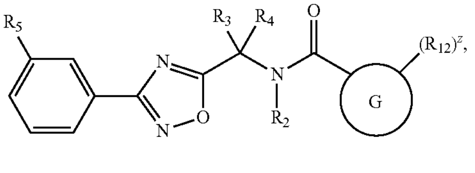

or a pharmaceutically acceptable salt thereof, wherein

G is selected from the group consisting of phenyl, 5-10 membered heterocyclyl comprising at least one unsaturated bond in the heterocyclyl ring, and 5-10 membered heteroaryl; provided that G is not pyrazolyl;

$R_2$ is hydrogen;

$R_3$ is $C_{1-6}$alkyl optionally substituted with $C_{1-6}$alkoxy;

$R_4$ is hydrogen;

$R_5$ is halogen;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In some embodiments, the compound of Formula I-I-I, I-I-I2, or I-I-I3 is a compound of Formula I-I-Ia or Formula I-I-Ib:

(I-I-Ia)

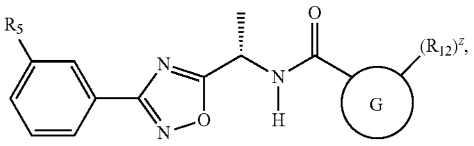

(I-I-Ib)

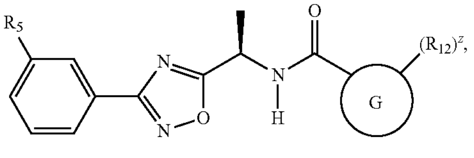

or a pharmaceutically acceptable salt thereof.

In some embodiments of Formula (I-I-I), (I-I-I2), (I-I-I3), (I-I-Ia), or (I-I-Ib), $R_5$ is selected from the group consisting of halogen, $C_{1-6}$haloalkyl, $C_{1-6}$alkoxy, and $C_{3-10}$cycloalkyl. For example, $R_5$ is —F, —$CF_3$, cyclopropyl, —$OCH_2CH_3$, or —$OCH(CH_3)_3$. In some embodiments of Formula (I-I-I), (I-I-I2), (I-I-I3), (I-I-Ia), or (I-I-Ib), $R_5$ is halogen. In some embodiments of Formula (I-I-I), (I-I-I2), (I-I-I3), (I-I-Ia), or (I-I-Ib), $R_5$ is —F.

In some embodiments of Formula (I-I-I), (I-I-I2), (I-I-I3), (I-I-Ia), or (I-I-Ib), $R_3$ is methyl or ethyl. In some embodiments of Formula (I-I-I), (I-I-I2), or (I-I-I3), $R_3$ is methyl. In some embodiments of Formula (I-I-I), (I-I-I2), or (I-I-I3), $R_3$ is ethyl.

In some embodiments of Formula (I-I-I), (I-I-I2), (I-I-I3), (I-I-Ia), or (I-I-Ib), G is selected from the group consisting of phenyl, cyclopropyl, cyclobutyl, cyclopentyl, cyclohexyl, imidazolyl, thiazolyl, pyridyl, tetrahydropyranyl, thiophenyl, isoxazolyl, isothiazolyl, pyridazinyl, piperidinyl, pyrrolidinyl, triazolyl, benzothiophenyl, pyrimidinyl, bicyclo[2.2.2]octanyl, bicyclo[1.1.1]pentanyl, spiro[2.4]heptanyl, spiro[3.3]heptanyl,

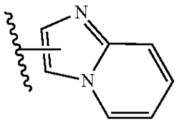
,
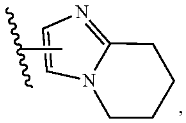
, and
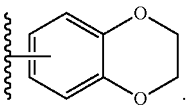
.

In some embodiments of Formula (I-I-I), (I-I-I2), (I-I-I3), (I-I-Ia), or (I-I-Ib), z is 0, 1, or 2. For example, z is 0. In another example, z is 1 or 2. In some embodiments of Formula (I-I-I), (I-I-I2), (I-I-I3), (I-I-Ia), or (I-I-Ib), z is 1. In some embodiments of Formula (I-I-I), (I-I-I2), (I-I-I3), (I-I-Ia), or (I-I-Ib), z is 2.

In some embodiments of Formula (I-I-I), (I-I-I2), (I-I-I3), (I-I-Ia), or (I-I-Ib), $R_{12}$ is each independently selected from the group consisting of halogen, cyano, hydroxyl, oxo, —$S(O)_2CH_3$, —$S(O)_2CH_2CH_3$, —$S(O)_2$(cyclopropyl), —$C(O)CH_3$, —$C(O)NH_2$, —$C(O)N(CH_3)_2$, methyl, ethyl, propyl, butyl, isopropyl, isobutyl, —$CF_3$, —$OCF_3$, —$OCH_3$, cyclopropyl, cyclobutyl, and phenyl. In some embodiments of Formula (I-I-I), (I-I-I2), (I-I-I3), (I-I-Ia), or (I-I-Ib), $R_{12}$ is each independently selected from the group consisting of —F, —Cl, —Br, —$CF_3$, cyano, oxo, methyl, phenyl, and ethyl. In some embodiments of Formula (I-I-I), (I-I-I2), (I-I-I3), (I-I-Ia), or (I-I-Ib), $R_{12}$ is each independently selected from the group consisting of —F, —Cl, —Br, —$CF_3$, cyano, oxo, methyl, and ethyl. In some embodiments of Formula (I-I-I), (I-I-I2), (I-I-I3), (I-I-Ia), or (I-I-Ib), $R_{12}$ is each independently selected from the group consisting of methyl, ethyl, phenyl, and —$CF_3$.

The present invention also provides for a compound of Formula I-I-II.

(I-I-II)

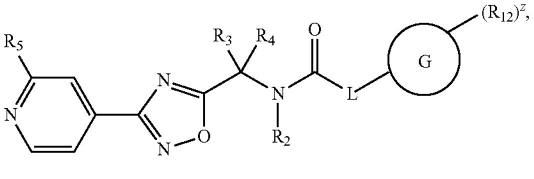

or a pharmaceutically acceptable salt thereof, wherein

L is bond or $C_{1-6}$alkyl;

G is selected from the group consisting of phenyl, $C_{3-10}$cycloalkyl, 5-10 membered heterocyclyl, and 5-10 membered heteroaryl;

$R_2$ is hydrogen;

$R_3$ is $C_{1-6}$alkyl optionally substituted with $C_{1-6}$alkoxy;

$R_4$ is hydrogen;

$R_5$ is selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In another aspect, the present invention also provides for a compound of Formula I-I-II2:

(I-I-II2)

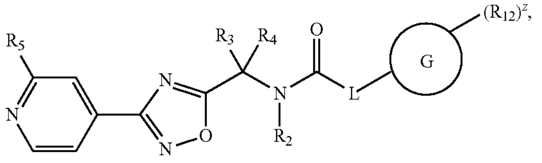

or a pharmaceutically acceptable salt thereof, wherein

L is bond or $C_{1-6}$alkyl;

G is selected from the group consisting of phenyl, $C_{3-10}$cycloalkyl, 5-10 membered heterocyclyl, and 5-10 membered heteroaryl; provided that G is not pyrazolyl;

$R_2$ is hydrogen;

$R_3$ is $C_{1-6}$alkyl optionally substituted with $C_{1-6}$alkoxy;

$R_4$ is hydrogen;

$R_5$ is selected from the group consisting of halogen, $C_{1-6}$alkyl, $C_{1-6}$haloalkyl, $C_{1-6}$ alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

In some embodiments, the compound is a compound of Formula I-I-IIa:

(I-I-11a)

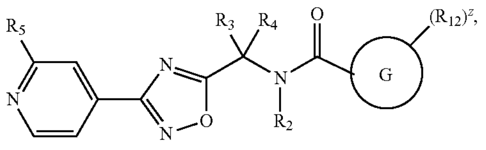

or a pharmaceutically acceptable salt thereof.

In some embodiments, the compound is a compound of Formula I-I-IIb or Formula I-I-IIc:

(I-I-IIb)

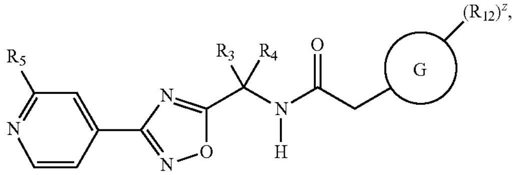

(I-I-IIc)

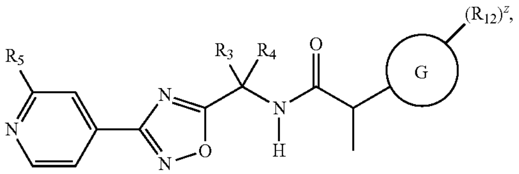

or a pharmaceutically acceptable salt thereof.

In some embodiments, the compound is a compound of Formula I-I-IId:

(I-I-IId)

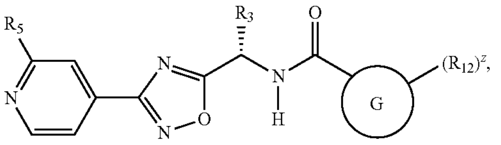

or a pharmaceutically acceptable salt thereof.

In some embodiments, the compound is a compound of Formula I-I-IIe or Formula I-I-IIf:

(I-I-IIb)

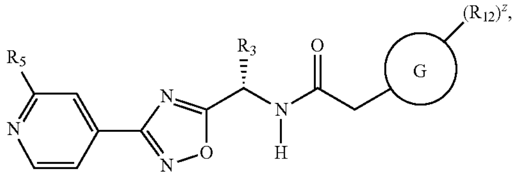

(I-I-IIc)

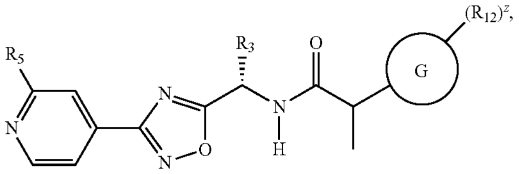

or a pharmaceutically acceptable salt thereof.

In some embodiments of Formula (I-I-II), (I-I-II2), (I-I-IIa), (I-I-IIb), (I-I-IIc), (I-I-IId), (I-I-IIe), or (I-I-IIf), $R_5$ is selected from the group consisting of halogen, $C_{1-6}$haloalkyl, $C_{1-6}$alkoxy, and $C_{3-10}$cycloalkyl. For example, $R_5$ is —F, —$CF_3$, cyclopropyl, —$OCH_2CH_3$, or —$OCH(CH_3)_3$.

In some embodiments of Formula (I-I-II), (I-I-II2), (I-I-IIa), (I-I-IIb), (I-I-IIc), (I-I-IId), (I-I-IIe), or (I-I-IIf), $R_3$ is methyl or ethyl.

In some embodiments of Formula (I-I-II), (I-I-II2), (I-I-IIa), (I-I-IIb), (I-I-IIc), (I-I-IId), (I-I-IIe), or (I-I-IIf), G is selected from the group consisting of phenyl, cyclopropyl, cyclobutyl, cyclopentyl, cyclohexyl, imidazolyl, thiazolyl, pyridyl, tetrahydropyranyl, thiophenyl, isoxazolyl, isothiazolyl, pyridazinyl, piperidinyl, pyrrolidinyl, triazolyl, benzothiophenyl, pyrimidinyl, bicyclo[2.2.2]octanyl, bicyclo[1.1.1]pentanyl, spiro[2.4]heptanyl, spiro[3.3]heptanyl,

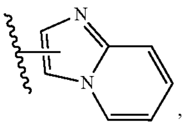,
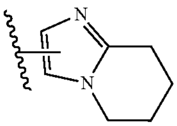, and
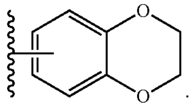.

In some embodiments of Formula (I-I-II), (I-I-II2), (I-I-IIa), (I-I-IIb), (I-I-IIc), (I-I-IId), (I-I-IIe), or (I-I-IIf), z is 0, 1, or 2. For example, z is 0. In another example, z is 1 or 2. In some embodiments of Formula (I-I-II), (I-I-II2), (I-I-IIa), (I-I-IIb), (I-I-IIc), (I-I-IId), (I-I-IIe), or (I-I-IIf), z is 1. In some embodiments of Formula (I-I-II), (I-I-II2), (I-I-IIa), (I-I-IIb), (I-I-IIc), (I-I-IId), (I-I-IIe), or (I-I-IIf) z is 2.

In some embodiments of Formula (I-I-II), (I-I-II2), (I-I-IIa), (I-I-IIb), (I-I-IIc), (I-I-IId), (I-I-IIe), or (I-I-IIf), $R_{12}$ is each independently selected from the group consisting of halogen, cyano, hydroxyl, oxo, $—S(O)_2CH_3$, $—S(O)_2CH_2CH_3$, $—S(O)_2$(cyclopropyl), $—C(O)CH_3$, $—C(O)NH_2$, $—C(O)N(CH_3)_2$, methyl, ethyl, propyl, butyl, isopropyl, isobutyl, $—CF_3$, $—OCF_3$, $—OCH_3$, cyclopropyl, cyclobutyl, and phenyl. In some embodiments of Formula (I-I-II), (I-I-II2), (I-I-IIa), (I-I-IIb), (I-I-IIc), (I-I-IId), (I-I-IIe), or (I-I-IIf), $R_{12}$ is each independently selected from the group consisting of —F, —Cl, —Br, $—CF_3$, cyano, oxo, methyl, and ethyl. In some embodiments of Formula (I-I-II), (I-I-II2), (I-I-IIa), (I-I-IIb), (I-I-IIc), (I-I-IId), (I-I-IIe), or (I-I-IIf), $R_{12}$ is each independently selected from the group consisting of methyl, ethyl, phenyl, and $—CF_3$.

In some embodiments of Formula I-I, the compound is selected from the group consisting of:

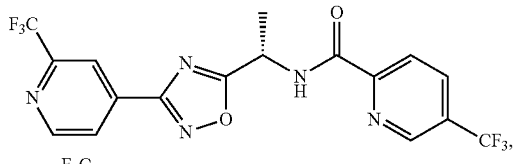,
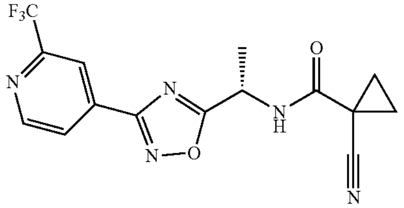,
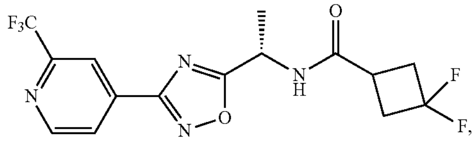,

-continued

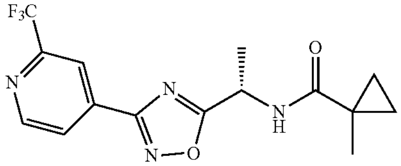,
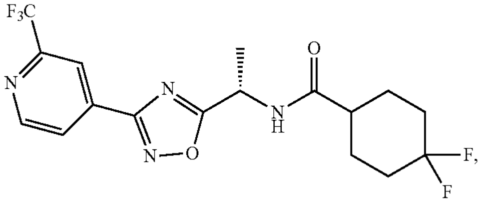,
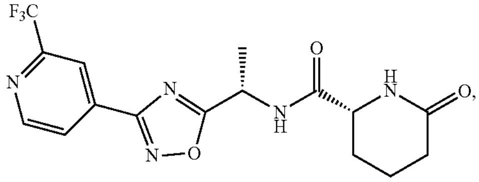,
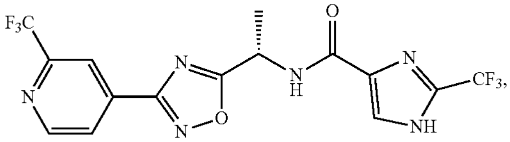,
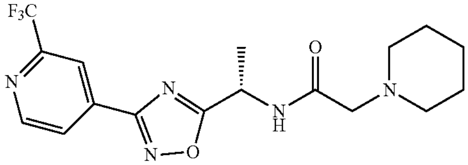,
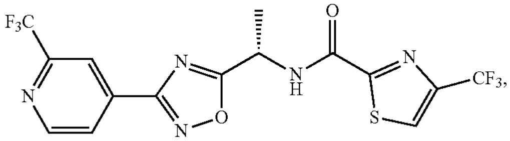,
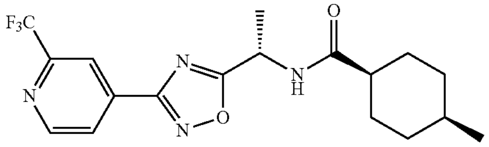,
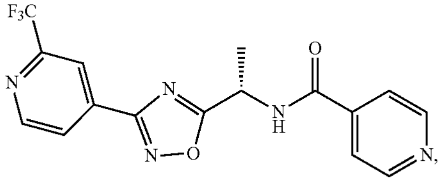,
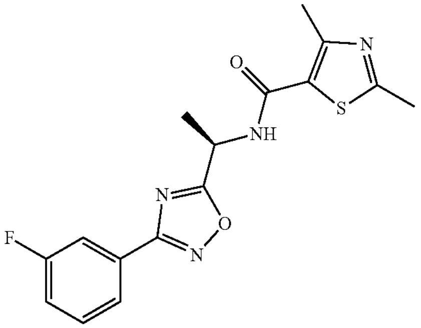, -continued
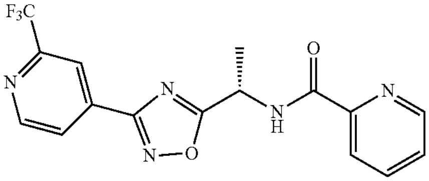
,
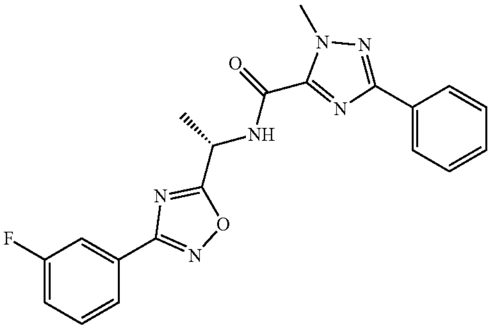
,
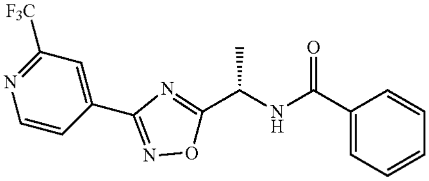
,
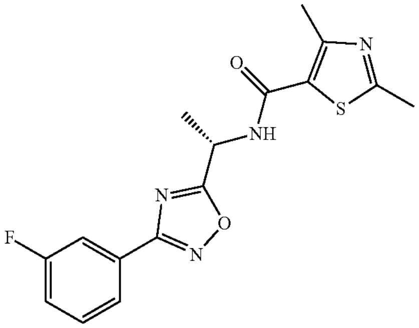
,
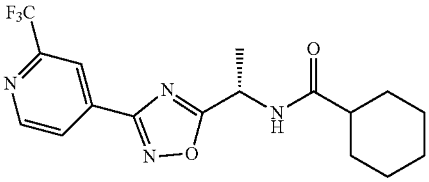
,
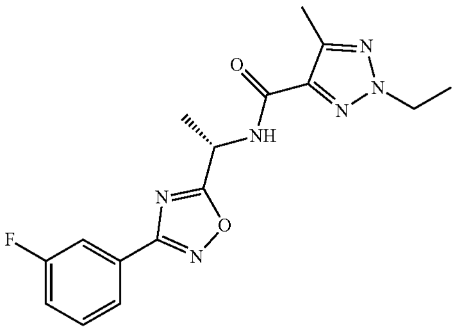
,
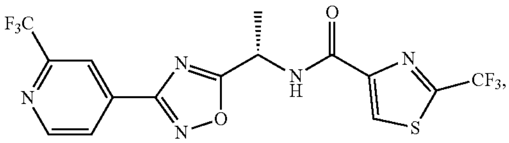
-continued
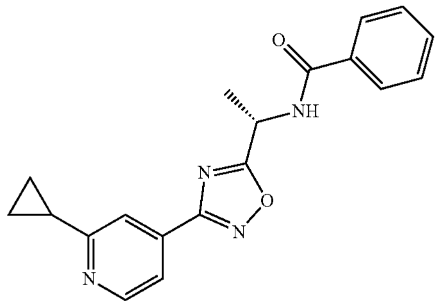
,
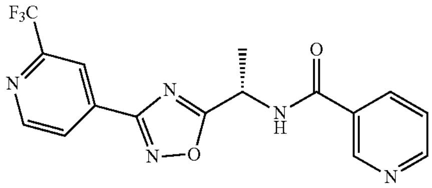
,
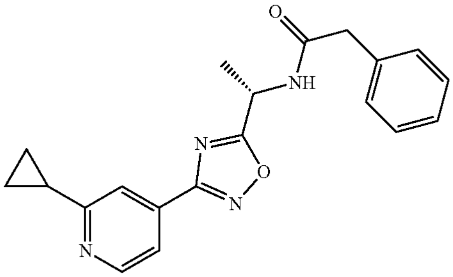
,
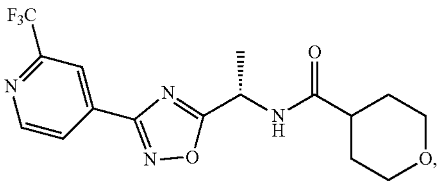
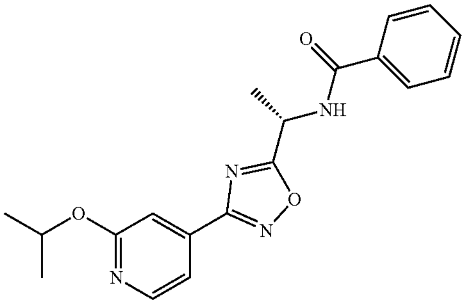
,
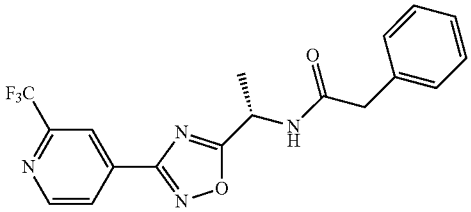
, -continued
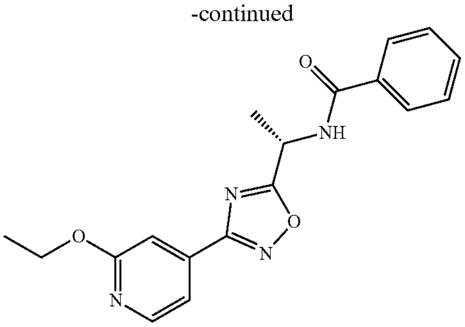
,
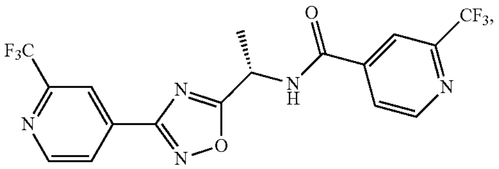
,
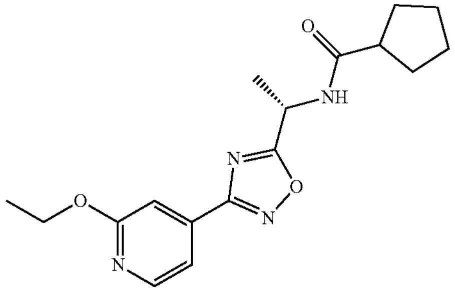
,
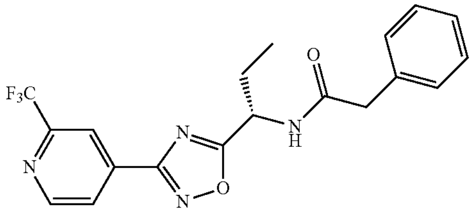
,
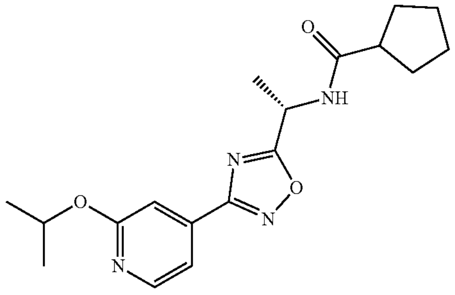
,
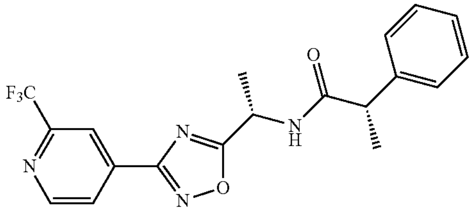
,
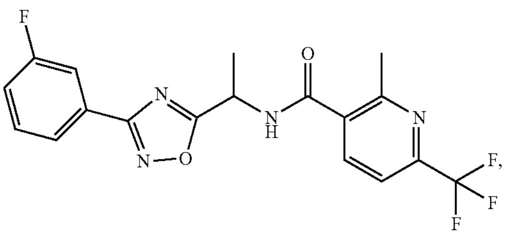
,
-continued
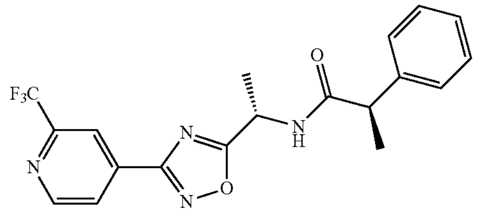
,
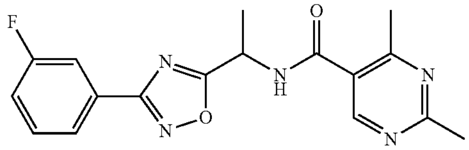
,
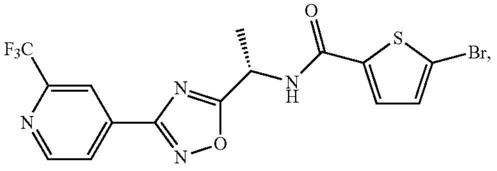
,
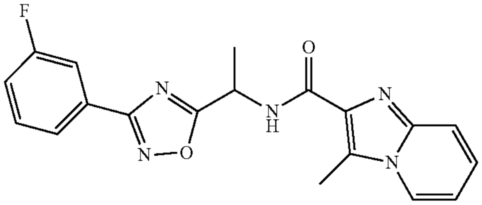
,
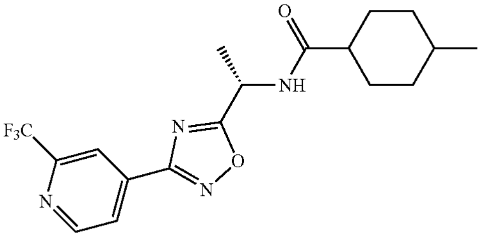
,
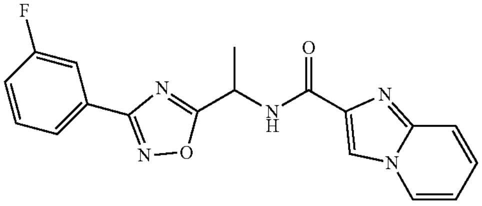
,
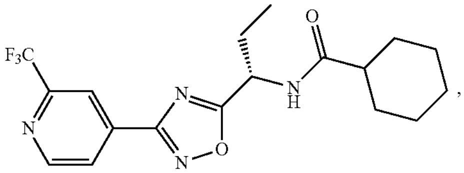
,
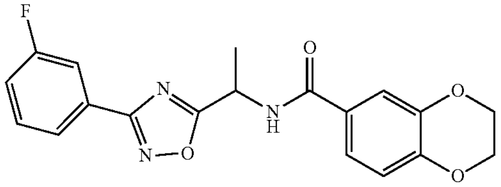
,
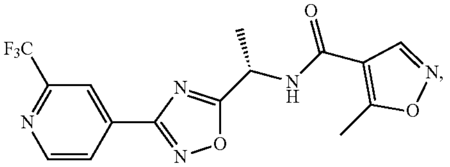

-continued
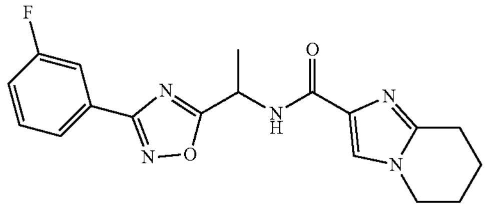
,
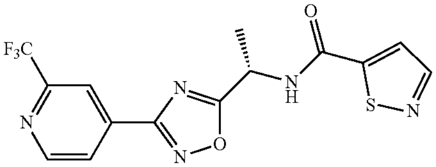
,
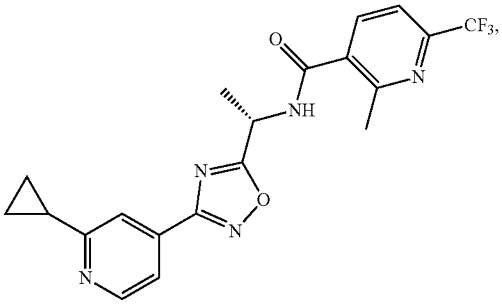
,
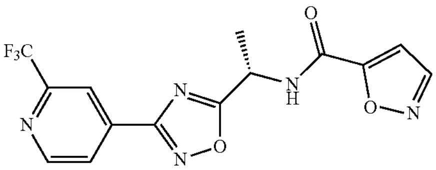
,
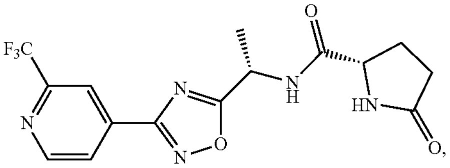
,
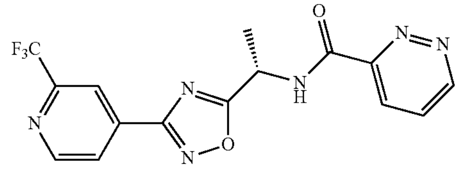
,
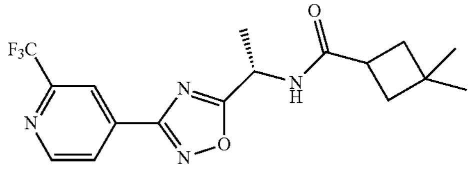
,
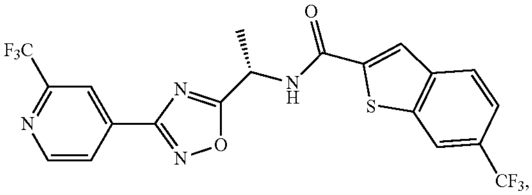
,
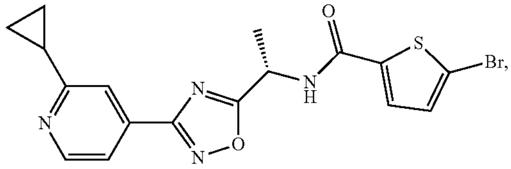
,
-continued
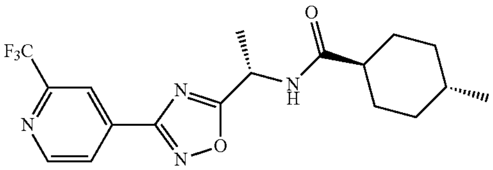
,
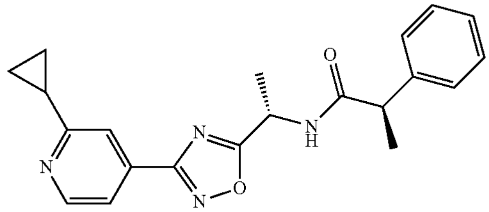
,
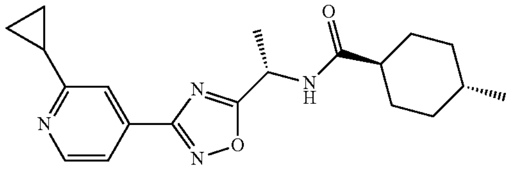
,
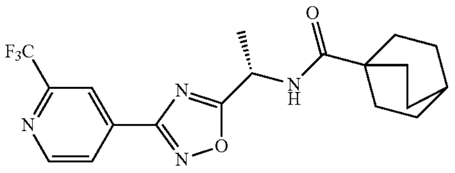
,
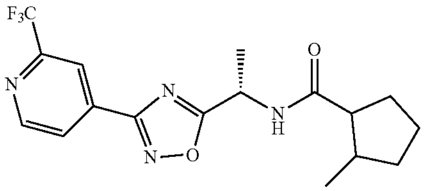
,
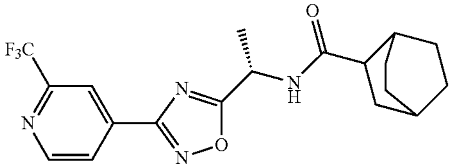
,
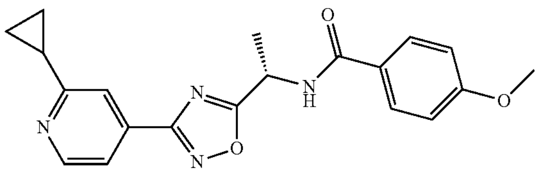
,
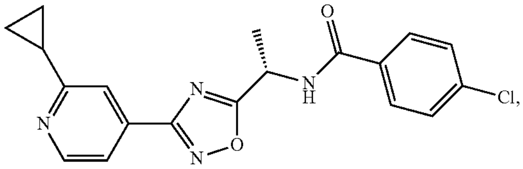
,
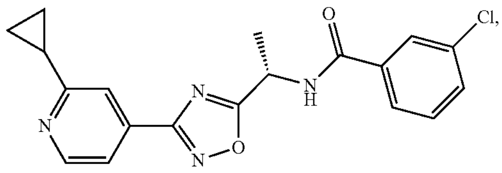
, -continued
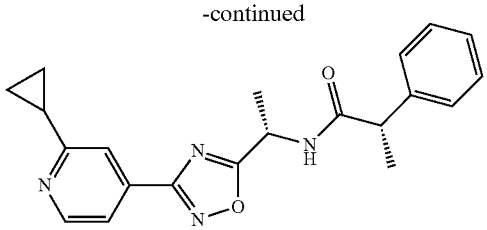
,
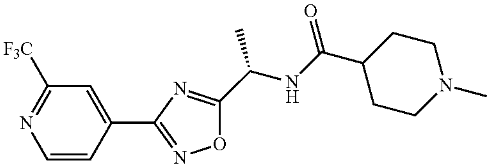
,
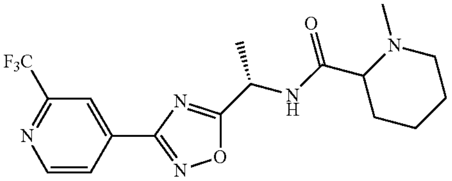
,
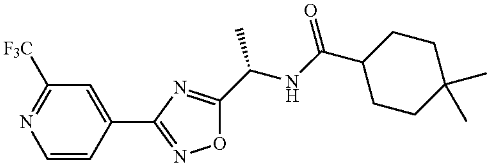
,
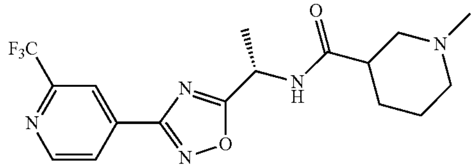
,
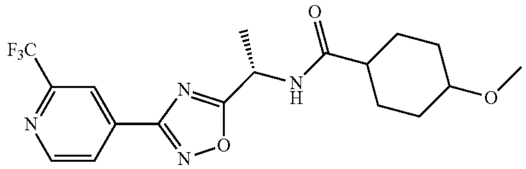
,
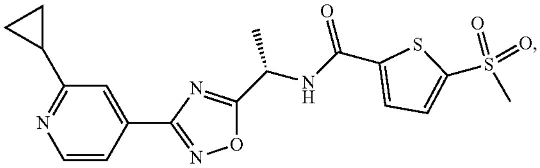
,
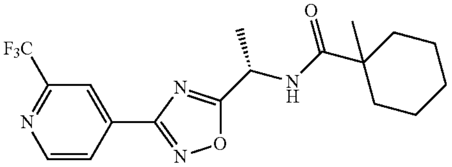
,
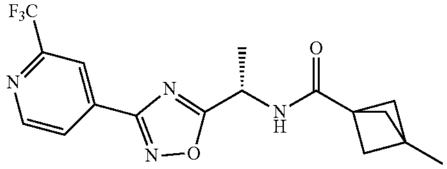
,
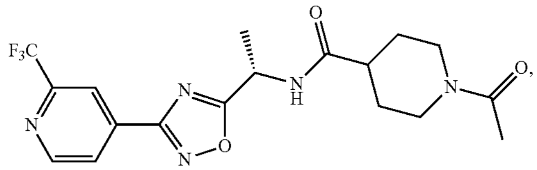
,
-continued
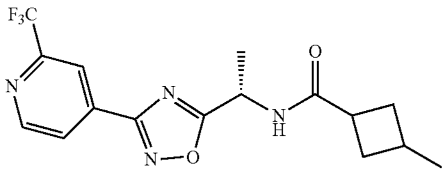
,
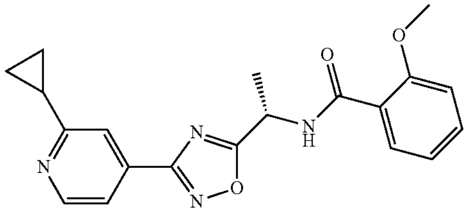
,
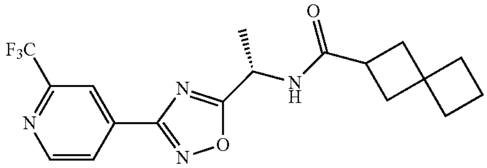
,
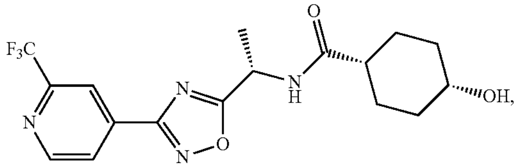
,
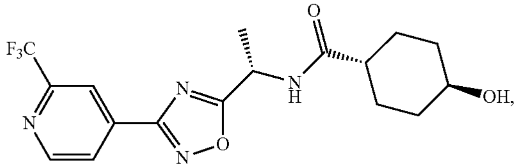
,
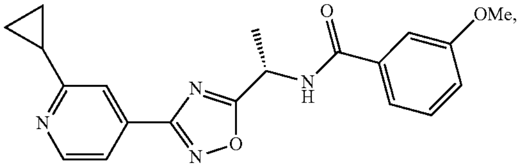
,
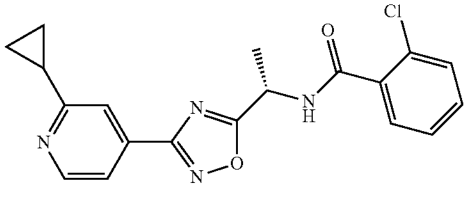
,
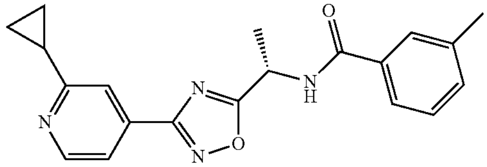
,
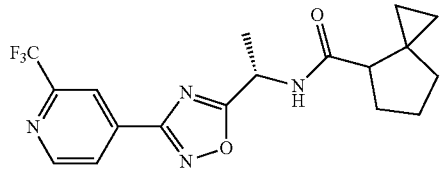
, -continued
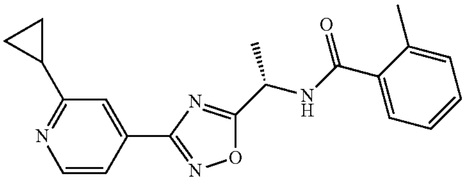
,
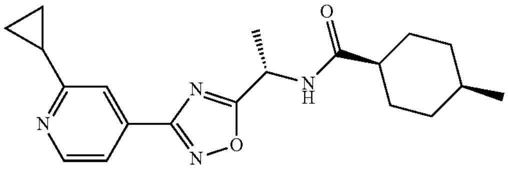
,
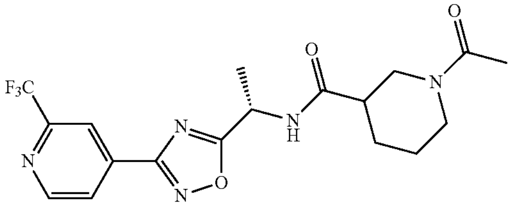
,
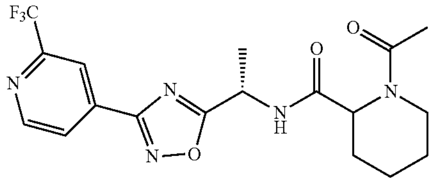
,
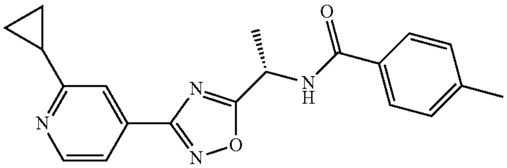
,
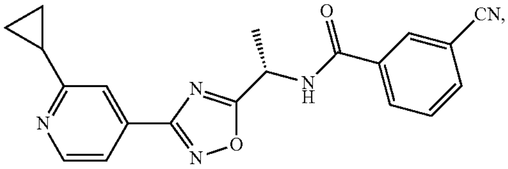
,
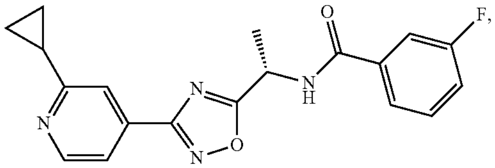
,
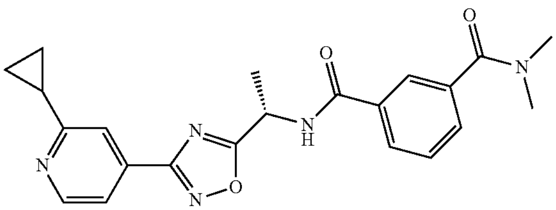
,
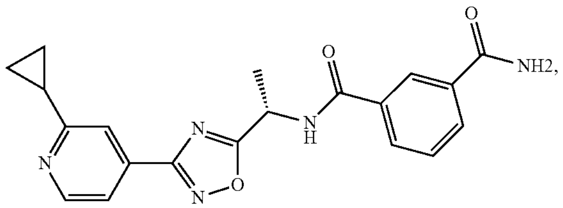
,
-continued
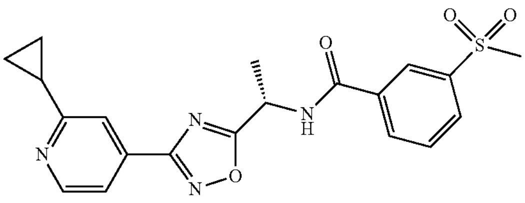
,
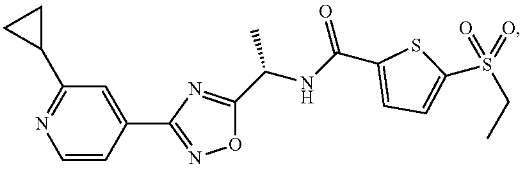
,
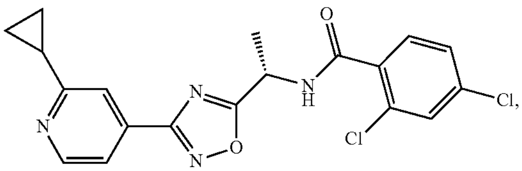
,
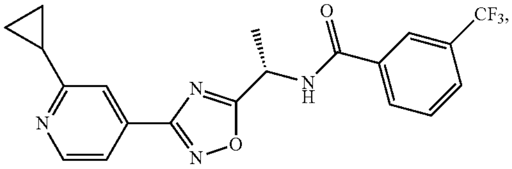
,
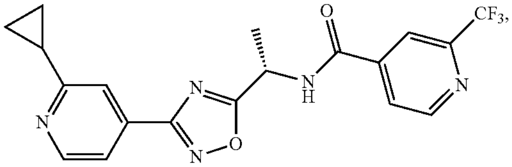
,
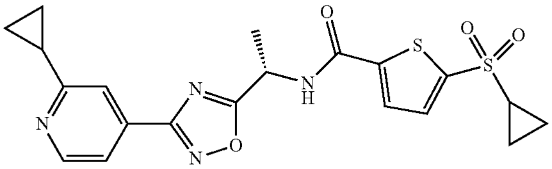
,
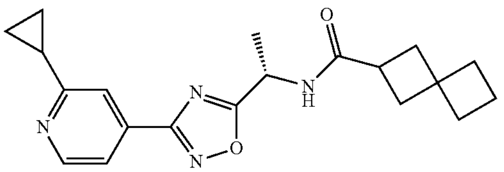
,
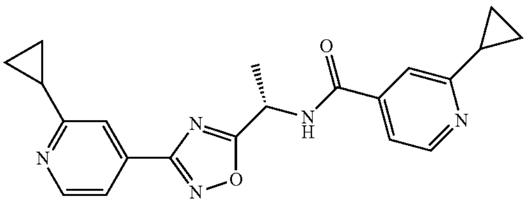
,
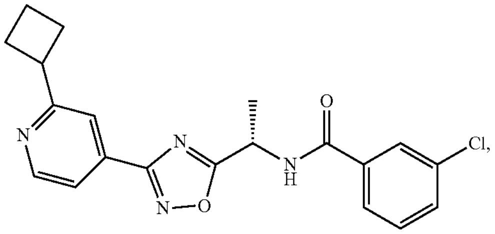

-continued

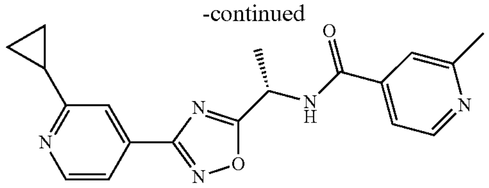

,

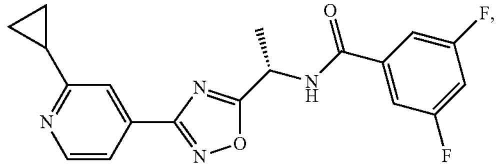

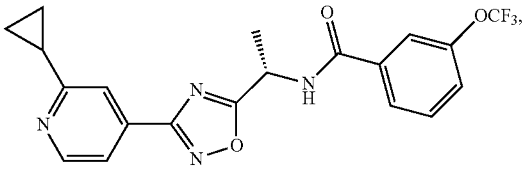

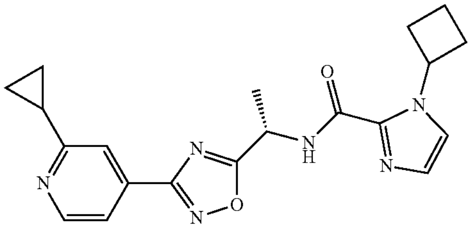

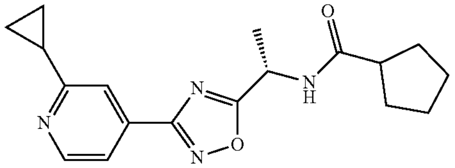

, or a pharmaceutically acceptable salt thereof.

In another aspect, provided herein is a pharmaceutical composition comprising a compound disclosed herein (e.g. a compound of Formula (I-I), or (e.g., (I-I-Ia), (I-I-Ib), (I-I-IIa), (I-I-IIb), (I-I-IIc), (I-I-IId), (I-I-IIe), or (I-I-IIf)), or a pharmaceutically acceptable salt thereof, and a pharmaceutically acceptable excipient.

In another aspect, the present invention features a compound of Formula (II-I):

(II-I)

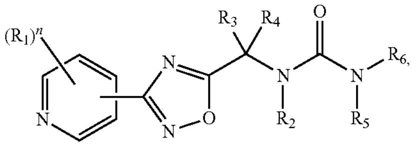

or a pharmaceutically acceptable salt thereof, wherein $R_1$ is each independently halogen, —CN, —OH, $C_{1-6}$alkyl, $C_{1-6}$haloalkyl, $C_{1-6}$alkoxy, $C_{1-6}$haloalkoxy, $C_{3-10}$cycloalkyl, phenyl, 3-10 membered heteroaryl, or 3-10 membered heterocyclyl;

$R_2$ is hydrogen or $C_{1-4}$alkyl;

$R_3$ is $C_{1-6}$alkyl optionally substituted with $C_{1-6}$alkoxy;

$R_4$ is hydrogen or $C_{1-6}$alkyl optionally substituted with $C_{1-6}$alkoxy;

$R_5$ and $R_6$ is each independently hydrogen, $C_{1-6}$alkyl, $C_{3-10}$cycloalkyl, phenyl, 3-10 membered heteroaryl, or 3-10 membered heterocyclyl, wherein the $C_{1-6}$alkyl, $C_{3-10}$cycloalkyl, phenyl, or 3-10 membered heterocyclyl may be optionally substituted with one or more of halogen, —CN, —OH, $C_{1-6}$alkyl, $C_{1-6}$haloalkyl, $C_{1-6}$alkoxy, aryl, $C_{3-10}$cycloalkyl, 3-10 membered heteroaryl, or 3-10 membered heterocyclyl; wherein $R_5$ and $R_6$ are not both hydrogen; or $R_5$ and $R_6$ can be taken together with the nitrogen attached to $R_5$ and $R_6$ to form a 3-10 membered heterocyclyl ring optionally substituted with one or more of halogen, —CN, —OH, $C_{1-6}$alkyl, $C_{1-6}$haloalkyl, aryl, $C_{3-10}$cycloalkyl, or 3-10 membered heterocyclyl; and n is 1 or 2.

In some embodiments of Formula II-I, the compound of Formula II-I is a compound of Formula II-I-a:

(II-I-a)

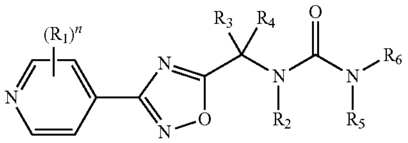

or a pharmaceutically acceptable salt thereof.

In some embodiments of Formula II-I, the compound of Formula II-I is a compound of Formula II-I-b:

(II-I-b)

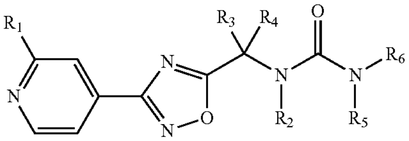

or a pharmaceutically acceptable salt thereof.

In some embodiments of Formula II-I, the compound of Formula II-I is a compound of Formula II-I-c:

(II-I-c)

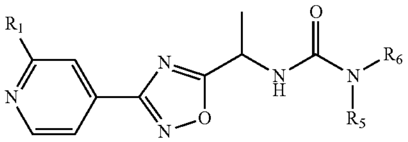

or a pharmaceutically acceptable salt thereof.

In some embodiments of Formula II-I, the compound of Formula II-I is a compound of Formula II-I-d:

(II-I-d)

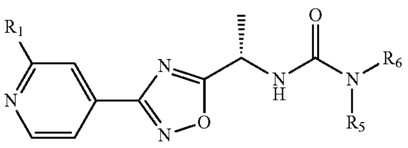

or a pharmaceutically acceptable salt thereof.

In some embodiments of Formula II-I (e.g., Formula II-I-a or II-I-b), $R_3$ is $C_{1-6}$alkyl and $R_4$ is hydrogen.

In some embodiments of Formula II-I (e.g., Formula II-I-a or II-I-b), $R_2$ is hydrogen.

In some embodiments of Formula II-I (e.g., Formula II-I-a), n is 1.

In some embodiments of Formula II-I (e.g., Formula II-I-a, II-I-b, II-I-c, or II-I-d), $R_5$ is hydrogen and $R_6$ $C_{1-6}$alkyl. In some embodiments of Formula II-I (e.g., Formula II-I-a, II-I-b, II-I-c, or II-I-d), $R_5$ and $R_6$ is each independently $C_{1-6}$alkyl. In some embodiments of Formula II-I (e.g., Formula II-I-a, II-I-b, II-I-c, or II-I-d), $R_5$ is $C_{1-6}$alkyl and $R_6$ is phenyl. In some embodiments of Formula II-I (e.g., Formula II-I-a, II-I-b, II-I-c, or II-I-d), $R_5$ and $R_6$ are taken together with the nitrogen attached to $R_5$ and $R_6$ to form a 3-10 membered heterocyclyl. In some embodiments, the 3-10 membered heterocyclyl is selected from the group consisting of 1,2,3,4-tetrahydroquinolinyl, 3,4-dihydro-2H-benzo[b][1,4]oxazinyl, 1,2,3,4-tetrahydroisoquinolinyl, and piperdinyl.

In some embodiments of Formula II-I (e.g., Formula II-I-a, II-I-b, II-I-c, or II-I-d), $R_1$ is selected from the group consisting of $C_{1-6}$haloalkyl, $C_{1-6}$alkoxy, and $C_{3-10}$cycloalkyl. In some embodiments of Formula II-I (e.g., Formula II-I-a, II-I-b, II-I-c, or II-I-d), $R_1$ is selected from the group consisting of cyclopropyl, isopropoxyl, and $-CF_3$.

In some embodiments of Formula II-I, the compound is selected from the group consisting of:

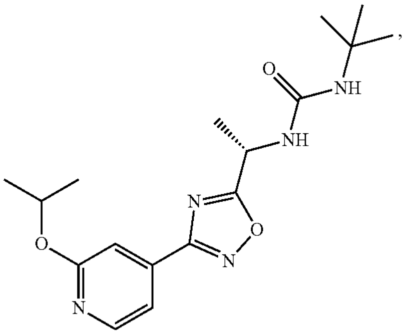
,

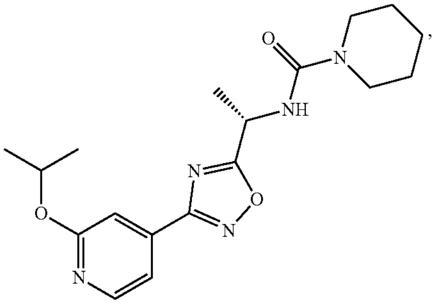
,

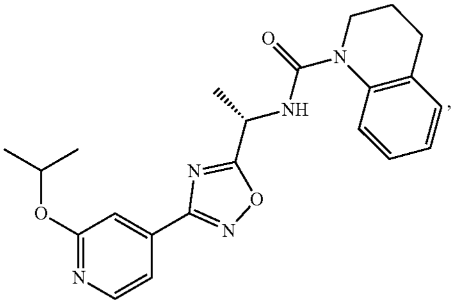
,

-continued

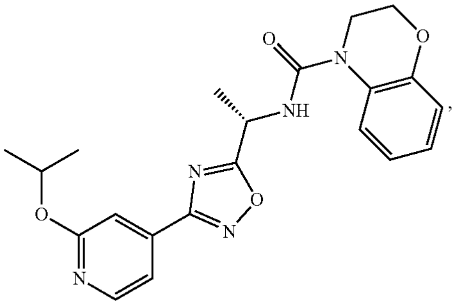
,

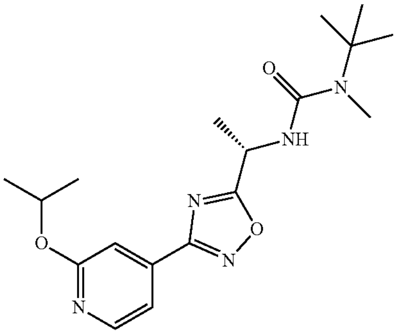
,

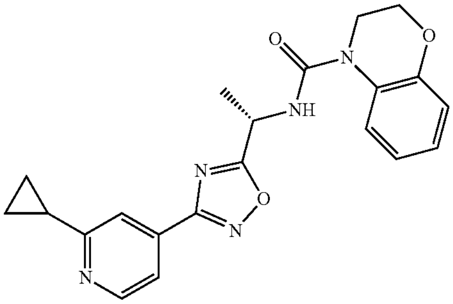
,

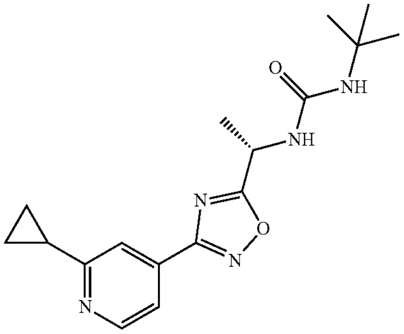
,

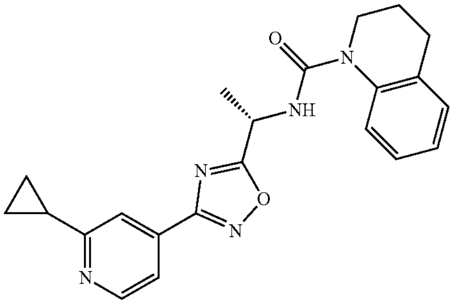
,

-continued

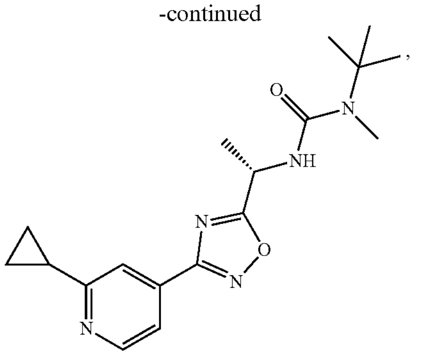

,

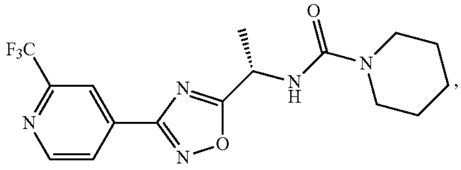

,

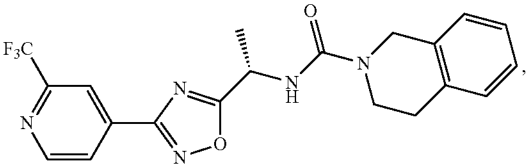

, and

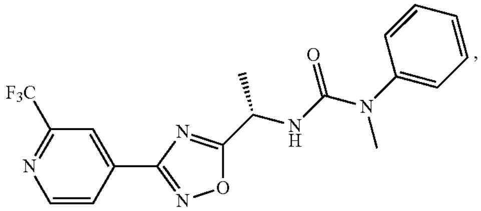

, or a pharmaceutically acceptable salt thereof.

In another aspect, provided herein is a pharmaceutical composition comprising a compound described herein (e.g., a compound of Formula (II-I) (e.g., (II-I-a), (II-I-b), (II-I-c), or (II-I-d))) or a pharmaceutically acceptable salt thereof and a pharmaceutically acceptable excipient.

In another aspect, the present invention features a compound of Formula (III-I):

(III-I)

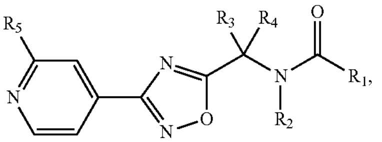

or a pharmaceutically acceptable salt thereof, wherein $R_1$ is $C_{1-6}$alkyl optionally substituted with one or more halogen, cyano, $C_{1-6}$haloalkyl, $C_{1-6}$alkoxy, $C_{1-6}$haloalkoxy, or $N(R^a)(R^b)$;

$R_2$ is hydrogen;

$R_3$ is $C_{1-6}$alkyl optionally substituted with $C_{1-6}$alkoxy;

$R_4$ is hydrogen;

$R_5$ is selected from the group consisting of halogen, $C_{1-6}$alkyl, $C_{1-6}$haloalkyl, $C_{1-6}$ alkoxy, $C_{1-6}$haloalkoxy, $N(R^c)(R^d)$, and $C_{3-10}$cycloalkyl; and $R^a$ and $R^b$ are each independently selected from the group consisting of $C_{1-6}$alkyl, $C_{1-6}$haloalkyl, and phenyl;

$R^c$ and $R^d$ are each independently selected from the group consisting of hydrogen, $C_{1-6}$alkyl, $C_{1-6}$haloalkyl, $C_{3-10}$cycloalkyl, and phenyl;

wherein, when $R_5$ is methoxy, $R_3$ is $C_{1-3}$alkyl.

In some embodiments of Formula III-I, the compound of Formula III-I is a compound of Formula III-Ia:

(III-Ia)

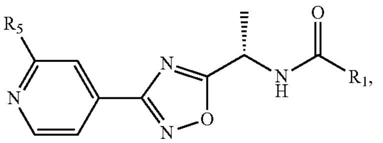

or a pharmaceutically acceptable salt thereof.

In some embodiments of Formula III-I (e.g., Formula III-Ia), $R_5$ is $C_{1-6}$haloalkyl or $C_{3-10}$cycloalkyl. In some embodiments of Formula III-I (e.g., Formula III-Ia), $R_5$ is $C_{1-6}$haloalkyl.

In some embodiments of Formula III-I (e.g., Formula III-Ia), $R_5$ is $CF_3$. In some embodiments of Formula III-I (e.g., Formula III-Ia), $R_5$ is cyclopropyl.

In some embodiments of Formula III-I (e.g., Formula III-Ia), $R_1$ is $C_{2-6}$alkyl optionally substituted with one or more halogen, cyano, $C_{1-6}$haloalkyl, $C_{1-6}$alkoxy, $C_{1-6}$haloalkoxy, or $N(R^a)(R^b)$. In some embodiments of Formula III-I (e.g., Formula III-Ia), $R_1$ is $C_{2-6}$alkyl optionally substituted with one or more halogen. In some embodiments of Formula III-I (e.g., Formula III-Ia), $R_1$ is $C_{1-6}$alkyl substituted with $N(R^a)(R^b)$. In some embodiments of Formula III-I (e.g., Formula III-Ia), $R_1$ is $C_{4-6}$alkyl. In some embodiments of Formula III-I (e.g., Formula III-Ia), $R_1$ is t-butyl.

In some embodiments of Formula III-I, $R_3$ is $C_{1-6}$alkyl. In some embodiments of Formula III-I, $R_3$ is methyl.

In some embodiments of Formula III-I (e.g., Formula III-Ia), $R^a$ and $R^b$ are each independently $C_{1-6}$alkyl or phenyl.

In some embodiments of Formula III-I, the compound of Formula III-I is selected from the group consisting of:

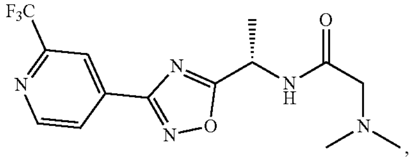

,

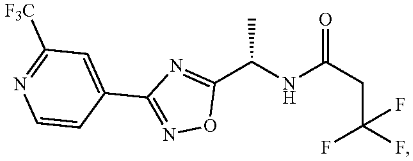

,

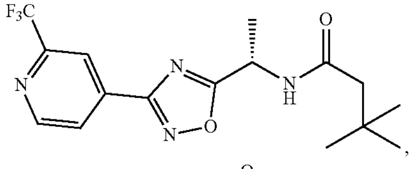

,

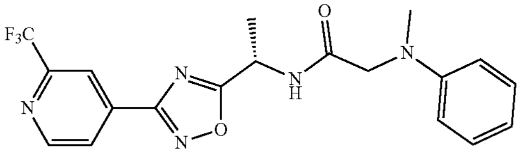

, and

-continued

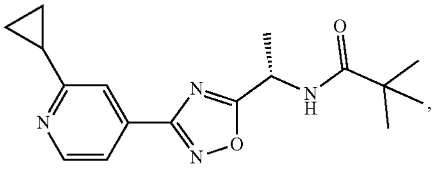

pharmaceutically acceptable salt thereof.

In another aspect, provided herein is a pharmaceutical composition comprising a compound disclosed herein (e.g. a compound of Formula (III-I) (e.g., Formula III-Ia))), or a pharmaceutically acceptable salt thereof, and a pharmaceutically acceptable excipient.

General Synthetic Schemes

Exemplary methods for preparing compounds described herein are illustrated in the following synthetic schemes. These schemes are given for the purpose of illustrating the invention, and should not be regarded in any manner as limiting the scope or the spirit of the invention.

SCHEME I-1

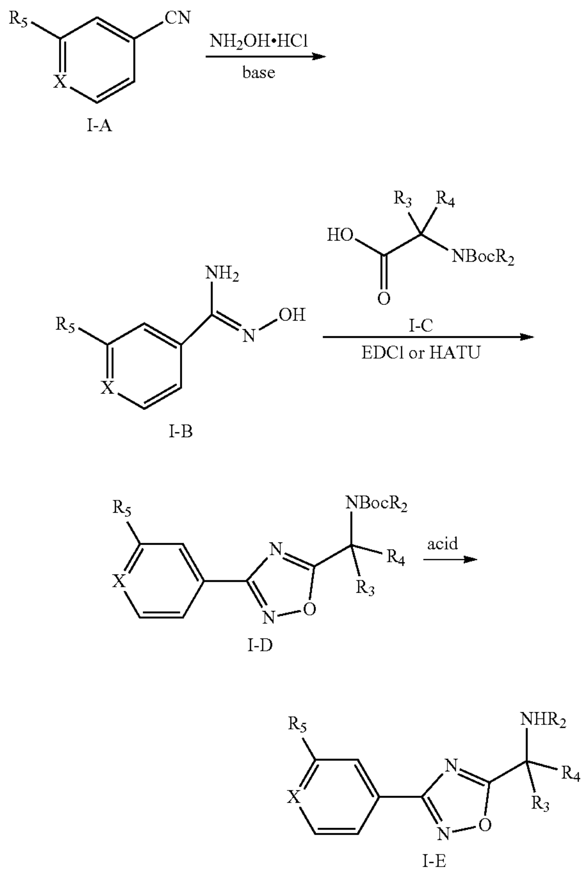

The synthetic route illustrated in Scheme I-1 depicts an exemplary procedure for preparing intermediate I-E. In the first step, I-A is treated with hydroxylamine to provide I-B. Then, HATU or EDCI-mediated cyclization of I-B with glycine I-C affords oxadiazole I-D. Deprotection of I-D under acidic conditions provides intermediate I-E.

SCHEME I-2

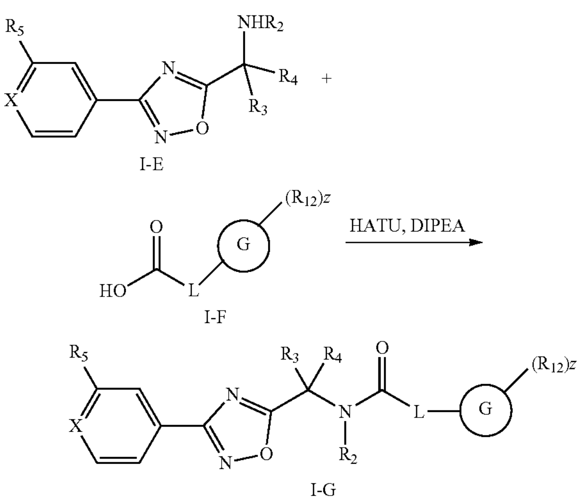

The synthetic route illustrated in Scheme I-2 depicts an exemplary procedure for preparing I-G (a compound of Formula I-I). Coupling of intermediate I-E and carboxylic acid I-F using standard peptide coupling procedures (e.g., HATU in dichloromethane in the presence of DIPEA) provides compound I-G (a compound of Formula I-I).

SCHEME II-1

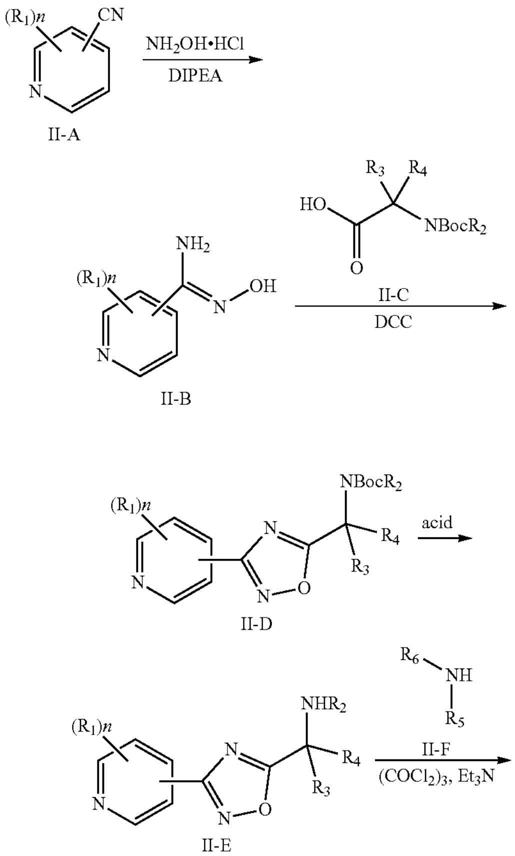

-continued

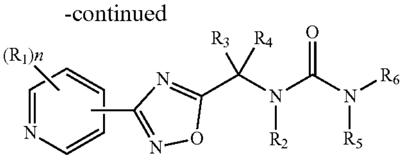

II-G

The synthetic route illustrated in Scheme II-1 depicts an exemplary procedure for preparing II-G (a compound of Formula II-I). In the first step, cyanopyridine II-A is reacted with hydroxylamine to provide nicotimidamide II-B. Then, N,N'-dicyclohexylcarbodiimide (DCC)-mediated cyclization of II-B with glycine II-C affords oxadiazole II-D. Deprotection of II-D under acidic conditions provides amine-substituted oxadiazole intermediate II-E, which is then treated with amine II-F to afford II-G (a compound of Formula II-I).

SCHEME III-1

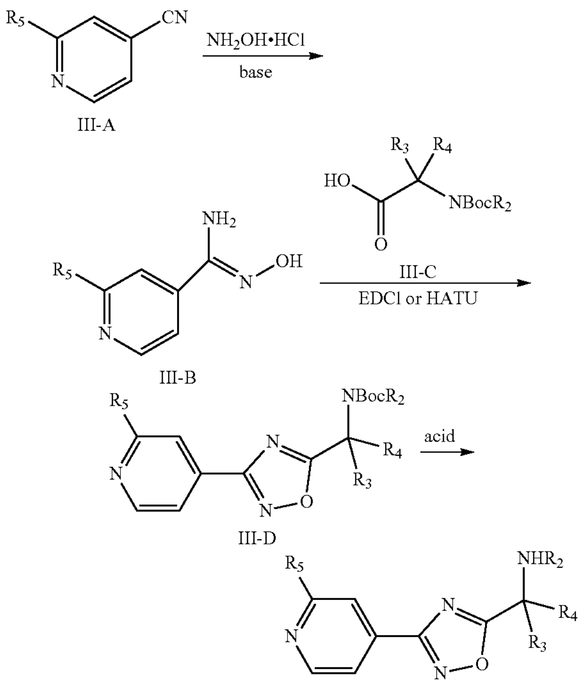

III-E

The synthetic route illustrated in Scheme III-1 depicts an exemplary procedure for preparing intermediate III-E. In the first step, III-A is treated with hydroxylamine to provide III-B. Then, HATU or EDCI-mediated cyclization of III-B with glycine III-C affords oxadiazole III-D. Deprotection of III-D under acidic conditions provides intermediate III-E.

SCHEME III-2

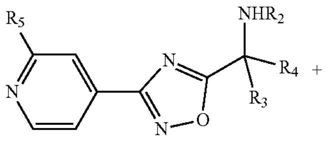

III-E

-continued

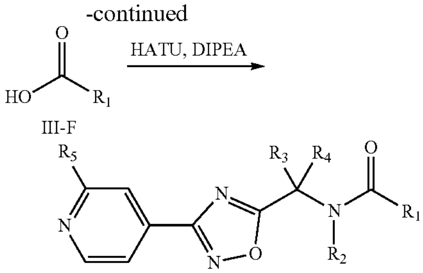

III-G

The synthetic route illustrated in Scheme III-2 depicts an exemplary procedure for preparing III-G (a compound of Formula III-I). Coupling of intermediate III-E and carboxylic acid III-F using standard peptide coupling procedures (e.g., HATU in dichloromethane in the presence of DIPEA) provides compound III-G (a compound of Formula III-I).

Methods of Treatment

The compounds and compositions described above and herein can be used to treat a neurological disease or disorder or a disease or condition associated with excessive neuronal excitability and/or a gain-of-function mutation in a gene (e.g., KCNT1). Exemplary diseases, disorders, or conditions include epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, developmental and epileptic encephalopathy (DEE), early infantile epileptic encephalopathy (EIEE), generalized epilepsy, focal epilepsy, multifocal epilepsy, temporal lobe epilepsy, Ohtahara syndrome, early myoclonic encephalopathy and Lennox Gastaut syndrome, drug resistant epilepsy, seizures (e.g., frontal lobe seizures, generalized tonic clonic seizures, asymmetric tonic seizures, focal seizures), leukodystrophy, hypomyelinating leukodystrophy, leukoencephalopathy, and sudden unexpected death in epilepsy, cardiac dysfunctions (e.g., cardiac arrhythmia, Brugada syndrome, myocardial infarction), pulmonary vasculopathy/hemorrhage, pain and related conditions (e.g. neuropathic pain, acute/chronic pain, migraine, etc), muscle disorders (e.g. myotonia, neuromyotonia, cramp muscle spasms, spasticity), itch and pruritis, movement disorders (e.g., ataxia and cerebellar ataxias), psychiatric disorders (e.g. major depression, anxiety, bipolar disorder, schizophrenia, attention-deficit hyperactivity disorder), neurodevelopmental disorder, learning disorders, intellectual disability, Fragile X, neuronal plasticity, and autism spectrum disorders.

In some embodiments, the neurological disease or disorder or the disease or condition associated with excessive neuronal excitability and/or a gain-of-function mutation in a gene (e.g., KCNT1) is selected from EIMFS, ADNFLE and West syndrome. In some embodiments, the neurological disease or disorder or the disease or condition associated with excessive neuronal excitability and/or a gain-of-function mutation in a gene (e.g., KCNT1) is selected from infantile spasms, epileptic encephalopathy, focal epilepsy, Ohtahara syndrome, developmental and epileptic encephalopathy and Lennox Gastaut syndrome. In some embodiments, the neurological disease or disorder or the disease or condition associated with excessive neuronal excitability and/or a gain-of-function mutation in a gene (e.g., KCNT1) is seizure. In some embodiments, the neurological disease or disorder or the disease or condition associated with excessive neuronal excitability and/or a gain-of-function mutation in a gene (e.g., KCNT1) is selected from cardiac arrhythmia, Brugada syndrome, and myocardial infarction.

In some embodiments, the neurological disease or disorder or the disease or condition associated with excessive neuronal excitability and/or a gain-of-function mutation in a gene (e.g., KCNT1) is selected from the group consisting of the learning disorders, Fragile X, intellectual function, neuronal plasticity, psychiatric disorders, and autism spectrum disorders.

Accordingly, the compounds and compositions thereof can be administered to a subject with a neurological disease or disorder or a disease or condition associated with excessive neuronal excitability and/or a gain-of-function mutation in a gene such as KCNT1 (e.g., EIMFS, ADNFLE, West syndrome, infantile spasms, epileptic encephalopathy, focal epilepsy, Ohtahara syndrome, developmental and epileptic encephalopathy, and Lennox Gastaut syndrome, seizures, cardiac arrhythmia, Brugada syndrome, and myocardial infarction).

EIMFS is a rare and debilitating genetic condition characterized by an early onset (before 6 months of age) of almost continuous heterogeneous focal seizures, where seizures appear to migrate from one brain region and hemisphere to another. Patients with EIMFS are generally intellectually impaired, non-verbal and non-ambulatory. While several genes have been implicated to date, the gene that is most commonly associated with EIMFS is KCNT1. Several de novo mutations in KCNT1 have been identified in patients with EIMFS, including V271F, G288S, R428Q, R474Q, R474H, R474C, 1760M, A934T, P924L, G243S, H257D, A259D, R262Q, Q270E, L2741, F346L, C377S, R398Q, P409S, A477T, F502V, M516V, Q550del, K629E, K629N, I760F, E893K, M896K, R933G, R950Q, K1154Q (Barcia et al. (2012) Nat Genet. 44: 1255-1260; Ishii et al. (2013) Gene 531:467-471; McTague et al. (2013) Brain. 136: 1578-1591; Epi4K Consortium & Epilepsy Phenome/Genome Project. (2013) Nature 501:217-221; Lim et al. (2016) Neurogenetics; Ohba et al. (2015) Epilepsia 56:el21-el28; Zhou et al. (2018) Genes Brain Behav. e12456; Moller et al. (2015) Epilepsia. el14-20; Numis et al. (2018) Epilepsia. 1889-1898; Madaan et al. Brain Dev. 40(3):229-232; McTague et al. (2018) Neurology. 90(1):e55-e66; Kawasaki et al. (2017) J Pediatr. 191:270-274; Kim et al. (2014) Cell Rep. 9(5):1661-1672; Ohba et al. (2015) Epilepsia. 56(9): e121-8; Rizzo et al. (2016) Mol Cell Neurosci. 72:54-63; Zhang et al. (2017) Clin Genet. 91(5):717-724; Mikati et al. (2015) Ann Neurol. 78(6):995-9; Baumer et al. (2017) Neurology. 89(21):2212; Dilena et al. (2018) Neurotherapeutics. 15(4):1112-1126). These mutations are gain-of-function, missense mutations that are dominant (i.e. present on only one allele) and result in change in function of the encoded potassium channel that causes a marked increase in whole cell current when tested in *Xenopus* oocyte or mammalian expression systems (see e.g. Milligan et al. (2015) Ann Neurol. 75(4): 581-590; Barcia et al. (2012) Nat Genet. 44(11): 1255-1259; and Mikati et al. (2015) Ann Neurol. 78(6): 995-999).

ADNFLE has a later onset than EIMFS, generally in mid-childhood, and is generally a less severe condition. It is characterized by nocturnal frontal lobe seizures and can result in psychiatric, behavioural and cognitive disabilities in patients with the condition. While ADNFLE is associated with genes encoding several neuronal nicotinic acetylcholine receptor subunits, mutations in the KCNT1 gene have been implicated in more severe cases of the disease (Heron et al. (2012) Nat Genet. 44: 1188-1190). Functional studies of the mutated KCNT1 genes associated with ADNFLE indicated that the underlying mutations (M896I, R398Q, Y796H and R928C) were dominant, gain-of-function mutations (Milligan et al. (2015) Ann Neurol. 75(4): 581-590; Mikati et al. (2015) Ann Neurol. 78(6): 995-999).

West syndrome is a severe form of epilepsy composed of a triad of infantile spasms, an interictal electroencephalogram (EEG) pattern termed hypsarrhythmia, and mental retardation, although a diagnosis can be made one of these elements is missing. Mutations in KCNT1, including G652V and R474H, have been associated with West syndrome (Fukuoka et al. (2017) *Brain Dev* 39:80-83 and Ohba et al. (2015) *Epilepsia* 56:el21-el28). Treatment targeting the KCNT1 channel suggests that these mutations are gain-of-function mutations (Fukuoka et al. (2017) Brain Dev 39:80-83).

In one aspect, the present invention features a method of treating treat a disease or condition associated with excessive neuronal excitability and/or a gain-of-function mutation in a gene such as KCNT1 (for example, epilepsy and other encephalopathies (e.g., epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy (DEE), and Lennox Gastaut syndrome, seizures, leukodystrophy, leukoencephalopathy, intellectual disability, Multifocal Epilepsy, Generalized tonic clonic seizures, Drug resistant epilepsy, Temporal lobe epilepsy, cerebellar ataxia, Asymmetric Tonic Seizures) and cardiac dysfunctions (e.g., cardiac arrhythmia, Brugada syndrome, sudden unexpected death in epilepsy, myocardial infarction), pain and related conditions (e.g. neuropathic pain, acute/chronic pain, migraine, etc), muscle disorders (e.g. myotonia, neuromyotonia, cramp muscle spasms, spasticity), itch and pruritis, ataxia and cerebellar ataxias, psychiatric disorders (e.g. major depression, anxiety, bipolar disorder, schizophrenia), learning disorders, Fragile X, neuronal plasticity, and autism spectrum disorders) comprising administering to a subject in need thereof a compound disclosed herein (e.g., a compound of Formula (I-I), (I-I-2), (I-I-I), (I-I-I2), (I-I-I3), (I-I-II), (I-I-II2), (II-I), or (III-I) or a pharmaceutically acceptable salt thereof) or a pharmaceutical composition disclosed herein (e.g., a pharmaceutical composition comprising a compound disclosed herein (e.g., a compound of Formula (I-I), (I-I-2), (I-I-I), (I-I-I2), (I-I-I3), (I-I-II), (I-I-II2), (II-I), or (III-I) or a pharmaceutically acceptable salt thereof), and a pharmaceutically acceptable excipient).

In some examples, the subject presenting with a disease or condition that may be associated with a gain-of-function mutation in KCNT1 is genotyped to confirm the presence of a known gain-of-function mutation in KCNT1 prior to administration of the compounds and compositions thereof. For example, whole exome sequencing can be performed on the subject. Gain-of-function mutations associated with EIMFS may include, but are not limited to, V271F, G288S, R428Q, R474Q, R474H, R474C, I760M, A934T, P924L, G243S, H257D, A259D, R262Q, Q270E, L2741, F346L, C377S, R398Q, P409S, A477T, F502V, M516V, Q550del, K629E, K629N, I760F, E893K, M896K, R933G, R950Q, and K1154Q. Gain-of-function mutations associated with ADNFLE may include, but are not limited to, M896I, R398Q, Y796H, R928C, and G288S. Gain-of-function mutations associated with West syndrome may include, but are not limited to, G652V and R474H. Gain-of-function mutations associated with temporal lobe epilepsy may include, but are not limited to, R133H and R565H. Gain-of-function mutations associated with Lennox-Gastaut may include, but are not limited to, R209C. Gain-of-function mutations associated with seizures may include, but are not limited to, A259D, G288S, R474C, R474H. Gain-of-function mutations associated with leukodystrophy may include, but are not limited to, G288S and Q906H.

Gain-of-function mutations associated with Multifocal Epilepsy may include, but are not limited to, V340M. Gain-of-function mutations associated with EOE may include, but are not limited to, F346L and A934T. Gain-of-function mutations associated with Early-onset epileptic encephalopathies (EOEE) may include, but are not limited to, R428Q. Gain-of-function mutations associated with developmental and epileptic encephalopathies may include, but are not limited to, F346L, R474H, and A934T. Gain-of-function mutations associated with epileptic encephalopathies may include, but are not limited to, L437F, Y796H, P924L, R961H. Gain-of-function mutations associated with Early Infantile Epileptic Encephalopathy (EIEE) may include, but are not limited to, M896K. Gain-of-function mutations associated with drug resistent epilepsy and generalized tonic-clonic seizure may include, but are not limited to, F346L. Gain-of-function mutations associated with migrating partial seizures of infancy may include, but are not limited to, R428Q. Gain-of-function mutations associated with Leukoencephalopathy may include, but are not limited to, F932I.

Gain-of-function mutations associated with NFLE may include, but are not limited to, A934T and R950Q. Gain-of-function mutations associated with Ohtahara syndrome may include, but are not limited to, A966T. Gain-of-function mutations associated with infantile spasms may include, but are not limited to, P924L. Gain-of-function mutations associated with Brugada Syndrome may include, but are not limited to, R1106Q. Gain-of-function mutations associated with Brugada Syndrome may include, but are not limited to, R474H.

In other examples, the subject is first genotyped to identify the presence of a mutation in KCNT1 and this mutation is then confirmed to be a gain-of-function mutation using standard in vitro assays, such as those described in Milligan et al. (2015) Ann Neurol. 75(4): 581-590. Typically, the presence of a gain-of-function mutation is confirmed when the expression of the mutated KCNT1 allele results an increase in whole cell current compared to the whole cell current resulting from expression of wild-type KCNT1 as assessed using whole-cell electrophysiology (such as described in Milligan et al. (2015) Ann Neurol. 75(4): 581-590; Barcia et al. (2012) Nat Genet. 44(11): 1255-1259; Mikati et al. (2015) Ann Neurol. 78(6): 995-999; or Rizzo et al. Mol Cell Neurosci. (2016) 72:54-63). This increase of whole cell current can be, for example, an increase of at least or about 50%, 100%, 150%, 200%, 250%, 300%, 350%, 400% or more. The subject can then be confirmed to have a disease or condition associated with a gain-of-function mutation in KCNT1.

In particular examples, the subject is confirmed as having a KCNT1 allele containing a gain-of-function mutation (e.g. V271F, G288S, R398Q, R428Q, R474Q, R474H, R474C, G652V, I760M, Y796H, M896I, P924L, R928C or A934T).

The compounds disclosed herein (e.g., a compound of Formula (I-I), (I-I-2), (I-I-I2), (I-I-I3), (I-I-II), (I-I-II2), (II-I), or (III-I) or a pharmaceutically acceptable salt thereof) or the pharmaceutical composition disclosed herein (e.g., a pharmaceutical composition comprising a compound disclosed herein (e.g., a compound of Formula (I-I), (I-I-2), (I-I-I), (I-I-I2), (I-I-I3), (I-I-II), (I-I-II2), (II-I), or (III-I) or a pharmaceutically acceptable salt thereof), and a pharmaceutically acceptable excipient) can also be used therapeutically for conditions associated with excessive neuronal excitability where the excessive neuronal excitability is not necessarily the result of a gain-of-function mutation in KCNT1. Even in instances where the disease is not the result of increased KCNT1 expression and/or activity, inhibition of KCNT1 expression and/or activity can nonetheless result in a reduction in neuronal excitability, thereby providing a therapeutic effect. Thus, the compounds disclosed herein (e.g., a compound of Formula (I-I), (I-I-2), (I-I-I), (I-I-I2), (I-I-I3), (I-I-II), (I-I-II2), (II-I), or (III-I) or a pharmaceutically acceptable salt thereof) or the pharmaceutical composition disclosed herein (e.g., a pharmaceutical composition comprising a compound disclosed herein (e.g., a compound of Formula (I-I), (I-I-2), (I-I-I2), (I-I3), (I-I-II), (I-I-II2), (II-I), or (III-I) or a pharmaceutically acceptable salt thereof), and a pharmaceutically acceptable excipient) can be used to treat a subject with conditions associated with excessive neuronal excitability, for example, epilepsy and other encephalopathies (e.g., epilepsy of infancy with migrating focal seizures (EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, and Lennox Gastaut syndrome, seizures) or cardiac dysfunctions (e.g., cardiac arrhythmia, Brugada syndrome, myocardial infarction), regardless of whether or not the disease or disorder is associated with a gain-of-function mutation in KCNT1.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.) The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, Protecting Groups in Organic Synthesis, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

List of Abbreviations
THE tetrahydrofuran
TFA trifluoroacetic acid
DMF N,N-dimethylformamide
MeOH methanol
DCM dichloromethane
MeCN or ACN acetonitrile
PE petroleum ether
EtOAc ethyl acetate
DIPEA N,N,-diisopropylethylamine
$Et_3N$ or TEA triethylamine
HATU o-(7-azabenzotriazol-1-yl)-N,N,N',N'-tetramethyluronium hexafluorophosphate
T3P propanephosphonic acid anhydride
DCC N,N'-dicyclohexylcarbodiimide
N-Boc-L-alanine (2S)-2-({[(2-methyl-2-propanyl)oxy]carbonyl}amino)propanoic acid
DMSO dimethyl sulfoxide
$Pd(OAc)_2$ palladium(II) acetate
RuPhos 2-dicyclohexylphosphino-2',6'-diisopropoxybiphenyl
EGTA ethylene glycol-bis(R-aminoethyl ether)-N,N,N',N'-tetraacetic acid
NMDG N-methyl-D-glucamine
HEPES 4-(2-hydroxyethyl)piperazine-1-ethanesulfonic acid
$IC_{50}$ half maximal inhibitory concentration TLC thin layer chromatography
LCMS liquid chromatography-mass spectrometry
HPLC high-performance liquid chromatagraphy
SFC supercritical fluid chromatography
MS mass spectrometry
NMR nuclear magnetic resonance

Example I-1: (S)-5-(trifluoromethyl)-N-(1-(3-(2-(trifluoromethyl)pyridin-4-yl)-1,2,4-oxadiazol-5-yl)ethyl)picolinamide

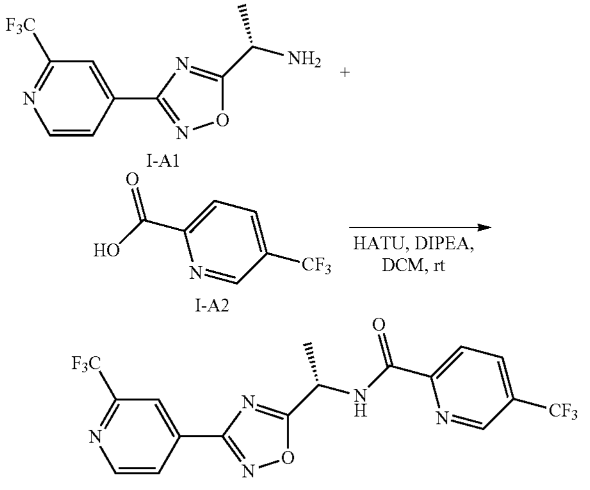

I-1

To a stirred solution of I-A2 (100 mg, 0.52 mmol) and I-A1 (0.15 g, 0.58 mmol) in DCM (10 mL) were added DIPEA (0.18 mL, 1.05 mmol) and HATU (298.44 mg, 0.78 mmol) at RT and stirred at RT for 2 h. Then, the reaction was quenched using water (100 mL) and diluted with DCM (100 mL×2). Combined organic layer was dried over sodium sulphate and evaporated to obtain the residue which was purified by column chromatography using 100-200 silica and 30-80% EtOAc/Hexane eluent to afford I-1 (70 mg, 0.16 mmol, 30% yield) as a solid. HPLC: Rt 9.11 min, 99.3%; Column: X-Select CSH C18 (4.6×150) mm, 3.5 μm; Mobile phase: A: 0.1% FA in water:ACN (95:05), B: ACN; Flow Rate: 1.0 mL/min. LCMS: 432.00 (M+H), Rt 2.10 min; Column: X-select CSH C18 (3×50) mm, 2.5 μm. $^1H$ NMR (400 MHz, DMSO-d6) δ 9.87 (d, 1H), 9.10-9.08 (m, 1H), 9.04-8.98 (m, 1H), 8.50-8.43 (m, 1H), 8.31-8.22 (m, 3H), 5.65-5.52 (m, 1H), 1.75 (d, 3H). Chiral method: Rt 3.63 min, 100%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 264 nm, Flow Rate: 3 mL/min.

Example I-2: (S)-3,3-difluoro-N-(1-(3-(2-(trifluoromethyl)pyridin-4-yl)-1,2,4-oxadiazol-5-yl)ethyl)cyclobutane-1-carboxamide

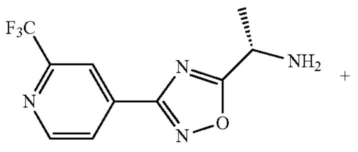

I-A1

-continued

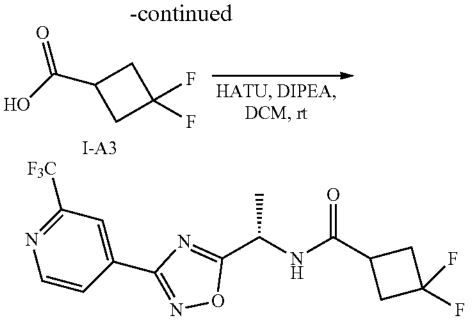

I-A3

I-2

To a stirred solution of I-A3 (0.1 g, 0.73 mmol) and I-A1 (216.5 mg, 0.73 mmol) in DCM (10 mL) were added DIPEA (0.26 mL, 1.47 mmol) and HATU (419.06 mg, 1.1 mmol) at RT and stirred at RT for 2 h. Then, the reaction was quenched using water (100 mL) and diluted with DCM (100 mL×2). Combined organic layer was dried over sodium sulphate and evaporated to obtain the residue which was purified by column chromatography using 100-200 silica and 30-80% EtOAc/Hexane eluent to afford I-2 (65 mg, 0.17 mmol, 23% yield) as a solid. HPLC: Rt 8.38 min, 99.1%; Column: X-Select CSH C18 (4.6×150) mm, 5 μm; Mobile phase: A: 0.1% FA in water:ACN (95:05), B: ACN; Flow Rate: 1.0 mL/min. LCMS: 377.00 (M+H), Rt 1.87 min; Column: X-select CSH C18 (3×50) mm, 2.5 μm. $^1H$ NMR (400 MHz, DMSO-d6) δ 9.04-8.90 (m, 2H), 8.32-8.23 (m, 2H), 5.35-5.22 (m, 1H), 2.99-2.95 (m, 1H), 2.75-2.64 (m, 4H), 1.62-1.54 (m, 3H). Chiral HPLC: Rt 3.05 min, 99.0%; SFC column: DIACEL CHIRALPAK-IG (250×4.6 mm, 5 um), Mobile Phase: A) $CO_2$ B) MeOH+0.1% $NH_3$, Gradient: 20-40% B in 5 min, hold 40% B till 9 min, 40-20% B at 10 min, hold 20% B till 12 min, Wavelength: 271 nm, Flow Rate: 3 mL/min.

Example I-3: (S)-4,4-difluoro-N-(1-(3-(2-(trifluoromethyl)pyridin-4-yl)-1,2,4-oxadiazol-5-yl)ethyl)cyclohexane-1-carboxamide

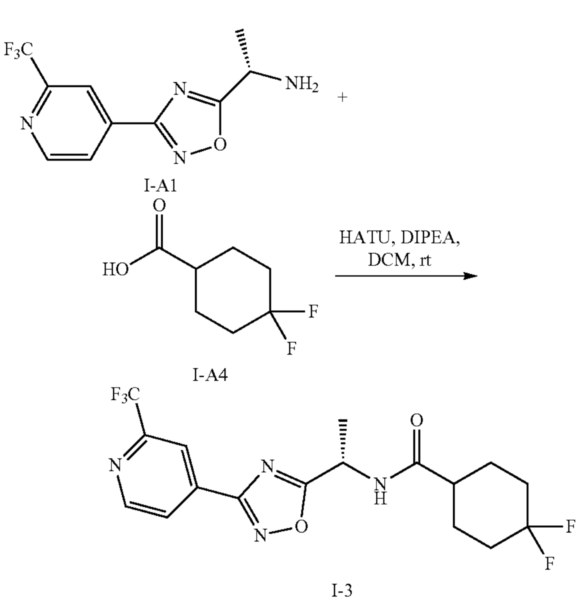

I-A1

I-A4

I-3

To a stirred solution of I-A4 (0.1 g, 0.61 mmol) and I-A1 (179.51 mg, 0.61 mmol) in DCM (10 mL) were added DIPEA (0.21 mL, 1.22 mmol) and HATU (347.45 mg, 0.91 mmol) at RT and stirred for 2 h. Then, the reaction was quenched using water (100 mL) and diluted with DCM (100 mL×2). Combined organic layer was dried over sodium sulphate and evaporated to give residue which was purified by column chromatography using 100-200 silica and 30-80% EtOAc/Hexane eluent to afford I-3 (60 mg, 0.14 mmol, 24% yield) as a solid. HPLC: Rt 8.58 min, 99.6%; Column: X-Select CSH C18 (4.6×150) mm, 5 μm; Mobile phase: A: 0.1% FA in water:ACN (95:05), B: ACN; Flow Rate: 1.0 mL/min. LCMS: 405.05 (M+H), Rt 1.95 min; Column: X-select CSH C18 (3×50) mm, 2.5 μm. $^1H$ NMR (400 MHz, DMSO-d6) δ 9.02 (d, 1H), 8.79 (d, 1H), 8.26-8.25 (m, 2H), 5.29-5.20 (m, 1H), 2.41-2.35 (m, 1H), 2.06-2.04 (m, 2H), 1.90-1.75 (m, 4H), 1.71-1.64 (m, 2H), 1.56 (d, 3H). Chiral HPLC: Rt 3.53 min, 100%; SFC column: DIACEL CHIRALPAK-IG (250×4.6 mm, 5 um), Mobile Phase: A) $CO_2$ B) MeOH+0.1% $NH_3$, Gradient:20-40% B in 5 min, hold 40% B till 9 min, 40-20% B at 10 min, hold 20% B till 12 min, Wavelength: 271 nm, Flow Rate: 3 mL/min.

Example I-4: (S)-2-(trifluoromethyl)-N-(1-(3-(2-(trifluoromethyl)pyridin-4-yl)-1,2,4-oxadiazol-5-yl)ethyl)-1H-imidazole-4-carboxamide

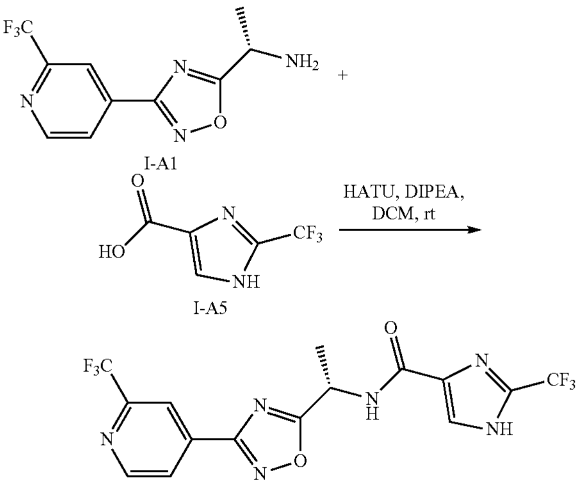

I-A1

I-A5

I-4

To a stirred solution of I-A5 (100 mg, 0.56 mmol) and I-A1 (163.63 mg, 0.56 mmol) in DCM (10 mL) were added DIPEA (0.19 mL, 1.11 mmol) and HATU (316.72 mg, 0.83 mmol) at RT and stirred at RT for 2 h. Then, the reaction was quenched using water (100 mL) and diluted with DCM (100 mL×2). Combined organic layer was dried over sodium sulphate and evaporated to obtain residue which was purified by column chromatography using 100-200 silica and 30-80% EtOAc/Hexane eluent to afford I-4 (25 mg, 0.05 mmol, 10% yield) as a solid. HPLC: Rt 7.99 min, 99.6%; Column: X-Select CSH C18 (4.6×150) mm, 3.5 μm; Mobile phase: A: 0.1% FA in water:ACN (95:05), B: ACN; Flow Rate: 1.0 mL/min. LCMS: 421.00 (M+H), Rt 1.86 min; Column: X-select CSH C18 (3×50) mm, 2.5 μm. $^1H$ NMR (400 MHz, DMSO-d6) δ 14.22 (bs, 1H), 9.08 (d, 1H), 9.01 (d, 1H), 8.3-8.22 (m, 2H), 8.01 (s, 1H), 5.54-5.42 (m, 1H), 1.70 (d, 3H). Chiral HPLC: Rt: 2.67 min, 100%, Column:

DIACEL CHIRALPAK-1G (250×4.6 mm, 5 um); Mobile phase: A) $CO_2$ B) MeOH+0.1% $NH_3$ Gradient: 10-40% B in 5 min, hold 40% B till 9 min, 40-10% B at 10 min, hold 10% B till 12 min, Wavelength: 280 nm, Flow Rate: 3 mL/min.

Example I-5: (S)-4-(trifluoromethyl)-N-(1-(3-(2-(trifluoromethyl)pyridin-4-yl)-1,2,4-oxadiazol-5-yl)ethyl)thiazole-2-carboxamide

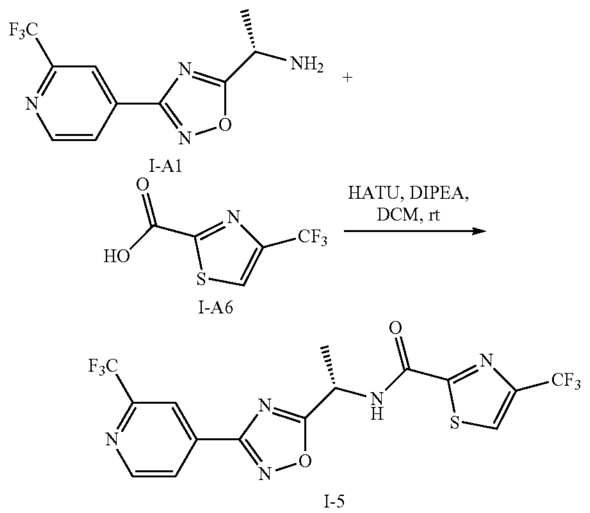

I-A1 I-A6 I-5

To a stirred solution of I-A6 (100 mg, 0.51 mmol) and I-A1 (149.47 mg, 0.51 mmol) in DCM (10 mL) were added DIPEA (0.18 mL, 1.01 mmol) and HATU (289.31 mg, 0.76 mmol) at RT and stirred at RT for 2 h. Then, the reaction was quenched using water (100 mL) and diluted with DCM (100 mL×2). The combined organic layer was dried over sodium sulphate and evaporated to obtain residue which was purified by column chromatography using 100-200 silica and 30-80% EtOAc/Hexane eluent to afford I-5 (80 mg, 0.18 mmol, 35% yield) as a solid. HPLC: Rt 9.24 min, 99.7%; Column: X-Select CSH C18 (4.6×150) mm, 5 μm; Mobile phase: A: 0.1% FA in water:ACN (95:05), B: ACN; Flow Rate: 1.0 mL/min. LCMS: 438.00 (M+H), Rt 2.06 min; Column: X-select CSH C18 (3×50) mm, 2.5 μm. $^1H$ NMR (400 MHz, DMSO-d6) δ 9.97 (d, 1H), 9.05-8.98 (m, 1H), 8.85 (s, 1H), 8.31-8.25 (m, 2H), 5.58-5.54 (m, 1H), 1.74 (d, 3H). Chiral HPLC: Rt: 2.89 min, 95.2%, Column: DIACEL CHIRALPAK-1G (250×4.6 mm, 5 um); Mobile phase: A) $CO_2$ B) MeOH+0.1% $NH_3$ Gradient: 10-40% B in 5 min, hold 40% B till 9 min, 40-10% B at 10 min, hold 10% B till 12 min, Wavelength: 261 nm, Flow Rate: 3 mL/min.

Example I-6: (S)—N-(1-(3-(2-(trifluoromethyl)pyridin-4-yl)-1,2,4-oxadiazol-5-yl)ethyl)isonicotinamide

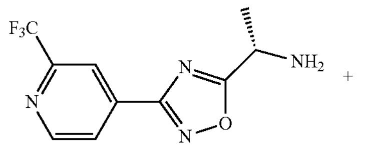

I-A1

-continued

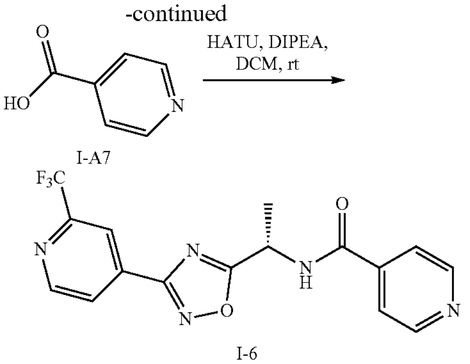

I-A7 I-6

To a stirred solution of I-A7 (100 mg, 0.81 mmol) and I-A1 (230.7 mg, 0.89 mmol) in DCM (5 mL) was added DIPEA (0.42 mL, 2.44 mmol) and HATU (463.28 mg, 1.22 mmol) at 0° C. and stirred at RT for 5 h. Then, the reaction was quenched by water added DCM (10 mL×3). The combined organic layer was dried over sodium sulphate and concentrated to obtain residue. The residue was purified by column chromatography on silica gel (100-200) using MeOH:DCM (2:98) eluent to afford I-6 (60 mg, 0.15 mmol, 19% yield) as a solid. HPLC: Rt 7.01 min, 97.0%; Column: X-Select CSH C18 (4.6×150) mm, 3.5 μm; Mobile phase: A: 0.1% FA in water:ACN (95:05), B: ACN; Flow Rate: 1.0 mL/min. LCMS: 364.00 (M+H), Rt 1.67 min; Column: X-select CSH C18 (3×50) mm, 2.5 μm. $^1H$ NMR (400 MHz, DMSO-d6) δ 9.60 (d, 1H), 9.01 (d, 1H), 8.79-8.75 (m, 2H), 8.28 (d, 2H), 7.84-7.76 (m, 2H), 5.56-5.48 (m, 1H), 1.72 (d, 3H). Chiral HPLC: Rt 4.72 min, 93.6%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 9 min, Wavelength: 270 nm, Flow Rate: 3 mL/min.

Example I-7: (S)—N-(1-(3-(2-(trifluoromethyl)pyridin-4-yl)-1,2,4-oxadiazol-5-yl)ethyl)picolinamide

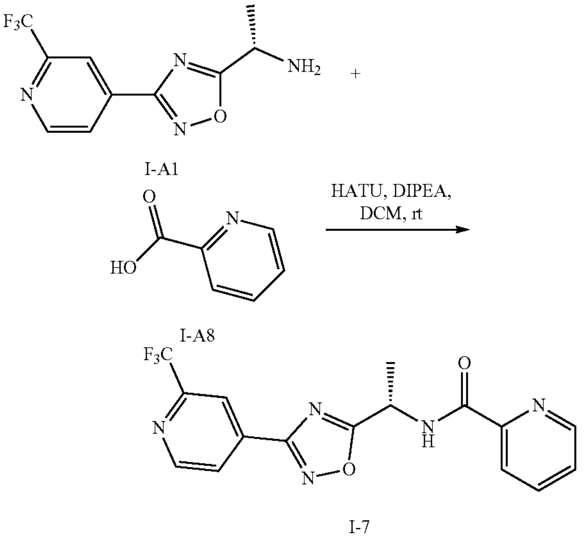

I-A1 I-A8 I-7

To a stirred solution of I-A8 (100 mg, 0.81 mmol) in DCM (5 mL) were added DIPEA (0.42 mL, 2.44 mmol) and HATU (463.28 mg, 1.22 mmol) at 0° C. To resulting reaction mixture I-A1 (230.7 mg, 0.89 mmol) was added at 0° C. and stirred at RT for 5 h. Then, the reaction was diluted with water and extracted with DCM (10 mL×3). Combined organic layer was dried over sodium sulphate and evaporated to obtain a residue. The residue was purified by column chromatography using silica gel (100-200) and MeOH: DCM (2:98) eluent to afford I-7 (70 mg, 0.18 mmol, 23% yield) as a solid. HPLC: Rt 8.34 min, 99.8%; Column: X-Select CSH C18 (4.6×150) mm, 5 μm; Mobile phase: A: 0.1% FA in water:ACN (95:05), B: ACN; Flow Rate: 1.0 mL/min. LCMS: 364.05 (M+H), Rt 1.92 min; Column: X-select CSH C18 (3×50) mm, 2.5 μm. $^1$H NMR (400 MHz, DMSO-d6) δ 9.65 (d, 1H), 9.05-8.96 (m, 1H), 8.72-8.68 (m, 1H), 8.30-8.25 (m, 2H), 8.11-7.99 (m, 2H), 7.68-7.64 (m, 1H), 5.58-5.52 (m, 1H), 1.74 (d, 3H). Chiral HPLC: Rt 5.33 min, 99.1%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 12 min, Wavelength: 265 nm, Flow Rate: 3 mL/min.

Example I-8: (S)—N-(1-(3-(2-(trifluoromethyl)pyridin-4-yl)-1,2,4-oxadiazol-5-yl)ethyl)benzamide

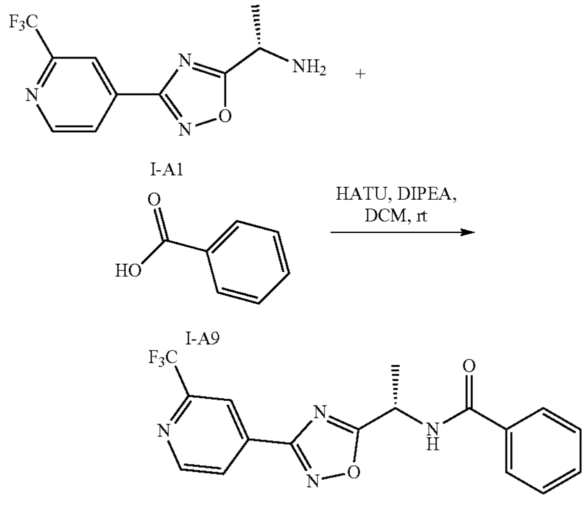

I-A1

I-A9

I-8

To a stirred solution of I-A9 (47.71 mg, 0.34 mmol) and I-A1 (0.1 g, 0.34 mmol) in DCM (10 mL) were added TEA (0.05 mL, 0.34 mmol) at RT and stirred for 2 h. Then, the reaction was quenched using water (100 mL) diluted with DCM (100 mL×2). The combined organic layer was dried over sodium sulphate and evaporated to obtain residue which was purified by column chromatography using 100-200 silica and 30-80% EtOAc/Hexane eluent to afford I-8 (22 mg, 0.06 mmol, 18% yield) as a solid. HPLC: Rt: 8.43 min, 99.8%; Column: X-Select CSH C18 (4.6×150) mm, 3.5 μm; Mobile phase: A: 0.1% FA in water:ACN (95:05), B: ACN; Flow Rate: 1.0 mL/min. LCMS: 363.20 (M+H), Rt 1.91 min; Column: X-select CSH C18 (3×50) mm, 2.5 μm. $^1$H NMR (400 MHz, DMSO-d6): δ 9.30 (d, 1H), 9.01 (d, 1H), 8.28-8.25 (m, 2H), 7.92-7.90 (m, 2H), 7.60-7.49 (m, 3H), 5.46-5.54 (m, 1H), 1.71 (d, 3H). Chiral HPLC: Rt 3.68 min, 100%; SFC column: DIACEL CHIRALPAK-IG (250×4.6 mm, 5 um), Mobile Phase: A) $CO_2$ B) MeOH+0.1% $NH_3$, Gradient:20-40% B in 5 min, hold 40% B till 9 min, 40-20% B in 10 min, hold 20% B till 12 min. Wavelength: 266 nm, Flow Rate: 3 mL/min.

Example I-9: S)—N-(1-(3-(2-(trifluoromethyl)pyridin-4-yl)-1,2,4-oxadiazol-5-yl)ethyl)cyclohexanecarboxamide

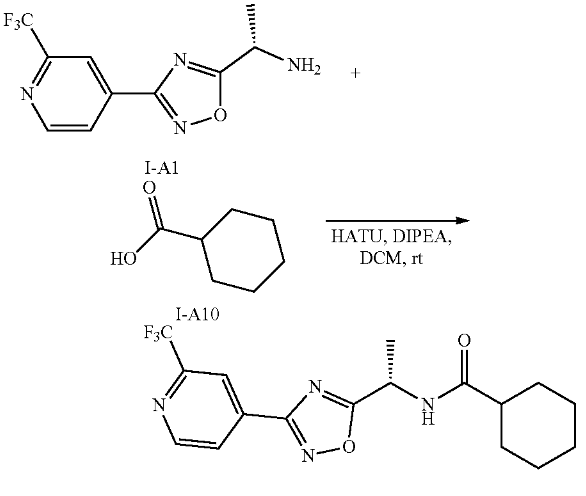

I-A1

I-A10

I-9

To a stirred solution of I-A10 (100 mg, 0.78 mmol) in DCM (5 mL) was added DIPEA (0.41 mL, 2.34 mmol) and HATU (444.99 mg, 1.17 mmol) at 0° C. To a resulting reaction mixture I-A1 (252.89 mg, 0.86 mmol) was added at 0° C. and stirred at RT for 16 h. Then, the reaction was diluted with water and extracted with DCM (10 mL×3). The combined organic layer was dried over sodium sulphate and evaporated to obtain the reaction product which was purified by prep HPLC to afford I-9 (75 mg, 0.20 mmol, 26% yield) as a solid. HPLC: Rt 8.80 min, 99.7%; Column: X-Select CSH C18 (4.6×150) mm, 3.5 μm; Mobile phase: A: 0.1% FA in water:ACN (95:05), B: ACN; Flow Rate: 1.0 mL/min. LCMS: 369.09 (M+H), Rt 2.01 min; Column: X-select CSH C18 (3×50) mm, 2.5 μm. $^1$H NMR (400 MHz, DMSO-d6): δ 9.01 (d, 1H), δ 8.61 (d, 1H), 8.26-8.25 (m, 2H), 5.28-5.20 (m, 1H), 2.20-2.17 (m, 1H), 1.72-1.59 (m, 4H), 1.62-1.59 (m, 1H), 1.54 (d, 3H), 1.35-1.15 (m, 5H). Chiral HPLC: Rt 3.57 min, 100%; SFC column: DIACEL CHIRALPAK-IG (250×4.6 mm, 5 um), Mobile Phase: A) $CO_2$ B) MeOH+0.1% $NH_3$, Gradient:20-40% B in 5 min, hold 40% B till 9 min, 40-20% B in 10 min, hold 20% B till 12 min. Wavelength: 270 nm, Flow Rate: 3 mL/min.

Example I-10: (S)-2-(trifluoromethyl)-N-(1-(3-(2-(trifluoromethyl)pyridin-4-yl)-1,2,4-oxadiazol-5-yl)ethyl)thiazole-4-carboxamide

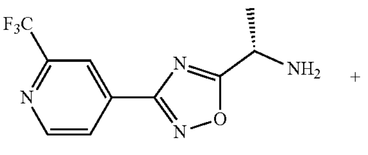

I-A1

-continued

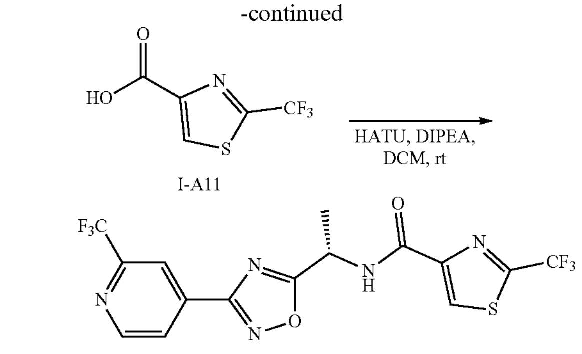

I-A11

I-10

To a stirred solution of I-A11 (80.29 mg, 0.41 mmol) and I-A1 (100 mg, 0.34 mmol) in DCM (10 mL) were added DIPEA (0.12 mL, 0.68 mmol) and HATU (193.56 mg, 0.51 mmol) at RT and stirred at RT for 2 h. Then, the reaction was quenched using water (100 mL) and diluted with DCM (100 mL×2). Combined organic layer was dried over sodium sulphate and evaporated to obtain residue which was purified by column chromatography using 100-200 silica and 30-80% EtOAc/Hexane eluent to afford I-10 (43 mg, 0.09 mmol, 28% yield) as a solid. HPLC: Rt 9.17 min, 99.9%; Column: X-Select CSH C18 (4.6×150) mm, 5 μm; Mobile phase: A: 0.1% FA in water:ACN (95:05), B: ACN; Flow Rate: 1.0 mL/min. LCMS: 437.95 (M+H), Rt 2.13 min; Column: X-select CSH C18 (3×50) mm, 2.5 μm. $^1$H NMR (400 MHz, DMSO-d6): δ 9.55 (d, 1H), 9.02-9.00 (m, 1H), 8.78 (s, 1H), 8.28-8.27 (m, 2H), 5.56-5.52 (m, 1H), 1.73 (d, 3H). Chiral method: Rt 3.54 min, 100%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 70% B till 9 min, 40-10% B in 10 min, hold 10% B till 12 min. Wavelength: 270 nm, Flow Rate: 3 mL/min.

Example I-11: (S)—N-(1-(3-(2-(trifluoromethyl)pyridin-4-yl)-1,2,4-oxadiazol-5-yl)ethyl)nicotinamide

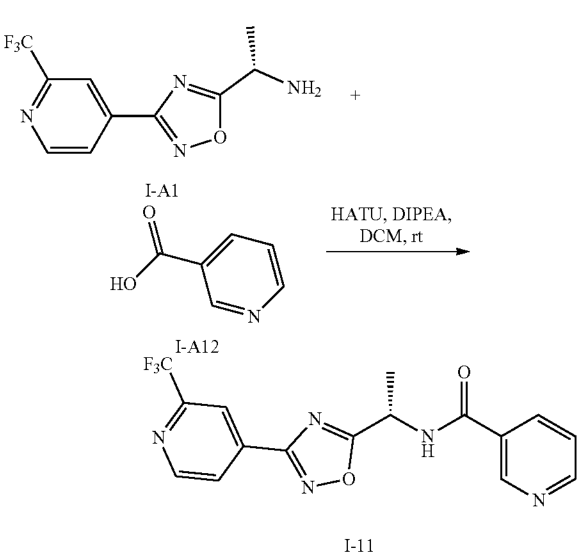

I-A1

I-A12

I-11

To a stirred solution of I-A12 (100 mg, 0.81 mmol) in DCM (5 mL) were added DIPEA (0.42 mL, 2.44 mmol) and HATU (463.28 mg, 1.22 mmol) at 0° C. To resulting reaction mixture I-A1 (263.28 mg, 0.89 mmol) was added at 0° C. and stirred at RT for 16 h. Then, the reaction was diluted with water and extracted with DCM (10 mL×3). Combined organic layer was dried over sodium sulphate and evaporated to obtain a residue. The residue was purified by prep-HPLC to afford I-11 (90 mg, 0.24 mmol, 30% yield) as a solid. HPLC: Rt:7.38 min, 99.7%; Column: X-Select CSH C18 (4.6×150) mm, 5 μm; Mobile phase: A: 0.1% FA in water:ACN (95:05), B: ACN; Flow Rate: 1.0 mL/min. LCMS: 364.20 (M+H), Rt 1.74 min; Column: X-select CSH C18 (3×50) mm, 2.5 μm. $^1$H NMR (400 MHz, DMSO-d6): δ 9.53 (d, 1H), 9.07 (d, 1H), 9.01 (d, 1H), 8.77 (d, 1H), 8.28-8.25 (m, 3H), 7.59-7.567 (m, 1H), 5.56-5.49 (m, 1H), 1.72 (d, 3H). Chiral HPLC: Rt 6.49 min, 100%; SFC column: DIACEL CHIRALPAK-IG (250×4.6 mm, 5 um), Mobile Phase: A) $CO_2$ B) MeOH+0.1% $NH_3$, Gradient:35-50% B in 5 min, hold 50% B till 9 min, 50-35% B in 10 min, hold 35% B till 12 min. Wavelength: 266 nm, Flow Rate: 3 mL/min.

Example I-12: (S)—N-(1-(3-(2-(trifluoromethyl)pyridin-4-yl)-1,2,4-oxadiazol-5-yl)ethyl)tetrahydro-2H-pyran-4-carboxamide

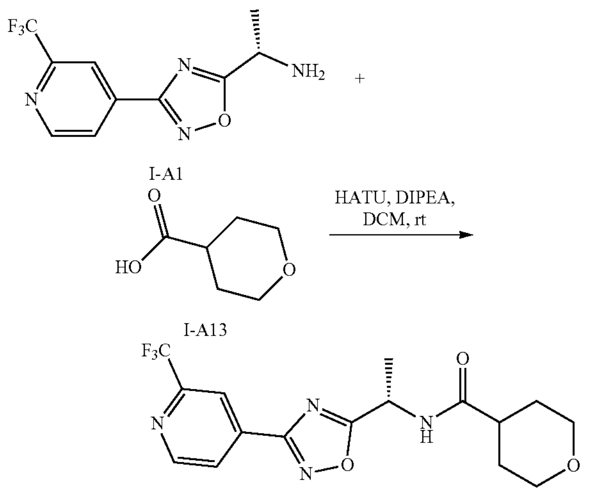

I-A1

I-A13

I-12

To a stirred solution of I-A13 (100 mg, 0.77 mmol) in DCM (5 mL) were added DIPEA (0.40 mL, 2.31 mmol) and HATU (438.25 mg, 1.15 mmol) at 0° C. To resulting reaction mixture, I-A1 (249.06 mg, 0.85 mmol) was added at 0° C. and stirred at RT for 10 h. Then, the reaction was diluted with water and extracted with DCM (10 mL×3). The combined organic layer was dried over sodium sulphate and evaporated to obtain a residue. The residue was purified by prep HPLC to afford I-12 (95 mg, 0.25 mmol, 33% yield) as a solid. HPLC: Rt 7.33 min, 99.8%; Column: X-Select CSH C18 (4.6×150) mm, 3.5 μm; Mobile phase: A: 0.1% FA in water:ACN (95:05), B: ACN; Flow Rate: 1.0 mL/min. LCMS: 371.20 (M+H), Rt 1.70 min; Column: X-select CSH C18 (3×50) mm, 2.5 μm. $^1$H NMR (400 MHz, DMSO-d6): δ 9.01 (d, 1H), δ 8.72 (d, 1H), 8.26-8.25 (m, 2H), 5.26-5.22 (m, 1H), 3.87-3.84 (m, 2H), 3.33-3.28 (m, 2H), 2.43-2.50

(m, 1H), 1.65-1.55 (m, 7H). Chiral HPLC: Rt 3.72 min, 100%; SFC column: DIACEL CHIRALPAK-IG (250×4.6 mm, 5 um), Mobile Phase: A) $CO_2$ B) MeOH+0.1% $NH_3$, Gradient:20-40% B in 5 min, hold 40% B till 9 min, 40-20% B in 10 min, hold 20% B till 12 min. Wavelength: 270 nm, Flow Rate: 3 mL/min.

Example I-13: (S)-2-phenyl-N-(1-(3-(2-(trifluoromethyl)pyridin-4-yl)-1,2,4-oxadiazol-5-yl)ethyl)acetamide

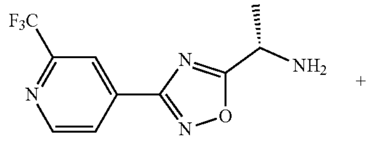

I-A1

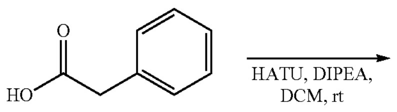

I-A14

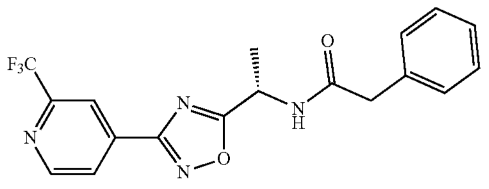

I-13

To a stirred solution of I-A14 (46.21 mg, 0.34 mmol) and I-A1 (100 mg, 0.34 mmol) in DCM (10 mL) was added DIPEA (0.12 mL, 0.68 mmol) and HATU (154.85 mg, 0.41 mmol) at 0° C. and stirred at RT for 3 h. Then, the reaction was quenched using DCM (20 mL) and washed with saturated sodium bicarbonate solution (3×25 mL) followed by water (3×20 mL). The organic layer was dried over sodium sulphate and evaporated to obtain residue which was purified by column chromatography 15 to 20% of EtOAc in hexane as an eluent to afford I-13 (40 mg, 0.10 mmol, 31% yield) as a solid. HPLC: Rt 8.75 min, 99.9%; Column: X-select CSH C18 (4.6×150) mm, 5 μm; Mobile phase: 10 mM ammonium bicarbonate in water, B: ACN; Flow Rate: 1.0 mL/min. LCMS: 376.95 (M+H), Rt 1.94 min; Column: X-select CSH C18 (3.0×50) mm, 2.5 μm. $^1H$ NMR (400 MHz, DMSO-d6): δ 9.07-8.98 (m, 2H), 8.24 (d, 2H), 7.34-7.17 (m, 5H), 5.28-5.20 (m, 1H), 3.56-3.46 (m, 2H), 1.57 (d, 3H). Chiral method: Rt 4.06 min, 100%; SFC column: DIACEL CHIRALPAK-IG (250×4.6 mm, 5 um), Mobile Phase: A) $CO_2$ B) MeOH+0.1% $NH_3$, Gradient:20-40% B in 5 min, hold 40% B till 9 min, 40-20% B in 10 min, hold 20% B till 12 min. Wavelength: 270 nm, Flow Rate: 3 mL/min.

Example I-14: (S)-2-(trifluoromethyl)-N-(1-(3-(2-(trifluoromethyl)pyridin-4-yl)-1,2,4-oxadiazol-5-yl)ethyl)isonicotinamide

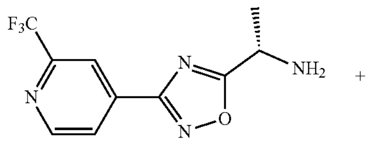

I-A1

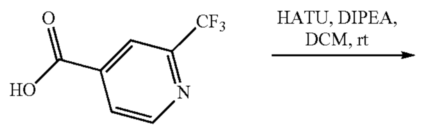

I-A15

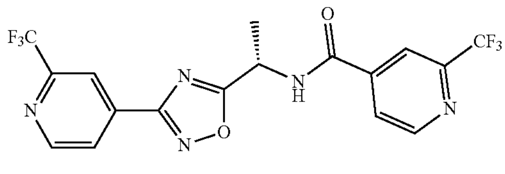

I-14

To a stirred solution of I-A15 (74.02 mg, 0.39 mmol) and I-A1 (100 mg, 0.39 mmol) in DCM (4 mL) was added DIPEA (0.17 mL, 0.97 mmol) and HATU (147.26 mg, 0.39 mmol) at RT and stirred at RT for 3 h. Then, the reaction was quenched using water and ethyl acetate (10 mL×3). The combined organic layer was dried over sodium sulphate and evaporated to obtain residue which was purified by Prep-HPLC to afford I-14 (70 mg, 0.16 mmol, 42% yield) as a solid. HPLC: Rt 8.87 min, 99.5%; Column: X-select CSH C18 (4.6×150) mm, 5 μm; Mobile phase: A: 0.1% FA in water:ACN (95:05), B: ACN; Flow Rate: 1.0 mL/min. LCMS: 432.15 (M+H), Rt 1.97 min; Column: X-select CSH C18 (3.0×50) mm, 2.5 μm. $^1H$ NMR (400 MHz, DMSO-d6): δ 9.83 (d, 1H), 9.05-8.95 (m, 2H), 8.32 (s, 1H), 8.30-8.25 (m, 2H), 8.14 (dd, 1H), 5.60-5.52 (m, 1H), 1.74 (d, 3H). Chiral method: Rt 3.37 min, 99.5%; SFC column: DIACEL CHIRALPAK-IG (250×4.6 mm, 5 um), Mobile Phase: A) $CO_2$ B) MeOH+0.1% $NH_3$, Gradient:40-10% B in 10 min, hold 40% B till 9 min, 40-10% B in 10 min, hold 10% B till 12 min. Wavelength: 261 nm, Flow Rate: 3 mL/min.

Example I-15: (S)-2-phenyl-N-(1-(3-(2-(trifluoromethyl)pyridin-4-yl)-1,2,4-oxadiazol-5-yl)propyl)acetamide

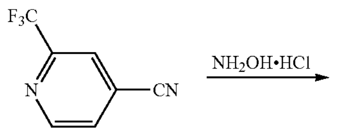

-continued

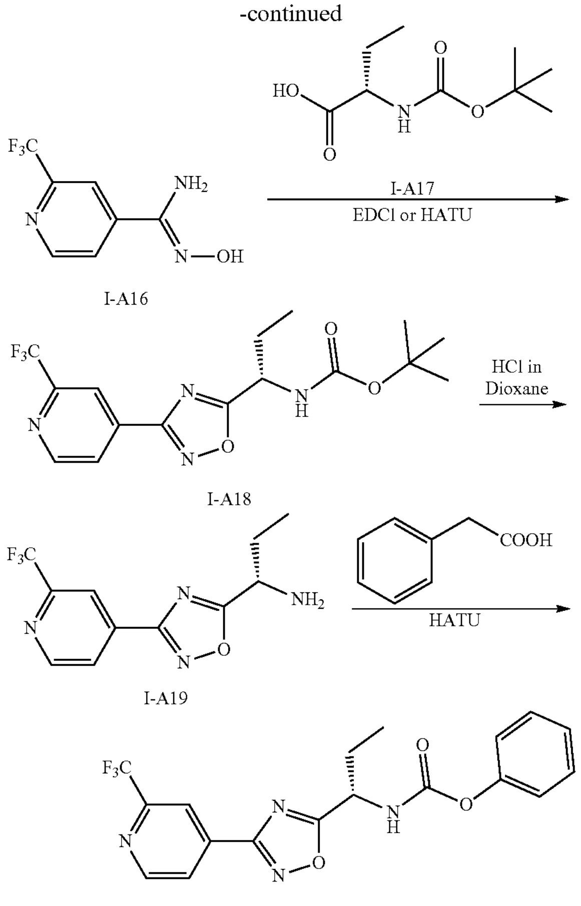

I-A16

I-A18

I-A19

I-15

I-A16: (Z)—N'-hydroxy-2-(trifluoromethyl)isonicotinimidamide

To a stirred solution of 2-(trifluoromethyl)isonicotinonitrile (4 g, 23.24 mmol) in ethanol (40 mL) was added hydroxyl amine hydrochloride (2.42 g, 34.86 mmol) and triethylamine (4.69 g, 46.48 mmol) at RT and the reaction mixture was stirred at 80° C. for 2 h. The reaction mixture was evaporated to dryness and resulting residue was diluted with EtOAc (100 mL), washed with water (2×30 mL), saturated brine solution (1×30 mL), and dried over $MgSO_4$. The organic layer was evaporated to give I-A16 (4 g, 18.36 mmol, 79% yield) as a solid.

I-A18: tert-butyl (S)-(1-(3-(2-(trifluoromethyl)pyridin-4-yl)-1,2,4-oxadiazol-5-yl)propyl)carbamate To a stirred solution of I-A16 (0.6 g, 2.92 mmol) in 1,4-Dioxane (15 mL) was added I-A17 (0.59 g, 2.92 mmol), DCC (0.6 g, 2.92 mmol) at RT and stirred at 100° C. for 16 h. The reaction mixture was cooled to RT, diluted with ethyl acetate (50 mL) and washed with water (2×15 mL) and brine solution (15 mL). The organic layer was separated, dried over $MgSO_4$ and evaporated to give a residue. The residue was purified by column chromatography using 50% EtOAc in hexane as an eluent to give I-A18 (0.60 g, 1.29 mmol, 44% yield) as a solid.

I-A19: (S)-1-(3-(2-(trifluoromethyl)pyridin-4-yl)-1,2,4-oxadiazol-5-yl)propan-1-amine To a stirred solution of I-A18 (0.6 g, 1.61 mmol) in 1,4-Dioxane (2 mL) was added 4M hydrochloric acid in dioxane (10 mL, 1.61 mmol) at 0° C. and stirred at RT for 6 h. Then, the reaction mixture was evaporated under reduced pressure to give I-A19 (0.48 g, 1.49 mmol, 92% yield) as a solid.

I-15: (S)-2-phenyl-N-(1-(3-(2-(trifluoromethyl)pyridin-4-yl)-1,2,4-oxadiazol-5-yl)propyl)acetamide To a stirred solution of I-A19 (136.04 mg, 0.44 mmol) and 2-phenylacetic acid (50 mg, 0.37 mmol) in DCM (10 mL) was added HATU (167.56 mg, 0.44 mmol) followed by DIPEA (0.13 mL, 0.73 mmol) at 0° C. and stirred at RT for 3 h. The reaction mixture was diluted with DCM (20 mL) and washed with saturated sodium bicarbonate solution (3×25 mL) followed by water (3×20 mL). The organic layer was separated, dried over $Na_2SO_4$ and evaporated to give a residue. The residue was purified by column chromatography using 100-200 silica and 15-20% EtOAc in hexane as an eluent to give I-15 (50 mg, 0.12 mmol, 34% yield) as a solid. HPLC: Rt 9.49 min, 99.6%; Column: X-select CSH C18 (4.6×150) mm, 5 μm; Mobile phase: 10 mM ammonium bicarbonate in water, B: ACN; Flow Rate: 1.0 mL/min. LCMS: 391.05 (M+H), Rt 2.14 min, Column: X-select CSH C18 (3.0×50) mm, 2.5 μm. $^1$H NMR (400 MHz, DMSO-d6): δ 9.04-8.95 (m, 2H), 8.25 (d, 2H), 7.35-7.17 (m, 5H), 5.15-5.05 (m, 1H), 3.54 (s, 2H), 2.04-1.86 (m, 2H), 0.95 (t, 3H).

Example I-16. (S)-2-phenyl-N—((S)-1-(3-(2-(trifluoromethyl)pyridin-4-yl)-1,2,4-oxadiazol-5-yl)ethyl)propanamide

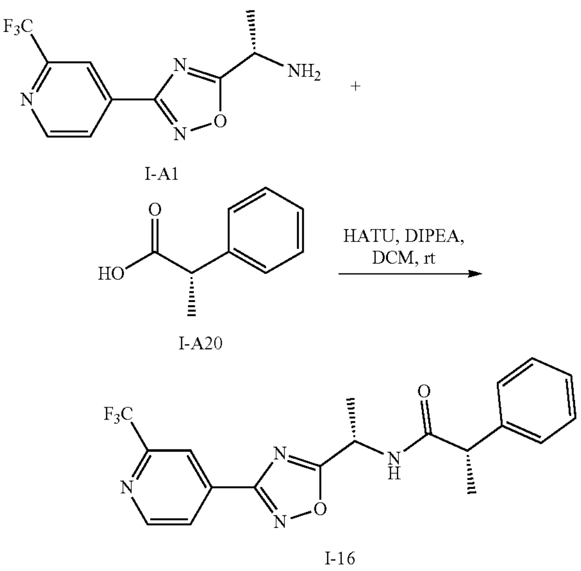

I-A1

I-A20

I-16

To a stirred solution of I-A20 (76.45 mg, 0.51 mmol) and I-A1 (100 mg, 0.34 mmol) in DCM (10 mL) were added DIPEA (0.12 mL, 0.68 mmol) and HATU (193.56 mg, 0.51 mmol) at RT and stirred at RT for 2 h. Then, the reaction was quenched using water (100 mL) and diluted with DCM (100 mL×2). Combined organic layer was dried over sodium sulphate and evaporated to obtain residue which was purified by column chromatography using 100-200 silica and 30-80% EtOAc/Hexane eluent to afford I-16 (90 mg, 0.22 mmol, 67% yield) as a solid. HPLC: Rt 8.89 min, 99.7%; Column: X-select CSH C18 (4.6×150) mm, 5 μm; Mobile phase: A: 0.1% FA in water:ACN (95:05), B: ACN; Flow Rate: 1.0 mL/min. LCMS: 391.05 (M+H), Rt 2.09 min; Column: X-select CSH C18 (3.0x50) mm, 2.5 μm. $^1H$ NMR (400 MHz, DMSO-d6): δ 9.00 (d, 1H), 8.90 (d, 1H), 8.18 (d, 2H), 7.38-7.17 (m, 5H), 5.28-5.21 (m, 1H), 3.76-3.68 (m, 1H), 1.56 (d, 3H), 1.34 (d, 3H). Chiral method: Rt 4.04 min, 96%; SFC column: DIACEL CHIRALPAK-IG (250x4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 280 nm, Flow Rate: 3 mL/min.

Example I-17: (R)-2-phenyl-N—((S)-1-(3-(2-(trifluoromethyl)pyridin-4-yl)-1,2,4-oxadiazol-5-yl)ethyl)propanamide

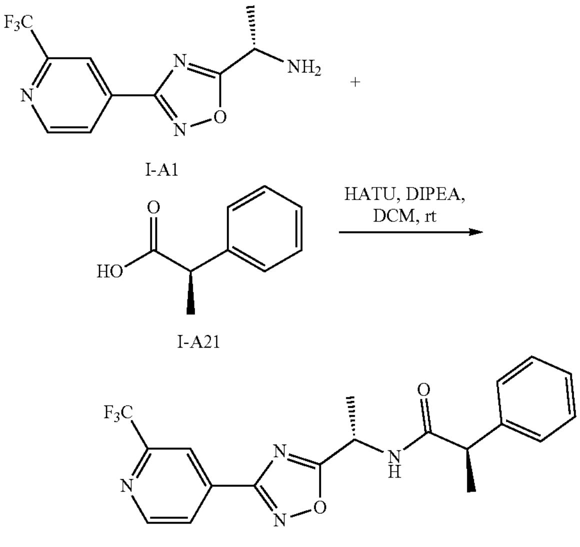

I-A1

I-A21

I-17

To a stirred solution of I-A21 (104.69 mg, 0.70 mmol) and I-A1 (150 mg, 0.58 mmol) in DCM (10 mL) were added DIPEA (0.2 mL, 1.16 mmol) and HATU (265.07 mg, 0.70 mmol) at 0° C. and stirred at RT for 3 h. Then, the reaction was quenched using water (15 mL) and diluted with DCM (30 mL). The aqueous layer was washed with DCM (2x30 mL). The combined organic layer was dried over sodium sulphate and evaporated to obtain residue which was purified by column chromatography using 100-200 silica and 25% EtOAc in hexane eluent to afford I-17 (40 mg, 0.10 mmol, 17% yield) as a solid. HPLC: Rt 9.43 min, 97.7%; Column: X-select CSH C18 (4.6×150) mm, 5 μm; Mobile phase: A: 10 mM ammonium bicarbonate in water B: ACN; Flow Rate: 1.0 mL/min. LCMS: 391.05 (M+H), Rt 2.16 min; Column: X-select CSH C18 (3.0x50) mm, 2.5 μm. $^1H$ NMR (400 MHz, DMSO-d6): δ 9.03 (d, 1H), 8.92 (d, 1H), 8.27 (d, 2H), 7.37-7.19 (m, 5H), 5.24-5.16 (m, 1H), 3.75-3.65 (m, 1H), 1.52 (d, 3H), 1.34 (d, 3H). Chiral method: Rt 4.90 min, 100%; SFC column: DIACEL CHIRALPAK-IG (250x4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 275 nm, Flow Rate: 3 mL/min.

Example I-18: (S)-5-bromo-N-(1-(3-(2-(trifluoromethyl)pyridin-4-yl)-1,2,4-oxadiazol-5-yl)ethyl)thiophene-2-carboxamide

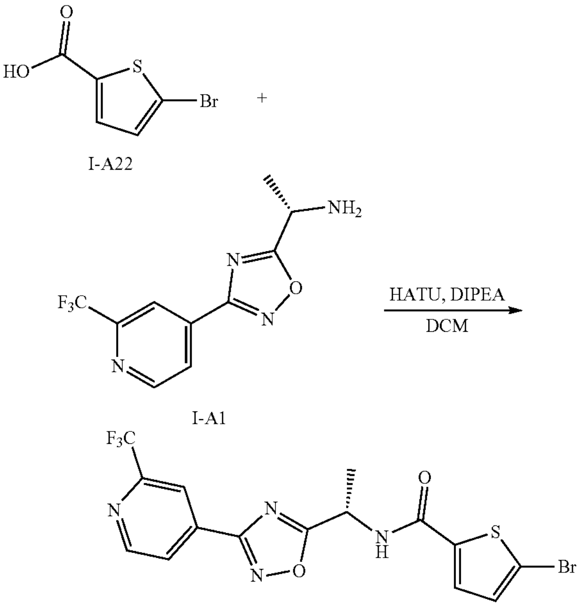

I-A22

I-A1

I-18

To a stirred solution of I-A22 (100 mg, 0.48 mmol) and I-A1 (149.65 mg, 0.58 mmol) in DCM (5 mL) were added DIPEA (0.25 mL, 1.45 mmol) and HATU (275.46 mg, 0.72 mmol) at 0° C. and stirred at RT for 3 h. The reaction was then quenched with water and the aqueous layer was washed with DCM (2x30 mL). The collected organic layer was washed using saturated brine solution (20 mL) and combined organic layer was dried over ($Na_2SO_4$) and evaporated to obtain a residue. The residue was then purified by flash column chromatography eluting by 20% EtOAc in hexane as eluent to give I-18 (30 mg, 0.06 mmol, 13% yield) as a solid. HPLC: Rt 7.76 min, 99.6%; Column: X-Bridge C18 (4.6×150) mm, 5 μm; Mobile phase: A: 0.1% $NH_3$ in water B: ACN; Flow Rate: 1.2 mL/min. LCMS: 446.84 (M+H), Rt 2.09 min; Column: X-select CSH C18 (3.0x50) mm, 2.5 μm. $^1H$ NMR (400 MHz, DMSO-d6): δ 9.40 (d, 1H), 9.01 (d, 1H), 8.28 (d, 2H), 7.76-7.69 (m, 1H), 7.34 (d, 1H), 5.48-5.42 (m, 1H), 1.69 (d, 3H).

Example I-19: (S)-4-methyl-N-(1-(3-(2-(trifluoromethyl)pyridin-4-yl)-1,2,4-oxadiazol-5-yl)ethyl)cyclohexane-1-carboxamide

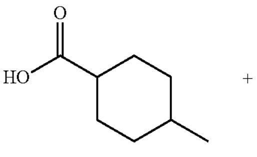

I-A23

-continued

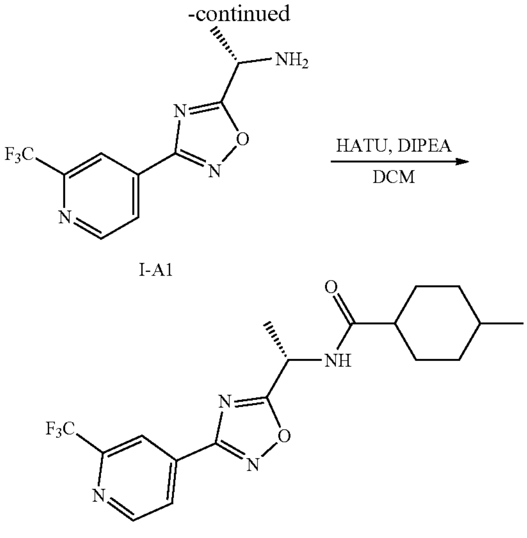

I-A1

I-19

To a stirred solution of I-A23 (100 mg, 0.70 mmol) and I-A1 (217.89 mg, 0.84 mmol) in DCM (5 mL) was added DIPEA (0.37 mL, 2.11 mmol) and HATU (401.09 mg, 1.05 mmol) at 0° C. and stirred at RT for 3 h. The reaction was diluted with DCM (30 mL), water (15 mL) and again washed with DCM (2x30 mL). The collected combined organic layer was washed using saturated brine solution (20 mL), dried over ($Na_2SO_4$) and evaporated to give the residue. The residue was then purified by flash column chromatography using 20% EtOAc in hexane as an eluent to give I-19 (45 mg, 0.11 mmol, 16% yield) as a solid. HPLC: Rt 7.91 min, 99.4%; Column: X-Bridge C18 (4.6×150) mm, 5 μm; Mobile phase: A: 0.1% $NH_3$ in water B: ACN; Flow Rate: 1.2 mL/min. LCMS: 383.05 (M+H), Rt 2.09 min; Column: X-select CSH C18 (3.0×50) mm, 2.5 μm. $^1$H NMR (400 MHz, DMSO-d6): δ 9.05-8.98 (m, 1H), 8.64-8.55 (m, 1H), 8.29-8.23 (m, 2H), 5.30-5.16 (m, 1H), 2.4-2.2 (m, 1H), 1.78-1.67 (m, 3H), 1.60-1.51 (m, 3H), 1.48-1.44 (m, 3H), 1.35-1.30 (m, 2H), 0.92-0.81 (m, 3H). Note: 1H not observed might have been merged under solvent peak.

Example I-20: (S)—N-(1-(3-(2-(trifluoromethyl)pyridin-4-yl)-1,2,4-oxadiazol-5-yl)propyl)cyclohexanecarboxamide

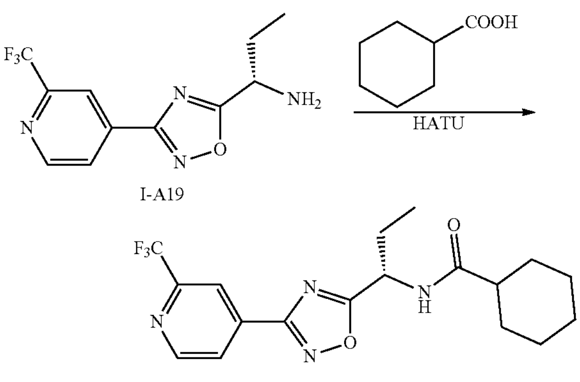

I-A19

I-20

To a stirred solution of I-A19 (50 mg, 0.16 mmol) and cyclohexanecarboxylic acid (24.91 mg, 0.19 mmol) in DCM (10 mL) were added HATU (92.38 mg, 0.24 mmol) followed by DIPEA (0.06 mL, 0.32 mmol) at 0° C. and stirred at RT for 3 h. The reaction mixture was diluted with DCM (10 mL), washed with water (3x15 mL), dried over $Na_2SO_4$ to give the residue. The residue was purified by column chromatography using 100-200 silica at 4-4.5% and EtOAc in hexane as an eluent to give I-20 (20 mg, 0.05 mmol, 32% yield) as a solid. HPLC: Rt 9.63 min, 99.8%; Column: X-select CSH C18 (4.6×150) mm, 5 μm; Mobile phase: 10 mM ammonium bicarbonate in water, B: ACN; Flow Rate: 1.0 mL/min. LCMS: 383.12 (M+H), Rt 2.14 min, Column: X-select CSH C18 (3.0×50) mm, 2.5 μm. $^1$H NMR (400 MHz, DMSO-d6): δ 9.02 (d, 1H), 8.57 (d, 1H), 8.30-8.23 (m, 2H), 5.9-5.02 (m, 1H), 2.27-2.02 (m, 1H), 1.99-1.86 (m, 2H), 1.72-1.61 (m, 4H), 1.40-1.10 (m, 6H), 0.95 (t, 3H).

Example I-21: (S)-5-methyl-N-(1-(3-(2-(trifluoromethyl)pyridin-4-yl)-1,2,4-oxadiazol-5-yl)ethyl)isoxazole-4-carboxamide

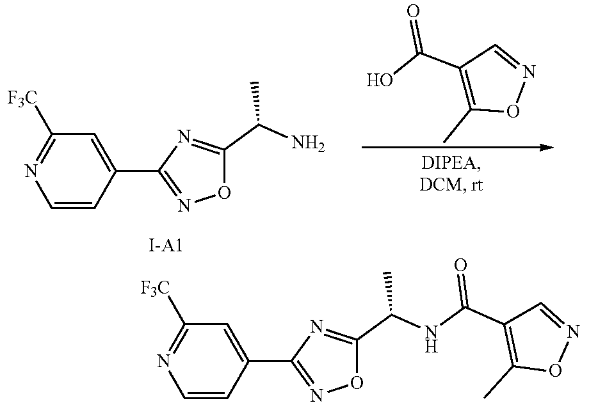

I-A1

I-21

To a stirred solution of 5-methylisoxazole-4-carboxylic acid (0.1 g, 0.79 mmol) and I-A1 (0.23 g, 0.79 mmol) in DCM (20 mL) were added DIPEA (0.27 mL, 1.57 mmol) and propylphosphonic anhydride (0.47 mg, 1.57 mmol) at 0° C. and stirred at RT for 6 h. The reaction mixture was diluted with DCM (30 mL) and washed with water (20 mL). The organic layer was washed using saturated brine solution (30 mL), separated, dried over ($MgSO_4$) and evaporated to give a residue. The residue was then purified by flash column chromatography using 50% EtOAc in hexane as an eluent to give I-21 (45 mg, 0.12 mmol, 15% yield) as a solid. HPLC: Rt 7.97 min, 98.7%; Column: X-select CSH C18 (4.6×150) mm, 5 μm; Mobile phase: A: 0.1% FA in water B: Acetonitrile (95:05); Flow Rate: 1.0 mL/min. LCMS: 368.10 (M+H), Rt 1.96 min; Column: X-select CSH (3.0×50) mm, 2.5 μm. $^1$H NMR (400 MHz, DMSO-d6): δ 9.13 (d, 1H), 9.05-8.95 (m, 2H), 8.31-8.24 (m, 2H), 5.52-5.40 (m, 1H), 2.63 (s, 3H), 1.75-1.58 (m, 3H). Chiral method: Rt 5.48 min, 98.9%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 270 nm, Flow Rate: 3 mL/min.

Example I-22: (S)—N-(1-(3-(2-(trifluoromethyl)pyridin-4-yl)-1,2,4-oxadiazol-5-yl)ethyl)isothiazole-5-carboxamide

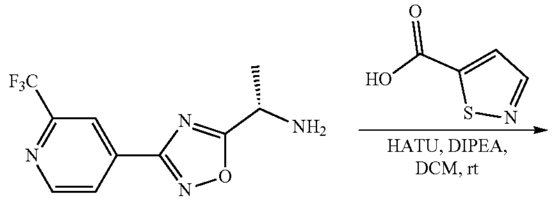

I-A1

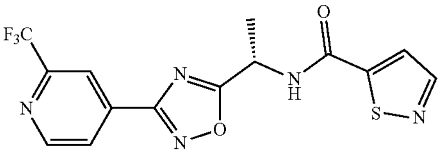

I-22

To a stirred solution of isothiazole-5-carboxylic acid (52.59 mg, 0.41 mmol) and I-A1 (0.1 g, 0.34 mmol) in DCM (10 mL) was added DIPEA (0.12 mL, 0.68 mmol) and HATU (193.56 mg, 0.51 mmol) at RT and stirred for 2 h. The reaction mixture was diluted with DCM (2×100 mL) and water (100 mL). The combined organic layer was separated, dried over ($Na_2SO_4$), filtered and evaporated to give the residue. The residue was then purified by flash column chromatography using 30-80% EtOAc in hexane as an eluent to give I-22 (55 mg, 0.14 mmol, 43% yield) as a solid. HPLC: Rt 8.02 min, 99.5%; Column: X-Select-CSH C18 (4.6×150) mm, 5 μm; Mobile phase: A: 0.1% FA in water: Acetonitrile (95:05), B-Acetonitrile; Flow Rate: 1.0 mL/min. LCMS: 369.90 (M+H), Rt 1.89 min; Column: X-select CSH C18 (3.0×50) mm, 2.5 μm. $^1$H NMR (400 MHz, DMSO-d6): δ 9.73 (d, 1H), 9.04-8.98 (m, 1H), 8.70 (d, 1H), 8.32-8.24 (m, 2H), 8.01 (d, 1H), 5.55-5.47 (m, 1H), 1.72 (d, 3H). Chiral method: Rt 4.83 min, 98.4%; SFC column: DIACEL CHIRALPAK-IG (250×4.6 mm, 5 um), Mobile Phase: A) $CO_2$ B) MeOH+0.1% $NH_3$, Gradient:35-50% B in 5 min, hold 50% B till 9 min, 50-35% B at 10 min, hold 35% B till 12 min, Wavelength: 272 nm, Flow Rate: 3 mL/min.

Example I-23: (S)—N-(1-(3-(2-(trifluoromethyl)pyridin-4-yl)-1,2,4-oxadiazol-5-yl)ethyl)isoxazole-5-carboxamide

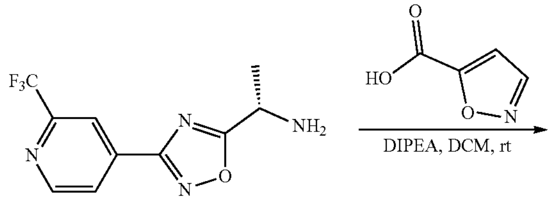

I-A1

-continued

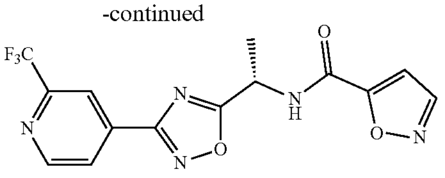

I-23

To a stirred solution of isoxazole-5-carboxylic acid (0.06 g, 0.53 mmol) and I-A1 (0.16 g, 0.53 mmol) in DCM (10 mL) was added DIPEA (0.18 mL, 1.06 mmol) and propanephosphonic acid anhydride (0.34 g, 1.06 mmol) at 0° C. and resulting reaction mixture was stirred at RT for 6 h. The reaction mixture was diluted with DCM (20 mL) and water (10 mL). The organic layer was washed with saturated brine solution (10 mL), separated, dried over (MgSO4) and evaporated to give the residue. The residue was then purified by flash column chromatography using 30% EtOAc in hexane as an eluent to give I-23 (120 mg, 0.33 mmol, 63% yield) as a solid. HPLC: Rt 7.94 min, 99.6%; Column: X-select CSH C18 (4.6×150) mm, 5 μm; Mobile phase: A: 0.1% FA in water B: Acetonitrile (95:05); Flow Rate: 1.0 mL/min. LCMS: 353.07 (M+H), Rt 1.82 min; Column: X-select CSH C18 (3.0×50) mm, 2.5 μm. $^1$H NMR (400 MHz, DMSO-d6): δ 9.85 (d, 1H), 9.05-8.98 (m, 1H), 8.80 (d, 1H), 8.31-8.23 (m, 2H), 7.19 (d, 1H), 5.56-5.48 (m, 1H), 1.71 (d, 3H). Chiral method: Rt 6.40 min, 100%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 270 nm, Flow Rate: 3 mL/min.

Example I-24: (S)—N-(1-(3-(2-(trifluoromethyl)pyridin-4-yl)-1,2,4-oxadiazol-5-yl)ethyl)pyridazine-3-carboxamide

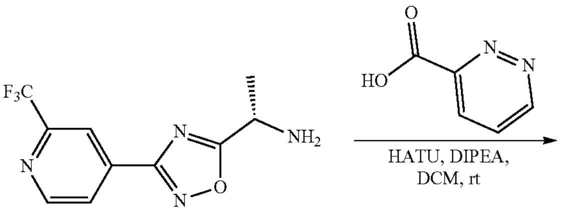

I-A1

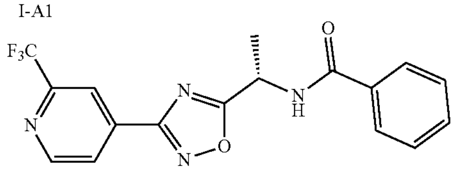

I-24

To a stirred solution of pyridazine-3-carboxylic acid (0.06 g, 0.48 mmol) and I-A1 (0.14 g, 0.48 mmol) in DCM (10 mL) was added DIPEA (0.17 mL, 0.97 mmol) and HATU (0.22 g, 0.58 mmol) at 0° C. and stirred at RT for 6 h. The reaction mixture was diluted with DCM (20 mL) and water (10 mL). The organic layer was washed with saturated brine solution (10 mL), separated, dried over (MgSO4) and evaporated to give a residue. The residue was then purified by flash column chromatography using 30% EtOAc in hexane as an eluent and fractions were evaporated to give I-24 (110 mg, 0.29 mmol, 61% yield) as a solid. HPLC: Rt 7.54 min, 98.9%; Column: X-Select CSH C18 (4.6×150) mm, 5 μm; Mobile phase: A: 0.1% FA in water B: Acetonitrile (95:05); Flow Rate: 1.0 mL/min. LCMS: 365.15 (M+H), Rt 1.77 min; Column: X-select CSH C18 (3.0×50) mm, 2.5 μm. $^1$H NMR (400 MHz, DMSO-d6): δ 10.17 (d, 1H), 9.48-9.42 (m, 1H), 9.04-8.92 (m, 1H), 8.31-8.15 (m, 3H), 7.99-7.91 (m, 1H), 5.65-5.58 (m, 1H), 1.77 (d, 3H). Chiral method: Rt 5.31 min, 98.14%; SFC column: DIACEL CHIRALPAK-IG (250×4.6 mm, 5 um), Mobile Phase: A) $CO_2$ B) MeOH+ 0.1% $NH_3$, Gradient:35-50% B in 5 min, hold 50% B till 9 min, 50-35% B at 10 min, hold 35% B till 12 min, Wavelength: 270 nm, Flow Rate: 3 mL/min.

Example I-25. (S)-6-(trifluoromethyl)-N-(1-(3-(2-(trifluoromethyl)pyridin-4-yl)-1,2,4-oxadiazol-5-yl)ethyl)benzo[b]thiophene-2-carboxamide

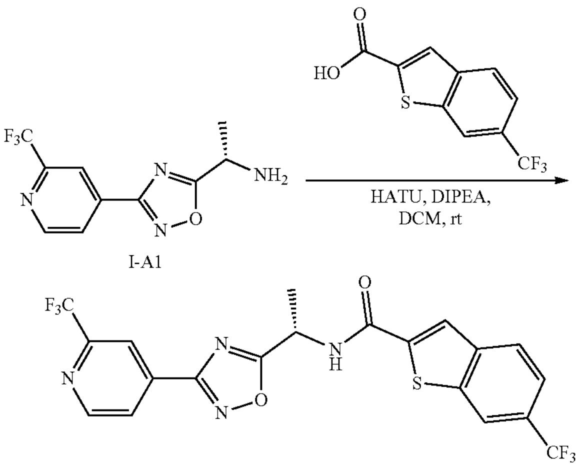

I-A1

I-25

To a stirred solution of 6-(trifluoromethyl)benzo[b]thiophene-2-carboxylic acid (100.27 mg, 0.41 mmol) and I-A1 (100 mg, 0.34 mmol) in DCM (3 mL) was added DIPEA (0.18 mL, 1.02 mmol) and HATU (193.56 mg, 0.51 mmol) at RT and stirred at RT for 3 h. The reaction mixture was diluted with DCM and organic layer was washed with water (3×3 mL). The organic layer was separated, dried over ($Na_2SO_4$), filtered and concentrated to obtain a residue. The residue was purified by flash column chromatography using 20-25% EtOAc in hexane as an eluent to give I-25 (70 mg, 0.14 mmol, 42% yield). HPLC: Rt 9.69 min, 99.7%; Column: X-Select-CSH C18 (4.6×150) mm, 3.5 μm; Mobile phase: A: 0.1% FA in water: Acetonitrile (95:05), B-Acetonitrile; Flow Rate: 1.0 mL/min. LCMS: 487.10 (M+H), Rt 2.21 min; Column: X-select CSH C18 (3.0×50) mm, 2.5 μm. $^1$H NMR (400 MHz, DMSO-d6): δ 9.75 (d, 1H), 9.04-8.97 (m, 1H), 8.59 (s, 1H), 8.33 (s, 1H), 8.29-8.27 (m, 2H), 8.25-8.18 (m, 1H), 7.79-7.71 (m, 1H), 5.58-5.49 (m, 1H), 1.73 (d, 3H). Chiral method: Rt 5.36 min, 100%; SFC column: DIACEL CHIRALPAK-IG (250×4.6 mm, 5 um), Mobile Phase: A) $CO_2$ B) MeOH+0.1% $NH_3$, Gradient: 10-40% B in 5 min, hold 40% B till 9 min, 40-10% B at 10 min, hold 10% B till 12 min, Wavelength: 275 nm, Flow Rate: 3 mL/min.

Example I-26: trans-4-methyl-N—((S)-1-(3-(2-(trifluoromethyl)pyridin-4-yl)-1,2,4-oxadiazol-5-yl)ethyl)cyclohexane-1-carboxamide

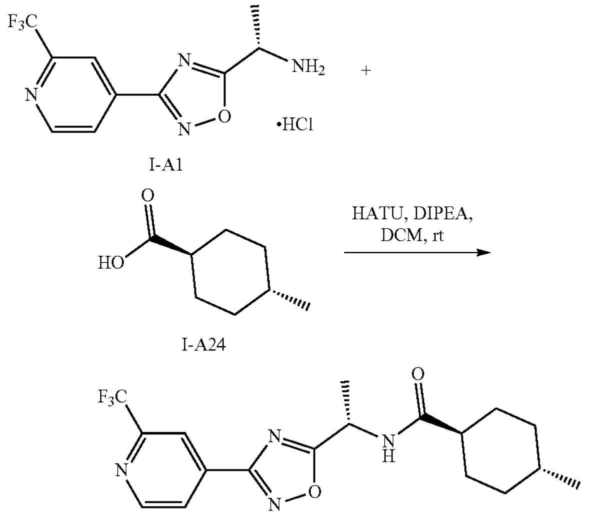

I-A1

I-A24

I-26

To a stirred solution of I-A24 (57.9 mg, 0.41 mmol) and I-A1 (HCl salt) (0.1 g, 0.34 mmol) in DCM (10 mL) was added DIPEA (0.12 mL, 0.68 mmol) and HATU (193.6 mg, 0.51 mmol) at RT and stirred at RT for 2 h. The reaction mixture was quenched using water (100 mL) and diluted with DCM (100 mL×2). Combined organic layer was dried over sodium sulphate and evaporated to obtain the residue which was purified by column chromatography using 100-200 silica and 30-80% EtOAc/Hexane eluent to afford I-26 (30 mg, 0.078 mmol, 23% yield) as a solid. HPLC: Rt 9.30 min, 99.5%; Column: X-Select CSH C18 (4.6×150) mm, 3.5 μm; Mobile phase: A: 0.1% FA in water:ACN (95:05), B: ACN; Flow Rate: 1.0 mL/min. LCMS: 382.7 (M+H), Rt 2.18 min; Column: X-select CSH C18 (3×50) mm, 2.5 μm. $^1$H NMR (400 MHz, DMSO-d6): δ 9.00 (d, 1H), 8.61 (d, 1H), 8.26-8.22 (m, 2H), 5.21 (d, 1H), 2.16-2.08 (m, 1H), 1.78-1.63 (m, 4H), 1.54 (d, 3H), 1.40-1.25 (m, 3H), 0.97-0.81 (m, 5H). Chiral method: Rt 6.85 min, 100%; column: DIACEL CHIRALPAK-IG (250×4.6 mm, 5 um), Mobile Phase: A) n-Hexane+0.1% Isopropylamine B) DCM:MeOH (1:1), Isocratic:20% B; Wavelength: 225 nm, Flow Rate: 1.0 mL/min.

Example I-29: (S)—N-(1-(3-(2-cyclopropylpyridin-4-yl)-1,2,4-oxadiazol-5-yl)ethyl)-4-methylcyclohexane-1-carboxamide

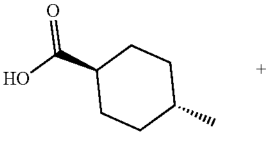

+

I-A24

-continued

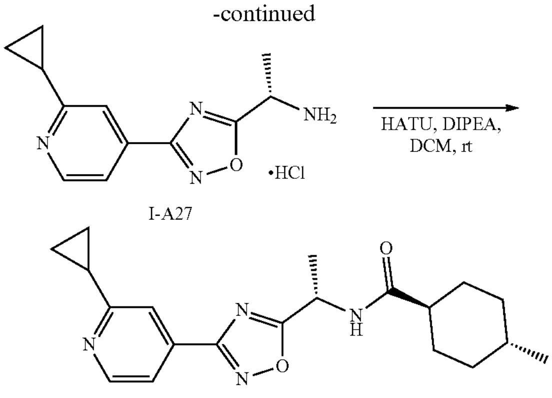

I-A27

I-29

To a stirred solution of I-A24 (64 mg, 0.45 mmol) and I-A27 (HCl salt) (0.1 g, 0.37 mmol) in DCM (2 mL) was added DIPEA (0.2 mL, 1.12 mmol) and HATU (213.8 mg, 0.56 mmol) at RT and stirred at RT for 2 h. The reaction mixture was quenched using water and diluted with DCM. The organic layer was dried over sodium sulphate and evaporated to give residue which was purified by prep HPLC to give I-29 (40 mg, 0.11 mmol, 30% yield) as a solid. HPLC: Rt 8.81 min, 99.2%; Column: X-Select CSH C18 (4.6×150) mm, 3.5 µm; Mobile phase: A: 0.1% FA in water:ACN (95:05), B: ACN; Flow Rate: 1.0 mL/min. LCMS: 355.25 (M+H), Rt 2.05 min; Column: X-select CSH C18 (3×50) mm, 2.5 µm. $^1$H NMR (400 MHz, DMSO-d6) δ 8.63-8.56 (m, 2H), 7.83 (s, 1H), 7.65-7.61 (m, 1H), 5.22-5.16 (m, 1H), 2.30-2.25 (m, 1H), 2.16-2.06 (m, 1H), 1.80-1.70 (m, 4H), 1.53 (d, 3H), 1.41-1.27 (m, 3H), 1.06-0.81 (m, 9H). Chiral method: Rt 8.98 min, 100%; column: DIACEL CHIRALPAK-IG (250×4.6 mm, 5 um), Mobile Phase: A) n-Hexane+0.1% Isopropylamine B) DCM: MeOH (1:1), Isocratic:20% B; Wavelength: 220 nm, Flow Rate: 1.0 mL/min.

Example I-30: 2-methyl-N—((S)-1-(3-(2-(trifluoromethyl)pyridin-4-yl)-1,2,4-oxadiazol-5-yl)ethyl) cyclopentane-1-carboxamide

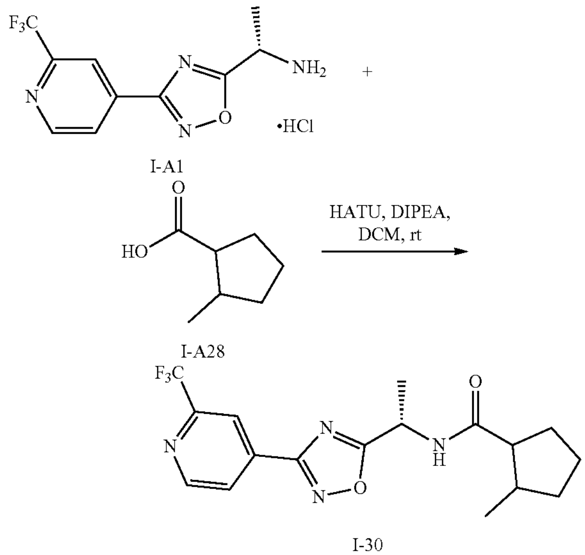

I-A1

I-A28

I-30

To a stirred solution of I-A28 (52 mg, 0.41 mmol) and I-A1 (HCl salt) (0.1 g, 0.34 mmol) in DCM (2 mL) was added DIPEA (0.18 mL, 1.02 mmol) and HATU (193.6 mg, 0.51 mmol) at RT and stirred at RT for 2 h. The reaction mixture was quenched using water (2 mL×3) and diluted with DCM. The organic layer was dried over sodium sulphate and evaporated to give the mixture which was purified by column chromatography using 50% ethyl acetate in hexane to give I-30 (45 mg, 0.12 mmol, 36% yield) as a solid. HPLC: Rt 8.99 min, 99.7%; Column: X-Select CSH C18 (4.6×150) mm, 5 µm; Mobile phase: A: 0.1% FA in water:ACN (95:05), B: ACN; Flow Rate: 1.0 mL/min. LCMS: 369 (M+H), Rt 2.09 min, Column: X-select CSH C18 (3×50) mm, 2.5 µm. $^1$H NMR (400 MHz, DMSO-d6) δ 9.02 (d, 1H), 8.78-8.72 (m, 1H), 8.30-8.22 (m, 2H), 5.28-5.22 (m, 1H), 2.22-2.11 (m, 1H), 2.10-1.90 (m, 1H), 1.86-1.80 (m, 2H), 1.75-1.53 (m, 6H), 1.16-1.10 (m, 1H), 1.04-0.96 (m, 3H).

Example I-32: (S)-1-cyano-N-(1-(3-(2-(trifluoromethyl)pyridin-4-yl)-1,2,4-oxadiazol-5-yl)ethyl)cyclopropane-1-carboxamide

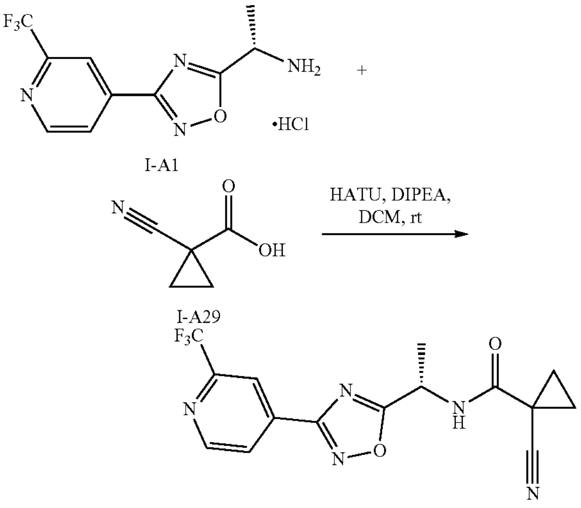

I-A1

I-A29

I-32

To a stirred solution of I-A29 (43 mg, 0.39 mmol) and I-A1 (HCl Salt) (0.11 g, 0.34 mmol) in DCM (2 mL) was added DIPEA (0.2 mL, 1.16 mmol) and HATU (220.9 mg, 0.58 mmol) at RT and stirred at RT for 2 h. The reaction mixture was quenched using water and diluted with DCM. The organic layer was dried over sodium sulphate and evaporated to give the residue which was purified by column chromatography using 6% ethyl acetate in hexane as an eluent to give I-32 (25 mg, 0.068 mmol, 17% yield) as a solid. HPLC: Rt 7.94 min, 95.5%; Column: X-Select CSH C18 (4.6×150) mm, 3.5 µm; Mobile phase: A: 0.1% FA in water:ACN (95:05), B: ACN; Flow Rate: 1.0 mL/min. LCMS: 352 (M+H), Rt 1.93 min; Column: X-select CSH C18 (3×50) mm, 2.5 µm. $^1$H NMR (400 MHz, DMSO-d6) δ 9.10-9.06 (m, 1H), 9.04-9.00 (m, 1H), 8.30-8.26 (m, 2H), 5.35-5.30 (m, 1H), 1.70-1.60 (m, 5H), 1.58-1.54 (m, 2H). Chiral method: Rt 5.36 min, 99.7%; column: DIACEL CHIRALPAK-IG (250×4.6 mm, 5 um), Mobile Phase: A)

n-Hexane+0.1% Isopropylamine B) DCM: MeOH (1:1), Isocratic:50% B; Wavelength: 225 nm, Flow Rate: 1.0 mL/min.

Example I-33. (S)-1-methyl-N-(1-(3-(2-(trifluoromethyl)pyridin-4-yl)-1,2,4-oxadiazol-5-yl)ethyl)cyclopropane-1-carboxamide

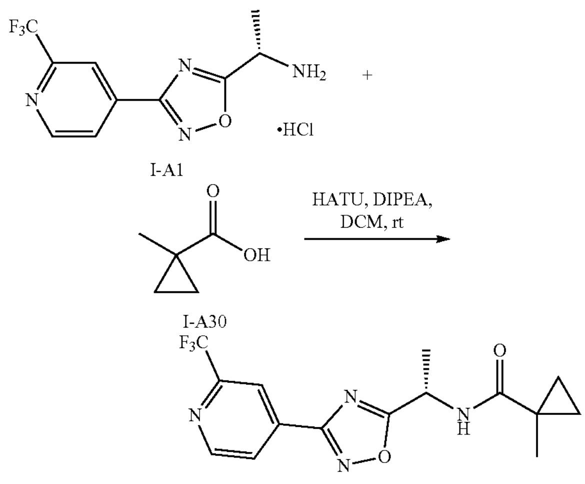

I-A1

I-A30

I-33

To a stirred solution of I-A30 (41 mg, 0.41 mmol) and I-A1 (HCl Salt) (0.1 g, 0.34 mmol) in DCM (2 mL) was added DIPEA (0.12 mL, 0.68 mmol) and HATU (193.6 mg, 0.51 mmol) at RT and stirred at RT for 2 h. The reaction mixture was quenched using water (100 mL) and diluted with DCM (2×100 mL). The organic layer was dried over sodium sulphate and evaporated to give the residue which was purified by column chromatography using 30-80% ethyl acetate in hexane as an eluent to give I-33 (20 mg, 0.058 mmol, 17% yield) as a solid. HPLC: Rt 8.41 min, 99.6%; Column: X-Select CSH C18 (4.6×150) mm, 5 µm; Mobile phase: A: 0.1% FA in water:ACN (95:05), B: ACN; Flow Rate: 1.0 mL/min. LCMS: 341.3 (M+H), Rt 1.97 min; Column: X-select CSH C18 (3×50) mm, 2.5 µm. $^1$H NMR (400 MHz, DMSO-d6) δ 9.05-8.98 (m, 1H), 8.33-8.24 (m, 3H), 5.30-5.24 (m, 1H), 1.60 (d, 3H), 1.30 (s, 3H), 1.00-0.95 (m, 2H), 0.60-0.55 (m, 2H). Chiral method: Rt 6.9 min, 96.1%; column: DIACEL CHIRALPAK-IG (250×4.6 mm, 5 um), Mobile Phase: A) n-Hexane+0.1% Isopropylamine B) DCM: MeOH (1:1), Isocratic:20% B; Wavelength: 225 nm, Flow Rate: 1.0 mL/min.

Example I-34: (R)-6-oxo-N—((S)-1-(3-(2-(trifluoromethyl)pyridin-4-yl)-1,2,4-oxadiazol-5-yl)ethyl) piperidine-2-carboxamide

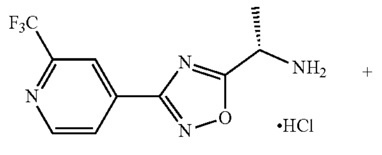

I-A1

-continued

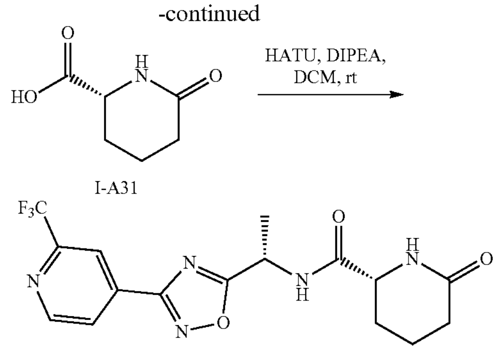

I-A31

I-34

To a stirred solution of I-A31 (58.3 mg, 0.41 mmol) and I-A1 (HCl Salt) (0.1 g, 0.34 mmol) in DCM (10 mL) were added DIPEA (0.12 mL, 0.68 mmol) and HATU (193.6 mg, 0.51 mmol) at RT and stirred at RT for 2 h. The reaction mixture was quenched using water (100 mL) and diluted with DCM (100 mL×2). The organic layer was dried over sodium sulphate and evaporated to give the residue which was purified by column chromatography using 30-80% ethyl acetate in hexane as an eluent to give I-34 (15 mg, 0.039 mmol, 1100 yield) as a solid. HPLC: Rt 8.97 min, 99.6%; Column: X-Select CSH C18 (4.6×150) mm, 3.5 µm; Mobile phase: A: 0.1% FA in water:ACN (95:05), B: ACN; Flow Rate: 1.0 mL/min. LCMS: 384.3 (M+H), Rt 1.68 min; Column: X-select CSH C18 (3×50) mm, 2.5 µm. $^1$H NMR (400 MHz, DMSO-d6) δ 9.02 (d, 1H), 8.86 (d, 1H), 8.30-8.22 (m, 2H), 7.60-7.56 (m, 1H), 5.33-5.28 (m, 1H), 3.98-3.92 (m, 1H), 2.14 (t, 2H), 1.86-1.57 (m, 7H). Chiral method: Rt 10.65 min, 93.4%; column: DIACEL CHIRALPAK-IG (250×4.6 mm, 5 um), Mobile Phase: A) n-Hexane+0.1% Isopropylamine B) DCM:MeOH (1:1), Isocratic:50% B; Wavelength: 227 nm, Flow Rate: 1.0 mL/min.

Example I-35. (S)-2-(piperidin-1-yl)-N-(1-(3-(2-(trifluoromethyl)pyridin-4-yl)-1,2,4-oxadiazol-5-yl) ethyl)acetamide

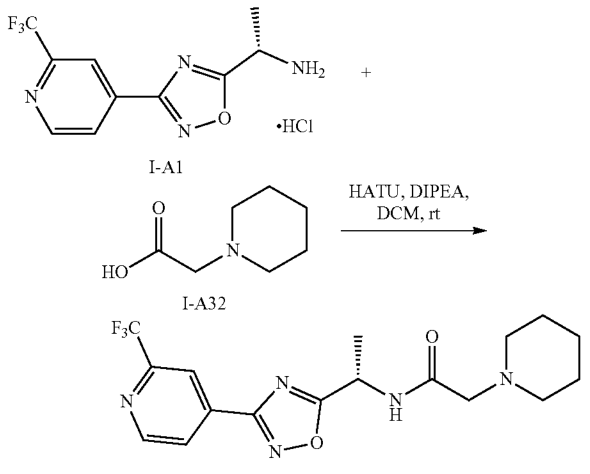

I-A1

I-A32

I-35

To a stirred solution of I-A32 (58.3 mg, 0.41 mmol) and I-A1 (HCl salt) (0.1 g, 0.34 mmol) in DCM (10 mL) was added DIPEA (0.12 mL, 0.68 mmol) and HATU (193.6 mg, 0.51 mmol) at RT and stirred at RT for 2 h. The reaction mixture was quenched using water (100 mL) and diluted with DCM (100 mL×2). The organic layer was dried over sodium sulphate and evaporated to give the residue which was purified by column chromatography using 30-80% ethyl acetate in hexane as an eluent to give I-35 (10 mg, 0.026 mmol, 8% yield) as a solid. HPLC: Rt 5.13 min, 99%; Column: X-Select CSH C18 (4.6×150) mm, 3.5 μm; Mobile phase: A: 0.1% FA in water:ACN (95:05), B: ACN; Flow Rate: 1.0 mL/min. LCMS: 384.5 (M+H), Rt 1.35 min; Column: X-select CSH C18 (3×50) mm, 2.5 μm. $^1$H NMR (400 MHz, DMSO-d6) δ 9.02 (d, 1H), 8.56 (d, 1H), 8.28-8.24 (m, 2H), 5.36-5.28 (m, 1H), 3.04-2.88 (m, 2H), 2.49-2.35 (m, 4H), 1.64-1.50 (m, 7H), 1.42-1.34 (m, 2H). Chiral method: Rt 6.98 min, 95.6%; column: DIACEL CHIRALPAK-IG (250×4.6 mm, 5 um), Mobile Phase: A) n-Hexane+0.1% Isopropylamine B) DCM:MeOH (1:1), Isocratic:20% B; Wavelength: 270 nm, Flow Rate: 1.0 mL/min.

Example I-36: cis-4-methyl-N—((S)-1-(3-(2-(trifluoromethyl)pyridin-4-yl)-1,2,4-oxadiazol-5-yl)ethyl)cyclohexane-1-carboxamide

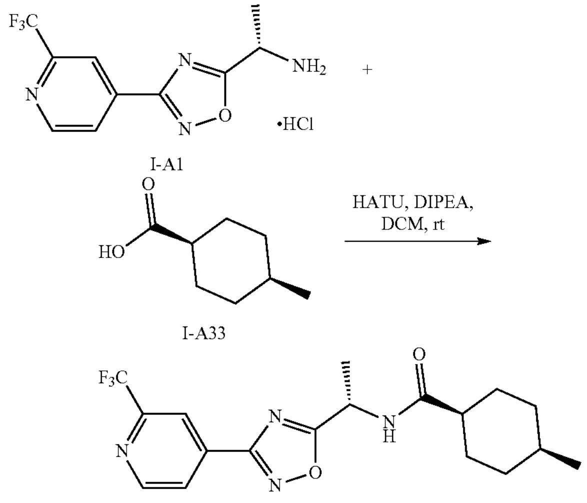

I-A1

I-A33

I-36

To a stirred solution of I-A33 (58.7 mg, 0.41 mmol) and I-A1 (HCl Salt) (0.1 g, 0.34 mmol) in DCM (10 mL) was added DIPEA (0.12 mL, 0.69 mmol) and HATU (196.2 mg, 0.52 mmol) at RT and stirred at RT for 2 h. The reaction mixture was quenched with water (100 mL) and diluted with DCM (100 mL×2). Combined organic layer was dried over sodium sulphate and evaporated to obtain residue which was purified by column chromatography using 100-200 silica and 30-80% EtOAc/Hexane eluent to afford the residue which was further separated using HPLC method developed on chiral column to give the cis-isomer I-36 (10 mg, 0.026 mmol, 7% yield) as a solid. HPLC: Rt 9.39 min, 99.5%; Column: X-Select CSH C18 (4.6×150) mm, 3.5 μm; Mobile phase: A: 0.1% FA in water:ACN (95:05), B: ACN; Flow Rate: 1.0 mL/min. LCMS: 383.35 (M+H), Rt 2.10 min; Column: X-select CSH C18 (3×50) mm, 2.5 μm. $^1$H NMR (400 MHz, DMSO-d6) δ 9.01 (d, 1H), 8.55 (d, 1H), 8.29-8.23 (m, 2H), 5.28-5.18 (m, 1H), 2.34-2.30 (m, 1H), 1.84-1.71 (m, 2H), 1.65-1.39 (m, 8H), 1.36-1.32 (m, 2H), 0.87 (d, 3H). Chiral method: Rt 7.07 min, 100%; column: DIACEL CHIRALPAK-IG (250×4.6 mm, 5 um), Mobile Phase: A) n-Hexane+0.1% Isopropylamine B) DCM:MeOH (1:1), Isocratic:20% B; Wavelength: 225 nm, Flow Rate: 1.0 mL/min.

Example I-37: (R)—N-(1-(3-(3-fluorophenyl)-1,2,4-oxadiazol-5-yl)ethyl)-2,4-dimethylthiazole-5-carboxamide

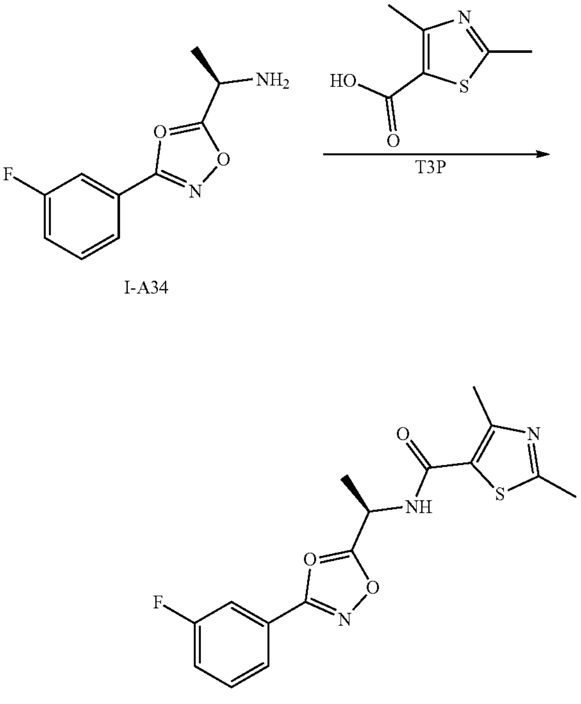

I-A34

I-37

To a stirred solution of (R)-1-(3-(3-fluorophenyl)-1,2,4-oxadiazol-5-yl)ethan-1-amine (200 mg, 0.97 mmol) in THE (5 mL) was added 2,4-dimethylthiazole-5-carboxylic acid (187 mg, 1.19 mmol) followed by T3P (50% in ethyl acetate, 1.72 mL, 2.9 mmol) and $Et_3N$ (0.4 mL, 2.9 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by column chromatography on silica gel with 35% EtOAc/PE to afford I-37 (75 mg, 0.21 mmol, 22% yield) as a solid. HPLC: Rt 3.89 min, 98.6%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 347.1 (M+H), Rt 2.05 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.84 min, SFC column: YMC Cellulose-SC; mobile phase: 70:30 (A:B), A=liquid $CO_2$, B=methanol; flow rate: 3.0 mL/min; wavelength: 210 nm. $^1$H NMR (400 MHz, $CDCl_3$): δ 7.90-7.88 (m, 1H), 7.81-7.78 (m, 1H), 7.51-7.46 (m, 1H), 7.26-7.22 (m, 1H), 6.40 (d, 1H), 5.64-5.60 (m, 1H), 2.74 (s, 3H), 2.73 (s, 3H), 1.76 (d, 3H).

Example I-38: (S)—N-(1-(3-(3-fluorophenyl)-1,2,4-oxadiazol-5-yl)ethyl)-1-methyl-3-phenyl-1H-1,2,4-triazole-5-carboxamide

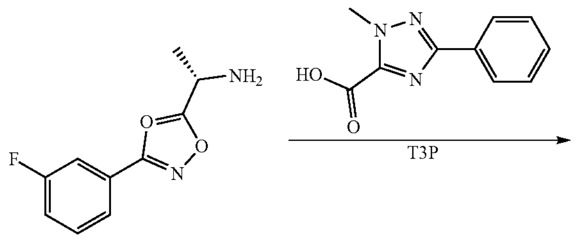

I-A35

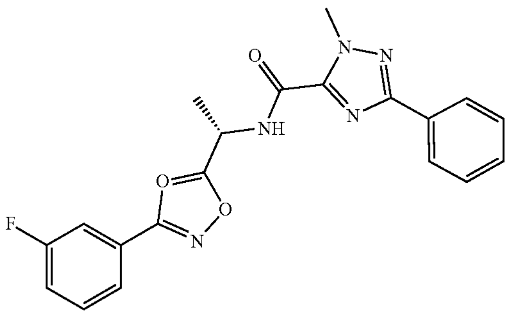

I-38

To a stirred solution of (S)-1-(3-(3-fluorophenyl)-1,2,4-oxadiazol-5-yl)ethan-1-amine (150 mg, 0.72 mmol) in THF (5 mL) was added 1-methyl-3-phenyl-1H-1,2,4-triazole-5-carboxylic acid (161 mg, 0.80 mmol) followed by T3P (50% in ethyl acetate, 1.29 mL, 2.17 mmol) and $Et_3N$ (0.3 mL, 2.17 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by column chromatography on silica gel with 35% EtOAc/PE to afford I-38 (35 mg, 0.086 mmol, 11% yield) as a solid. HPLC: Rt 5.30 min, 96.8%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 393.1 (M+H), Rt 2.71 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.36 min, SFC column: YMC Cellulose-SC; mobile phase: 70:30 (A:B), A=liquid $CO_2$, B=methanol; flow rate: 3.0 mL/min; wavelength: 210 nm. $^1H$ NMR (400 MHz, $CDCl_3$): δ 8.14-8.11 (m, 2H), 8.03 (d, 1H), 7.93-7.91 (m, 1H), 7.84-7.81 (m, 1H), 7.51-7.44 (m, 4H), 7.26-7.21 (m, 1H), 5.67-5.60 (m, 1H), 4.34 (s, 3H), 1.85 (d, 3H).

Example I-39: (S)—N-(1-(3-(3-fluorophenyl)-1,2,4-oxadiazol-5-yl)ethyl)-2,4-dimethylthiazole-5-carboxamide

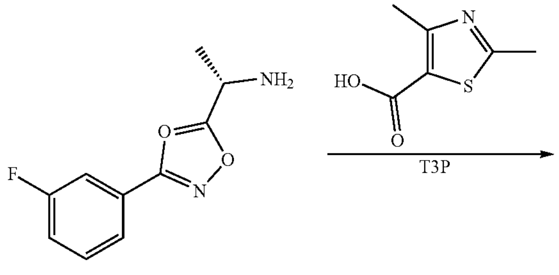

I-A35

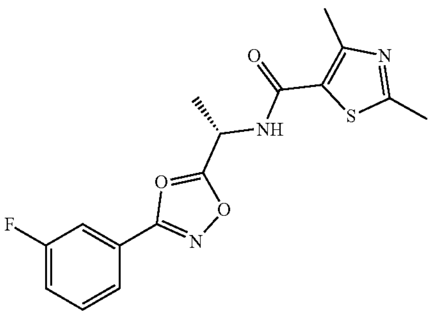

I-39

To a stirred solution of (S)-1-(3-(3-fluorophenyl)-1,2,4-oxadiazol-5-yl)ethan-1-amine (170 mg, 0.82 mmol) in THF (5 mL) was added 2,4-dimethylthiazole-5-carboxylic acid (159 mg, 1.01 mmol) followed by T3P (50% in ethyl acetate, 1.47 mL, 2.46 mmol) and $Et_3N$ (0.34 mL, 2.46 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by column chromatography on silica gel with 35% EtOAc/PE to afford I-39 (110 mg, 0.31 mmol, 37% yield) as a solid. HPLC: Rt 3.89 min, 98.0%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 347.0 (M+H), Rt 2.05 min, Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.29 min, SFC column: YMC Cellulose-SC; mobile phase: 70:30 (A:B), A=liquid $CO_2$, B=methanol; flow rate: 3.0 mL/min; wavelength: 210 nm. $^1H$ NMR (400 MHz, $CDCl_3$): δ 7.90-7.88 (m, 1H), 7.80-7.78 (m, 1H), 7.52-7.46 (m, 1H), 7.26-7.22 (m, 1H), 6.40 (d, 1H), 5.66-5.58 (m, 1H), 2.74 (s, 3H), 2.73 (s, 3H), 1.76 (d, 3H).

Example I-40: (S)-2-ethyl-N-(1-(3-(3-fluorophenyl)-1,2,4-oxadiazol-5-yl)ethyl)-5-methyl-2H-1,2,3-triazole-4-carboxamide

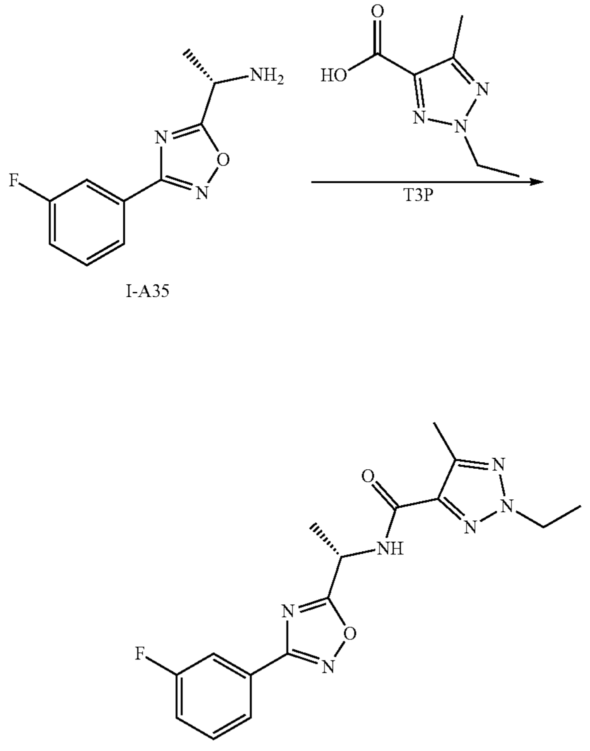

I-A35

I-40

To a stirred solution of (S)-1-(3-(3-fluorophenyl)-1,2,4-oxadiazol-5-yl)ethan-1-amine (200 mg, 0.97 mmol) in THE (5 mL) was added 2-ethyl-5-methyl-2H-1,2,3-triazole-4-carboxylic acid (187 mg, 1.21 mmol) followed by T3P (50% in ethyl acetate, 1.72 mL, 2.9 mmol) and $Et_3N$ (0.4 mL, 2.9 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by column chromatography on silica gel with 35% EtOAc/PE to afford I-40 (175 mg, 0.49 mmol, 51% yield) as a solid. HPLC: Rt 4.55 min, 98.7%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 345.1 (M+H), Rt 2.36 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.79 min, SFC column: YMC Cellulose-SC; mobile phase: 70:30 (A:B), A=liquid $CO_2$, B=methanol; flow rate: 3.0 mL/min; wavelength: 210 nm. $^1H$ NMR (400 MHz, $CDCl_3$): δ 7.92-7.89 (m, 1H), 7.83-7.80 (m, 1H), 7.50-7.45 (m, 1H), 7.32-7.28 (m, 1H), 7.25-7.20 (m, 1H), 5.70-5.62 (m, 1H), 4.45 (q, 2H), 2.56 (s, 3H), 1.78 (d, 3H), 1.61 (t, 3H).

Example I-41: (S)—N-(1-(3-(2-cyclopropylpyridin-4-yl)-1,2,4-oxadiazol-5-yl)ethyl)benzamide

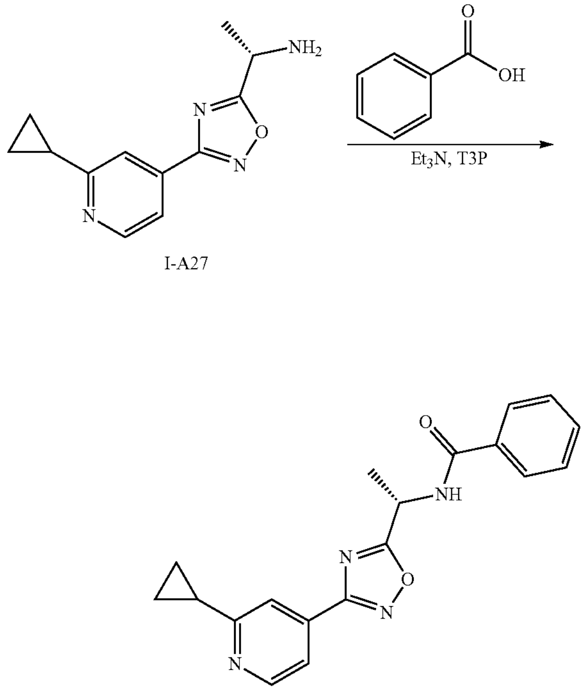

I-A27

I-41

To a stirred solution of (S)-1-(3-(2-cyclopropylpyridin-4-yl)-1,2,4-oxadiazol-5-yl)ethan-1-amine (100 mg, 0.43 mmol) in THE (8.0 mL) was added benzoic acid (84 mg, 0.69 mmol) followed by $Et_3N$ (0.18 mL, 1.3 mmol) and T3P (50% in ethyl acetate, 0.8 mL, 1.3 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-41 (75 mg, 0.22 mmol, 50% yield) as a solid. Prep. HPLC method: Rt 12.5; Column: X-Bridge (150×19 mm), 5.0 μm; Mobile phase: 0.1% TFA in water/acetonitrile; Flow Rate: 15.0 mL/min. HPLC: Rt 2.75 min, 98.4%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 335.1 (M+H), Rt 1.90 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 2.23 min, SFC column: YMC Amylose-C; mobile phase: 60:40 (A:B), A=liquid $CO_2$, B=0.5% isopropyl amine in methanol; flow rate: 3.0 mL/min; wavelength: 210 nm. $^1H$ NMR (400 MHz, DMSO-$d_6$): 9.28 (d, 1H), 8.60 (d, 1H), 7.92 (d, 2H), 7.86 (s, 1H), 7.66 (dd, 1H), 7.61-7.49 (m, 3H), 5.51-5.47 (m, 1H), 2.33-2.26 (m, 1H), 1.70 (d, 3H), 1.01-0.97 (m, 4H).

Example I-42: (S)—N-(1-(3-(2-cyclopropylpyridin-4-yl)-1,2,4-oxadiazol-5-yl)ethyl)-2-phenylacetamide

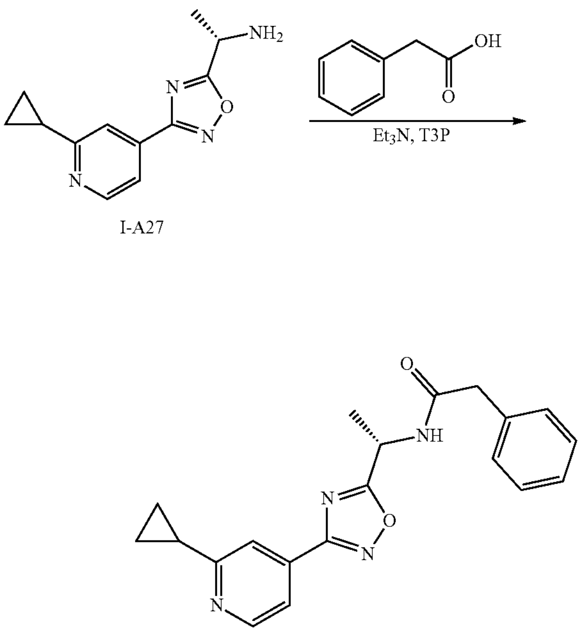

I-A27

I-42

To a stirred solution of (S)-1-(3-(2-cyclopropylpyridin-4-yl)-1,2,4-oxadiazol-5-yl)ethan-1-amine (100 mg, 0.43 mmol) in THE (8.0 mL) was added 2-phenylacetic acid (84 mg, 0.62 mmol) followed by $Et_3N$ (0.18 mL, 1.3 mmol) and T3P (50% in ethyl acetate, 0.8 mL, 1.3 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-42 (92 mg, 0.26 mmol, 60% yield) as a solid. Prep. HPLC method: Rt 12.3; Column: X-Bridge (150×19 mm), 5.0 μm; Mobile phase: 0.1% TFA in water/acetonitrile; Flow Rate: 15.0 mL/min. HPLC: Rt 5.39 min, 99.6%; Column: X-Bridge C8 (50×4.6) mm, 3.5 μm; Mobile phase: A: 10 mM ammonium bicarbonate in water, B: ACN; Flow Rate: 1.0 mL/min. LCMS: 349.0 (M+H), Rt 1.76 min; Column: ZORBAX XDB C-18 (50×4.6 mm), 3.5 μm; Mobile Phase: A: 0.1% HCOOH in water, B: 0.1% HCOOH in ACN; Flow Rate: 1.5 mL/min. Chiral method: Rt 1.71 min, SFC column: YMC Amylose-SA; mobile phase: 60:40 (A:B), A=liquid $CO_2$, B=0.5% isopropyl amine in methanol; flow rate: 4.0 mL/min; wavelength: 210 nm. $^1$H NMR (400 MHz, $CD_3OD$): 8.53 (d, 1H), 7.82 (d, 1H), 7.73 (dd, 1H), 7.36-7.26 (m, 5H), 5.35-5.31 (m, 1H), 3.66-3.58 (m, 2H), 2.23-2.19 (m, 1H), 1.67 (d, 3H), 1.13-1.03 (m, 4H).

Example I-43: (S)—N-(1-(3-(2-isopropoxypyridin-4-yl)-1,2,4-oxadiazol-5-yl)ethyl)benzamide

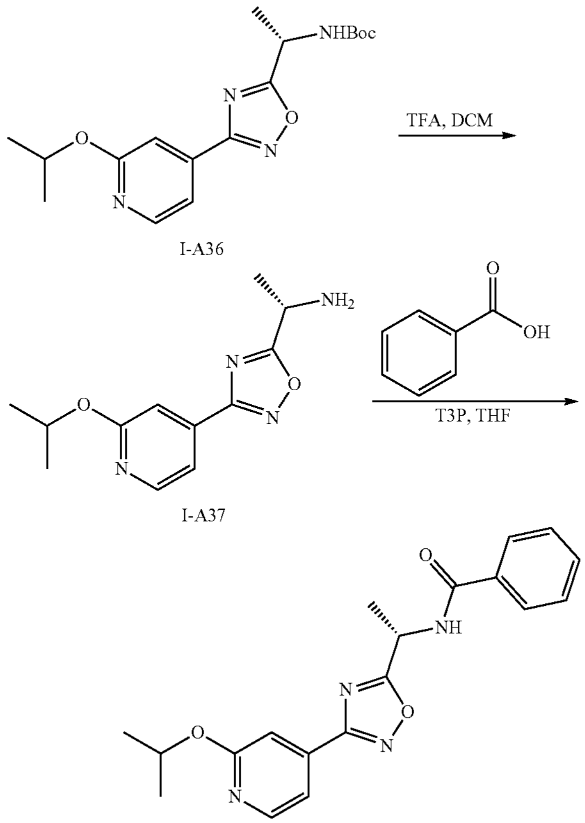

I-A36

I-A37

I-43

I-A37: (S)-1-(3-(2-isopropoxypyridin-4-yl)-1,2,4-oxadiazol-5-yl)ethan-1-amine

To a stirred solution of tert-butyl (S)-(1-(3-(2-isopropoxypyridin-4-yl)-1,2,4-oxadiazol-5-yl)ethyl)carbamate (580 mg, 1.66 mmol) in DCM (10.0 mL) was added TFA (2.43 mL) at 0° C. under nitrogen. The reaction mixture was slowly warmed to room temperature and stirred for 3 h. The mixture was concentrated under reduced pressure and treated with ice water (30 mL). The mixture was treated with 10% $NaHCO_3$ solution (10.0 mL) and extracted with DCM (2×30 mL). The organic layer was washed with brine (50 mL), dried over anhydrous $Na_2SO_4$ and concentrated to afford I-A37 (350 mg). The compound was used for the next step without further purification.

I-43: (S)—N-(1-(3-(2-isopropoxypyridin-4-yl)-1,2,4-oxadiazol-5-yl)ethyl)benzamide To a stirred solution of I-A37 (160 mg, 0.64 mmol) in THE (5.0 mL) was added benzoic acid (78 mg, 0.64 mmol) followed by TEA (0.27 mL, 1.92 mmol) and T3P (50% in ethyl acetate, 1.14 mL, 1.92 mmol) at 0° C. under nitrogen. The reaction mixture was slowly warmed to room temperature and stirred for 3 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-43 (110 mg, 0.31 mmol, 48% yield) as a solid. Prep. HPLC method: Rt 9.75; Column: X-Bridge C-18 (150×19 mm), 5.0 μm; Mobile phase: 0.1% TFA in water/acetonitrile; Flow Rate: 15.0 mL/min. HPLC: Rt 4.55 min, 99.1%; Column: X-Bridge C8 (50×4.6) mm, 3.5 μm; Mobile phase: A: 0.1% TFA in water, B: ACN; Flow Rate: 2.0 mL/min. LCMS: 353.2 (M+H), Rt 2.33 min; Column: Zorbax Eclipse Plus C-18 (50×2.1 mm), 1.8 μm; Mobile Phase: A: 0.1% HCOOH in water:ACN (95:5), B: ACN; Flow Rate: 0.8 mL/min. Chiral method: Rt 2.66 min, SFC column: Lux C3; mobile phase: 85:15 (A:B), A=liquid $CO_2$, B=methanol; flow rate: 3.0 mL/min; wavelength: 210 nm. $^1H$ NMR (400 MHz, DMSO-$d_6$): δ 9.27 (d, 1H), 8.36 (d, 1H), 7.92-7.90 (m, 2H), 7.61-7.46 (m, 4H), 7.21 (s, 1H), 5.50-5.47 (m, 1H), 5.33-5.27 (m, 1H), 1.69 (d, 3H), 1.32 (d, 6H).

Example I-44: (S)—N-(1-(3-(2-ethoxypyridin-4-yl)-1,2,4-oxadiazol-5-yl)ethyl)benzamide

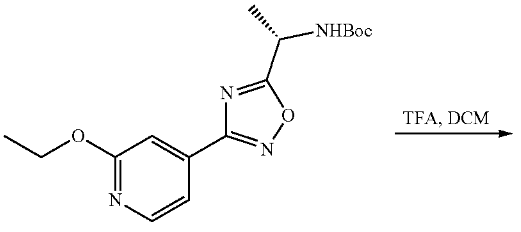

I-A38

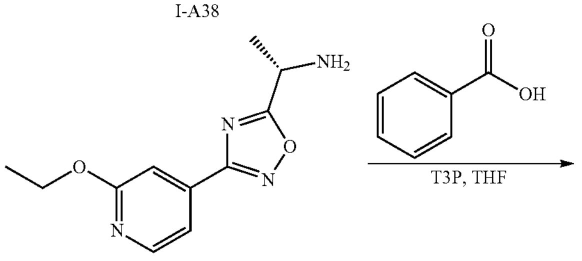

I-A39

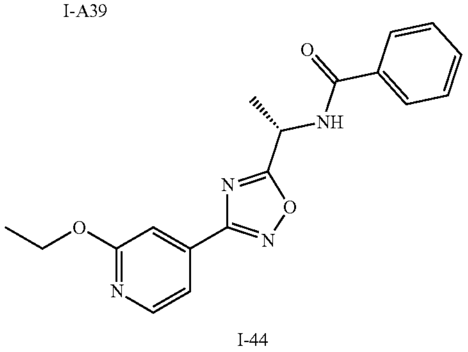

I-44

I-A39: (S)-1-(3-(2-ethoxypyridin-4-yl)-1,2,4-oxadiazol-5-yl)ethan-1-amine

To a stirred solution of tert-butyl (S)-(1-(3-(2-ethoxypyridin-4-yl)-1,2,4-oxadiazol-5-yl)ethyl)carbamate (800 mg, 2.39 mmol) in DCM (10 mL) was added TFA (3.45 mL) at 0° C. under nitrogen. The reaction mixture was slowly warmed to room temperature and stirred for 3 h. The mixture was concentrated under reduced pressure and treated with ice water (20 mL). The mixture was treated with 10% $NaHCO_3$ solution (20 mL) and extracted with EtOAc (2×30 mL). The organic layer was washed with brine (20 mL), dried over $Na_2SO_4$ and concentrated to afford I-A39 (380 mg). The residue was used for the next step without further purification.

I-44: (S)—N-(1-(3-(2-ethoxypyridin-4-yl)-1,2,4-oxadiazol-5-yl)ethyl)benzamide

To a stirred solution of I-A39 (150 mg, 0.64 mmol) in THF (5.0 mL) was added benzoic acid (78 mg, 0.64 mmol) followed by TEA (0.27 mL, 1.92 mmol) and T3P (50% in ethyl acetate, 1.14 mL, 1.92 mmol) at 0° C. under nitrogen. The reaction mixture was slowly warmed to room temperature and stirred for 5 h. The reaction mixture was diluted with water (25 mL) and extracted with ethyl acetate (2×25 mL). The organic layer was washed with brine (20 mL), dried over $Na_2SO_4$ and concentrated. The residue was purified by preparative HPLC to afford I-44 (152 mg, 0.45 mmol, 70% yield) as a solid. Prep. HPLC method: Rt 11.82; Column: Sunfire C18 (150×19 mm), 5.0 μm; Mobile phase: 0.1% TFA in water/acetonitrile; Flow Rate: 15.0 mL/min. HPLC: Rt 4.24 min, 99.8%; Column: X-Bridge C8 (50×4.6) mm, 3.5 μm; Mobile phase: A: 0.1% TFA in water, B: ACN; Flow Rate: 2.0 mL/min. LCMS: 339.1 (M+H), Rt 2.27 min; Column: ZORBAX XDB C-18 (50×4.6 mm), 3.5 μm. Mobile Phase: A: 0.1% HCOOH in water:ACN (95:5), B: ACN; Flow Rate: 1.5 mL/min. Chiral method: Rt 2.94 min, SFC column: Lux C3; mobile phase: 85:15 (A:B), A=liquid $CO_2$,B=methanol; flow rate: 3.0 mL/min; wavelength: 210 nm. $^1H$ NMR (400 MHz, DMSO-$d_6$): δ 9.27 (d, 1H), 8.37 (d, 1H), 7.91 (d, 2H), 7.61-7.50 (m, 4H), 7.26 (s, 1H), 5.50-5.46 (m, 1H), 4.37 (q, 2H), 1.69 (d, 3H), 1.34 (t, 3H).

Example I-45: (S)—N-(1-(3-(2-ethoxypyridin-4-yl)-1,2,4-oxadiazol-5-yl)ethyl)cyclopentanecar-boxamide

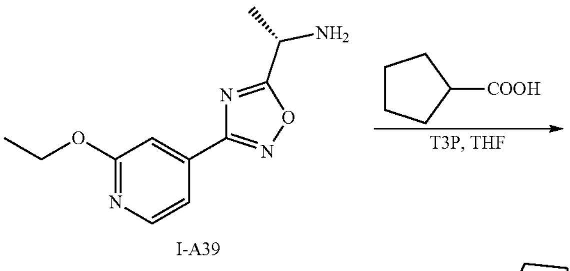

I-A39

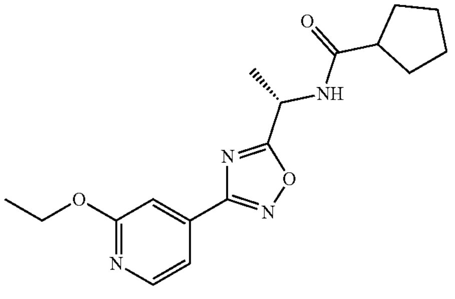

I-45

To a stirred solution of (S)-1-(3-(2-ethoxypyridin-4-yl)-1,2,4-oxadiazol-5-yl)ethan-1-amine (200 mg, 0.85 mmol) in THF (5.0 mL) was added cyclopentanecarboxylic acid (97 mg, 0.85 mmol) followed by TEA (0.36 mL, 2.56 mmol) and T3P (50% in ethyl acetate, 1.52 mL, 2.56 mmol) at 0° C. under nitrogen. The reaction mixture was slowly warmed to room temperature and stirred for 5 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-45 (238 mg, 0.72 mmol, 84% yield) as a solid. Prep. HPLC method: Rt 12.25; Column: Sunfire C18 (150×19 mm), 5.0 μm; Mobile phase: 0.1% TFA in water/acetonitrile; Flow Rate: 15.0 mL/min. HPLC: Rt 4.20 min, 99.8%; Column: X-Bridge C8 (50×4.6) mm, 3.5 μm; Mobile phase: A: 0.1% TFA in water, B: ACN; Flow Rate: 2.0 mL/min. LCMS: 331.2 (M+H), Rt 2.28 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.51 min, SFC column: YMC Cellulose-SB; mobile phase: 60:40 (A:B), A=liquid $CO_2$, B=0.5% isopropyl amine in methanol; flow rate: 3.0 mL/min; wavelength: 210 nm. $^1H$ NMR (400 MHz, DMSO-$d_6$): δ 8.64 (d, 1H), 8.37 (d, 1H), 7.48 (dd, 1H), 7.25 (s, 1H), 5.22-5.19 (m, 1H), 4.37 (q, 2H), 2.67-2.63 (m, 1H), 1.80-1.75 (m, 2H), 1.68-1.54 (m, 9H), 1.34 (t, 3H).

Example I-46: (S)—N-(1-(3-(2-isopropoxypyridin-4-yl)-1,2,4-oxadiazol-5-yl)ethyl)cyclopentane-carboxamide

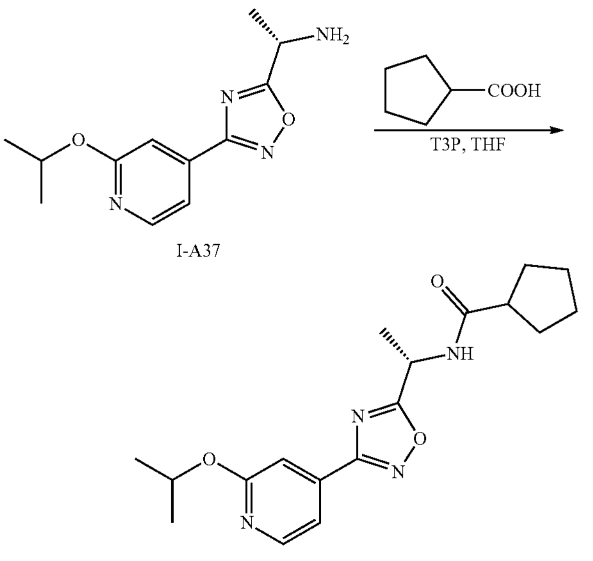

I-A37

I-46

To a stirred solution of (S)-1-(3-(2-isopropoxypyridin-4-yl)-1,2,4-oxadiazol-5-yl)ethan-1-amine (160 mg, 0.64 mmol) in THE (5.0 mL) was added cyclopentanecarboxylic acid (73 mg, 0.64 mmol) followed by TEA (0.27 mL, 1.92 mmol) and T3P (50% in ethyl acetate, 1.14 mL, 1.92 mmol) at 0° C. under nitrogen. The reaction mixture was slowly warmed to room temperature and stirred for 3 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-46 (134 mg, 0.72 mmol, 61% yield) as a solid. Prep. HPLC method: Rt 9.90; Column: X-Bridge C-18 (150×19 mm), 5.0 μm; Mobile phase: 0.1% TFA in water/acetonitrile; Flow Rate: 15.0 mL/min. HPLC: Rt 4.59 min, 99.8%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 345.0 (M+H), Rt 2.47 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.87 min, SFC column: Lux C3; mobile phase: 85:15 (A:B), A=liquid $CO_2$, B=methanol; flow rate: 3.0 mL/min; wavelength: 210 nm. $^1H$ NMR (400 MHz, DMSO-$d_6$): δ 8.64 (d, 1H), 8.37 (d, 1H), 7.45 (dd, 1H), 7.19 (s, 1H), 5.34-5.17 (m, 2H), 2.67-2.63 (m, 1H), 1.80-1.76 (m, 2H), 1.68-1.55 (m, 9H), 1.34 (d, 6H).

Example I-47: N-[1-[3-(3-fluorophenyl)-1,2,4-oxadiazol-5-yl]ethyl]-2-methyl-6-(trifluoromethyl)pyridine-3-carboxamide

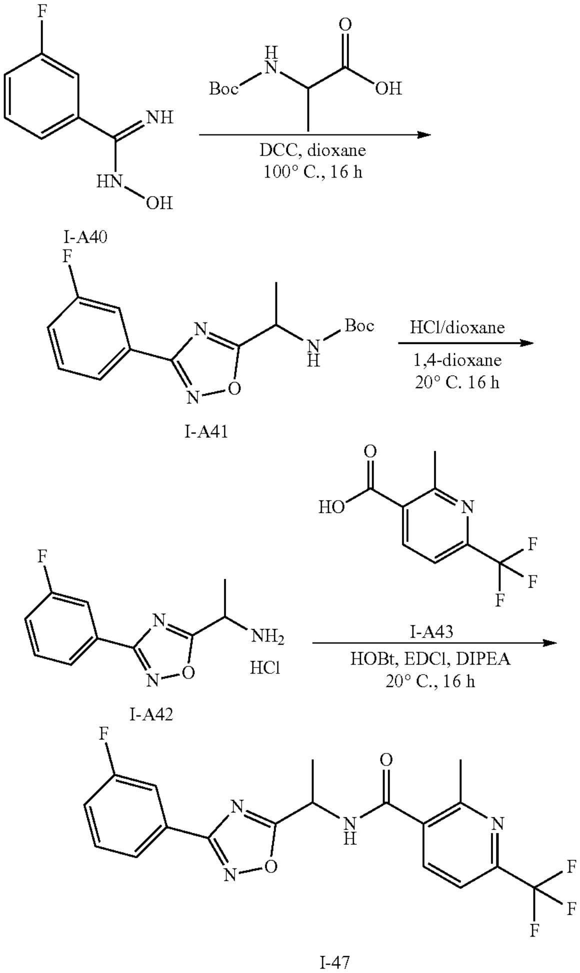

I-A40

I-A41

I-A43

I-A42

I-47

I-A41: tert-butyl N-[1-[3-(3-fluorophenyl)-1,2,4-oxadiazol-5-yl]ethyl]carbamate

A mixture of 3-fluoro-N-hydroxy-benzamidine (1.8 g, 11.68 mmol), 2-(tert-butoxycarbonylamino)propanoic acid (2.43 g, 12.85 mmol), and DCC (4.81 g, 23.36 mmol) in 1,4-Dioxane (30 mL) was stirred at 100° C. for 16 hours. After cooling to RT, the mixture was concentrated to give a residue. The residue was diluted with $H_2O$ (25 mL), and the mixture was extracted with EtOAc (25 mL×2). The combined organic phase was washed with brine (20 mL), dried over $Na_2SO_4$, filtered and concentrated to give a residue. The residue was purified by flash chromatography on silica gel (EtOAc in PE=0% to 10% to 30%) to give the product (3 g, 8.26 mmol, 71% yield) as an oil. LCMS $R_t$=0.91 min in 1.5 min chromatography, 5-95AB, MS ESI calcd. for $C_{15}H_{19}FN_3O_3$[M+H-tBu] 252.1, found 251.8.

I-A42: 1-[3-(3-fluorophenyl)-1,2,4-oxadiazol-5-yl] ethanamine;hydrochloride

To a mixture of tert-butyl N-[1-[3-(3-fluorophenyl)-1,2,4-oxadiazol-5-yl]ethyl]carbamate (3 g, 9.76 mmol) in 1,4-Dioxane (15 mL) was added 4M HCl/dioxane (20 mL). The mixture was stirred at 20° C. for 16 hours. The mixture was concentrated to give a residue (4 g, 15.16 mmol) as an oil. LCMS $R_t$=0.59 min in 1.5 min chromatography, 5-95AB, MS ESI calcd. for $C_{10}H_{11}FN_3O$ [M+H] 208.1, found 207.8.

Example I-47: N-[1-[3-(3-fluorophenyl)-1,2,4-oxadiazol-5-yl]ethyl]-2-methyl-6-(trifluoromethyl)pyridine-3-carboxamide A mixture of 2-methyl-6-(trifluoromethyl)pyridine-3-carboxylic acid (100 mg, 0.49 mmol), EDCI (186.91 mg, 0.97 mmol) and DIPEA (0.26 mL, 1.46 mmol), HOBt (131.75 mg, 0.97 mmol) and 1-[3-(3-fluorophenyl)-1,2,4-oxadiazol-5-yl]ethanamine;hydrochloride (130.67 mg, 0.54 mmol) in DCM (2 mL) was stirred at 20° C. for 16 hours. The residue was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-HPLC (Waters Xbridge (150 mm×25 mm, 5 um), A=$H_2O$ (10 mM $NH_4HCO_3$) and B=$CH_3CN$; 40-70% B over 10 minutes) to give the product (58.6 mg, 0.15 mmol, 30% yield) as a solid. $^1H$ NMR (400 MHz, $CDCl_3$) $\delta_H$=7.95 (d, 1H), 7.87 (d, 1H), 7.80-7.74 (m, 1H), 7.61 (d, 1H), 7.52-7.42 (m, 1H), 7.26-7.20 (m, 1H), 6.58 (d, 1H), 5.71-5.62 (m, 1H), 2.80 (s, 3H), 1.80 (d, 3H). LCMS $R_t$=1.25 min in 2 min chromatography, 10-80AB, MS ESI calcd. for $C_{18}H_{15}F_4N_4O_2$[M+H]$^+$ 395.1, found 395.1.

Example I-48: N-[1-[3-(3-fluorophenyl)-1,2,4-oxadiazol-5-yl]ethyl]-2,4-dimethyl-pyrimidine-5-carboxamide

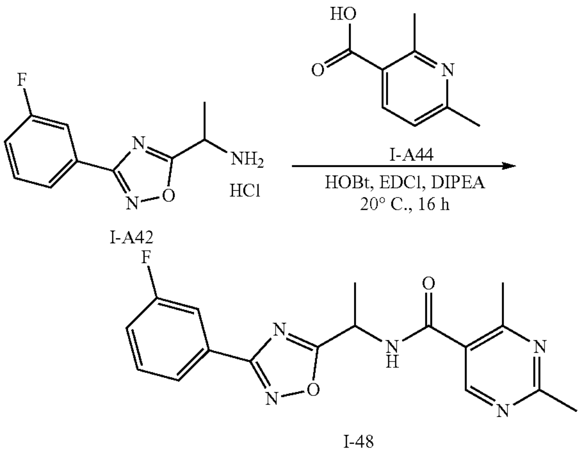

I-A42

I-48

A mixture of 2,4-dimethylpyrimidine-5-carboxylic acid (100 mg, 0.66 mmol), EDCI (251.99 mg, 1.31 mmol) and DIPEA (0.34 mL, 1.97 mmol), HOBt (177.63 mg, 1.31 mmol) and 1-[3-(3-fluorophenyl)-1,2,4-oxadiazol-5-yl] ethanamine hydrochloride (176.17 mg, 0.72 mmol) in DCM (2 mL) was stirred at 20° C. for 16 hours. The residue was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-HPLC (Waters Xbridge (150 mm×25 mm, 5 um) A=$H_2O$ (10 mM $NH_4HCO_3$) and B=$CH_3CN$; 22-52% B over 10 minutes) to give the product (63.7 mg, 0.19 mmol, 28% yield) as a solid. $^1H$ NMR (400 MHz, $CDCl_3$) $\delta_H$=8.72 (s, 1H), 7.87 (d, 1H), 7.80-7.73 (m, 1H), 7.52-7.42 (m, 1H), 7.26-7.20 (m, 1H), 6.61 (br d, 1H), 5.70-5.58 (m, 1H), 2.76 (s, 3H), 2.70 (s, 3H), 1.79 (d, 3H). LCMS $R_t$=1.06 min in 2 min chromatography, 10-80AB, MS ESI calcd. for $C_{17}H_{17}FN_5O_2$[M+H]$^+$ 342.1, found 342.1.

Example I-49: N-[1-[3-(3-fluorophenyl)-1,2,4-oxadiazol-5-yl]ethyl]-3-methyl-imidazo[1,2-a]pyridine-2-carboxamide

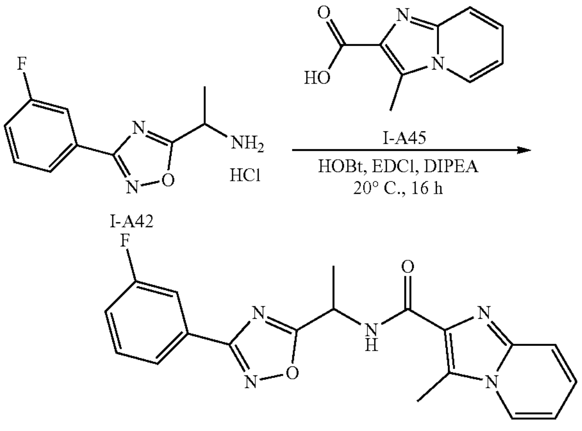

I-A42

I-49

A mixture of 3-methylimidazo[1,2-a]pyridine-2-carboxylic acid (100 mg, 0.57 mmol), EDCI (217.63 mg, 1.14 mmol) and DIPEA (0.3 mL, 1.7 mmol), HOBt (153.41 mg, 1.14 mmol) and 1-[3-(3-fluorophenyl)-1,2,4-oxadiazol-5-yl] ethanamine hydrochloride (152.15 mg, 0.62 mmol) in DCM (5 mL) was stirred at 20° C. for 16 hours. The mixture was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-HPLC (Waters Xbridge 150 mm×25 mm×5 um; mobile phase: A=$H_2O$ (10 mM $NH_4HCO_3$) and B=MeCN; B %: 35%-65%, 10 min) to give the product (14.7 mg, 0.04 mmol, 7% yield) as a solid. $^1H$ NMR (400 MHz, $CDCl_3$) $\delta_H$=8.09 (d, 1H), 7.95 (d, 1H), 7.89 (d, 1H), 7.80 (d, 1H), 7.60 (d, 1H), 7.49-7.39 (m, 1H), 7.32-7.28 (m, 1H), 7.23-7.16 (m, 1H), 6.96-6.90 (m, 1H), 5.74-5.64 (m, 1H), 2.85 (s, 3H), 1.81 (d, 3H). LCMS $R_t$=1.06 min in 2 min chromatography, 10-80AB, MS ESI calcd. for $C_{19}H_{17}FN_5O_2$ [M+H]$^+$ 366.1, found 366.1.

Example I-50: N-[1-[3-(3-fluorophenyl)-1,2,4-oxadiazol-5-yl]ethyl]imidazo[1,2-a]pyridine-2-carboxamide

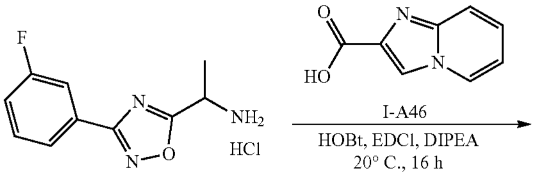

I-A42

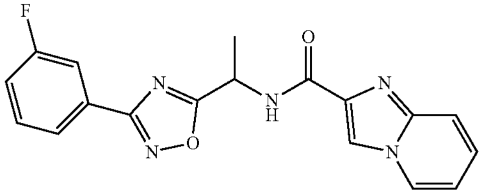

I-50

A mixture of imidazo[1,2-a]pyridine-2-carboxylic acid (100 mg, 0.62 mmol), EDCI (236.45 mg, 1.23 mmol) and DIPEA (0.32 mL, 1.85 mmol), HOBt (166.67 mg, 1.23 mmol) and 1-[3-(3-fluorophenyl)-1,2,4-oxadiazol-5-yl]ethanamine hydrochloride (165.30 mg, 0.68 mmol) in DCM (5 mL) was stirred at 20° C. for 16 hours. The mixture was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-HPLC (Waters Xbridge (150 mm×25 mm, 5 um), A=$H_2O$ (10 mM $NH_4HCO_3$) and B=$CH_3CN$; 30-60% B over 10 minutes) to give the product (42.3 mg, 0.12 mmol, 19% yield) as a solid. $^1$H NMR (400 MHz, $CDCl_3$) $\delta_H$=8.25-8.13 (m, 2H), 7.96 (d, 1H), 7.89 (d, 1H), 7.84-7.76 (m, 1H), 7.62 (d, 1H), 7.51-7.39 (m, 1H), 7.33-7.28 (m, 1H), 7.24-7.15 (m, 1H), 6.96-6.81 (m, 1H), 5.77-5.66 (m, 1H), 1.81 (d, 3H). LCMS $R_t$=1.01 min in 2 min chromatography, 10-80AB, MS ESI calcd. for $C_{18}H_{15}FN_5O_2[M+H]^+$ 352.1, found 352.1.

Example I-51: N-[1-[3-(3-fluorophenyl)-1,2,4-oxadiazol-5-yl]ethyl]-2,3-dihydro-1,4-benzodioxine-6-carboxamide

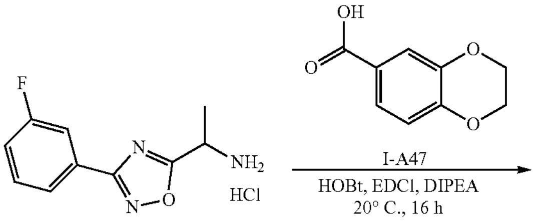

I-A42

-continued

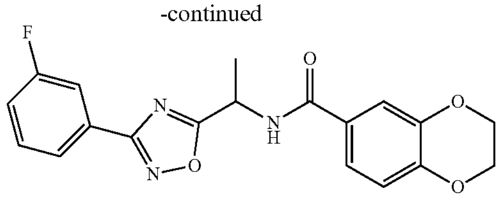

I-51

A mixture of tetralin-6-carboxylic acid (100 mg, 0.57 mmol), EDCI (217.58 mg, 1.14 mmol), DIPEA (0.3 mL, 1.7 mmol), HOBt (153.37 mg, 1.14 mmol) and 1-[3-(3-fluorophenyl)-1,2,4-oxadiazol-5-yl]ethanamine hydrochloride (152.11 mg, 0.62 mmol) in DCM (5 mL) was stirred at 20° C. for 16 hours. The residue was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-IPLC (Waters Xbridge (150 mm×25 mm, 5 um) A=$H_2O$ (10 mM $NH_4HCO_3$) and B=$CH_3CN$; 35-65% B over 10 minutes) to give the product (35.56 mg, 0.09 mmol, 16% yield) as a solid. $^1$H NMR (400 MHz $CDCl_3$) $\delta_H$=7.88 (d, 1H), 7.83-7.72 (m, 1H), 7.51-7.43 (m, 1H), 7.41 (d, 1H), 7.39-7.33 (m, 1H), 7.25-7.18 (m, 1H), 6.94 (d, 1H), 6.67 (br d, 1H), 5.71-5.61 (m, 1H), 4.35-4.28 (m, 4H), 1.75 (d, 3H). LCMS $R_t$=1.12 min in 2 min chromatography, 10-80AB, MS ESI calcd. for $C_{19}H_{17}FN_3O_4[M+H]^+$ 370.1, found 369.9.

Example I-52: N-[1-[3-(3-fluorophenyl)-1,2,4-oxadiazol-5-yl]ethyl]-5,6,7,8-tetrahydroimidazo[1,2-a]pyridine-2-carboxamide

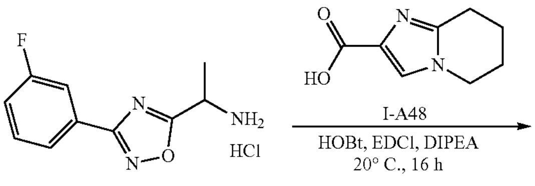

I-A42

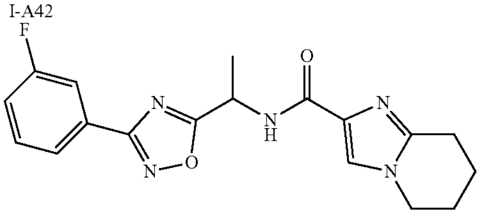

I-52

A mixture of 2-ethyl-1-propyl-imidazole-4-carboxylic acid (100 mg, 0.55 mmol), EDCI (210.41 mg, 1.1 mmol) and DIPEA (0.29 mL, 1.65 mmol), HOBt (148.32 mg, 1.1 mmol) and 1-[3-(3-fluorophenyl)-1,2,4-oxadiazol-5-yl]ethanamine hydrochloride (147.10 mg, 0.60 mmol) in DCM (5 mL) was stirred at 20° C. for 16 hours. The residue was diluted with water (20 mL), extracted with DCM (20 mL×2). The combined organic phase was washed with brine (15 mL), dried over anhydrous $Na_2SO_4$, filtered and concentrated to give a residue. The residue was purified by Prep-HPLC (Waters Xbridge (150 mm×25 mm, 5 um) A=$H_2O$ (10 mM $NH_4HCO_3$) and B=$CH_3CN$; 35-58% B over 8 minutes) to give the product. The product was purified by Prep-HPLC (Waters Xbridge (150 mm×25 mm, 5 um) A=$H_2O$ (10 mM $NH_4HCO_3$) and B=$CH_3CN$; 30-60% B over 10 minutes) to give the product (2.3 mg, 6.5 ummol, 1% yield) as a solid. $^1$H NMR (400 MHz, $CDCl_3$) $\delta_H$=8.63 (d, 1H), 7.82 (d, 1H), 7.74-7.67 (m, 1H), 7.65-7.57 (m, 1H), 7.54 (s, 1H), 7.48-7.40 (m, 1H), 5.43-5.29 (m, 1H), 3.96 (t, 2H), 2.74 (t, 2H), 1.92-1.78 (m, 4H), 1.62 (d, 3H). LCMS $R_t$=0.95 min in 2 min chromatography, 10-80AB, MS ESI calcd. for $C_{18}H_{19}FN_5O_2$ $[M+H]^+$ 356.1, found 356.0.

Example I-53: (S)—N-(1-(3-(2-cyclopropylpyridin-4-yl)-1,2,4-oxadiazol-5-yl)ethyl)-2-methyl-6-(trifluoromethyl)nicotinamide

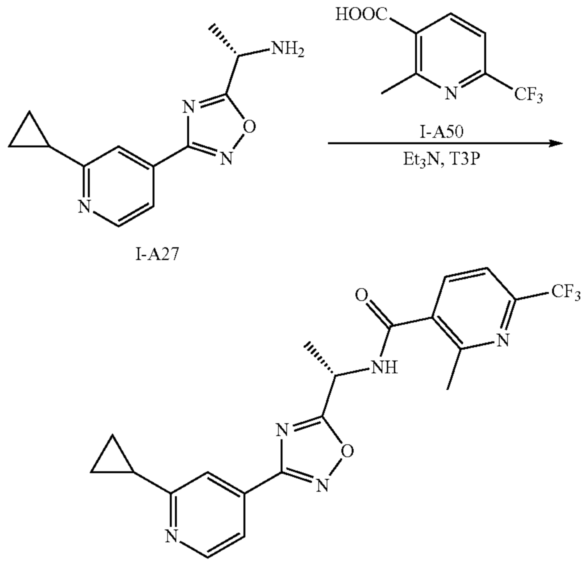

I-A27

I-53

To a stirred solution of (S)-1-(3-(2-cyclopropylpyridin-4-yl)-1,2,4-oxadiazol-5-yl)ethan-1-amine (100 mg, 0.43 mmol) in THE (8.0 mL) was added 2-methyl-6-(trifluoromethyl)nicotinic acid (126 mg, 0.62 mmol) followed by $Et_3N$ (0.18 mL, 1.3 mmol) and T3P (50% in ethyl acetate, 0.8 mL, 1.3 mmol) at 0° C. under nitrogen. The reaction mixture was slowly warmed to room temperature and stirred for 16 h. The reaction mixture was diluted with water (20 mL) and extracted with ethyl acetate (2×25 mL). The organic layer was washed with brine (20 mL), dried over $Na_2SO_4$ and concentrated. The residue was purified by preparative HPLC to afford I-53 (58 mg, 0.13 mmol, 31% yield) as a solid. Prep. HPLC method: Rt 9.8; Column: X-Select C-18 (150×19 mm), 5.0 μm; Mobile phase: 0.1% TFA in water/acetonitrile; Flow Rate: 15.0 mL/min. HPLC: Rt 3.14 min, 99.1%; Column: X-Bridge C8 (50×4.6) mm, 3.5 μm; Mobile phase: A: 0.1% TFA in water, B: 0.1% TFA in ACN; Flow Rate: 2.0 mL/min. LCMS: 418.1 (M+H), Rt 2.15 min; Column: ZORBAX XDB C-18 (50×4.6 mm), 3.5 μm; Mobile Phase: A: 0.1% HCOOH in water:ACN (95:5), B: ACN; Flow Rate: 1.5 mL/min. Chiral method: Rt 1.46 min, SFC column: YMC Cellulose-SB; mobile phase: 60:40 (A:B), A=liquid $CO_2$, B=0.5% isopropyl amine in methanol; flow rate: 3.0 mL/min; wave length: 220 nm. $^1$H NMR (400 MHz, $CD_3OD$): $\delta_H$=8.56 (s, 1H), 8.07 (d, 1H), 7.87 (s, 1H), 7.78 (s, 2H), 5.59-5.57 (m, 1H), 2.74 (s, 3H), 2.23 (m, 1H), 1.79 (d, 3H), 1.11-1.06 (m, 4H).

Example I-54: (S)-5-oxo-N—((S)-1-(3-(2-(trifluoromethyl)pyridin-4-yl)-1,2,4-oxadiazol-5-yl)ethyl) pyrrolidine-2-carboxamide

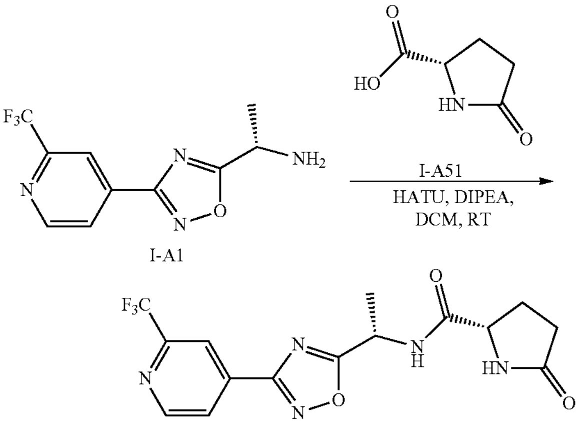

I-A1

I-54

To a stirred solution of I-A51 (78.87 mg, 0.61 mmol) in DCM (2 mL) were added DIPEA (0.27 mL, 1.53 mmol) and HATU (290.34 mg, 0.76 mmol) at RT and stirred at RT for 10 min. To this solution, I-A1 (150 mg, 0.51 mmol) was added and the reaction mixture was stirred at RT for 2 h. The reaction mixture was diluted with DCM (10 mL×2) and washed with water (10 mL). The organic layer was dried over anhydrous sodium sulphate, filtered and evaporated to give the residue. The residue was purified by prep. HPLC to give I-54 (115 mg, 0.311 mmol, 61% yield) as a solid. HPLC: Rt 6.432 min, 99.8%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 369.9 (M+H), Rt 1.677 min; Column: X-select CSH C18 (3×50) mm, 2.5 μm. $^1$H NMR (400 MHz, DMSO-d6) $\delta_H$=9.02 (d, 1H), 8.93 (d, 1H), 8.28-8.25 (m, 2H), 7.86-7.84 (m, 1H), 5.31-5.27 (m, 1H), 4.12-4.06 (m, 1H), 2.33-2.29 (m, 1H), 2.16-2.08 (m, 2H), 2.00-1.92 (m, 1H), 1.59 (d, 3H). Chiral method: Rt 10.681 min, 94.7%; column: DIACEL CHIRALPAK-IG (250×4.6 mm, 5 um), –Mobile Phase: A) n-Hexane+0.1% Isopropylamine B) DCM: MeOH (1:1), Isocratic:50% B; Wavelength: 225 nm, Flow Rate: 1.0 mL/min.

Example I-56: (S)-3,3-dimethyl-N-(1-(3-(2-(trifluoromethyl)pyridin-4-yl)-1,2,4-oxadiazol-5-yl)ethyl) cyclobutane-1-carboxamide

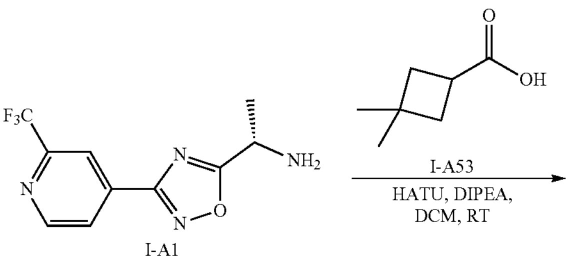

I-A1

-continued

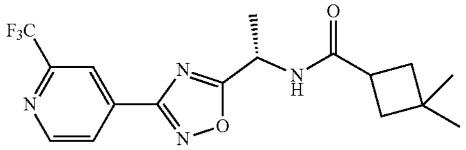

I-56

To a stirred solution of I-A53 (104.39 mg, 0.81 mmol) in DCM (2 mL) were added DIPEA (0.35 mL, 2.04 mmol) and HATU (387.12 mg, 1.02 mmol) at RT and stirred for 10 min. To this solution, I-A1 (200 mg, 0.68 mmol) was added and the reaction mixture was stirred at RT for 2 h. The reaction mixture was diluted with DCM (10 mL×2) and washed with water (10 mL). The organic layer was dried over anhydrous sodium sulphate, filtered and evaporated to give a residue. The residue was purified by flash column chromatography using 100-200 mesh silica and 30-35% EtOAc in hexane as an eluent to give I-56 (110 mg, 0.29 mmol, 42% yield) as a solid. HPLC: Rt 8.8 min, 96%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 369 (M+H), Rt 2.173 min; Column: X-select CSH C18 (3×50) mm, 2.5 μm. $^1$H NMR (400 MHz, DMSO-d6) $\delta_H$=9.02 (d, 1H), 8.56 (d, 1H), 8.28-8.25 (m, 2H), 5.27-5.19 (m, 1H), 3.07-2.98 (m, 1H), 1.93-1.80 (m, 4H), 1.55 (d, 3H), 1.14 (s, 3H), 1.03 (s, 3H). Chiral method: Rt 7.29 min, 95.1%; column: DIACEL CHIRALPAK-IG (250×4.6 mm, 5 um), –Mobile Phase: A) n-Hexane+0.1% Isopropylamine B) DCM: MeOH (50:50), Isocratic:20% B; Wavelength: 270 nm, Flow Rate: 1.0 mL/min.

Example I-57: Synthesis of (S)-5-bromo-N-(1-(3-(2-cyclopropylpyridin-4-yl)-1,2,4-oxadiazol-5-yl)ethyl)thiophene-2-carboxamide

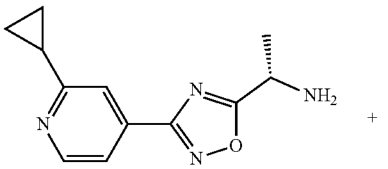

I-A27

+

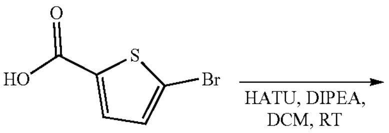

I-A54

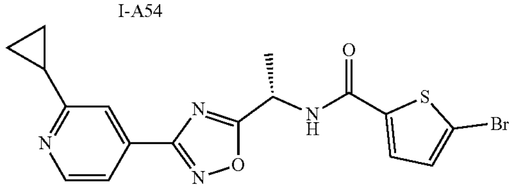

I-57

To the stirred solution of I-A54 (93.15 mg, 0.45 mmol) in DCM (2 mL) were added DIPEA (0.2 mL, 1.12 mmol) and HATU (213.83 mg, 0.56 mmol) at RT and stirred for 10 min. To resulting reaction mixture was added (1S)-1-[3-(2-cyclopropyl-4-pyridyl)-1,2,4-oxadiazol-5-yl]ethanamine hydrochloride (100 mg, 0.37 mmol) and stirred at RT for 2 h. The reaction mixture was diluted with DCM and organic layer was washed with water (2 mL×3). Organic layer dried over sodium sulphate and concentrated completely under reduced pressure to obtain a residue as a liquid. The residue was purified using prep-HPLC to give I-57 (45 mg, 0.10 mmol, 28% yield) as a solid. HPLC: Rt 8.553 min, 96.6%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 419.10 (M+H), Rt 2.03 min; Column: X-select CSH C18 (3×50) mm, 2.5 μm. $^1$H NMR (400 MHz, DMSO-d6) $\delta_H$=9.36 (d, 1H), 8.61 (d, 1H), 7.86-7.84 (m, 1H), 7.71 (d, 1H), 7.68-7.65 (m, 1H), 7.34 (d, 1H), 5.45-5.40 (m, 1H), 2.33-2.25 (m, 1H), 1.67 (d, 3H), 1.04-0.96 (m, 4H). Chiral method: Rt 15.32 min, 91.9%; column: DIACEL CHIRALPAK-IG (250×4.6 mm, 5 um), –Mobile Phase: A) n-Hexane+0.1% Isopropylamine B) DCM: MeOH (1:1), Isocratic: 20% B; Wavelength: 280 nm, Flow Rate: 1.0 mL/min.

Example I-58: Synthesis of (R)—N—((S)-1-(3-(2-cyclopropylpyridin-4-yl)-1,2,4-oxadiazol-5-yl)ethyl)-2-phenylpropanamide

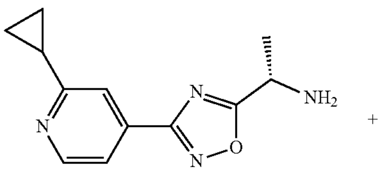

I-A27

+

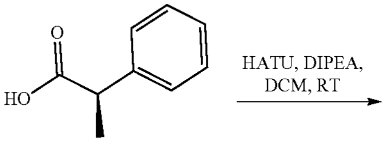

I-A55

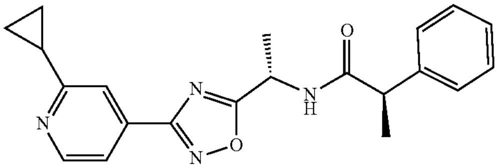

I-58

To a stirred solution of I-A27 (100 mg, 0.43 mmol) and I-A55 (0.07 mL, 0.52 mmol) in DCM (10 mL) were added HATU (247.69 mg, 0.65 mmol) and DIPEA (0.15 mL, 0.87 mmol) at RT. The reaction mixture was stirred at RT for 2 h. The reaction mixture was diluted with DCM (100 mL×2) and washed with water (100 mL). The organic layer was separated and dried over anhydrous sodium sulphate and evaporated to dryness to give the residue which was purified by flash column chromatography using silica gel and 30-35% EtOAc in hexane as an eluent to give I-58 (30 mg, 0.08 mmol, 18% yield). HPLC: Rt 8.879 min, 96.8%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 363 (M+H), Rt 1.972 min; Column: X-select CSH C18 (3×50) mm, 2.5 μm. $^1$H NMR (400 MHz, DMSO-d6) $\delta_H$=8.90 (d, 1H), 8.64 (d, 1H), 7.89 (s, 1H), 7.76-7.73 (m, 1H), 7.33-7.27 (m, 4H), 7.25-7.19 (m, 1H), 5.22-5.14 (m, 1H), 3.73-3.67 (m, 1H), 2.36-2.29 (m, 1H), 1.51 (d, 3H), 1.34 (d, 3H), 1.16-1.04 (m, 4H). Chiral method: Rt 7.961 min, 98.4%; column: DIACEL CHIRALPAK-IG (250×4.6 mm, 5 um), –Mobile Phase: A) n-Hexane+0.1% Isopropylamine B) DCM: MeOH (1:1), Isocratic:20% B; Wavelength: 293 nm, Flow Rate: 1.0 mL/min.

Example I-59: (S)—N-(1-(3-(2-(trifluoromethyl)pyridin-4-yl)-1,2,4-oxadiazol-5-yl)ethyl)bicyclo[2.2.2]octane-1-carboxamide

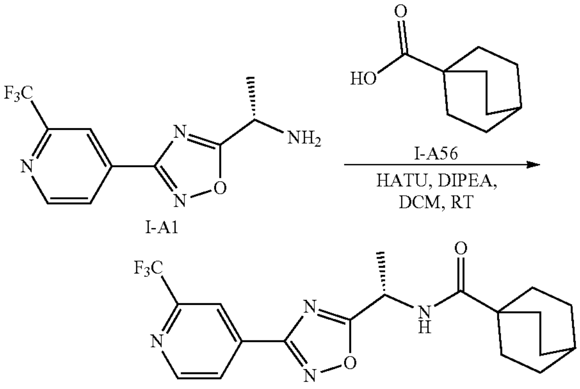

I-59

To a stirred solution of I-A1 (100 mg, 0.39 mmol) and I-A56 (71.67 mg, 0.46 mmol) in DCM (10 mL) was added HATU (220.89 mg, 0.58 mmol) and DIPEA (0.13 mL, 0.77 mmol) at RT. The reaction mixture was stirred at RT for 2 h. The reaction mixture was diluted with DCM (100 mL×2) and washed with water (100 mL). The organic layer was dried over anhydrous sodium sulphate, filtered and evaporated to give the residue. The residue was purified by flash column chromatography 100-200 mesh silica and 25-30% EtOAc in hexane as an eluent to give I-59 (20 mg, 0.050 mmol, 13% yield). HPLC: Rt 9.522 min, 99.8%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 394.90 (M+H), Rt 2.202 min; Column: X-select CSH C18 (3×50) mm, 2.5 μm. $^{1}$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 7.184 min, 94.4%; column: DIACEL CHIRALPAK-IG (250×4.6 mm, 5 um), –Mobile Phase: A) n-Hexane+0.1% Isopropylamine B) DCM: MeOH (1:1), Isocratic:20% B; Wavelength: 225 nm, Flow Rate: 1.0 mL/min.

Example I-60: Synthesis of N—((S)-1-(3-(2-(trifluoromethyl)pyridin-4-yl)-1,2,4-oxadiazol-5-yl)ethyl)bicyclo[2.2.2]octane-2-carboxamide

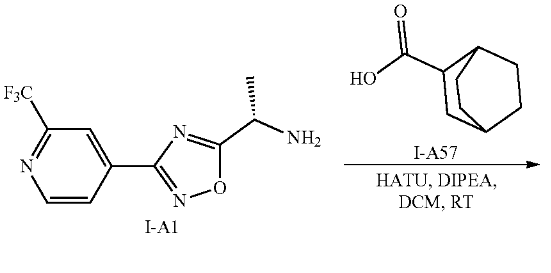

I-A1

-continued

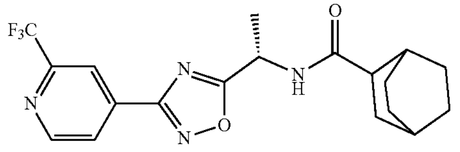
I-60

To a stirred solution of I-A1 (100 mg, 0.39 mmol) and I-A57 (71.67 mg, 0.46 mmol) in DCM (10 mL) was added HATU (220.89 mg, 0.58 mmol) and DIPEA (0.13 mL, 0.77 mmol) at RT and stirred at RT for 2 h. The reaction mixture was diluted with DCM (100 mL×2) and washed with water (100 mL). The organic layer was dried over anhydrous sodium sulphate, filtered and evaporated to give the residue. The residue was purified by flash column chromatography using 100-200 mesh silica and 30-35% EtOAc in hexane as an eluent to give I-60 (20 mg, 0.051 mmol, 13% yield). HPLC: Rt 9.647 min, 99.8%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 395.15 (M+H), Rt 2.23 min, Column: X-select CSH C18 (3×50) mm, 2.5 μm. $^{1}$H NMR (400 MHz, DMSO-d6) $\delta_H$=9.02 (d, 1H), 8.62-8.58 (m, 1H), 8.28-8.24 (m, 2H), 5.26-5.21 (m, 1H), 1.96-1.76 (m, 2H), 1.57-1.46 (m, 11H), 1.40-1.30 (m, 3H).

Example I-61: (S)—N-(1-(3-(2-cyclopropylpyridin-4-yl)-1,2,4-oxadiazol-5-yl)ethyl)-4-methoxybenzamide

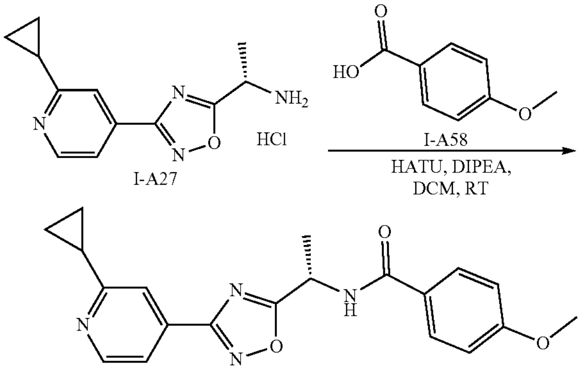

I-61

To a stirred solution of I-A27 (70. mg, 0.26 mmol, HCl salt) and I-A58 (47.92 mg, 0.31 mmol) in DCM (10 mL) were added HATU (149.68 mg, 0.39 mmol) and DIPEA (0.09 mL, 0.52 mmol) at RT. The reaction mixture was stirred at RT for 2 h. The mixture was quenched with water (10 mL) and diluted with DCM (50×2 mL). The organic layer was dried over anhydrous sodium sulphate, filtered and evaporated to give a residue. The residue was purified by column chromatography using 100-200 silica and 30-80% EtOAc/hexane as an eluent to give I-61 (30 mg, 0.078 mmol, 30% yield). HPLC: Rt 7.53 min, 94.9%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 364.9 (M+H), Rt 1.884 min, Column: X-select CSH C18 (3*50) mm, 2.5 μm. $^{1}$H NMR (400 MHz, DMSO-d6) $\delta_H$=9.02 (d, 1H), 8.28-8.25 (m, 2H), 8.16-8.13

(m, 1H), 5.27-5.19 (m, 1H), 1.68-1.64 (m, 6H), 1.63-1.53 (m, 10H). Chiral method: Rt 17.184 min, 99.8%; column: DIACEL CHIRALPAK-IG (250×4.6 mm, 5 u), –Mobile Phase: A) n-Hexane+0.1% Iso-propyl-amine B) DCM: MeOH (1:1), Isocratic:25% B; Wavelength: 254 nm, Flow: 1.0 mL/min.

Example I-62: (S)-4-chloro-N-(1-(3-(2-cyclopropylpyridin-4-yl)-1,2,4-oxadiazol-5-yl)ethyl)benzamide

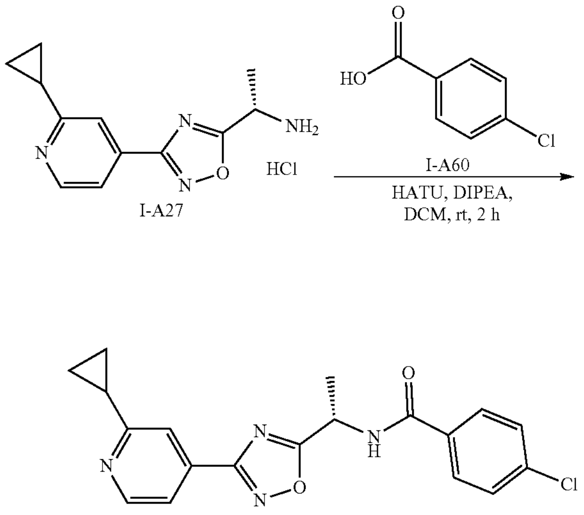

I-62

To a stirred solution of I-A27 HCl salt (0.070 g, 0.262 mmol) and I-A60 (0.049 g, 0.312 mmol) in DCM (10 mL) was added DIPEA (0.090 mL, 0.520 mmol) followed by HATU (0.149 g, 0.390 mmol) at room temperature and stirred for 2 h. After completion of reaction the reaction mixture was quenched with water (10 mL) and extracted with ethyl acetate (2×10 mL). The combined organic layer was dried over anhydrous $Na_2SO_4$, filtered and concentrated under reduced pressure to afford the residue. The residue was purified by 100-200 mesh size silica gel column chromatography eluting with 30-80% ethyl acetate in n-hexane to afford I-62 (0.020 g, 0.054 mmol, 21% yield) as a solid. LCMS: 368.90 (M+H), $R_t$=2.036 min; Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: $R_t$=8.580 min, 97.0%; Column: X-Select CSH C18 (150×4.6 mm, 3.5 μm); Mobile phase: A: 0.05% TFA:ACETONITRILE (95:05), B: ACETONITRILE: 0.05% TFA (95:05); Programme: T/B %: 0.01/10, 12/90, 16/90. Flow Rate: 1.0 mL/min; Diluent: Acetonitrile:Water. CHIRAL HPLC: $R_t$=7.184 min, 94.40%; Column: CHIRAL PAK IG (250×4.6 mm, 5 μm); Mobile phase A) n-Hexane+0.1% Iso-propyl-amine B) DCM: MeOH (1:1), Isocratic:25% B; Wavelength: 292 nm, Flow: 1.0 mL/min. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H).

Example I-63: 3-chloro-N-[(1S)-1-[3-(2-cyclopropyl-4-pyridyl)-1,2,4-oxadiazol-5-yl]ethyl]benzamide

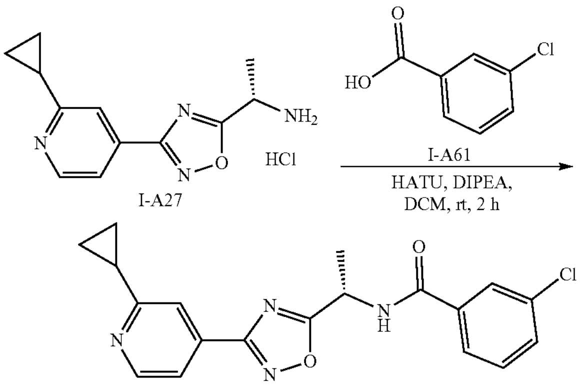

I-63

To a stirred solution of I-A27 HCl salt (70. mg, 0.26 mmol, HCl salt) and I-A61 (49.31 mg, 0.31 mmol) in DCM (10 mL) were added HATU (149.68 mg, 0.39 mmol) and DIPEA (0.09 mL, 0.52 mmol) at RT. The reaction mixture was stirred at RT for 2 h. The reaction mixture was quenched with water (10 mL) and diluted with DCM (50×2 mL). The organic layer was dried over anhydrous sodium sulphate, filtered and evaporated to get a residue. The residue was purified by column chromatography using 100-200 silica and 30-80% EtOAc/Hexane as an eluent to give I-63 (20 mg, 0.05 mmol, 20% yield). HPLC: Rt 8.671 min, 98.2%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 368.9 (M+H), Rt 2.054 min, Column: X-select CSH C18 (3*50) mm, 2.5 μm. $^1$H NMR (400 MHz, DMSO-d6) $\delta_H$=9.41 (d, 1H), 8.63 (d, 1H), 7.97 (s, 1H), 7.89-7.86 (m, 2H), 7.73-7.71 (m, 1H), 7.68-7.65 (m, 1H), 7.55 (t, 1H), 5.50-5.46 (m, 1H), 2.33-2.29 (m, 1H), 1.69 (d, 3H), 1.06-1.01 (m, 4H).

Example I-64: (2S)—N-[(1S)-1-[3-(2-cyclopropyl-4-pyridyl)-1,2,4-oxadiazol-5-yl]ethyl]-2-phenylpropanamide

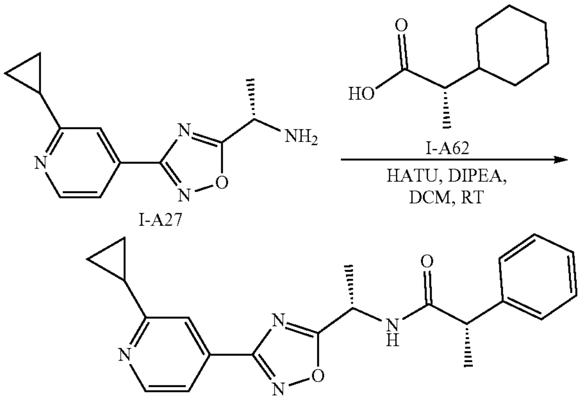

I-64

To a stirred solution of I-A27 (100. mg, 0.37 mmol) and I-A62 (0.06 mL, 0.45 mmol) in DCM (2 ml) were added HATU (213.83 mg, 0.56 mmol)) and DIPEA (0.2 mL, 1.12 mmol) at RT and stirred for 2 hr at RT. The reaction mixture was diluted with DCM (3 mL) and quenched using water (2×3 mL) and organic layer separated. The organic layer was dried over $Na_2SO_4$, filtered and evaporated by rotavapor. The reaction mixture was purified Prep HPLC to give I-64 (85 mg, 0.23 mmol, 61% yield) as a solid. HPLC: Rt 8.04 min, 97.9%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 363.20 (M+H), Rt 1.948 min, Column: X-select CSH C18 (3*50) mm, 2.5 μm. $^1H$ NMR (400 MHz, DMSO-d6) $\delta_H$=8.87 (d, 1H), 8.59 (d, 1H), 7.76 (s, 1H), 7.58-7.56 (m, 1H), 7.33-7.27 (m, 4H), 7.25-7.22 (m, 1H), 5.25-5.21 (m, 1H), 3.73-3.68 (m, 1H), 2.27-2.22 (m, 1H), 1.55 (d, 3H), 1.33 (d, 3H), 1.04-0.96 (m, 4H).

Example I-65: (S)-1-methyl-N-(1-(3-(2-(trifluoromethyl)pyridin-4-yl)-1,2,4-oxadiazol-5-yl)ethyl)piperidine-4-carboxamide

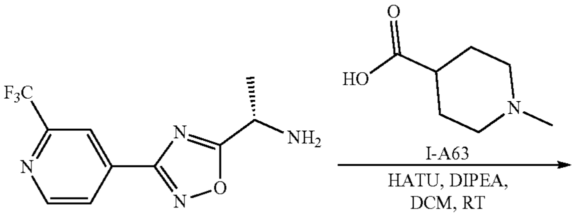

I-A1

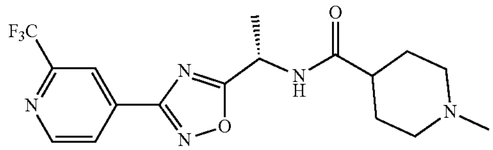

I-65

To a stirred solution of compound I-A1 (100 mg, 0.34 mmol, HCl salt) and I-A63 (0.06 mL, 0.41 mmol) in DCM (3 mL) were added HATU (193.6 mg, 0.51 mmol) and DIPEA (0.18 mL, 1.02 mmol) at RT. The reaction mixture was stirred at RT for 2 h. The reaction mixture was diluted with DCM (3 mL) and washed with water (2×3 mL). The organic layer was dried over anhydrous sodium sulphate, filtered and evaporated to give a residue. The residue was purified using prep-HPLC to give I-65 (40 mg, 0.103 mmol, 30% yield). HPLC: Rt 8.610 min, 98.7%; Column: X-Select CSH C18 (4.6×150) mm, 5 μm; Mobile phase: A: 10 mM ammonium bicarbonate in water, B: ACN; Flow Rate: 1.0 mL/min. LCMS: 384.05 (M+H), Rt 1.635 min, Column: X-select CSH C18 (3*50) mm, 2.5 μm. $^1H$ NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 7.133 min, 97.4%; column: DIACEL CHIRALPAK-IG (250×4.6 mm, 5 u), −Mobile Phase: A) n-Hexane+0.1% Iso-propyl-amine B) IPA, Isocratic:35% B; Wavelength: 270 nm, Flow: 1.0 mL/min.

Example I-66: 1-methyl-N—((S)-1-(3-(2-(trifluoromethyl)pyridin-4-yl)-1,2,4-oxadiazol-5-yl)ethyl)piperidine-2-carboxamide

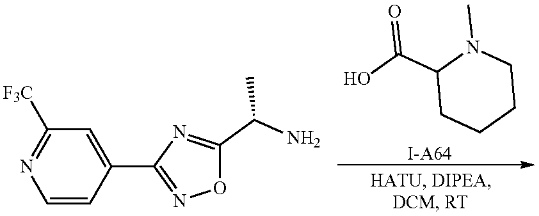

I-A1

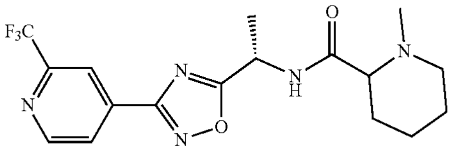

I-66

To a stirred solution of compound I-A1 (100 mg, 0.34 mmol, HCl salt) and I-A64 (0.06 mL, 0.41 mmol) in DCM (2 mL) were added HATU (193.56 mg, 0.51 mmol) and DIPEA (0.18 mL, 1.02 mmol) at RT. The reaction mixture was stirred at RT for 2 h. The reaction mixture was diluted with DCM (3 mL) and washed with water (2×5 mL). The organic layer was dried over anhydrous sodium sulphate, filtered and evaporated to give a residue. The residue was purified by using prep-HPLC to give I-66 (30 mg, 0.078 mmol, 23% yield). HPLC: Rt 5.050 min (48.63%) and 5.127 (51.37%); total: 100%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 384.20 (M+H), Rt 1.499 min, Column: X-select CSH C18 (3*50) mm, 2.5 μm. $^1H$ NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 9.904 min (47.37%); 10.424 (48.697%) total=96.1%; column: DIACEL CHIRALPAK-IG (250×4.6 mm, 5 u), −Mobile Phase: A) n-Hexane+0.1% Iso-propyl-amine B) DCM: MeOH (1:1), Isocratic:15% B; Wavelength: 225 nm, Flow: 1.0 mL/min.

Example I-67: (S)-4,4-dimethyl-N-(1-(3-(2-(trifluoromethyl)pyridin-4-yl)-1,2,4-oxadiazol-5-yl)ethyl)cyclohexane-1-carboxamide

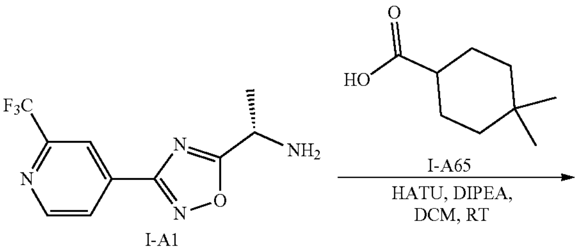

I-A1

-continued

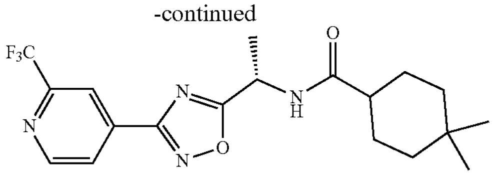

I-67

To a stirred solution of compound I-A1 (100. mg, 0.34 mmol, HCl salt) and I-A65 (0.06 mL, 0.41 mmol) in DCM (3 mL) were added HATU (193.56 mg, 0.51 mmol) and DIPEA (0.18 mL, 1.02 mmol) at RT. The reaction mixture was stirred at RT for 2 h. The reaction mixture was diluted with DCM (3 mL) and washed with water (2×3 mL). The organic layer was dried over anhydrous sodium sulphate, filtered and evaporated to give a residue. The residue was purified using prep-HPLC to give I-67 (17 mg, 0.043 mmol, 13% yield) as a solid. HPLC: Rt 9.707 min, 99.9%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 397.1 (M+H), Rt 2.262 min, Column: X-select CSH C18 (3*50) mm, 2.5 μm. $^{1}$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 8.188 min, 96.2%; column: DIACEL CHIRALPAK-IG (250×4.6 mm, 5 u), –Mobile Phase: A) n-Hexane+0.1% Iso-propyl-amine B) DCM: MeOH (1:1), Isocratic:20% B; Wavelength: 271 nm, Flow: 1.0 mL/min.

Example I-68: 1-methyl-N—((S)-1-(3-(2-(trifluoromethyl)pyridin-4-yl)-1,2,4-oxadiazol-5-yl)ethyl)piperidine-3-carboxamide

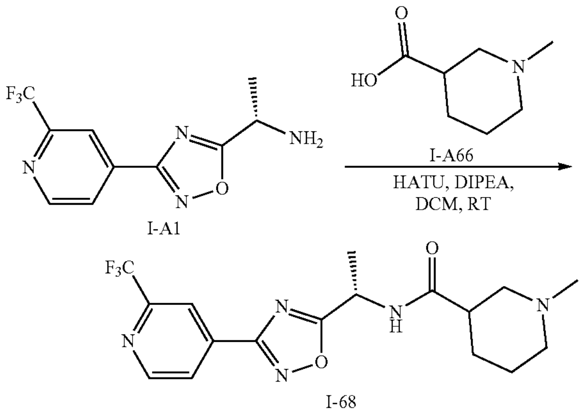

I-68

To a stirred solution of compound I-A1 (210 mg, 0.7 mmol) and I-A66 (0.1 g, 0.7 mmol) in DCM (10 mL) were added HATU (270 mg, 0.7 mmol) and DIPEA (0.24 mL, 1.4 mmol) at 0° C. The reaction mixture was stirred at RT for 6 h. The reaction mixture was diluted with DCM (20 mL) and washed with water (10 mL). The organic layer was dried over anhydrous sodium sulphate, filtered and evaporated to give a residue. The residue was purified by flash column chromatography 100-200 mesh silica and 80% EtOAc in hexane as an eluent to give residue which was purified by prep HPLC to give I-68 (20 mg, 0.05 mmol, 7% yield) as a solid. Note:mixture of diastereomer. HPLC: Rt 8.076 min, 99.2%; Column: X-Select CSH C18 (4.6×150) mm, 5 μm; Mobile phase: A: 10 mM ammonium bicarbonate in water: ACN, B: ACN; Flow Rate: 1.0 mL/min; Gradient program: 0.01/5, 1/5, 18/100, 12/100, 14/5, 18/5. LCMS: 383.91 (M+H), Rt 1.725 min, Column: X-select CSH C18 (3*50) mm, 2.5 μm. $^{1}$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 15.672 min (73.667%), 23.206 (21.598%), 95.3%; column: DIACEL CHIRALPAK-IG (250×4.6 mm, 5 u), –Mobile Phase: A) n-Hexane+0.1% Iso-propyl-amine B) EtOH: MeOH (1:1), Isocratic:20% B; Wavelength: 271 nm, Flow: 1.0 mL/min.

Example I-69: (S)-4-methoxy-N-(1-(3-(2-(trifluoromethyl)pyridin-4-yl)-1,2,4-oxadiazol-5-yl)ethyl)cyclohexane-1-carboxamide

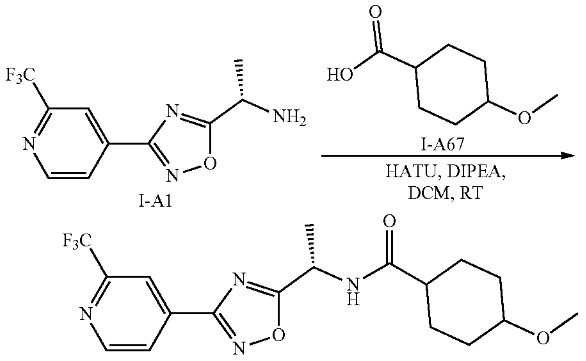

I-69

To a stirred solution of compound I-A1 (100 mg, 0.34 mmol) and I-A67 (0.06 mL, 0.41 mmol) in DCM (2 mL) were added HATU (193.56 mg, 0.51 mmol) and DIPEA (0.18 mL, 1.02 mmol) at RT. The reaction mixture was stirred at RT for 2 h. The reaction mixture was diluted with DCM (3 mL) and washed with water (3 mL×2). The organic layer was dried over anhydrous sodium sulphate, filtered and evaporated to give a liquid product which was purified using Prep HPLC to give I-69 (50 mg, 0.12 mmol, 36% yield) as a solid. HPLC: Rt 8.155 min, 99.5%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 399.20 (M+H), Rt 2.202 min, Column: X-select CSH C18 (3*50) mm, 2.5 μm. $^{1}$H NMR (400 MHz, DMSO-d6) $\delta_H$=9.02 (d, 1H), 8.69-8.67 (m, 1H), 8.28-8.24 (m, 2H), 5.25-5.20 (m, 1H), 3.22 (s, 3H), 3.10-3.05 (m, 1H), 2.20-2.10 (m, 1H), 2.05-2.00 (m, 2H), 1.80-1.75 (m, 2H), 1.54 (d, 3H), 1.45-1.35 (m, 2H), 1.12-1.07 (m, 2H). Chiral method: Rt 4.561 min, 98.9%; column: DIACEL CHIRALPAK-IG (250×4.6 mm, 5 u), –Mobile Phase: A) n-Hexane+0.1% Iso-propyl-amine B) DCM: MeOH (1:1), Isocratic: 40% B; Wavelength: 271 nm, Flow: 1.0 mL/min.

Example I-70: (S)—N-(1-(3-(2-cyclopropylpyridin-4-yl)-1,2,4-oxadiazol-5-yl)ethyl)-5-(methylsulfonyl)thiophene-2-carboxamide

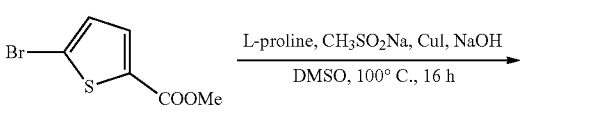

I-A68

-continued

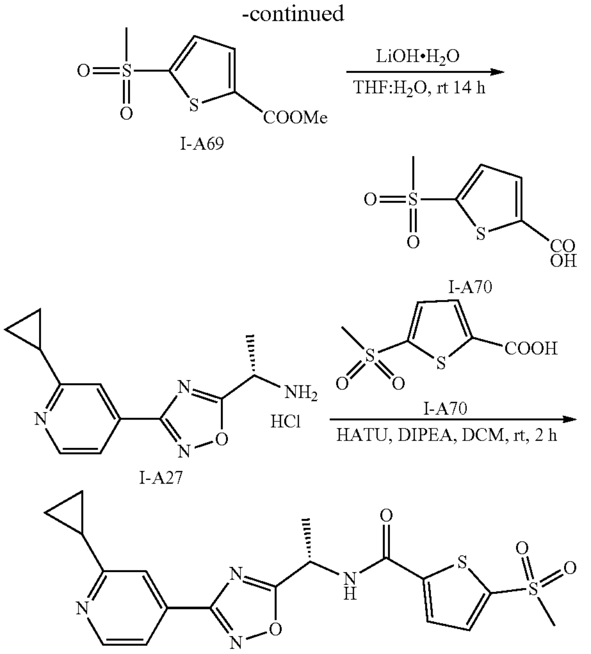

I-A69, I-A70, I-A27, I-70

I-A69: methyl 5-(methylsulfonyl)thiophene-2-carboxylate

To a stirred solution of I-A68 (2.00 g, 9.050 mmol) in DMSO (30 mL) was added sodium methanesulfinate (1.85 g, 18.09 mmol), copper iodide (0.343 g, 1.810 mmol), L-proline (0.208 g, 1.810 mmol) and sodium hydroxide (0.036 g, 0.900 mmol) at room temperature. The reaction mixture was further heated at 100° C. for 16 h. After completion of the reaction the mixture was concentrated under reduced pressure to dryness. The residue was diluted with ethyl acetate and washed with water (2×10 mL) followed by brine (10 mL). The organic layer was separated, dried over anhydrous $Na_2SO_4$, filtered and concentrated under reduced pressure to afford the residue. The residue was purified by flash column chromatography eluting with 0-30% ethyl acetate in n-hexane to afford I-A69 (0.800 g, 3.630 mmol, 40% yield).

I-A70: 5-(methylsulfonyl)thiophene-2-carboxylic acid

To a stirred solution of I-A69 (0.800 g, 3.631 mmol) in THF:$H_2O$ (7:3 mL) was added LiOH.$H_2O$ (0.305 g, 7.264 mmol) at room temperature and stirred for 14 h. After completion of reaction, the mixture was concentrated under reduced pressure to remove THF. The aqueous layer obtained was acidified with 1N HCl solution and the solid precipitated was filtered and dried under vacuum to afford I-A70 (0.500 g, 2.424 mmol, 67% yield).

I-70: (S)—N-(1-(3-(2-cyclopropylpyridin-4-yl)-1,2,4-oxadiazol-5-yl)ethyl)-5-(methylsulfonyl)thiophene-2-carboxamide To a stirred solution of I-A27 HCl salt (0.300 g, 1.120 mmol) and I-A70 (0.278 g, 1.350 mmol) in DCM (10 mL) was added DIPEA (0.590 mL, 3.370 mmol) followed by HATU (0.641 g, 1.690 mmol) at room temperature and stirred for 2 h. After completion of the reaction the mixture was concentrated under reduced pressure to dryness. The residue was diluted with ethyl acetate and washed with water (2×10 mL) followed by brine (10 mL). The organic layer was separated, dried over anhydrous $Na_2SO_4$, filtered and concentrated under reduced pressure to afford the residue. The residue was purified by flash column chromatography eluting with 0-40% ethyl acetate in n-hexane to afford I-70 (0.204 g, 0.470 mmol, 42% yield) as a solid. LCMS: 419.10 (M+H), $R_t$=2.252 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: $R_t$=5.838 min, 97.38%; Column: ATLANTIS T3 (150×4.6 mm, 3.5 μm); Mobile phase: A: 0.05% TFA in Water:ACETONITRILE (95:05), B: ACETONITRILE: 0.05% TFA in Water (5:95); Programme: T/B %: 0.01/10, 12/90, 16/90. Flow Rate: 1.0 mL/min; Diluent: Acetonitrile:Water. CHIRAL HPLC: $R_t$=15.07 min, 98.24%; Column: CHIRAL PAK IC (150×4.6 mm, 3 μm), Mobile Phase: A) 0.1% DEA in n-Hexane, B) DCM: MeOH (50:50), A:B: 70:30; Flow: 0.7 mL/min. $^1$H NMR (400 MHz, DMSO-d6) $\delta_H$=ppm 9.64 (d, 1H), 8.60 (d, 1H), 7.94 (d, 1H), 7.84-7.87 (m, 2H), 7.65 (dd, 1H), 5.44-5.59 (m, 1H), 3.39 (s, 3H), 2.27-2.31 (m, 1H), 1.70 (d, 3H), 0.96-1.01 (m, 4H).

Example I-71: 1-methyl-N-[(1S)-1-[3-[2-(trifluoromethyl)-4-pyridyl]-1,2,4-oxadiazol-5-yl]ethyl]cyclohexanecarboxamide

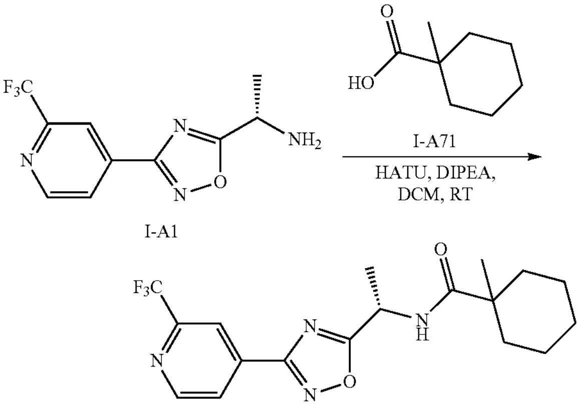

I-A1, I-71

To a stirred solution of compound I-A1 (100 mg, 0.34 mmol, HCl salt) and I-A71 (0.06 mL, 0.41 mmol) in DCM (2 mL) were added HATU (193.56 mg, 0.51 mmol) and DIPEA (0.18 mL, 1.02 mmol) at RT. The reaction mixture was stirred at RT for 2 h. The reaction mixture was diluted with DCM (3 mL) and washed with water (2×3 mL). The organic layer was dried over anhydrous sodium sulphate, filtered and evaporated to give a residue. The residue was purified using prep-HPLC to give I-71 (40 mg, 0.10 mmol, 31% yield) as a solid. HPLC: Rt 9.24 min, 99.9%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 383.15 (M+H), Rt 2.290 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 5.735 min, 96.1%; column: DIACEL CHIRALPAK-IG (250×4.6 mm, 5 u), –Mobile Phase: A) n-Hexane+0.1% Iso-propyl-amine B) DCM: MeOH (1:1), Isocratic:20% B; Wavelength: 271 nm, Flow: 1.0 mL/min.

Example I-72: 3-methyl-N-[(1S)-1-[3-[2-(trifluoromethyl)-4-pyridyl]-1,2,4-oxadiazol-5-yl]ethyl] bicyclo[1.1.1]pentane-1-carboxamide

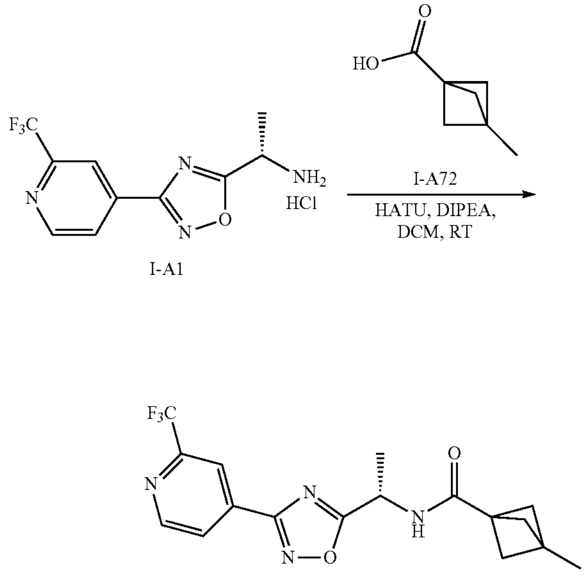

I-A1

I-72

To a stirred solution of compound I-A1 HCl salt (100 mg, 0.34 mmol, HCl salt) and I-A72 (0.06 mL, 0.41 mmol) in DCM (2 mL) were added HATU (193.56 mg, 0.51 mmol) and DIPEA (0.18 mL, 1.02 mmol) at RT for 10 min. The reaction mixture was stirred at RT for 2 h. The reaction mixture was diluted with DCM (3 mL) and washed with water (2×3 mL) The organic layer was dried over anhydrous magnesium sulphate, filtered and evaporated to give a residue. The residue was purified by prep HPLC to give I-72 (30 mg, 0.08 mmol, 23% yield) as a solid. HPLC: Rt 8.810 min, 95.1%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 367.15 (M+H), Rt 2.21 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 10.68 min, 95.7%; column: DIACEL CHIRALPAK-IG (250×4.6 mm, 5 u), –Mobile Phase: A) n-Hexane+0.1% Iso-propyl-amine B) isopropyl alcohol (1:1), Isocratic:20% B; Wavelength: 271 nm, Flow: 1.0 mL/min.

Example I-73: 1-acetyl-N-[(1S)-1-[3-[2-(trifluoromethyl)-4-pyridyl]-1,2,4-oxadiazol-5-yl]ethyl]piperidine-4-carboxamide

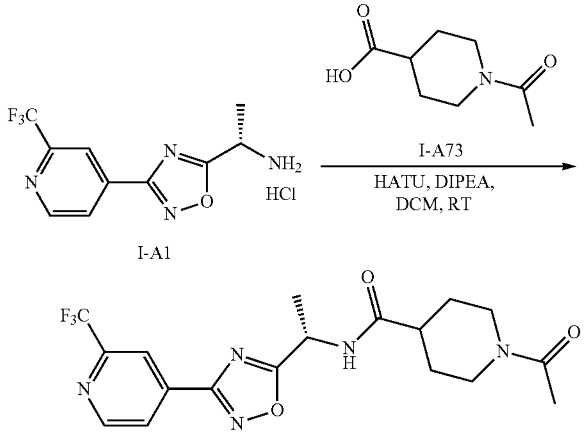

I-A1

I-73

To a stirred solution of compound I-A1 HCl (0.17 g, 0.58 mmol, HCl salt) and I-A73 (0.1 g, 0.58 mmol) in DCM (10 mL) were added HATU (0.27 g, 0.7 mmol) and DIPEA (0.2 mL, 1.17 mmol) at 0° C. The reaction mixture was stirred at RT for 6 h. The reaction mixture was diluted with DCM (20 mL) and washed with water (10 mL). The organic layer was dried over anhydrous magnesium sulphate, filtered and evaporated to give a residue. The residue was purified by prep HPLC to give I-73 (80 mg, 0.19 mmol, 33% yield) as a solid. HPLC: Rt 6.871 min, 99.7%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 412 (M+H), Rt 1.726 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 8.608 min, 100%; column: DIACEL CHIRALPAK-IG (250×4.6 mm, 5 u), –Mobile Phase: A) n-Hexane+0.1% Iso-propyl-amine B) DCM: MeOH (9:1), Isocratic:20% B; Wavelength: 225 nm, Flow: 1.0 mL/min.

Example I-74: 3-methyl-N-[(1S)-1-[3-[2-(trifluoromethyl)-4-pyridyl]-1,2,4-oxadiazol-5-yl]ethyl] cyclobutanecarboxamide

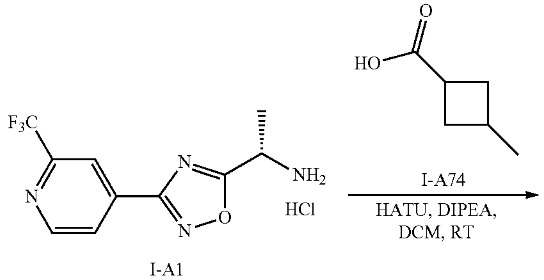

I-A1

-continued

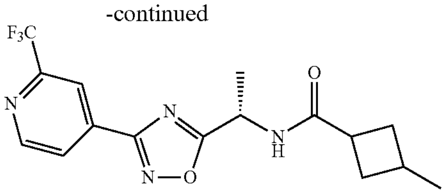

I-74

To a stirred solution of compound I-A1 (100 mg, 0.34 mmol, HCl salt) and I-A74 (38.74 mg, 0.34 mmol) in DCM (2 mL) were added HATU (193.56 mg, 0.51 mmol) and DIPEA (0.18 mL, 1.02 mmol) at RT for 10 min. The reaction mixture was stirred at RT for 2 h. The reaction mixture was diluted with DCM (5 mL) and washed with water (2×10 mL). The organic layer was dried over anhydrous sodium sulfate, filtered and evaporated to give a residue. The residue was purified by prep HPLC to give I-74 (67 m, 0.19 mmol, 56% yield) as a solid. HPLC: Rt 8.431 (47%) and 8.476 (53%) total: 99.9%; (Note: cis trans isomers not separated); Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 354.9 (M+H), Rt 2.093 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 16.622 min (49.846%) and 20.119 (46.334%) column: DIACEL CHIRALPAK-IG (250×4.6 mm, 5 u), –Mobile Phase: A) n-Hexane+0.1% Iso-propyl-amine B) DCM: MeOH (1:1), Isocratic:10% B; Wavelength: 225 nm, Flow: 1.0 mL/min. Note: cis and trans isomer mixture (~50:50).

Example I-75: N-[(1S)-1-[3-(2-cyclopropyl-4-pyridyl)-1,2,4-oxadiazol-5-yl]ethyl]-2-methoxybenzamide

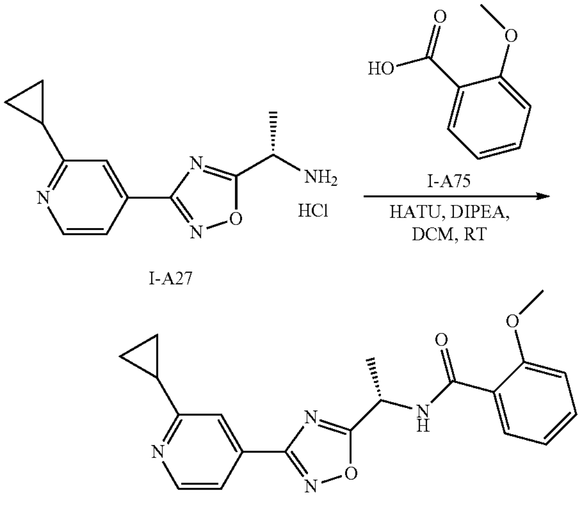

I-A27

I-75

To a stirred solution of I-A27 HCl salt (61.96 mg, 0.41 mmol) and I-A75 (90.52 mg, 0.34 mmol) in DCM (2 mL) were added HATU (193.56 mg, 0.51 mmol) and DIPEA (0.18 mL, 1.02 mmol) at RT for 10 min. The reaction mixture was stirred at RT for 2 h. The reaction mixture was diluted with DCM (5 mL) and washed with water (2×10 mL) The organic layer was dried over anhydrous sodium sulfate, filtered and evaporated to give a residue. The residue was purified by prep HPLC to give I-75 (17 mg, 0.0456 mmol, 13% yield) as a solid. HPLC: Rt 8.499 min, 97.8%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 365 (M+H), Rt 1.994 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 11.47 min, 93%; column: DIACEL CHIRALPAK-IG (250×4.6 mm, 5 u), –Mobile Phase: A) n-Hexane+0.1% Iso-propyl-amine B) DCM: MeOH (1:1), Isocratic:30% B; Wavelength: 290 nm, Flow: 1.0 mL/min.

Example I-76: N-[(1S)-1-[3-[2-(trifluoromethyl)-4-pyridyl]-1,2,4-oxadiazol-5-yl]ethyl]spiro[3.3]heptane-2-carboxamide

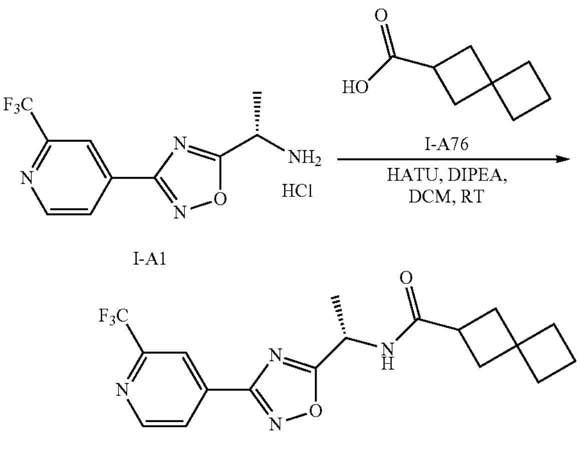

I-A1

I-76

To a stirred solution of compound I-A1 (0.21 g, 0.71 mmol, HCl salt) and I-A76 HCl salt (0.1 g, 0.71 mmol) in DCM (2 mL) were added HATU (0.27 g, 0.71 mmol) and DIPEA (0.25 mL, 1.43 mmol) at 0° C. The reaction mixture was stirred at RT for 6 h. The reaction mixture was diluted with DCM (20 mL) and washed with water (10 mL). The organic layer was dried over anhydrous sodium sulphate, filtered and evaporated to give a residue. The residue was purified by flash column chromatography using 80% EtOAc in hexane as an eluent to give I-76 (115 mg, 0.29 mmol, 41% yield). HPLC: Rt 9.018 min, 96.6%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 381.1 (M+H), Rt 2.181 min, Column: X-select CSH C18 (3*50) mm, 2.5 μm. $^1$H NMR (400 MHz, DMSO-d6) $\delta_H$=9.02 (d, 1H), 8.28-8.25 (m, 2H), 8.16-8.13 (m, 1H), 5.27-5.19 (m, 1H), 1.68-1.64 (m, 6H), 1.63-1.53 (m, 10H). Chiral method: Rt 7.862 min, 95.8%; column: DIACEL CHIRALPAK-IG (250×4.6 mm, 5 u), –Mobile Phase: A) n-Hexane+0.1% Iso-propyl-amine B) DCM: MeOH (1:1), Isocratic:20% B; Wavelength: 271 nm, Flow: 1.0 mL/min.

Examples I-77 and I-78: Cis-4-hydroxy-N-[(1S)-1-[3-[2-(trifluoromethyl)-4-pyridyl]-1,2,4-oxadiazol-5-yl]ethyl]cyclohexanecarboxamide & Trans-4-hydroxy-N-[(1S)-1-[3-[2-(trifluoromethyl)-4-pyridyl]-1,2,4-oxadiazol-5-yl]ethyl]cyclohexanecarboxamide

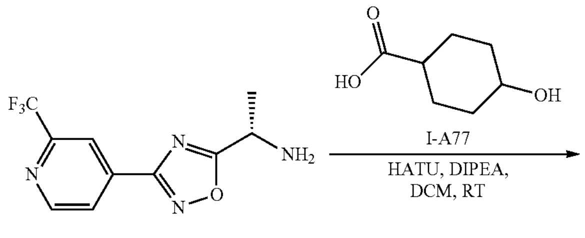

I-A1

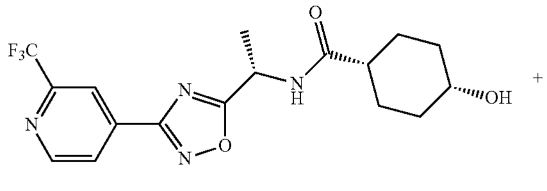

I-77

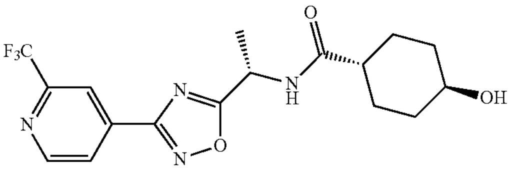

I-78

To a stirred solution of compound I-A1 (100 mg, 0.34 mmol, HCl salt) and I-A77 (0.06 mL, 0.41 mmol) in DCM (2 mL) were added HATU (193.56 mg, 0.51 mmol) and DIPEA (0.18 mL, 1.02 mmol) at RT. The reaction mixture was stirred at RT for 2 h. The reaction mixture was diluted with DCM (3 mL) and washed with water (2x3 mL). The organic layer was dried over anhydrous sodium sulphate, filtered and evaporated to get a residue. The residue was purified by prep HPLC and subsequently repurified using chiral column chromatography to give two products cis and trans isomers I-77 (34 mg, 0.09 mmol, 26% yield) and I-78 (18 mg, 0.04 mmol, 13% yield). Note that stereochemistry was randomly assigned.

I-77: HPLC: Rt 6.9 min, 99.8%; Column: X-Select CSH C18 (4.6x150) mm, 3.5 μm; Mobile phase: A: 0.1% Formic acid in water:ACN (95:05), B: ACN; Flow Rate: 1.0 mL/min. LCMS: 385.15 (M+H), Rt 1.78 min, Column: X-select CSH C18 (3*50) mm, 2.5 μm. $^1$H NMR (400 MHz, DMSO-d6) $\delta_H$=9.02 (d, 1H), 8.65 (d, 1H), 8.28-8.24 (m, 2H), 5.24-5.20 (m, 1H), 4.55 (d, 1H), 2.15-2.08 (m, 1H), 1.86-1.84 (m, 2H), 1.18-1.70 (m, 2H), 1.54 (d, 3H), 1.43-1.30 (m, 2H), 1.17-1.08 (m, 2H), 1H merged in solvent peak. Chiral method: Rt 7.87 min, 98.9%; column: DIACEL CHIRALPAK-IG (250×4.6 mm, 5 u), –Mobile Phase: A) n-Hexane+0.1% Iso-propyl-amine B) Iso-propyl-Alcohol, Isocratic:20% B; Wavelength: 270 nm, Flow: 1.0 mL/min.

I-78: HPLC: Rt 7.02 min, 97.4%; Column: X-Select CSH C18 (4.6x150) mm, 3.5 μm; Mobile phase: A: 0.1% Formic acid in water:ACN (95:05), B: ACN; Flow Rate: 1.0 mL/min. LCMS: 385.15 (M+H), Rt 1.90 min, Column: X-select CSH C18 (3*50) mm, 2.5 μm. $^1$H NMR (400 MHz, DMSO-d6) $\delta_H$=9.02 (d, 1H), 8.59-8.57 (m, 1H), 8.28-8.25 (m, 2H), 5.25-5.20 (m, 1H), 4.32-4.30 (m, 1H), 3.80-3.70 (m, 1H), 2.25-2.15 (m, 1H), 1.85-1.75 (m, 2H), 1.61-1.57 (m, 2H), 1.55 (d, 3H), 1.45-1.42 (m, 4H). Chiral method: Rt 15.167 min, 97.2%; column: DIACEL CHIRALPAK-IG (250×4.6 mm, 5 u), –Mobile Phase: A) n-Hexane+0.1% Iso-propyl-amine B) DCM:MeOH (50:50), Isocratic:20% B; Wavelength: 270 nm, Flow: 1.0 mL/min.

Example I-79: (N-[(1S)-1-[3-(2-cyclopropyl-4-pyridyl)-1,2,4-oxadiazol-5-yl]ethyl]-3-methoxy-benzamide

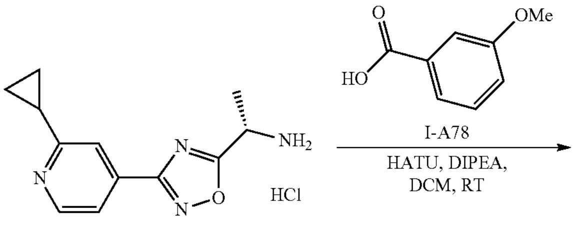

I-A27

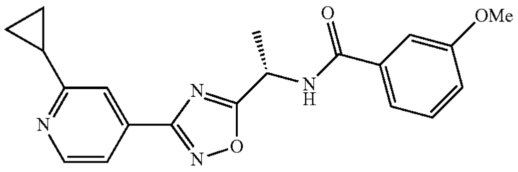

I-79

To a stirred solution of I-A27 (100.0 mg, 0.43 mmol, HCl salt) and I-A78 (66.07 mg, 0.43 mmol) in DCM (3 mL) were added HATU (247.69 mg, 0.65 mmol) and DIPEA (0.19 mL, 1.09 mmol) at RT. The reaction mixture was stirred at RT for 3 h. The reaction mixture was diluted with DCM (20 mL) and washed with water thrice. The organic layer was dried over anhydrous sodium sulphate, filtered and evaporated to afford a residue. The residue was purified by prep HPLC to afford I-79 (18 mg, 0.0494 mmol, 11% yield) as a solid. HPLC: Rt 7.957 min, 99.7%; Column: X-Select CSH C18 (4.6x150) mm, 3.5 μm; Mobile phase: A: 0.1% Formic acid in water:ACN (95:05), B: ACN; Flow Rate: 1.0 mL/min. LCMS: 365.4 (M+H), Rt 1.766 min, Column: X-select CSH (3*50) mm, 2.5 μm. $^1$H NMR (400 MHz, DMSO-d6) $\delta_H$=9.25 (d, 1H), 8.60 (d, 1H), 7.85 (s, 1H), 7.65 (d, 1H), 7.30-7.57 (m, 3H), 7.14 (d, 1H), 5.34-5.58 (m, 1H), 3.82 (s, 3H), 2.26-2.38 (m, 1H), 1.69 (d, 3H), 0.90-1.05 (m, 4H). Chiral method: Rt 9.657 min, 99.4%; column: DIACEL CHIRALPAK-IG (250 mm×4.6 mm, 5 u), –Mobile Phase: A) n-Hexane+0.1% Iso-propyl-amine B) EtOH:MeOH (50:50), Isocratic:30% B; Wavelength: 291 nm, Flow: 1.0 mL/min.

Example I-80: 2-chloro-N-[(1S)-1-[3-(2-cyclopropyl-4-pyridyl)-1,2,4-oxadiazol-5-yl]ethyl]benzamide

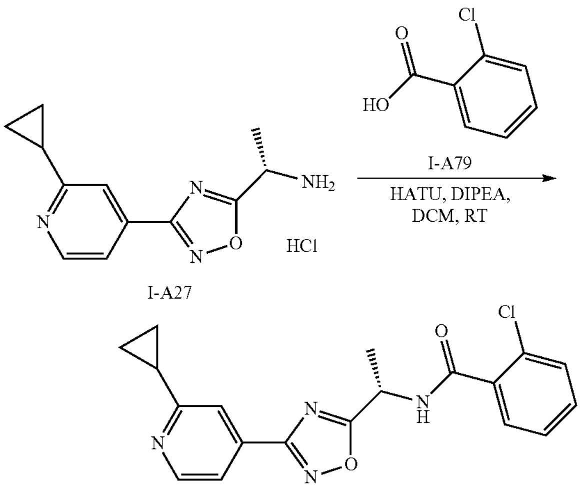

I-A27

I-80

To a stirred solution of I-A27 (100.0 mg, 0.43 mmol HCl salt) and I-A79 (67.99 mg, 0.43 mmol) in DCM (3 mL) were added HATU (247.69 mg, 0.65 mmol) and DIPEA (0.19 mL, 1.09 mmol) at RT. The reaction mixture was stirred at RT for 3 h. The reaction mixture was diluted with DCM (20 mL) and washed with water (thrice). The organic layer was dried over anhydrous sodium sulphate, filtered and evaporated to afford a residue. The residue was purified by prep HPLC as an eluent to afford I-80 (40 mg, 0.109 mmol, 25% yield) as a solid. HPLC: Rt 8.006 min, 99.8%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 369.35 (M+H), Rt 1.772 min, Column: X-select CSH (3*50) mm, 2.5 μm. $^1$H NMR (400 MHz, DMSO-d6) $\delta_H$=9.35 (d, 1H), 8.62 (d, 1H), 7.87 (s, 1H), 7.67 (d, 1H), 7.36-7.60 (m, 4H), 5.42-5.50 (m, 1H), 2.26-2.36 (m, 1H), 1.65 (d, 3H), 0.92-1.08 (m, 4H). Chiral method: Rt 6.81 min, 100%; column: DIACEL CHIRALPAK-IG (250 mm×4.6 mm, 5 u), –Mobile Phase: A) CO2 B) MeOH+0.1% NH3, Gradient:25-50% B in 5 min, hold 50% B till 9 min, 50-25% B at 10 min hold 25% B till 12 min, Flow: 1.0 mL/min.

Example I-81: N-[(1S)-1-[3-(2-cyclopropyl-4-pyridyl)-1,2,4-oxadiazol-5-yl]ethyl]-3-methyl-benzamide

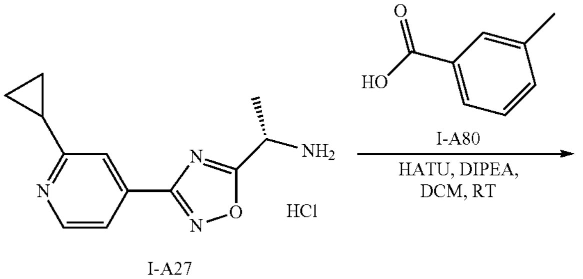

I-A27

-continued

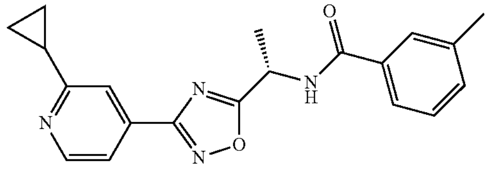

I-81

To a stirred solution of I-A8i (51.04 mg, 0.37 mmol) in DCM (3 mL) were added HATU (142.55 mg, 0.37 mmol) and DIPEA (0.07 mL, 0.37 mmol) at RT and the reaction mixture was stirred for 10 min followed by addition of I-A27 (100.0 mg, 0.37 mmol HCl salt). The reaction mixture was stirred at RT for 2 h. The reaction mixture was diluted with DCM (5 mL) and washed with water (10 mL×2). The organic layer was dried over anhydrous sodium sulphate, filtered and evaporated to afford a residue. The residue was purified by prep HPLC to afford I-81 (80 mg, 0.213 mmol, 57% yield) as a solid. HPLC: Rt 8.131 min, 92.6%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 348.8 (M+H), Rt 2.012 min, Column: X-select CSH (3*50) mm, 2.5 μm. $^1$H NMR (400 MHz, DMSO-d6) $\delta_H$=9.21 (d, 1H), 8.61 (d, 1H), 7.87 (s, 1H), 7.59-7.78 (m, 3H), 7.27-7.49 (m, 2H), 5.48 (quin, 1H), 2.38 (m, 3H), 2.26-2.36 (m, 1H), 1.69 (d, 3H), 0.94-1.07 (m, 4H). Chiral method: Rt 8.937 min, 93.4%; column: DIACEL CHIRALPAK-IG (250 mm×4.6 mm, 5 u), –Mobile Phase: A) n-Hexane+0.1% Iso-propyl-amine B) EtOH:MeOH (50:50), Isocratic:25% B; Wavelength: 292 nm, Flow: 1.0 mL/min.

Example A-82: N-[(1S)-1-[3-[2-(trifluoromethyl)-4-pyridyl]-1,2,4-oxadiazol-5-yl]ethyl]spiro[2.4]heptane-7-carboxamide

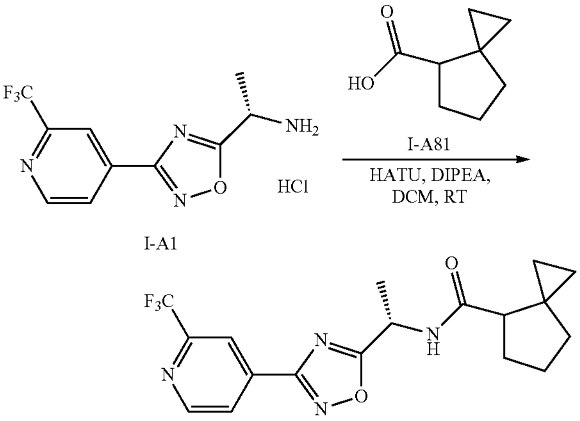

I-A1

I-82

To a stirred solution of I-A81 (57.09 mg, 0.41 mmol) in DCM (3 mL) were added HATU (129.04 mg, 0.34 mmol) and DIPEA (0.18 mL, 1.02 mmol) at RT and the reaction mixture was stirred for 10 min followed by addition of I-A1 (100.0 mg, 0.34 mmol HCl salt). The reaction mixture was stirred at RT for 2 h. The reaction mixture was diluted with DCM (5 mL) and washed with water (10 mL×2). The organic layer was dried over anhydrous sodium sulphate, filtered and evaporated to afford a residue. The residue was purified by prep HPLC to afford I-82 (35 mg, 0.091 mmol, 27% yield) as a solid. HPLC: Rt 8.825 min, 98.8%; Column: X-Select CSH C18 (4.6×150) mm, 3.5 µm; Mobile phase: A: 0.1% Formic acid in water:ACN (95:05), B: ACN; Flow Rate: 1.0 mL/min. LCMS: 381.0 (M+H), Rt 2.098 min, Column: X-select CSH 18 (3*50) mm, 2.5 µm. $^1H$ NMR (400 MHz, DMSO-d6) $\delta_H$=9.02 (t, 1H), 8.41-8.68 (m, 1H), 8.27 (t, 2H), 5.18-5.28 (m, 1H), 2.44 (t, 1H), 1.83-1.97 (m, 2H), 1.58-1.82 (m, 3H), 1.54 (t, 3H), 1.30-1.42 (m, 1H), 0.30-0.69 (m, 4H). Chiral method: Rt 6.130 min, 42% and Rt 7.147 min, 53%; column: DIACEL CHIRALPAK-IG (250 mm×4.6 mm, 5 u), –Mobile Phase: A) n-Hexane+0.1% Iso-propyl-amine B) EtOH:MeOH (50:50), Isocratic:20% B; Wavelength: 292 nm, Flow: 1.0 mL/min.

Example I-83: N-[(1S)-1-[3-(2-cyclopropyl-4-pyridyl)-1,2,4-oxadiazol-5-yl]ethyl]-2-methyl-benzamide

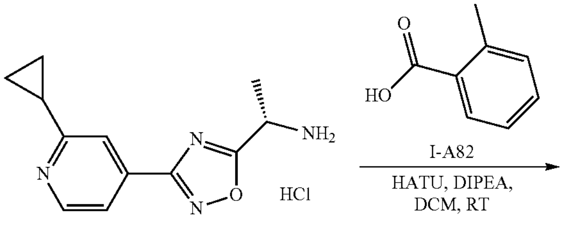

I-A27

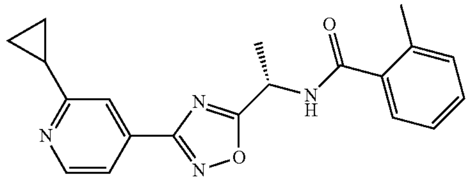

I-83

To a stirred solution of I-A27 (100 mg, 0.43 mmol, HCl salt) and I-A82 (59.13 mg, 0.43 mmol) in DCM (3 mL) were added HATU (247.69 mg, 0.65 mmol) and DIPEA (0.19 mL, 1.09 mmol) at RT. The reaction mixture was stirred at RT for 3 h. The reaction mixture was diluted with DCM (20 mL) and washed with water thrice. The organic layer was dried over anhydrous sodium sulphate, filtered and concentrated under reduced pressure. The residue was purified by prep HPLC to afford I-83 (30 mg, 0.0861 mmol, 20% yield) as a solid. HPLC: Rt 7.818 min, 98.9%; Column: X-Select CSH C18 (4.6×150) mm, 3.5 µm; Mobile phase: A: 0.1% Formic acid in water:ACN (95:05), B: ACN; Flow Rate: 1.0 mL/min. LCMS: 349.45 (M+H), Rt 1.797 min, Column: X-select CSH (3*50) mm, 2.5 µm. $^1H$ NMR (400 MHz, DMSO-d6) $\delta_H$=9.14 (d, 1H), 8.61 (d, 1H), 7.85 (s, 1H), 7.66 (d, 1H), 7.32-7.51 (m, 2H), 7.28 (d, 2H), 5.38-5.48 (m, 1H), 2.37 (s, 3H), 2.24-2.34 (m, 1H), 1.65 (d, 3H), 0.94-1.09 (m, 4H). Chiral method: Rt 6.28 min, 99%; column: DIACEL CHIRALPAK-IG (250 mm×4.6 mm, 5 u), –Mobile Phase: A) CO2 B) MeOH+0.1% NH3, Gradient:25-50% B in 5 min, hold 50% B till 9 min, 50-25% B at 10 min hold 25% B till 12 min, Flow: 3.0 mL/min.

Example I-84: (1S,4R)—N—((S)-1-(3-(2-cyclopropylpyridin-4-yl)-1,2,4-oxadiazol-5-yl)ethyl)-4-methylcyclohexane-1-carboxamide

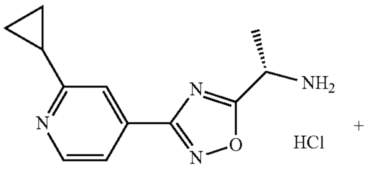

I-A27

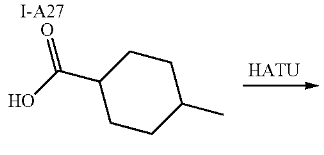

I-A83

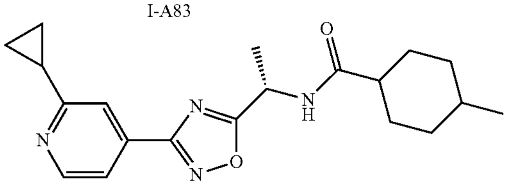

I-A84

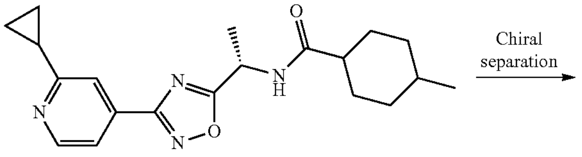

I-A84

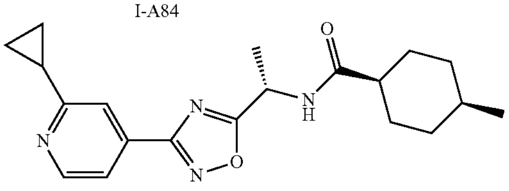

I-84

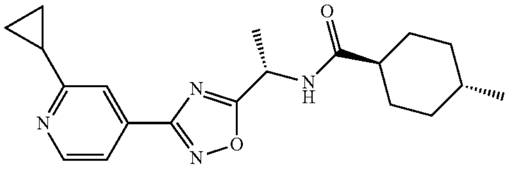

I-29

I-A84: (1s,4R)—N—((S)-1-(3-(2-cyclopropylpyridin-4-yl)-1,2,4-oxadiazol-5-yl)ethyl)-4-methylcyclohexane-1-carboxamide To a stirred solution of I-A83 (127.95 mg, 0.9 mmol) in DCM (3 mL) was added DIPEA (0.39 mL, 2.25 mmol) and HATU (427.66 mg, 1.12 mmol) at RT and stirred for 10 min followed by addition of I-A27 (200 mg, 0.75 mmol, HCl salt) at RT. The reaction mixture was stirred for 2 h at RT. The reaction mixture was diluted with DCM (5 mL). The organic layer was washed with water (10 mL×2), dried over sodium sulfate and evaporated completely under reduced pressure, to afford a residue which was purified by column chromatography using 25-30% of ethyl acetate to afford a residue (I-A84). The compound was purified by chiral HPLC to give I-84 (35 mg, 0.0972 mmol, 13% yield) and I-29 (20 mg, 0.056 mmol, 7% yield) as solids. Chiral HPLC purification conditions: column: Chiralpak IG (250×30 mm) 5 μM, Mobile phase: A) 0.1% isopropyl amine in n-hexane B) isopropyl alcohol Method: 15% B isocratic Flow: 25 mL/min. PK-1 RT-21 min (I-84) and PK-2 RT-31 min (I-29). Stereochemistry was randomly assigned.

I-84: HPLC: Rt 8.697 min, 98.4%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 355.05 (M+H), Rt 1.939 min, Column: X-select CSH (3*50) mm, 2.5 μm. $^1$H NMR (400 MHz, DMSO-d6) $\delta_H$=8.60 (d, 1H), 8.52-8.51 (m, 1H), 7.83 (s, 1H), 7.64-7.63 (m, 1H), 5.23-5.20 (m, 1H), 2.32-2.24 (m, 2H), 1.77-1.73 (m, 2H), 1.60 (brs, 1H), 1.54 (d, 3H), 1.50-1.46 (m, 4H), 1.33-1.30 (m, 2H), 1.04-0.97 (m, 4H), 0.88 (d, 3H). Chiral method: Rt 10.318 min, 100%; column: DIACEL CHIRALPAK YMC CHIRAL AMYLOSE-SA (250×4.6 mm, 5 u), –Mobile Phase: A) n-Hexane+0.1% Isopropyl amine B) Isopropyl alcohol, Isocratic: 20% B; Wavelength: 220 nm, Flow: 1.0 mL/min.

Example I-85: 1-acetyl-N-[(1S)-1-[3-[2-(trifluoromethyl)-4-pyridyl]-1,2,4-oxadiazol-5-yl]ethyl]piperidine-3-carboxamide

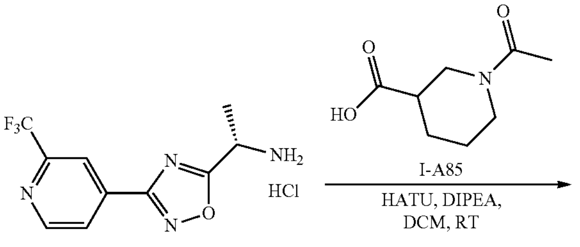

I-A1

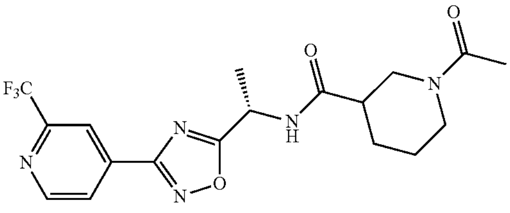

I-85

To a stirred solution of compound I-A1 (112.13 mg, 0.43 mmol, HCl salt) and I-A85 (74.34 mg, 0.43 mmol) in DCM (3 mL) were added HATU (247.69 mg, 0.65 mmol) and DIPEA (0.19 mL, 1.09 mmol) at 0° C. The reaction mixture was stirred at RT for 3 h. The reaction mixture was diluted with DCM (20 mL) and washed with water (10 mL). The organic layer was dried over anhydrous sodium sulphate, filtered and evaporated to afford a residue. The residue was purified by prep HPLC to afford I-85 (30 mg, 0.0728 mmol, 17% yield) as a solid. Note: mixture of isomers. HPLC: Rt 7.872 min, 99.9%; Column: X-Select CSH C18 (4.6×150) mm, 3.5 μm; Mobile phase: A: 0.1% Formic acid in water: ACN (95:05), B: ACN; Flow Rate: 1.0 mL/min. LCMS: 412.05 (M+H), Rt 1.705 min, Column: X-select CSH C18 (3*50) mm, 2.5 μm. $^1$H NMR (400 MHz, DMSO-d6) $\delta_H$=9.02 (d, 1H), 8.71-8.59 (m, 1H), 8.27 (s, 2H), 5.33-5.24 (m, 1H), 5.10 (s, 1H), 4.58 (s, 1H), 3.74-3.69 (m, 1H), 3.28-3.22 (m, 1H), 2.18-2.16 (m, 1H), 2.05-1.98 (m, 3H), 1.61-1.59 (m, 5H), 1.43-1.30 (m, 2H). Chiral method: Rt 5.067 min, 50.8% and 9.618 min, 47.42% min; column: DIACEL CHIRALPAK-IG (250×4.6 mm, 5 u), –Mobile Phase: A) n-Hexane+0.1% Iso-propyl-amine B) DCM: MeOH (1:1), Isocratic:50% B; Wavelength: 271 nm, Flow: 1.0 mL/min.

Example I-86: 1-acetyl-N-[(1S)-1-[3-[2-(trifluoromethyl)-4-pyridyl]-1,2,4-oxadiazol-5-yl]ethyl]piperidine-2-carboxamide

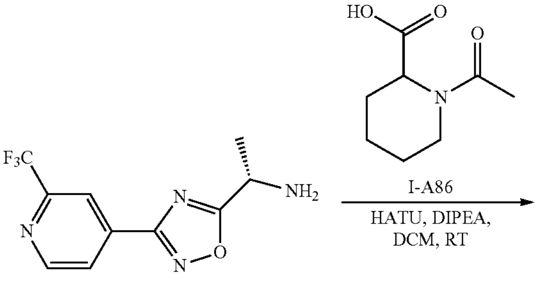

I-A1

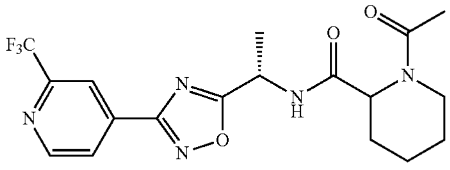

I-86

To a stirred solution of compound I-A1 (100 mg, 0.39 mmol) and I-A86 (66.3 mg, 0.3900 mmol) in DCM (3 mL) were added HATU (220.89 mg, 0.58 mmol) and DIPEA (0.17 mL, 0.97 mmol) at 0° C. The reaction mixture was stirred at RT for 3 h. The reaction mixture was diluted with DCM (20 mL) and washed with water trice. The organic layer was dried over anhydrous sodium sulphate, filtered and evaporated to afford a residue. The residue was purified by prep HPLC to afford I-86 (35 mg, 0.085 mmol, 22% yield) as an oil. Note: mixture of isomers. HPLC: Rt 7.398 min, 99.9%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 412.05 (M+H), Rt 1.607 min, Column: X-select CSH C18 (3*50) mm, 2.5 μm. $^1$H NMR (400 MHz, DMSO-d6) $\delta_H$=9.02 (d, 1H), 8.88-8.83 (m, 1H), 8.27 (s, 2H), 5.28-5.22 (m, 1H), 4.40-4.07 (m, 1H), 3.76-3.73 (m, 1H), 3.20-2.94 (m, 1H), 2.67-2.53 (m, 1H), 2.44-2.26 (m, 1H), 2.01-1.99 (m, 3H), 1.90-1.86 (m, 1H), 1.71-1.62 (m, 2H), 1.61-1.57 (m, 3H), 1.40-1.29 (m, 1H). Chiral method: Rt 15.145 min, 50.4% and 17.282 min, 45.3% min; column: DIACEL CHIRALPAK-IG (250×4.6 mm, 5 u), –Mobile Phase: A) n-Hexane+0.1% Iso-propyl-amine B) DCM: MeOH (1:1), Isocratic:20% B; Wavelength: 271 nm, Flow: 1.0 mL/min.

Example I-87: (S)—N-(1-(3-(2-cyclopropylpyridin-4-yl)-1,2,4-oxadiazol-5-yl)ethyl)-4-methylbenzamide

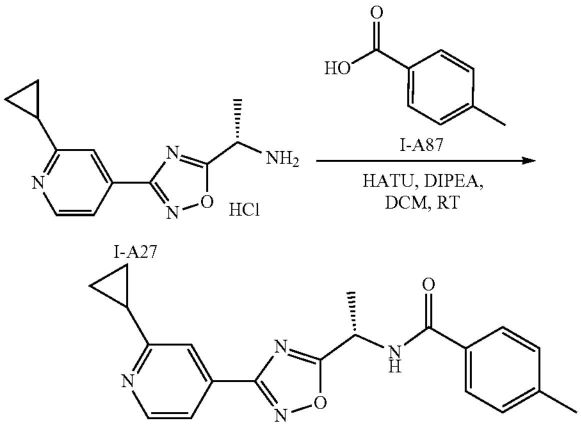

I-A27

I-87

To a stirred solution of I-A27 (150 mg, 0.56 mmol, HCl salt) and I-A87 (91.88 mg, 0.67 mmol) in DCM (3 ml) were added HATU (320.74 mg, 0.84 mmol) and DIPEA (0.29 mL, 1.69 mmol) at RT and stirred for 2 hr at RT. The reaction mixture was diluted with DCM (5 mL) and quenched using water (2x10 mL) and organic layer separated. The organic layer dried over $Na_2SO_4$, filtered and evaporated by rotavapor. The reaction mixture was purified by column chromatography using 25-30% ethyl acetate in hexane to afford I-87 (40 mg, 0.1125 mmol, 20% yield) as a solid. HPLC: Rt 8.309 min, 98%; Column: X-Select CSH C18 (4.6x150) mm, 3.5 μm; Mobile phase: A: 0.1% Formic acid in water: ACN (95:05), B: ACN; Flow Rate: 1.0 mL/min. LCMS: 349.05 (M+H), Rt 1.950 min, Column: X-select CSH C18 (3*50) mm, 2.5 μm. $^1$H NMR (400 MHz, DMSO-d6) $\delta_H$=9.17 (d, 1H), 8.59 (d, 1H), 7.85-7.80 (m, 3H), 7.65-7.64 (m, 1H), 7.31 (d, 2H), 5.48-5.44 (m, 1H), 2.36 (s, 3H), 2.28-2.27 (m, 1H), 1.68 (d, 3H), 1.00-0.97 (m, 4H). Chiral method: Rt 5.785 min, 99.8%; column: DIACEL CHIRALPAK-IG (250x4.6 mm, 5 u), −Mobile Phase: A) n-Hexane+0.1% Iso-propyl-amine B) DCM: MeOH (1:1), Isocratic: 50% B; Wavelength: 292 nm, Flow: 1.0 mL/min.

Example I-88: (S)-3-cyano-N-(1-(3-(2-cyclopropylpyridin-4-yl)-1,2,4-oxadiazol-5-yl)ethyl)benzamide

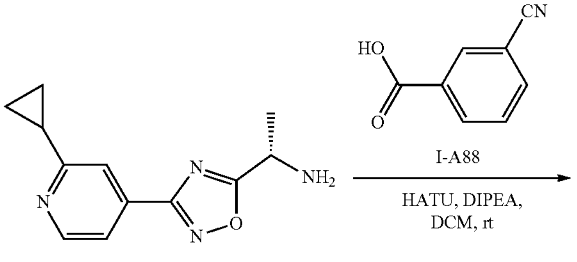

I-A27

-continued

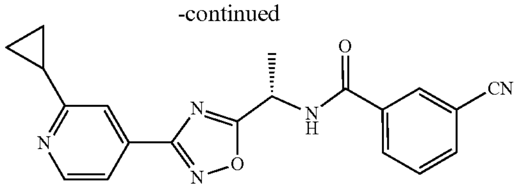

I-88

To a stirred solution of I-A27 (70 mg, 0.26 mmol) and I-A88 (46 mg, 0.31 mmol) in DCM (5 mL), HATU (7.67 mg, 0.04 mmol) and DIPEA (0.14 mL, 0.79 mmol) were added at RT. The reaction mixture was stirred at RT for 2 h. The reaction mixture was quenched with water (5 mL) and diluted with DCM (3x10 mL). The organic layer was dried over anhydrous sodium sulphate, filtered and evaporated to afford a residue. The residue was purified by column chromatography using 100-200 silica and 5-10% EtOAc/hexane as an eluent to afford I-88 (50 mg, 0.1387 mmol, 26% yield) as a solid. HPLC: Rt 8.25 min, 99.67%; Column: X-Bridge C18 (4.6x150) mm, 3.5 μm; Mobile phase: A: 10 mM Ammonium bicarbonate in water, B: ACN; Flow Rate: 1.0 mL/min. LCMS: 360.05 (M+H), Rt 1.923 min, Column: X-select CSH C18 (3*50) mm, 2.5 μm. $^1$H NMR (400 MHz, DMSO-d6) $\delta_H$=9.47 (d, 1H), 8.59 (d, 1H), 8.34 (s, 1H), 8.19 (d, 1H), 8.05 (d, 1H), 7.84 (s, 1H), 7.73 (t, 1H), 7.64 (d, 1H), 5.51-5.47 (m, 1H), 2.30-2.26 (m, 1H), 1.69 (d, 3H), 1.00-0.95 (m, 4H).

Example I-89: (S)—N-(1-(3-(2-cyclopropylpyridin-4-yl)-1,2,4-oxadiazol-5-yl)ethyl)-3-fluorobenzamide

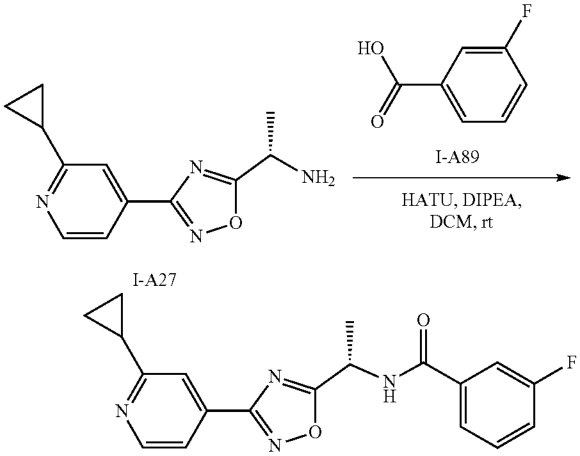

I-A27

I-89

To a stirred solution of I-A27 (70 mg, 0.26 mmol) and I-A89 (44.12 mg, 0.31 mmol) in DCM (5 mL), HATU (7.67 mg, 0.04 mmol) and DIPEA (0.14 mL, 0.79 mmol) were added at RT. The reaction mixture was stirred at RT for 2 h. The reaction mixture was quenched with water (5 mL) and diluted with DCM (3x10 mL). The organic layer was dried over anhydrous sodium sulphate, filtered and evaporated to get a residue. The residue was purified by prep. HPLC to afford I-89 (40 mg, 0.112 mmol, 43% yield) as a solid. HPLC: Rt 8.50 min, 98.74%; Column: X-Bridge C18 (4.6x150) mm, 5 μm; Mobile phase: A:10 mM Ammmonium bicarbonate in water, B: ACN; Flow Rate: 1.0 mL/min. LCMS: 352.95 (M+H), Rt 1.981 min, Column: X-select CSH C18 (3*50) mm, 2.5 μm. $^1$H NMR (400 MHz, DMSO-d6) $\delta_H$=9.35 (d, 1H), 8.59 (d, 1H), 7.84 (s, 1H), 7.76 (d, 1H), 7.72-7.68 (m, 1H), 7.65-7.63 (m, 1H), 7.59-7.53 (m, 1H), 7.46-7.41 (m, 1H). 5.49-5.45 (m, 1H), 2.30-2.24 (m, 1H), 9.35 (d, 3H), 1.00-0.95 (m, 4H).

Examples I-90 and I-91: Synthesis of (S)—N1-(1-(3-(2-cyclopropylpyridin-4-yl)-1,2,4-oxadiazol-5-yl) ethyl)-N3,N3-dimethylisophthalamide & (S)—N-(1-(3-(2-cyclopropylpyridin-4-yl)-1,2,4-oxadiazol-5-yl) ethyl)isophthalamide

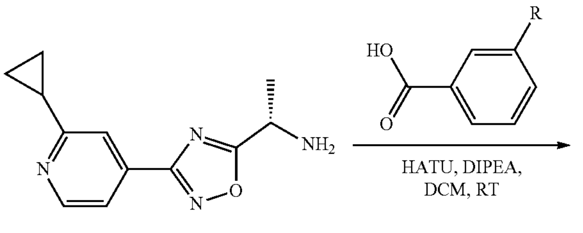

I-A27

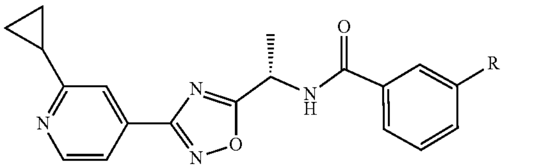

I-90, I-91

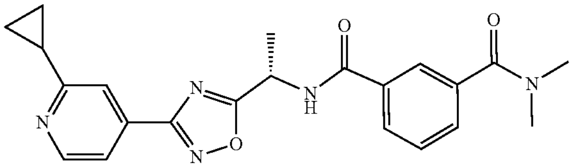

I-90

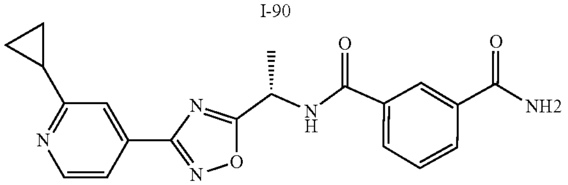

I-91

General Procedure for Amidation:

To a stirred solution of the acid (1 eq.) and I-A27 (1.1 eq.) in DMF/DCM wAS added DIPEA (2 eq.) followed by HATU (1.5 eq.) at 0° C. and the resulting reaction mixture was stirred for 16 h. The reaction mixture was diluted with water and extracted with ethyl acetate. The combined organic layer was separated, dried over anhydrous sodium sulphate, filtered and concentrated under reduced pressure to afford the residue. The residue was purified by silica gel column chromatography/prep. HPLC to afford the desired compound.

I-90: (S)—N1-(1-(3-(2-cyclopropylpyridin-4-yl)-1,2,4-oxadiazol-5-yl)ethyl)-N3,N3-dimethylisophthalamide Yield: 21 mg, 0.048 mmol, 13% yield, Appearance: solid; HPLC: Rt 6.411 min, 93.11%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 406.10 (M+H), Rt 1.939 min, Column: X-select CSH C18 (3*50) mm, 2.5 μm. $^1$H NMR (400 MHz, DMSO-d6) $\delta_H$=9.37 (d, 1H), 8.61 (d, 1H), 8.01-7.92 (m, 2H), 7.87 (s, 1H), 7.69 (d, 1H), 7.64-7.52 (m, 2H), 5.50 (p, 1H), 3.00 (s, 3H), 2.91 (s, 3H), 2.29 (q, 1H), 1.69 (d, 3H), 1.03-0.98 (m, 4H). Chiral method: Rt: 9.640 min, 91.78%; column: YMC CHIRAL ART CELLULOSE-SC (250×4.6 mm, 5 u), Mobile Phase: A) n-Hexane+0.1% TFA, B) DCM: MeOH (50:50), Isocratic:40% B; Wavelength: 288 nm, Flow: 1.0 mL/min.

I-91: (S)—N-(1-(3-(2-cyclopropylpyridin-4-yl)-1,2,4-oxadiazol-5-yl) ethyl) isophthalamide Yield: 15 mg, 0.0387 mmol, 6%, Appearance: solid; HPLC: Rt 6.346 min, 97.30%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 378 (M+H), Rt 1.794 min, Column: X-select CSH C18 (3*50) mm, 2.5 μm. $^1$H NMR (400 MHz, DMSO-d6) $\delta_H$=9.40 (d, 1H), 8.61 (d, 1H), 8.41 (s, 1H), 8.11-8.00 (m, 3H), 7.87 (s, 1H), 7.68 (d, 1H), 7.59 (t, 1H), 7.50 (s, 1H), 5.51 (p, 1H), 2.30-2.28 (m, 1H), 1.71 (d, 3H), 1.04-0.95 (m, 4H). Chiral method: Rt: 9.988 min, 95.89%; column: YMC CHIRAL ART CELLULOSE-SC (250×4.6 mm, 5 u), Mobile Phase: A) n-Hexane+0.1% TFA, B) DCM: MeOH (50:50), Isocratic: 35% B; Wavelength: 288 nm, Flow: 1.0 mL/min.

Example I-92: (S)—N-(1-(3-(2-cyclopropylpyridin-4-yl)-1,2,4-oxadiazol-5-yl)ethyl)-3-(methylsulfonyl) benzamide

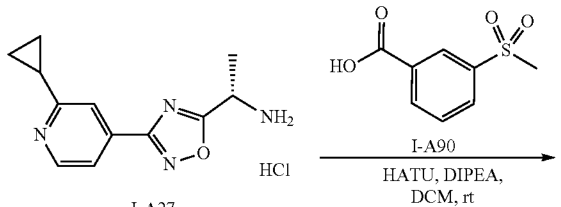

I-A27

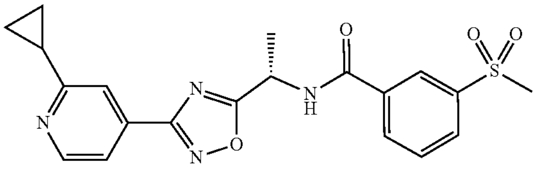

I-92

To a stirred solution of I-A90 (63.05 mg, 0.31 mmol) in DCM (2 mL) was added HATU (99.79 mg, 0.26 mmol) and DIPEA (0.05 mL, 0.26 mmol) and stirred for 15 min. To this solution, I-A27 HCl salt (70 mg, 0.26 mmol) was added at 0° C. The reaction mixture was stirred for at RT 2 h. Reaction was monitored by TLC. After completion, reaction mass was diluted with DCM (20 mL), water (5 mL) and extracted with DCM (3×20 mL). The organic layer was separated, dried over anhydrous $Na_2SO_4$ and concentrated under reduced pressure to afford a residue. The residue was purified by PREP-HPLC to afford desired compound I-92 (40 mg, 0.1 mmol, 37%) as a solid. HPLC: Rt 7.796 min, 99.22%; Column: X-Bridge C18 (4.6×150) mm, 5 μm; Mobile phase: A: 10 mM Ammonium bicarbonate in water, B: ACN; Flow Rate: 1.0 mL/min. LCMS: 412.95 (M+H), Rt 1.775 min, Column: Atlantis Premier BEH C 18 (2.1*50 mm), 2.5 μm. $^1$H NMR (400 MHz, DMSO-d6) $\delta_H$=9.59 (d, 1H), 8.60 (d, 1H), 8.45 (s, 1H), 8.24 (d, 1H), 8.14 (d, 1H), 7.85-7.77 (m, 2H), 7.66-7.64 (m, 1H), 5.55-5.52 (m, 1H), 3.28-3.26 (m, 3H), 2.30-2.25 (m, 1H), 1.72 (d, 3H), 1.00-0.96 (m, 4H). Chiral method: Rt: 7.376 min, 99.07%; column: YMC CHIRAL ART CELLULOSE-SC (250x4.6 mm, 5 u), Mobile Phase: A) n-Hexane+0.1% Iso-propyl amine, B) DCM: MeOH (50:50), Isocratic: 40% B; Wavelength: 292 nm, Flow: 1.0 mL/min.

Example I-93: (S)—N-(1-(3-(2-cyclopropylpyridin-4-yl)-1,2,4-oxadiazol-5-yl)ethyl)-5-(ethylsulfonyl) thiophene-2-carboxamide

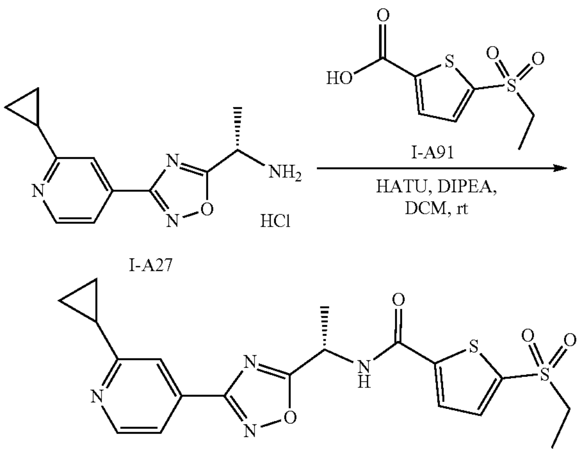

I-A27

I-93

Synthesis of (S)—N-(1-(3-(2-cyclopropylpyridin-4-yl)-1,2,4-oxadiazol-5-yl)ethyl)-5-(ethylsulfonyl) thiophene-2-carboxamide (PRX-0003499-001)

To a stirred solution of I-A91 (69.37 mg, 0.31 mmol) in DCM (5 mL) was added HATU (249.47 mg, 0.66 mmol) and DTPEA (0.14 mL, 0.79 mmol) and stirred for 15 mi. To this solution, I-A27 HCl salt (70 mg, 0.26 mmol) was added at 0° C. The reaction mixture was stirred for at RT 2 h. Reaction was monitored by TLC. After completion, reaction mass was diluted with DCM (20 mL), water (5 mL) and extracted with DCM (3x20 mL). The organic layer was separated, dried over $Na_2SO_4$ and concentrated under reduced pressure to afford a residue. The residue was purified by PREP-HPLC to afford desired compound I-93 (12 mg, 0.03 mmol, 11%) as a solid. HPLC: Rt 8.159 min 99.27%; Column: X-Bridge C18 (4.6x150) mm, s m; Mobile phase: A: 10 mM Ammonium bicarbonate in water, B: ACN; Flow Rate: 1.0 mL/min. LCMS: 432.90 (M+H), Rt 1.867 min, Column: Atlantis Premier BEH C 18 (2.1*50 mm), 2.5 μm. $^1$H NMR (400 MHz, DMSO-d6) $\delta_H$=9.66 (s, 1H), 8.60 (d, 1H), 7.97 (d, 1H), 7.88-7.80 (m, 2H), 7.65 (d, 1H), 5.50-5.46 (m, 1H), 3.45 (q, 2H), 2.30-2.25 (m, 1H), 1.70 (d, 3H), 1.18 (t, 3H), 1.03-0.94 (i, 4H). Chiral method: Rt: 7.319 min 97.09%; column: YMC CHIRAL ART CELLULOSE-SC (250x4.6 mm, 5 u), Mobile Phase: A) n-Hexane+0.1% Iso-propyl amine, B) DCM: MeOH (50: 50), Isocratic: 40% B; Wavelength: 262 nm, Flow: 1.0 mL/min.

Example I-94: (S)-2,4-dichloro-N-(1-(3-(2-cyclopropylpyridin-4-yl)-1,2,4-oxadiazol-5-yl)ethyl)benzamide

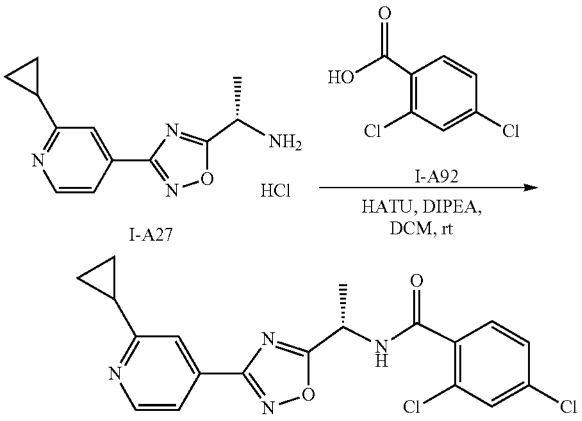

I-A27

I-94

To a stirred solution of I-A92 (60.15 mg, 0.31 mmol) in DCM (5 mL) was added HATU (249.47 mg, 0.66 mmol) and DIPEA (0.14 mL, 0.79 mmol) and stirred for 15 min. To this solution, I-A27 HCl salt (70 mg, 0.26 mmol) was added at 0° C. The reaction mixture was stirred at RT for 2 h. Reaction was monitored by TLC. After completion, reaction mass was diluted with DCM (20 mL), water (5 mL) and extracted with DCM (3x20 mL). The organic layer was separated, dried over $Na_2SO_4$ and concentrated under reduced pressure to afford a residue. The residue was purified by PREP-HPLC to afford desired compound I-94 (25 mg, 0.06 mmol, 23%) as a solid. HPLC: Rt 9.010 min, 99.37%; Column: X-Bridge C18 (4.6x150) mm, 5 μm; Mobile phase: A: 10 mM Ammonium bicarbonate in water, B: ACN; Flow Rate: 1.0 mL/min. LCMS: 402.80 (M+H), Rt 2.236 min, Column: Atlantis Premier BEH C 18 (2.1*50 mm), 2.5 μm. $^1$H NMR (400 MHz, DMSO-d6) $\delta_H$=9.41 (d, 1H), 8.62 (d, 1H), 7.86 (s, 1H), 7.73 (s, 1H), 7.70-7.63 (m, 1H), 7.55-7.53 (m, 2H), 5.44 (p, 1H), 2.32-2.27 (m, 1H), 1.65 (d, 3H), 1.02-0.98 (m, 4H). Chiral method: Rt: 9.507 min, 98.01%; column: DIACEL CHIRALPAK-IG, (250x4.6 mm, 5 u), Mobile Phase: A) n-Hexane+0.1% Iso-propyl amine, B) DCM: MeOH (50:50), Isocratic: 30% B; Wavelength: 291 nm, Flow: 1.0 mL/min.

Example I-95: (S)—N-(1-(3-(2-cyclopropylpyridin-4-yl)-1,2,4-oxadiazol-5-yl)ethyl)-3-(trifluoromethyl) benzamide

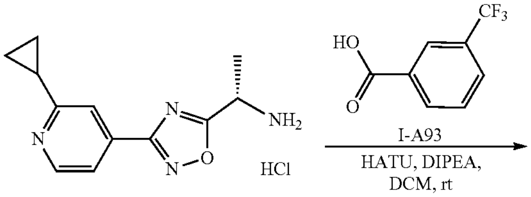

I-A27

-continued

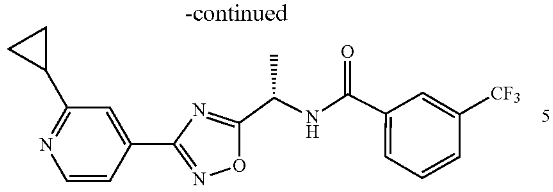

I-95

To a stirred solution of I-A93 (59.87 mg, 0.31 mmol) in DCM (2 mL) was added HATU (249.47 mg, 0.66 mmol) and DIPEA (0.14 mL, 0.79 mmol) and stirred for 15 min. To this solution, I-A27 HCl salt (70. mg, 0.26 mmol) was added at 0° C. The reaction mixture was stirred for at RT for 2 h. Reaction was monitored by TLC. After completion, reaction mass was diluted with DCM (20 mL), water (5 mL) and extracted with DCM (3x20 mL). The organic layer was separated, dried over $Na_2SO_4$ and concentrated under reduced pressure to afford a residue. The residue was purified by PREP-HPLC to afford desired compound I-95 (30 mg, 0.07 mmol, 28%) as a solid. HPLC: Rt 9.125 min, 99.78%; Column: X-Bridge C18 (4.6x150) mm, 5 μm; Mobile phase: A: 10 mM Ammonium bicarbonate in water, B: ACN; Flow Rate: 1.0 mL/min. LCMS: 402.95 (M+H), Rt 2.100 min, Column: Atlantis Premier BEH C 18 (2.1*50 mm), 2.5 μm. $^1$H NMR (400 MHz, DMSO-d6) $\delta_H$=9.54 (d, 1H), 8.60 (d, 1H), 8.29-8.18 (m, 2H), 7.97 (d, 1H), 7.85 (s, 1H), 7.77 (t, 1H), 7.68-7.62 (m, 1H), 5.52 (p, 1H), 2.30-2.26 (m, 1H), 1.71 (d, 3H), 1.05-0.92 (m, 4H). Chiral method: Rt: 6.465 min, 98.60%; column: YMC CHIRAL ART CELLUULOSE-SC, (250x4.6 mm, 5 u), Mobile Phase: A) n-Hexane+0.1% Iso-propyl amine, B) DCM: MeOH (50:50), Isocratic: 20% B; Wavelength: 292 nm, Flow: 1.0 mL/min.

Example I-96: (S)—N-(1-(3-(2-cyclopropylpyridin-4-yl)-1,2,4-oxadiazol-5-yl)ethyl)-2-(trifluoromethyl)isonicotinamide

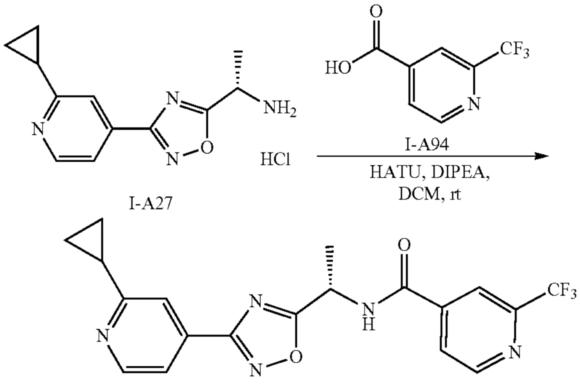

I-96

To a stirred solution of I-A94 (60.19 mg, 0.31 mmol) in DCM (2 mL) was added HATU (99.79 mg, 0.26 mmol) and DIPEA (0.05 mL, 0.26 mmol) and stirred for 15 min. To this solution, I-A27 HCl salt (70 mg, 0.26 mmol) was added at 0° C. The reaction mixture was stirred for 2 h at RT. Reaction was monitored by TLC. After completion, reaction mass was diluted with DCM (20 mL), water (5 mL) and extracted with DCM (3x20 mL). The organic layer was separated, dried over $Na_2SO_4$ and concentrated under reduced pressure to afford a residue. The residue was purified by PREP-HPLC to afford desired compound I-96 (22 mg, 0.05 mmol, 21%) as an oil. HPLC: Rt 8.664 min, 99.81%; Column: X-Bridge C18 (4.6x150) mm, 5 μm; Mobile phase: A: 10 mM Ammonium bicarbonate in water, B: ACN; Flow Rate: 1.0 mL/min. LCMS: 403.90 (M+H), Rt 2.074 min, Column: X-Select CSH C18 (4.6x150) mm, 2.5 μm. $^1$H NMR (400 MHz, DMSO-d6) $\delta_H$=9.80-9.78 (m, 1H), 8.97 (d, 1H), 8.58 (d, 1H), 8.31 (s, 1H), 8.14 (d, 1H), 7.84 (s, 1H), 7.65 (d, 1H), 5.55-5.52 (m, 1H), 2.30-2.25 (m, 1H), 1.72 (d, 3H), 1.00-0.96 (m, 4H). Chiral method: Rt: 7.241 min, 99.96%; column: DIACEL CHIRALPAK-IG, (250x4.6 mm, 5 u), Mobile Phase: A) n-Hexane+0.1% Iso-propyl amine, B) DCM: MeOH (50:50), Isocratic: 20% B; Wavelength: 295 nm, Flow: 1.0 mL/min.

Example I-97: (S)—N-(1-(3-(2-cyclopropylpyridin-4-yl)-1,2,4-oxadiazol-5-yl)ethyl)-5-(cyclopropylsulfonyl)thiophene-2-carboxamide

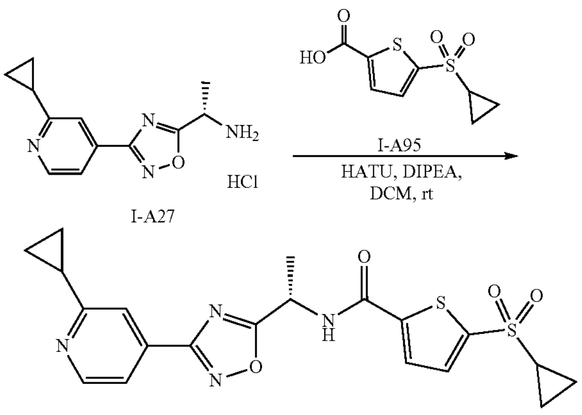

I-97

To a stirred solution of I-A27 HCl salt (97.07 mg, 0.36 mmol) and I-A95 (101.44 mg, 0.44 mmol) in DCM (5 mL) were added HATU (166.05 mg, 0.44 mmol) and DIPEA (0.13 mL, 0.73 mmol) at RT. The reaction mixture was stirred at RT for 2 h. Reaction was monitored by TLC. After completion, reaction was quenched by water (10 mL) and extracted with DCM (2x50 mL). Organic layer was separated, dried over anhydrous $Na_2SO_4$, then filtered. Organic layer was concentrated under reduced pressure. The residue was purified by silica gel column chromatography using 30-80% EtOAc/Hexane as eluent to afford the title compound I-97 (25 mg, 0.05 mmol, 15%) as a solid. HPLC: Rt 7.953 min, 95.09%; Column: X-Select CSH C18 (4.6x150) mm, 3.5 μm; Mobile phase: A: 0.1% Formic acid in water: ACN (95:05), B: ACN; Flow Rate: 1.0 mL/min. LCMS: 445 (M+H), Rt 1.934 min, Column: X-select CSH C18 (3*50) mm, 2.5 μm. $^1$H NMR (400 MHz, DMSO-d6) $\delta_H$=9.64 (d, 1H), 8.60-8.58 (m, 1H), 7.96-7.94 (m, 1H), 7.86-7.82 (m, 2H), 7.66-7.64 (m, 1H), 5.50-5.46 (m, 1H), 3.10-3.00 (m, 1H), 2.30-2.25 (m, 1H), 1.70 (d, 3H), 1.22-1.10 (m, 4H), 1.05-0.98 (m, 4H). Chiral method: Rt: 7.205 min, 97.58%; column: DIACEL CHIRALPAK-IG, (250x4.6 mm, 5 u), Mobile Phase: A) n-Hexane+0.1% Iso-propyl amine, B) DCM: MeOH (50:50), Isocratic: 20% B; Wavelength: 287 nm, Flow: 1.0 mL/min.

Example I-98: (S)—N-(1-(3-(2-cyclopropylpyridin-4-yl)-1,2,4-oxadiazol-5-yl)ethyl) spiro[3.3]heptane-2-carboxamide

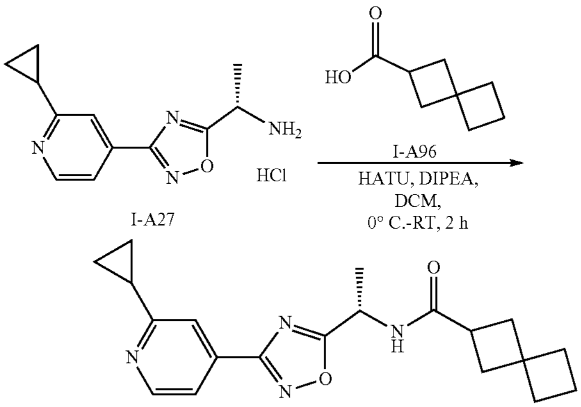

I-A27

I-98

To a stirred solution of I-A27 HCl salt (100 mg, 0.37 mmol) and I-A96 (63.07 mg, 0.45 mmol) in DCM (5 mL) were added HATU (171.06 mg, 0.45 mmol) and DIPEA (0.07 mL, 0.37 mmol) at RT. The reaction mixture was stirred at RT for 2 h. Reaction was monitored by TLC. After completion, reaction was quenched with water (10 mL) and extracted with DCM (2x50 mL). Organic layer was separated, dried over anhydrous $Na_2SO_4$, filtered and concentrated under reduced pressure. The residue was purified by silica gel column chromatography using 30-80% EtOAc/Hexane as eluent to afford the title compound I-98 (28 mg, 0.08 mmol, 21% yield) as a an oil. HPLC: Rt 8.436 min, 99.50%; Column: X-Select CSH C18 (4.6x150) mm, 3.5 µm; Mobile phase: A: 0.1% Formic acid in water:ACN (95:05), B: ACN; Flow Rate: 1.0 mL/min. LCMS: 353.3 (M+H), Rt 1.999 min, Column: X-select CSH C18 (3*50) mm, 2.5 µm. $^1H$ NMR (400 MHz, DMSO-d6) $\delta_H$=8.59 (d, 1H), 8.52 (d, 1H), 7.82 (s, 1H), 7.62 (d, 1H), 5.22-5.18 (m, 1H), 2.95-2.85 (m, 1H), 2.30-2.25 (m, 1H), 2.10-2.05 (m, 4H), 2.00-1.95 (m, 2H), 1.85-1.70 (m, 4H), 1.52 (d, 3H), 1.05-0.95 (m, 4H). Chiral method: Rt: 9.762 min, 99.42%; column: DIACEL CHIRALPAK-IG, (250x4.6 mm, 5 u), Mobile Phase: A) n-Hexane+0.1% Iso-propyl amine, B) DCM: MeOH (50:50), Isocratic: 20% B; Wavelength: 292 nm, Flow: 1.0 mL/min.

Example I-99: (S)-2-cyclopropyl-N-(1-(3-(2-cyclopropylpyridin-4-yl)-1,2,4-oxadiazol-5-yl)ethyl)isonicotinamide

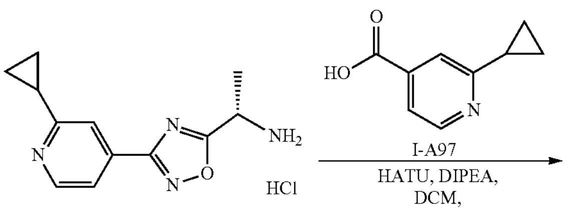

I-A27

-continued

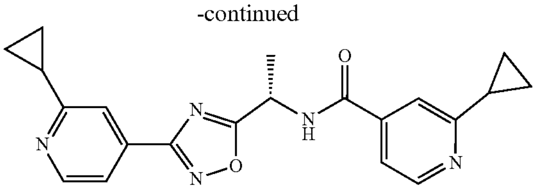
I-99

To a stirred solution of I-A27 HCl salt (0.150, 0.562 mmol) and I-A97 (0.110 g, 0.674 mmol) in DCM (10 mL) was added DIPEA (0.147 mL, 0.843 mmol) followed by HATU (0.320 g, 0.843 mmol) at room temperature and stirred for 2 h. After completion of reaction (monitored by TLC), the reaction mixture was concentrated under reduced pressure and the residue was diluted with ethyl acetate. The organic layer was separated, washed with water followed by brine, dried over anhydrous $Na_2SO_4$, filtered and concentrated under reduced pressure to afford the residue. The residue was purified by flash column chromatography eluting with 0-40% ethyl acetate in n-hexane to afford I-99 (0.050 g, 0.133 mmol, 22% yield) as an oil. LCMS: 376.00 (M+H), $R_t$=2.965 min, Column: Kinetex EVO-C18 (3.0*50 mm, 2.6 µm); Mobile Phase: A: 2.5 mM $NH_4OAc$ in water, B: Acetonitrile; (Gradient) T/B %: 0.01/5, 3/90, 5/90, 5.5/5, 6/5; Flow rate: 0.8 mL/min. HPLC: $R_t$=4.486 min, 96.61%; Column: X-Select CSH C18 (150x4.6 mm, 3.5 µm); Mobile phase: A: 0.05% TFA:ACETONITRILE (95:05), B: ACETONITRILE: 0.05% TFA (95:05); Programme: T/B %: 0.01/10, 12/90, 16/90. Flow Rate: 1.0 mL/min; Diluent: Acetonitrile:Water. CHIRAL HPLC: $R_t$=7.785 in, 96.05%; Column: CHIRAL PAK IC (150x4.6 mm, 5 µm), Mobile Phase: A) 0.1% DEA in n-Hexane, B) EtOH:MeOH (1:1), A:B:: 65:35; Flow: 0.7 mL/min. $^1H$ NMR (400 MHz, DMSO-d6) $\delta_H$=9.49 (d, 1H), 8.60 (d, 1H), 8.56 (d, 1H), 7.85 (s, 1H), 7.69 (s, 1H), 7.65 (dd, 1H), 7.52 (dd, 1H), 5.46-5.53 (m, 1H), 2.24-2.31 (m, 1H), 2.14-2.23 (m, 1H), 1.70 (d, 3H), 0.95-1.02 (m, 8H).

Example I-100: (S)-3-chloro-N-(1-(3-(2-cyclobutylpyridin-4-yl)-1,2,4-oxadiazol-5-yl)ethyl) benzamide

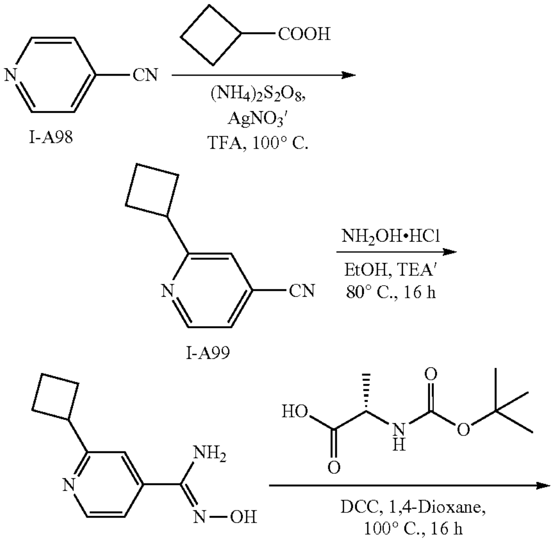

I-A98

I-A99

I-A100

-continued

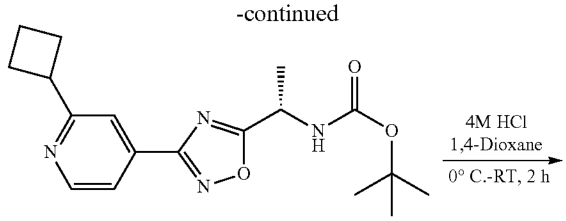

I-A101

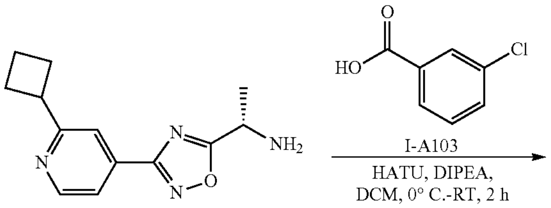

I-A102

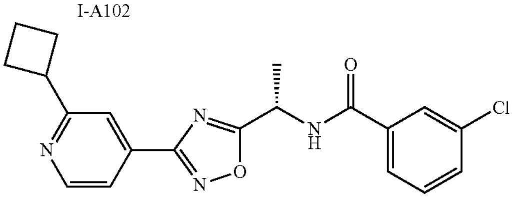

I-100

I-A99: Synthesis of 2-cyclobutylisonicotinonitrile

To a stirred solution of I-A98 (2 g, 19.21 mmol) in water (20 mL):chlorobenzene (20 mL) were added cyclobutanecarboxylic acid (5.77 g, 57.63 mmol), ammonium persulfate (8.77 g, 38.42 mmol), TFA (1.41 mL, 18.37 mmol), silver nitrate (0.326 g, 1.92 mmol). The reaction mixture was stirred at 120° C. for 3 h. After completion, the reaction mixture was diluted with water and extracted with EtOAc. The organic layer was dried over $Na_2SO_4$, filtered and evaporated to get residue which was purified by combiflash column chromatography using 8% Ethyl acetate/hexane as an eluent to afford I-A99 (2 g, 12.65 mmol, 67%) as an oil.

I-A100: (Z)-2-cyclobutyl-N'-hydroxyisonicotinimidamide

To a stirred solution of I-A99 (2 g, 12.64 mmol) in EtOH (20 mL) were added hydroxylamine hydrochloride (1.32 g, 18.96 mmol) and TEA (2.55 g, 25.28 mmol) and stirred at 80° C. for 3 h. The reaction mixture was evaporated under reduced pressure. The residue was diluted with water and extracted with EtOAc. The organic layer dried over $Na_2SO_4$ filtered and evaporated to afford a residue which was purified by silica gel column chromatography using 100-200 mesh silica and 8% Ethyl acetate/hexane as an eluent to afford I-A100 (2 g, 10.47 mmol, 83%) as an oil.

I-A101: tert-butyl (S)-(1-(3-(2-cyclobutylpyridin-4-yl)-1,2,4-oxadiazol-5-yl)ethyl)carbamate To a stirred solution of I-A100 (2 g, 10.46 mmol) in 1,4-dioxane (20 mL). (2S)-2-(tert-butoxycarbonylamino) propanoic acid (2.18 g, 11.5 mmol) DCC (2.37 g, 11.5 mmol) were added. The reaction mixture was stirred at 100° C. for 16 h. The reaction mixture was diluted with water and extracted with EtOAc. The organic layer dried over $Na_2SO_4$ filtered and evaporated to afford a residue which was purified by combi flash column chromatography using 8% Ethyl acetate/hexane as an eluent to get I-A101 (3 g, 8.71 mmol, 83%) as an oil.

I-A102: (S)-1-(3-(2-cyclobutylpyridin-4-yl)-1,2,4-oxadiazol-5-yl)ethan-1-amine

To a stirred solution of I-A101 (3 g, 8.71 mmol) in 1,4-dioxane (10 mL) was added 4M HCl in 1,4-dioxane (30 mL, 214.94 mmol) and stirred at RT for 2 h. The reaction mixture was concentrated under reduced pressure. The residue was triturated with diethyl ether to afford I-A102 as HCl salt (2.5 g) as a solid.

I-100: (S)-3-chloro-N-(1-(3-(2-cyclobutylpyridin-4-yl)-1,2,4-oxadiazol-5-yl)ethyl) benzamide To a stirred solution of I-A103 (67 mg, 0.43 mmol) in DCM (5 mL) were added HATU (380 mg, 1 mmol) and DIPEA (0.26 mL, 1.49 mmol) stirred at RT for 15 min. To this solution, I-A102 (100 mg, 0.41 mmol) was added and reaction mixture was stirred at RT for 2 h. Reaction was monitored by TLC. After completion, reaction mass was quenched with water and extracted with DCM (3×20 mL). Organic layer was separated, dried over $Na_2SO_4$, filtered and evaporated to afford a residue which was purified by prep. HPLC to afford I-100 (20 mg, 0.05 mmol, 15%) as an oil. HPLC: Rt 9.213 min, 99.25%; Column: X-Bridge C18 (4.6×150) mm, 5 μm; Mobile phase: A: 10 mM Ammonium bicarbonate in water, B: ACN; Flow Rate: 1.0 mL/min. LCMS: 382.95 (M+H), Rt 2.258 min, Column: X-select CSH C18 (3*50) mm, 2.5 μm. $^1$H NMR (400 MHz, DMSO-d6) $\delta_H$=9.38 (d, 1H), 8.74 (d, 1H), 7.97 (s, 1H), 7.86 (d, 1H), 7.75-7.70 (m, 2H), 7.66 (d, 1H), 7.55 (t, 1H), 5.50-5.46 (m, 1H), 3.80-3.75 (m, 1H), 2.32-2.26 (m, 4H), 2.06-1.98 (m, 1H), 1.87-1.85 (m, 1H), 1.69 (d, 3H). Chiral method: Rt: 7.590 min, 100%; column: DIACEL CHIRALPAK-IG, (250×4.6 mm, 5 u), Mobile Phase: A) n-Hexane+0.1% TEA, B) DCM: MeOH (50:50), Isocratic:20% B; Wavelength: 281 nm, Flow: 1.0 mL/min.

Example I-101: (S)—N-(1-(3-(2-cyclopropylpyridin-4-yl)-1,2,4-oxadiazol-5-yl)ethyl)-2-methyl isonicotinamide

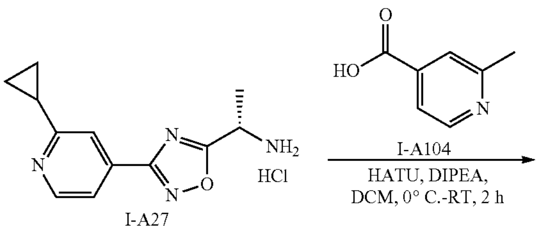

I-A27

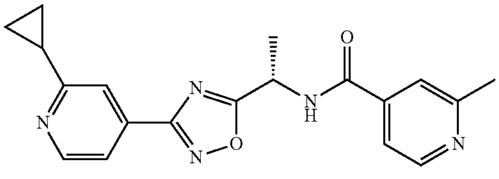

I-101

To a stirred solution of I-A27 HCl salt (100 mg, 0.43 mmol) and I-A104 (71.47 mg, 0.52 mmol) in DCM (5 mL) were added DIPEA (0.23 mL, 1.3 mmol) and HATU (247.69 mg, 0.65 mmol) at RT. The reaction mixture was stirred at RT for 2 h. Reaction was monitored by TLC. After completion, reaction was quenched with water and extracted with DCM. Organic layer was separated, dried over anhydrous $Na_2SO_4$, filtered and concentrated under reduced pressure. The residue was purified by prep. HPLC to afford the title compound I-101 (32.1 mg, 0.09 mmol, 21% yield) as a solid. HPLC: Rt 5.253 min, 97.74%; Column: X-Select CSH C18 (4.6×150) mm, 3.5 μm; Mobile phase: A: 0.1% Formic acid in water:ACN (95:05), B: ACN; Flow Rate: 1.0 mL/min. LCMS: 350.1 (M+H), Rt 1.433 min, Column: X-select CSH C18 (3*50) mm, 2.5 μm. $^1$H NMR (400 MHz, DMSO-d6) $\delta_H$=9.51 (d, 1H), 8.65-8.58 (m, 2H), 7.85 (s, 1H), 7.68-7.59 (m, 3H), 5.52-5.47 (m, 1H), 2.55 (s, 3H), 2.32-2.25 (m, 1H), 1.69 (d, 3H), 1.05-0.95 (m, 4H). Chiral method: Rt: 7.814 min, 99.18%; column: DIACEL CHIRALPAK-IG, (250×4.6 mm, 5 u), Mobile Phase: A) n-Hexane+0.1% Iso-propyl amine, B) DCM: MeOH (50:50), Isocratic: 30% B; Wavelength: 282 nm, Flow: 1.0 mL/min.

Example I-102: (S)—N-(1-(3-(2-cyclopropylpyridin-4-yl)-1,2,4-oxadiazol-5-yl)ethyl)-3,5-difluorobenzamide

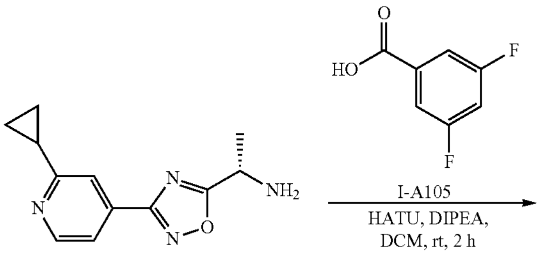

I-A27

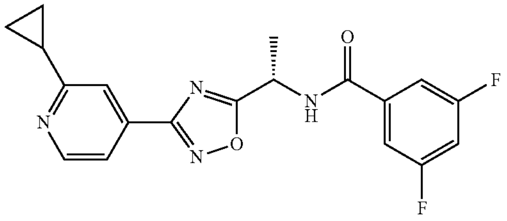

I-102

To a stirred solution of I-A27 (0.200 g, 0.750 mmol) and I-A105 (0.177 g, 1.120 mmol) in DCM (10 mL) were added HATU (0.285 g, 0.750 mmol) and DIPEA (0.196 mL, 1.120 mmol) at room temperature and stirred for 2 h. After completion of reaction (monitored by TLC), the reaction mixture was quenched with water (10 mL) and extracted with DCM (2×50 mL). The combined organic layer was dried over anhydrous $Na_2SO_4$, filtered and concentrated under reduced pressure resulting in the residue. The residue was purified by CombiFlash column chromatography eluting with 0-40% ethyl acetate in n-hexane to afford I-102 (0.080 g, 0.210 mmol, 29%) as a solid. LCMS: 371.20 (M+H), $R_t$=2.715 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: $R_t$=7.979 min, 99.35%; Column: X-Select CSH C18 (150×4.6 mm, 3.5 μm); Mobile phase: A: 0.05% TFA: ACETONITRILE (95:05), B: ACETONITRILE: 0.05% TFA (95:05); Programme: T/B %: 0.01/10, 12/90, 16/90. Flow Rate: 1.0 mL/min; Diluent: Acetonitrile:Water. CHIRAL HPLC: $R_t$=15.22 min, 99.36%; Column: CHIRAL PAK IA (150×4.6 mm, 3 μm), Mobile Phase: A) 0.1% DEA in n-Hexane, B) EtOH:MeOH (50:50), A:B:: 95:05; Flow: 0.7 mL/min. $^1$H NMR (400 MHz, DMSO-d6) $\delta_H$=9.43 (d, 1H), 8.60 (d, 1H), 7.85 (s, 1H), 7.61-7.67 (m, 3H), 7.48-7.57 (m, 1H), 5.44-5.53 (m, 1H), 2.25-2.34 (m, 1H), 1.69 (d, 3H), 0.95-1.02 (m, 4H).

Example I-103: (S)—N-(1-(3-(2-cyclopropylpyridin-4-yl)-1,2,4-oxadiazol-5-yl)ethyl)-3-(trifluoromethoxy)benzamide

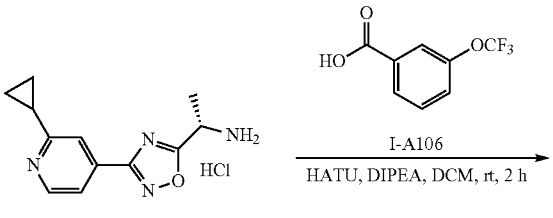

I-A27

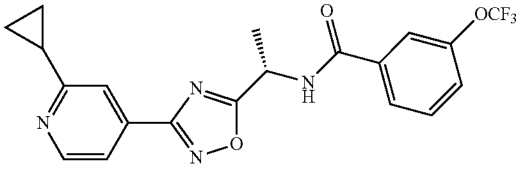

I-103

To a stirred solution of I-A27 HCl salt (0.100 g, 0.434 mmol) and I-A106 (0.134 g, 0.651 mmol) in DCM (5 mL) was added DIPEA (0.113 mL, 0.651 mmol) followed by HATU (0.247 g, 0.651 mmol) at room temperature and stirred for 2 h. After completion of reaction (monitored by TLC), the reaction mixture was diluted with water (15 mL) and extracted with DCM (3×15 mL). The combined organic layer was dried over anhydrous $Na_2SO_4$, filtered and concentrated under reduced pressure to afford the residue. The residue was purified by Combiflash column chromatography to afford I-103 (0.045 g, 0.107 mmol, 24%) a solid. LCMS: 419.20 (M+H), $R_t$=2.932 min, Column: Kinetex EVO-C18 (3.0*50 mm, 2.6 μm); Mobile Phase: A: 0.025% Formic acid, B: Acetonitrile; T/B %: 0.01/5, 3/90, 5/90, 5.5/5, 6/5; Flow rate: 0.8 mL/min (Gradient). HPLC: $R_t$=9.563 min, 98.05%; Column: X-Select CSH C18 (150×4.6 mm, 3.5 μm); Mobile phase: A: 0.05% TFA: ACETONITRILE (95: 05), B: ACETONITRILE: 0.05% TFA (95:05); Programme: T/B %: 0.01/10, 12/90, 16/90. Flow Rate: 1.0 mL/min; Diluent: Acetonitrile:Water. CHIRAL HPLC: $R_t$=4.775 min, 96.03%; Column: CHIRAL PAK IG (250×4.6 mm, 5 μm); Mobile phase: A: 0.1% DEA:n-Hexane; B: DCM: MeOH (1:1); A:B 70:30; Flow Rate: 1.0 mL/min. $^1$H NMR (400 MHz, DMSO-d6) $\delta_H$=ppm 9.45 (d, 1H), 8.60 (d, 1H), 7.97 (d, 1H), 7.86 (d, 2H), 7.58-7.70 (m, 3H), 5.45-5.55 (m, 1H), 2.24-2.32 (m, 1H), 1.70 (d, 3H), 0.94-1.02 (m, 4H).

Example I-104: (S)-1-cyclobutyl-N-(1-(3-(2-cyclopropylpyridin-4-yl)-1,2,4-oxadiazol-5-yl)ethyl)-1H-imidazole-2-carboxamide

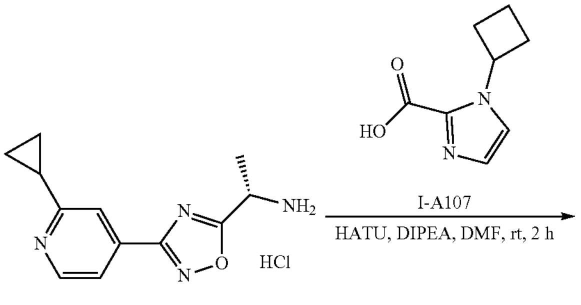

I-A27

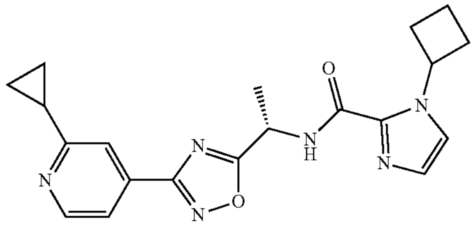

I-104

To a stirred solution of I-A27 HCl salt (200 mg, 0.8700 mmol) and I-A107 (168.59 mg, 1.01 mmol) in DMF (5 mL) was added DIPEA (560.21 mL, 4.34 mmol) followed by HATU (495 mg, 1.3 mmol) at room temperature and stirred for 15 h. After completion of reaction (monitored by TLC), the reaction mixture was concentrated under reduced pressure and the residue was diluted with ethyl acetate. The organic layer was separated, washed with water followed by brine, dried over anhydrous $Na_2SO_4$, filtered and concentrated under reduced pressure to afford the residue. The residue was purified by flash column chromatography eluting with 0-40% ethyl acetate in n-hexane to afford I-104 (38 mg, 0.1002 mmol, 12%) as a solid. LCMS: 376.00 (M+H), $R_t$=2.965 min, Column: Kinetex EVO-C18 (3.0*50 mm, 2.6 μm); Mobile Phase: A: 2.5 mM $NH_4OAc$ in water, B: Acetonitrile; (Gradient) T/B %: 0.01/5, 3/90, 5/90, 5.5/5, 6/5; Flow rate: 0.8 mL/min. HPLC: $R_t$=4.486 min, 96.61%; Column: X-Select CSH C18 (150×4.6 mm, 3.5 μm); Mobile phase: A: 0.05% TFA: ACETONITRILE (95:05), B: ACETONITRILE: 0.05% TFA (95:05); Programme: T/B %: 0.01/10, 12/90, 16/90. Flow Rate: 1.0 mL/min; Diluent: Acetonitrile:Water. CHIRAL HPLC: $R_t$=7.785 in, 96.05%; Column: CHIRAL PAK IC (150×4.6 mm, 5 μm), Mobile Phase: A) 0.1% DEA in n-Hexane, B) EtOH:MeOH (1:1), A:B:: 65:35; Flow: 0.7 mL/min. $^1$H NMR (400 MHz, DMSO-d6) $\delta_H$=9.28-9.19 (m, 1H), 8.63-8.55 (m, 1H), 7.85 (s, 1H), 7.80-7.72 (m, 1H), 7.70-7.60 (m, 1H), 7.14-7.03 (m, 1H), 5.66-5.54 (m, 1H), 5.48-5.35 (m, 1H), 2.44-2.22 (m, 5H), 1.82-1.61 (m, 5H), 1.06-0.90 (m, 4H).

Example I-105: (S)—N-(1-(3-(2-cyclopropylpyridin-4-yl)-1,2,4-oxadiazol-5-yl)ethyl)cyclopentanecarboxamide

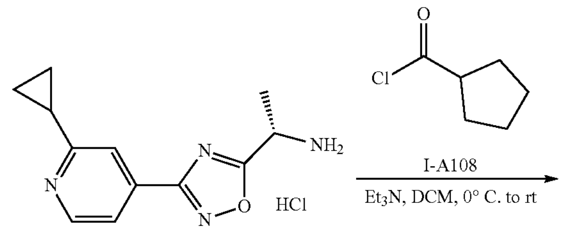

I-A27

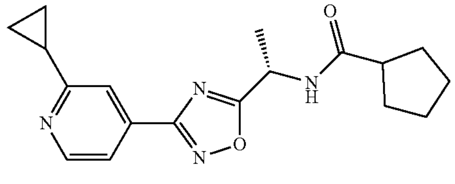

I-105

To a stirred solution of I-A27 HCl (200 mg, 0.87 mmol) in DCM (3 mL) was added TEA (175.78 mg, 1.7371 mmol) dropwise, followed by I-A108 (115.16 mg, 0.8685 mmol) at 0° C. The reaction mixture was allowed to warm room temperature and continued stirring for 16 hrs. After completion of the reaction, the mixture was quenched with water and extracted with DCM, washed with water followed by brine, dried over anhydrous $Na_2SO_4$, filtered and concentrated under reduced pressure. The residue was purified by flash column chromatography eluting with 0-40% ethyl acetate in n-hexane to afford I-105 (88.8 mg, 0.2710 mmol, 31%) as a solid. HPLC: $R_t$=6.332 min, 99.63%; Column: XSELECT CSH C18 (150×4.6 mm, 3.5); Mobile Phase-A: 0.05% TFA: ACETONITRILE (95:05); Mobile Phase-B: ACETONITRILE:0.05% TFA (95:05); Programme:T/B %: 0.01/10, 12/90, 16/90; Flow: 1.0 mL/min; Diluent:ACN: WATER. LCMS: 327.2 (M+H), $R_t$=2.115 min, Column: X-Bridge BEH C-18(3.0×50 mm, 2.5 m); Mobile Phase: A: 0.025% FA in Water, B: ACN. $^1$H NMR (400 MHz, DMSO-d6) $\delta_H$=8.70-8.52 (m, 2H), 7.83 (s, 1H), 7.71-7.55 (m, 1H), 5.31-5.12 (m, 1H), 2.75-2.56 (m, 1H), 2.36-2.19 (m, 1H), 1.89-1.70 (m, 2H), 1.69-1.43 (m, 9H), 1.08-0.88 (m, 4H).

Example I-A. Synthesis of Intermediates

Synthesis of I-A1

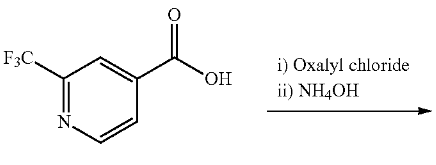

I-B1

-continued

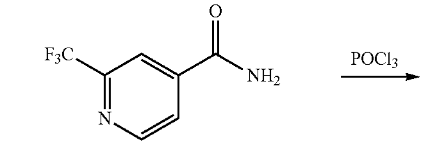

I-B2

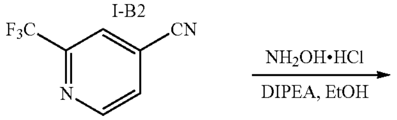

I-B3

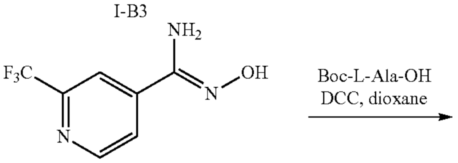

I-B4

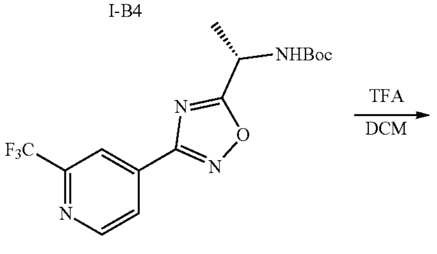

I-B5

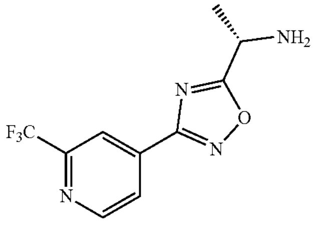

I-A1

I-B2: 2-(trifluoromethyl)isonicotinamide

To a stirred solution of 2-(trifluoromethyl)pyridine-4-carboxylic acid (I-B1, 2.0 g, 10.47 mmol) in DCM (20.0 mL) was added oxalyl chloride (1.39 g, 10.99 mmol) and a catalytic amount of DMF (0.05 mL) at 0° C. The reaction mixture was warmed to room temperature and stirred for 2 h. The reaction mixture was concentrated under reduced pressure and aqueous $NH_4OH$ (2.0 mL) was added at 0° C. dropwise followed by MeCN (10.0 mL). The reaction mixture was stirred at room temperature for 30 min and diluted with ethyl acetate (100 mL). The organic layer was washed with water (2×50 mL), washed with brine (20 mL), dried over $Na_2SO_4$ and concentrated to afford I-B2 (1.3 g).

I-B3: 2-(trifluoromethyl)pyridine-4-carbonitrile $POCl_3$ (3.04 mL, 32.61 mmol) was added dropwise to I-B2 (1.3 g, 6.84 mmol) at 0° C. The reaction mixture was heated at 100° C. for 3 h. The reaction mixture was cooled to room temperature and treated with 50% NaOH solution (10 mL). The reaction mixture was diluted with water (50 mL) and extracted with ethyl acetate (2×70 mL). The organic layer was washed with brine (40 mL), dried over $Na_2SO_4$ and concentrated. The residue was purified by column chromatography on silica gel with 8% ethyl acetate/PE to afford I-B3 (520 mg, 3.0 mmol, 44% yield). LCMS: 173.1 (M+H), Rt 1.84 min; Column: ZORBAX XDB C-18 (50×4.6 mm), 3.5 μm; Mobile Phase: A: 0.1% HCOOH in water:ACN (95:5), B: ACN; Flow Rate:1.5 mL/min.

I-B4: N'-hydroxy-2-(trifluoromethyl)pyridine-4-carboxamidine

To a stirred solution of I-B3 (520 mg, 3.02 mmol) in ethanol (10.0 mL) was added hydroxylamine hydrochloride (314 mg, 4.53 mmol) and DIPEA (1.58 mL, 9.05 mmol) at room temperature under nitrogen atmosphere. The reaction mixture was heated at 80° C. for 2 h. The reaction mixture was cooled to room temperature and concentrated under reduced pressure. The residue was treated with water (15 mL) followed by saturated sodium bicarbonate solution (10 mL) and extracted with ethyl acetate (2×30 mL). The organic layer was washed with brine (20 mL), dried over $Na_2SO_4$ and concentrated to afford I-B4 (580 mg). It was used for the next step without further purification.

I-B5: tert-butyl (S)-(1-(3-(2-(trifluoromethyl)pyridin-4-yl)-1,2,4-oxadiazol-5-yl)ethyl)carbamate To a stirred solution of I-B4 (580 mg, 2.83 mmol) in 1,4-dioxane (20.0 mL) was added (2S)-2-(tert-butoxycarbonylamino)propanoic acid (534 mg, 2.83 mmol) and DCC (640 mg, 3.11 mmol). The reaction mixture was stirred at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The residue was purified by column chromatography on silica gel with 12% ethyl acetate/PE to afford I-B5 (840 mg, 2.34 mmol, 82% yield). LCMS: 359.2 (M+H), Rt 2.42 min; Column: ZORBAX XDB C-18 (50×4.6 mm), 3.5 μm; Mobile Phase: A: 0.1% HCOOH in water:ACN (95:5), B: ACN; Flow Rate:1.5 mL/min I-A1: (1S)-1-[3-[2-(trifluoromethyl)-4-pyridyl]-1,2,4-oxadiazol-5-yl]ethanamine To a stirred solution of I-B5 (400 mg, 1.12 mmol) in DCM (8.0 mL) was added TFA (1.5 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford I-A1 (260 mg).

Synthesis of I-A34

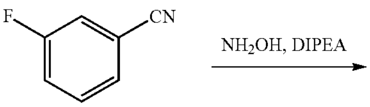

I-B6

-continued

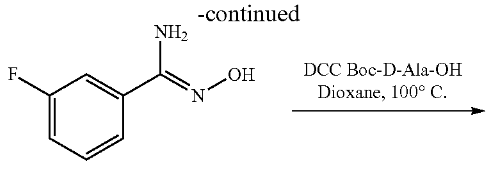

I-B7

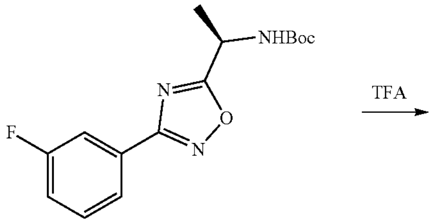

I-B8

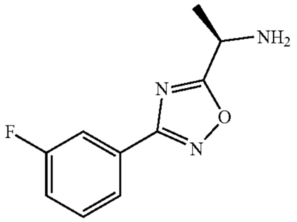

I-A34

I-B7: 3-fluoro-N'-hydroxybenzimidamide

To a solution of 3-fluorobenzonitrile (10.0 g, 82.57 mmol) in ethanol (200 mL) was added hydroxylamine hydrochloride (17.21 g, 247.71 mmol) and DIPEA (43.96 mL, 247.71 mmol). The reaction mixture was heated at 70° C. for 16 h. The reaction mixture was cooled to room temperature and concentrated. The mixture was treated with water (100 mL) and extracted with ethyl acetate (2×100 mL). The organic layer was washed with brine (50 mL), dried over anhydrous $Na_2SO_4$ and concentrated to afford I-B7 (10.5 g).

I-B8: tert-butyl (R)-(1-(3-(3-fluorophenyl)-1,2,4-oxadiazol-5-yl)ethyl)carbamate To a solution of compound I-B7 (0.25 g, 1.62 mmol) in 1,4-dioxane (10.0 mL) was added (2R)-2-(tert-butoxycarbonylamino)propanoic acid (0.33 g, 1.76 mmol) and DCC (0.37 g, 1.78 mmol the reaction mixture was heated at 100° C. for 16 h. The reaction mixture was cooled to room temperature and concentrated. The mixture was treated with water (15 mL) and extracted with ethyl acetate (2×20 mL). The organic layer was washed with brine (10 mL), dried over anhydrous $Na_2SO_4$ and concentrated. The residue was purified by column chromatography on silica gel with 8% EtOAc/PE to afford I-B8 (270 mg, 0.86 mmol, 53% yield) as a solid. HPLC: Rt 5.02 min, 99.3%; Column: XBridge C8 (50×4.6) mm, 3.5 μm; Mobile phase: A: 0.1% TFA in water, B: 0.1% TFA in ACN; Flow Rate: 2.0 mL/min. LCMS: 306.1 (M−H), Rt 2.51 min, Column: ZORBAX XDB C-18 (50×4.6 mm), 3.5 μm; Mobile Phase: A: 0.1% HCOOH in water:ACN (95:5), B: ACN; Flow Rate:1.5 mL/min. Chiral method: Rt 1.94 min, SFC column: YMC Amylose-C; mobile phase: 60:40 (A:B), A=liquid $CO_2$, B=0.5% isopropyl amine in methanol; flow rate: 3.0 mL/min; wave length: 220 nm. $^1H$ NMR (400 MHz, $CDCl_3$): $\delta_H$=7.89 (d, 1H), 7.82-7.78 (m, 1H), 7.50-7.45 (m, 1H), 7.25-7.20 (m, 1H), 5.19 (m, 2H), 1.65 (d, 3H), 1.49 (s, 9H).

I-A34: (R)-1-(3-(3-fluorophenyl)-1,2,4-oxadiazol-5-yl)ethan-1-amine

To a solution of compound I-B8 (270 mg, 0.88 mmol) in DCM (5 mL) was added TFA (1.3 mL) and the mixture stirred at room temperature for 3 h. The reaction mixture was treated with saturated $NaHCO_3$ solution (10 mL) and extracted with DCM (2×20 mL). The organic layer was washed with brine (10 mL), dried over anhydrous $Na_2SO_4$ and concentrated to afford I-A34 (170 mg) as a liquid.

Synthesis of I-A35

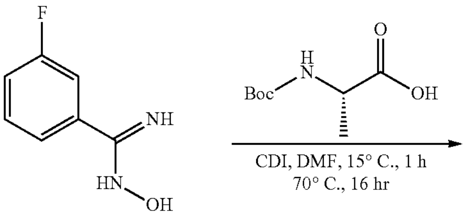

I-B7

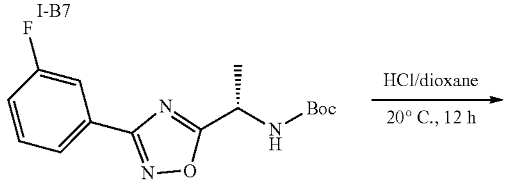

I-B9

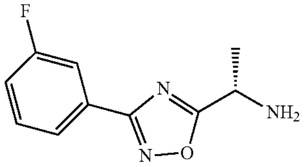

I-A35

I-B9: A mixture of (2S)-2-(tert-butoxycarbonylamino)propanoic acid (0.74 g, 3.89 mmol) and CDI (0.69 g, 4.28 mmol) in DMF (18 mL) was stirred at 15° C. for 1 hour and then 3-fluoro-N'-hydroxy-benzamidine (0.6 g, 3.89 mmol) was added. The reaction mixture was stirred at 70° C. for 16 hours. After cooling to r.t., the mixture was diluted with $H_2O$ (30 mL) and extracted with EtOAc (30 mL×3). The combined organic phase was washed with brine (50 mL), dried over $Na_2SO_4$, filtered and concentrated to give a residue. The residue was purified by flash column chromatography on silica gel (EtOAc in PE=0% to 15% to 40%) to give the product (420 mg, 1.37 mmol, 35% yield) as an oil. LCMS $R_t$=0.91 min in 1.5 min chromatography, 5-95AB, MS ESI calcd. for $C_{11}H_{11}FN_3O_3$[M+H-t-Bu]$^+$ 252.07, found 252.1.

I-A35: To tert-butyl N-[(1S)-1-[3-(3-fluorophenyl)-1,2,4-oxadiazol-5-yl]ethyl]carbamate (420 mg, 1.37 mmol) was added 4M HCl in 1,4-dioxane (10 mL, 40 mmol) and the reaction mixture was stirred at 20° C. for 12 hours. The mixture was concentrated under reduced pressure and diluted with $H_2O$ (20 mL) and basified with $NaHCO_3$ (solid) to a pH~8. The mixture was extracted with EtOAc (20 mL×2), and the combined organic phase was washed with brine (30 mL), dried over $Na_2SO_4$, filtered and concentrated to give a residue (270 mg, 1.30 mmol, 95% yield) as an oil. LCMS $R_t$=0.41 min in 2.0 min chromatography, 10-80AB, MS ESI calcd. for $C_{10}H_{11}FN_3O$ $[M+H]^+$ 208.08, found 207.9.

Synthesis of I-A36

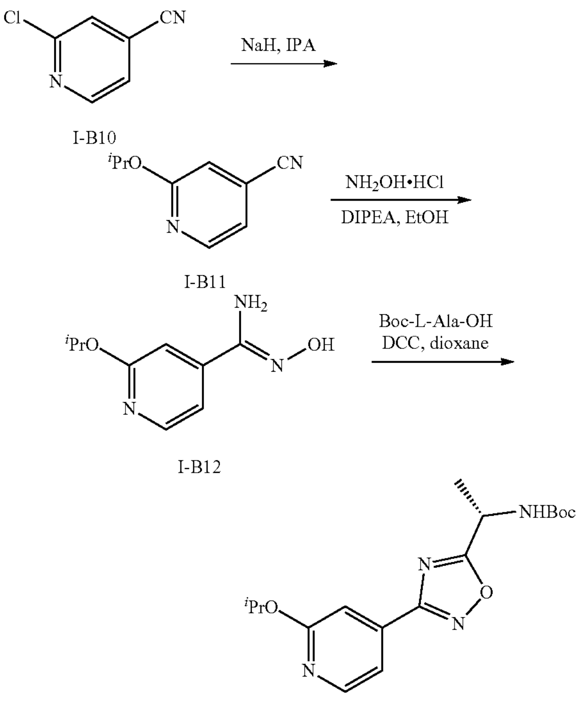

I-B10, I-B11, I-B12, I-A36

I-B11: 2-isopropoxyisonicotinonitrile

To the isopropyl alcohol (45.0 mL) at 0° C. was added NaH (60% in mineral oil, 952 mg, 23.8 mmol) in small portions. The resulting suspension was stirred for 5 min and 2-chloropyridine-4-carbonitrile (3.0 g, 21.65 mmol) was added in small portions. The reaction mixture was heated at 80° C. for 1 h. The reaction mixture was cooled to 10° C. and treated with ice water (50 mL). The mixture was extracted with ethyl acetate (2×50 mL). The organic layer was washed with brine (50 mL), dried over anhydrous $Na_2SO_4$ and concentrated. The residue was purified by column chromatography on silica gel with 10% ethyl acetate/PE to afford I-B11 (980 mg, 6.0 mmol, 27% yield). LCMS: 163.1 (M+H), Rt 2.32 min; Column: ZORBAX XDB C-18 (50×4.6 mm), 3.5 μm; Mobile Phase: A: 0.1% HCOOH in water:ACN (95:5), B: ACN; Flow Rate:1.5 mL/min I-B12: (Z)—N'-hydroxy-2-isopropoxyisonicotinimidamide To a stirred solution of I-B11 (0.98 g, 6.0 mmol) in ethanol (20.0 mL) was added hydroxylamine hydrochloride (0.63 g, 9.0 mmol) followed by DIPEA (3.16 mL, 18.13 mmol). The reaction mixture was heated at 80° C. for 2 h. The reaction mixture was cooled to room temperature and treated with water (30 mL). The mixture was treated with 10% sodium carbonate solution (10 mL) and extracted with ethyl acetate (2×50 mL). The organic layer was washed with brine (50 mL), dried over anhydrous $Na_2SO_4$ and concentrated to afford I-B12 (1.1 g).

I-A36: tert-butyl (S)-(1-(3-(2-isopropoxypyridin-4-yl)-1,2,4-oxadiazol-5-yl)ethyl)carbamate To a stirred solution of I-B12 (1.1 g, 5.6 mmol) in 1,4-dioxane (20.0 mL) was added (2S)-2-(tert-butoxycarbonylamino)propanoic acid (1.07 g, 5.6 mmol) and DCC (1.28 g, 6.2 mmol). The reaction mixture was heated to 100° C. for 16 h. The reaction mixture was cooled to room temperature and concentrated under reduced pressure. The mixture was treated with water (30 mL) and extracted with ethyl acetate (2×50 mL). The organic layer was washed with brine (50 mL), dried over anhydrous $Na_2SO_4$ and concentrated. The residue was purified by column chromatography on silica gel with 14% EtOAc/PE to afford I-A36 (1.5 g, 4.3 mmol, 76% yield) as a solid. LCMS: 349.1 (M+H), Rt 2.64 min; Column: ZORBAX XDB C-18 (50×4.6 mm), 3.5 μm; Mobile Phase: A: 0.1% HCOOH in water:ACN (95:5), B: ACN; Flow Rate:1.5 mL/min.

Synthesis of I-A27

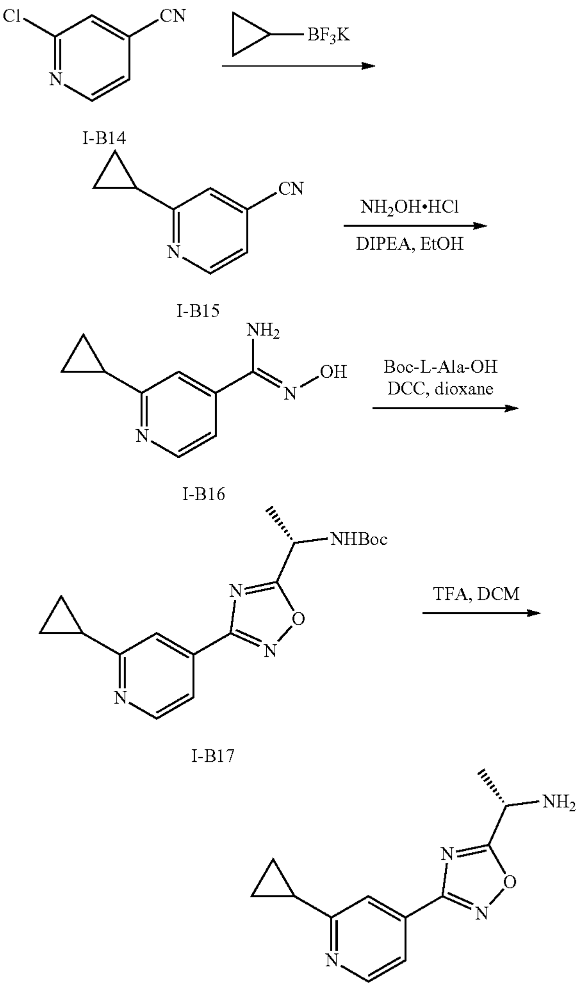

I-B14, I-B15, I-B16, I-B17, I-A27

I-B15: 2-cyclopropylisonicotinonitrile

To a solution of 2-chloropyridine-4-carbonitrile (2.0 g, 14.4 mmol) in 1,4-dioxane (25 mL) was added potassium cyclopropyltrifluoroborate (6.41 g, 43.3 mmol) followed by $K_2CO_3$ (7.98 g, 57.7 mmol) and RuPhos (1.35 g, 2.89 mmol). The resulting mixture was degassed with $N_2$ gas for 10 min and $Pd(OAc)_2$ (324 mg, 1.44 mmol) was added. The mixture was stirred at 100° C. for 1 h. The reaction mixture was cooled to room temperature and filtered through celite. The filtrate was concentrated under reduced pressure and the residue was purified by column chromatography on silica gel with 15% EtOAc/PE to afford I-B15 (1.1 g, 7.6 mmol, 50% yield) as a solid. LCMS: 145.1 (M+H), Rt 1.87 min; Column: ZORBAX XDB C-18 (50×4.6 mm), 3.5 μm; Mobile Phase: A: 0.1% TFA in water:ACN (95:5), B: 0.1% TFA in ACN; Flow Rate:1.5 mL/min I-B16: (Z)-2-cyclopropyl-N'-hydroxyisonicotinimidamide To a solution of I-B15 (450 mg, 3.1 mmol) in ethanol (15.0 mL) was added hydroxylamine hydrochloride (312 mg, 4.4 mmol) followed by DIPEA (1.49 mL, 8.99 mmol) at room temperature. The reaction mixture was heated at 80° C. for 5 h. The reaction mixture was cooled to room temperature and concentrated under reduced pressure. The residue was treated with water (30 mL) followed by saturated sodium bicarbonate solution (20 mL) and extracted with ethyl acetate (2×25 mL). The organic layer was washed with brine (10 mL), dried over $Na_2SO_4$ and concentrated to afford I-B16 (420 mg) as a solid.

I-B17: tert-butyl (S)-(1-(3-(2-cyclopropylpyridin-4-yl)-1,2,4-oxadiazol-5-yl)ethyl)carbamate To a solution of (2S)-2-(tert-butoxycarbonylamino)propanoic acid (0.44 g, 2.31 mmol) in 1,4-dioxane (10.0 mL) was added I-B16 (0.41 g, 2.31 mmol) followed by DCC (0.52 g, 2.55 mmol). The resulting mixture was stirred at 100° C. for 16 h. The reaction mixture was cooled to room temperature and concentrated under reduced pressure. The mixture was treated with water (30 mL) and extracted with ethyl acetate (2×25 mL). The organic layer was washed with brine (20 mL), dried over $Na_2SO_4$ and concentrated. The residue was purified by column chromatography on silica gel with 15% ethyl acetate/PE to afford I-B17 (570 mg, 1.72 mmol, 74% yield) as a solid. LCMS: 331.3 (M+H), Rt 2.22 min; Column: ZORBAX XDB C-18 (50×4.6 mm), 3.5 μm; Mobile Phase: A: 0.1% TFA in water:ACN (95:5), B: 0.1% TFA in ACN; Flow Rate:1.5 mL/min I-A27: (S)-1-(3-(2-cyclopropylpyridin-4-yl)-1,2,4-oxadiazol-5-yl)ethan-1-amine To a solution of I-B17 (410 mg, 1.24 mmol) in DCM (5.0 mL) was added TFA (1.36 mL) at 0° C. The reaction mixture was slowly warmed to room temperature and stirred for 3 h. The mixture was concentrated under reduced pressure and treated with ice water (20 mL). The mixture was treated with 10% aqueous $NaHCO_3$ solution (5 mL) and extracted with EtOAc (2×25 mL). The organic layer was washed with brine (20 mL), dried over anhydrous $Na_2SO_4$ and concentrated to afford I-A27 (240 mg).

Synthesis of I-A38

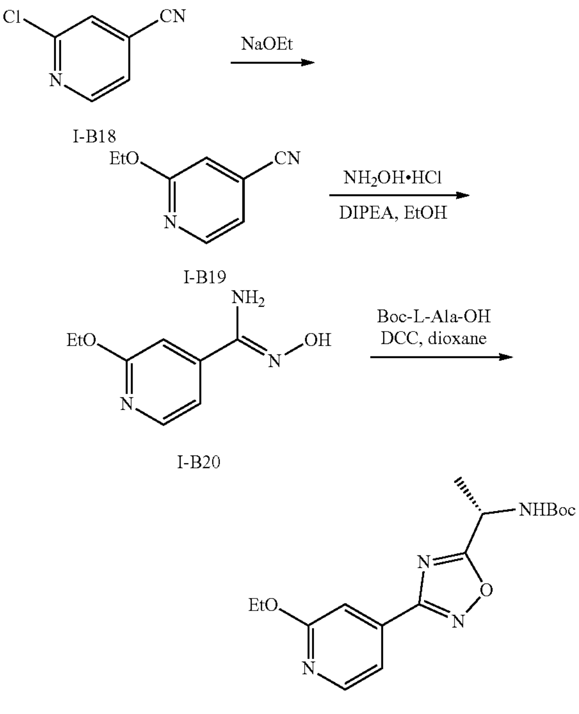

I-B18, I-B19, I-B20, I-A38

I-B19: 2-ethoxyisonicotinonitrile

To a stirred solution of 2-chloropyridine-4-carbonitrile (5.0 g, 36.1 mmol) in 1,4-dioxane (50.0 mL) was added NaOEt (2.46 g, 36.1 mmol) at one portion. The reaction mixture was heated at 60° C. for 4 h. The reaction mixture was cooled to room temperature, treated with ice cold water (50 mL) and extracted with ethyl acetate (2×100 mL). The organic layer was washed with brine (100 mL), dried over anhydrous $Na_2SO_4$ and concentrated. The residue was purified by column chromatography on silica with 6% EtOAc/PE to afford I-B19 (3.5 g, 23.5 mmol, 65% yield). LCMS: 149.1 (M+H), Rt 2.06 min; Column: ZORBAX XDB C-18 (50×4.6 mm), 3.5 μm; Mobile Phase: A: 0.1% HCOOH in water:ACN (95:5), B: ACN; Flow Rate:1.5 mL/min I-B20: (Z)-2-ethoxy-N'-hydroxyisonicotinimidamide To a stirred solution of 2-ethoxypyridine-4-carbonitrile (1.5 g, 10.12 mmol) in ethanol (30.0 mL) was added hydroxylamine hydrochloride (1.06 g, 15.19 mmol) followed by DIPEA (5.29 mL, 30.37 mmol). The reaction mixture was heated at 80° C. for 2 h. The reaction mixture was cooled to room temperature and concentrated under reduced pressure. The residue was treated with water (30 mL) followed by saturated sodium bicarbonate solution (20 mL) and extracted with ethyl acetate (2×50 mL). The organic layer was washed with brine (100 mL), dried over anhydrous $Na_2SO_4$ and concentrated to afford I-B20 (1.7 g).

I-A38: tert-butyl (S)-(1-(3-(2-ethoxypyridin-4-yl)-1,2,4-oxadiazol-5-yl)ethyl)carbamate To a stirred solution of (2S)-2-(tert-butoxycarbonylamino)propanoic acid (1.78 g, 9.38 mmol) in 1,4-dioxane (34.0 mL) was added I-B20 (1.7 g, 9.38 mmol) and DCC (2.13 g, 10.32 mmol). The reaction mixture was heated at 100° C. for 16 h. The reaction mixture was cooled to room temperature and concentrated under reduced pressure. The mixture was treated with water (100 mL) and extracted with ethyl acetate (2×100 mL). The organic layer was washed with brine (100 mL), dried over anhydrous $Na_2SO_4$ and concentrated. The residue was purified by column chromatography on silica gel with 14% EtOAc/PE to afford I-A38 (2.4 g, 7.07 mmol, 75% yield) as a solid. LCMS: 335.1 (M+H), Rt 3.22 min; Column: XBridge C8 (50×4.6 mm), 3.5 μm; Mobile Phase: A: 10 mM $NH_4HCO_3$ in $H_2O$, B: ACN; Flow Rate:0.8 mL/min.

Example II-1. Synthesis of Compound II-1

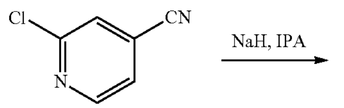

II-A1

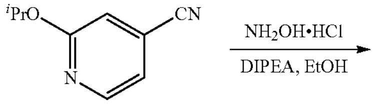

II-A2

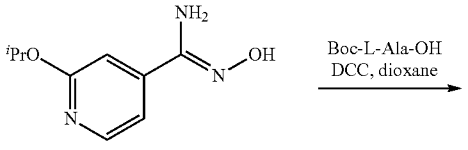

II-A3

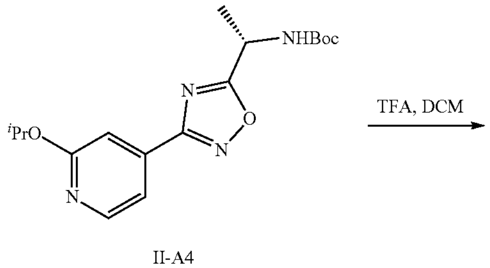

II-A4

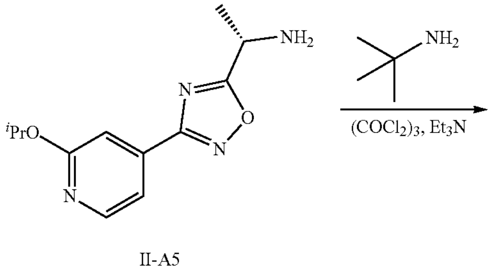

II-A5

-continued

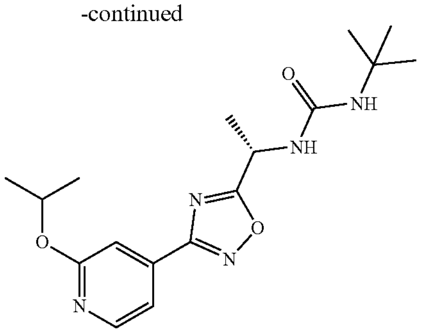

II-1

II-A2: To the isopropyl alcohol (45.0 mL) at 0° C. was added NaH (60% in mineral oil, 952 mg, 23.8 mmol) in small portions. The resulting suspension was stirred for 5 min and 2-chloropyridine-4-carbonitrile (3.0 g, 21.65 mmol) was added in small portions. The reaction mixture was heated at 80° C. for 1 h. The reaction mixture was cooled to 10° C. and treated with ice water (50 mL). The mixture was extracted with ethyl acetate (2×50 mL). The organic layer was washed with brine (50 mL), dried over anhydrous $Na_2SO_4$ and concentrated. The residue compound was purified by column chromatography on silica gel with 10% ethyl acetate/PE to afford II-A2 (980 mg, 6.0 mmol, 27% yield). LCMS: 163.1 (M+H), Rt 2.32 min Column: ZORBAX XDB C-18 (50×4.6 mm), 3.5 μm Mobile Phase: A: 0.1% HCOOH in water:ACN (95:5), B: ACN; Flow Rate:1.5 mL/min.

II-A3: To a stirred solution of II-A2 (0.98 g, 6.0 mmol) in ethanol (20.0 mL) was added hydroxylamine hydrochloride (0.63 g, 9.0 mmol) followed by DIPEA (3.16 mL, 18.13 mmol). The reaction mixture was heated at 80° C. for 2 h. The reaction mixture was cooled to room temperature and treated with water (30 mL). The mixture was treated with 10% sodium carbonate solution (10 mL) and extracted with ethyl acetate (2×50 mL). The organic layer was washed with brine (50 mL), dried over anhydrous $Na_2SO_4$ and concentrated to afford II-A3 (1.1 g). It was used in the next step without further purification.

II-A4: To a stirred solution of II-A3 (1.1 g, 5.6 mmol) in 1,4-dioxane (20.0 mL) was added (2S)-2-(tert-butoxycarbonylamino)propanoic acid (1.07 g, 5.6 mmol) and DCC (1.28 g, 6.2 mmol). The reaction mixture was heated to 100° C. for 16 h. The reaction mixture was cooled to room temperature and concentrated under reduced pressure. The mixture was treated with water (30 mL) and extracted with ethyl acetate (2×50 mL). The organic layer was washed with brine (50 mL), dried over anhydrous $Na_2SO_4$ and concentrated. The residue was purified by column chromatography on silica gel with 14% EtOAc/PE to afford II-A4 (1.5 g, 4.3 mmol, 76% yield) as a solid. LCMS: 349.1 (M+H), Rt 2.64 min Column: ZORBAX XDB C-18 (50×4.6 mm), 3.5 μm Mobile Phase: A: 0.1% HCOOH in water:ACN (95:5), B: ACN; Flow Rate:1.5 mL/min.

II-A5: To a stirred solution of II-A4 (700 mg, 2.01 mmol) in DCM (14.0 mL) was added TFA (0.77 mL) at 0° C. The reaction mixture was slowly warmed to room temperature and stirred for 2 h. The mixture was concentrated under reduced pressure and treated with ice water (10 mL). The mixture was treated with 10% $Na_2CO_3$ solution (5.0 mL) and extracted with ethyl acetate (2×25 mL). The organic layer was washed with brine (25 mL), dried over anhydrous $Na_2SO_4$ and concentrated to afford II-A5 (280 mg). The compound was used for the next step without further purification.

II-1: To a stirred solution of 2-methylpropan-2-amine (44 mg, 0.60 mmol) in DCM (10.0 mL) was added $Et_3N$ (0.1 mL, 0.72 mmol) followed by triphosgene (59 mg, 0.20 mmol) at 0° C. The reaction mixture was stirred for 10 min and II-A5 (150 mg, 0.60 mmol) in DCM (2.0 mL) was added at 0° C. The reaction mixture was warmed to room temperature and stirred for 2 h. The reaction mixture was treated with 10% $NaHCO_3$ solution (30 mL) and extracted with ethyl acetate (2×50 mL). The organic layer was washed with brine (25 mL), dried over anhydrous $Na_2SO_4$ and concentrated. The residue was purified by preparative HPLC to afford Compound II-1 (40 mg, 0.12 mmol, 19% yield) as a solid. Prep. HPLC method: Rt 12.5; Column: X-Bridge (150×19 mm), 5.0 μm; Mobile phase: 0.1% TFA in water/acetonitrile; Flow Rate: 15.0 mL/min. HPLC: Rt 4.67 min, 99.4% Column: X-Bridge C8 (50×4.6) mm, 3.5 μm Mobile phase: A: 0.1% TFA in water, B: 0.1% TFA in ACN; Flow Rate: 2.0 mL/min. LCMS: 348.2 (M+H), Rt 2.34 min, Column: ZORBAX XDB C-18 (50×4.6 mm), 3.5 μm Mobile Phase: A: 0.1% HCOOH in water:ACN (95:5), B: ACN; Flow Rate:1.5 mL/min. $^1H$ NMR (400 MHz, $CD_3OD$): $\delta_H$=8.28 (dd, 1H), 7.51 (dd, 1H), 7.33-7.32 (m, 1H), 5.36-5.30 (m, 1H), 5.15 (q, 1H), 1.59 (d, 3H), 1.38 (d, 6H), 1.32 (s, 9H).

Example II-2. Synthesis of Compound II-2

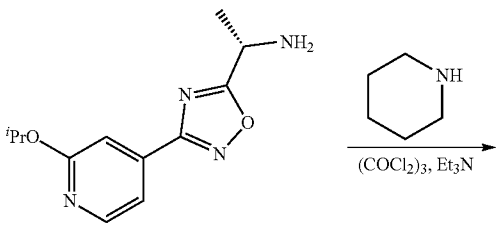

II-A5

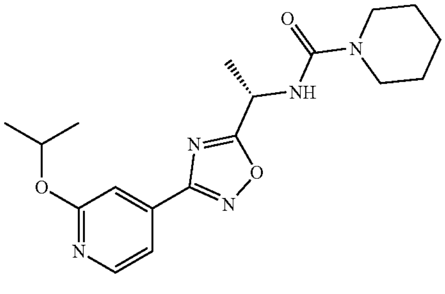

II-2

To a stirred solution of (S)-1-(3-(2-isopropoxypyridin-4-yl)-1,2,4-oxadiazol-5-yl)ethan-1-amine (II-A5, 150 mg, 0.60 mmol) and piperidine (0.06 mL, 0.60 mmol) in DCM (8.0 mL) was added $Et_3N$ (0.1 mL, 0.72 mmol) at 0° C. The reaction mixture was stirred for 10 min and triphosgene (59 mg, 0.20 mmol) was added. The reaction mixture was slowly warmed to room temperature and stirred for 1 h. The reaction mixture was treated with 10% $NaHCO_3$ solution (20 mL) and extracted with DCM (2×30 mL). The organic layer was washed with brine (25 mL), dried over anhydrous $Na_2SO_4$ and concentrated. The residue was purified by preparative HPLC to afford Compound II-2 (86 mg, 0.24 mmol, 40% yield) as a solid. Prep. HPLC method: Rt 11.5; Column: X-Bridge (150×19 mm), 5.0 μm; Mobile phase: 0.1% TFA in water/acetonitrile; Flow Rate: 15.0 mL/min. HPLC: Rt 4.28 min, 99.5% Column: X-Bridge C8 (50×4.6) mm, 3.5 μm Mobile phase: A: 0.1% TFA in water, B: 0.1% TFA in ACN; Flow Rate: 2.0 mL/min. LCMS: 360.2 (M+H), Rt 2.31 min, Column: ZORBAX XDB C-18 (50×4.6 mm), 3.5 μm Mobile Phase: A: 0.1% HCOOH in water:ACN (95:5), B: ACN; Flow Rate:1.5 mL/min. $^1H$ NMR (400 MHz, $CD_3OD$): $\delta_H$=8.28 (d, 1H), 7.52 (dd, 1H), 7.36 (s, 1H), 5.35-5.29 (m, 1H), 5.20 (q, 1H), 3.43 (t, 4H), 1.66-1.58 (m, 9H), 1.38 (d, 6H).

Example II-3. Synthesis of Compound II-3

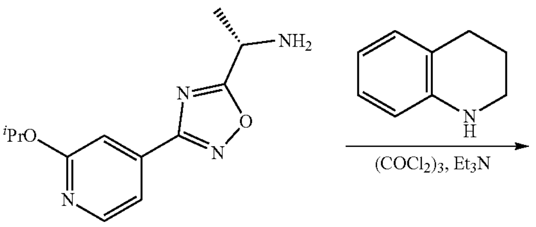

II-A5

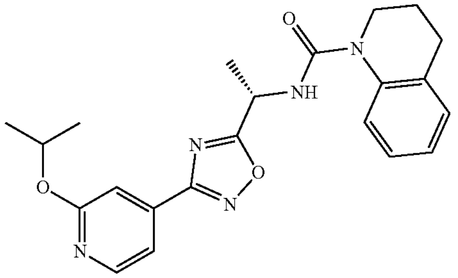

II-3

To a stirred solution of (S)-1-(3-(2-isopropoxypyridin-4-yl)-1,2,4-oxadiazol-5-yl)ethan-1-amine (II-A5, 150 mg, 0.60 mmol) and 1,2,3,4-tetrahydroquinoline (80 mg, 0.60 mmol) in DCM (10.0 mL) was added $Et_3N$ (0.1 mL, 0.72 mmol) at 0° C. The reaction mixture was stirred for 10 min and triphosgene (59 mg, 0.20 mmol) was added. The reaction mixture was slowly warmed to room temperature and stirred for 1 h. The reaction mixture was treated with 10% $NaHCO_3$ solution (20 mL) and extracted with DCM (2×30 mL). The organic layer was washed with brine (30 mL), dried over anhydrous $Na_2SO_4$ and concentrated. The residue was purified by preparative HPLC to afford Compound II-3 (30 mg, 0.07 mmol, 12% yield) as a solid. Prep. HPLC method: Rt 13.5; Column: YMC-C18 (150×19 mm), 5.0 μm; Mobile phase: 10 mM $NH_4OAc$ in water/acetonitrile; Flow Rate: 15.0 mL/min. HPLC: Rt 5.15 min, 98.5% Column: X-Bridge C8 (50×4.6) mm, 3.5 μm Mobile phase: A: 0.1% TFA in water, B: 0.1% TFA in ACN; Flow Rate: 2.0 mL/min. LCMS: 408.3 (M+H), Rt 2.72 min, Column: ZORBAX XDB C-18 (50×4.6 mm), 3.5 μm Mobile Phase: A: 0.1% HCOOH in water:ACN (95:5), B: ACN; Flow Rate:1.5 mL/min. $^1H$ NMR (400 MHz, $CD_3OD$): $\delta_H$=8.28 (d, 1H), 7.52-7.48 (m, 2H), 7.32 (d, 1H), 7.22-7.18 (m, 2H), 7.06 (t, 1H), 5.36-5.26 (m, 2H), 3.78-3.66 (m, 2H), 2.80 (t, 2H), 2.02-1.96 (m, 2H), 1.69 (d, 3H), 1.37 (d, 6H).

Example II-4. Synthesis of Compound II-4

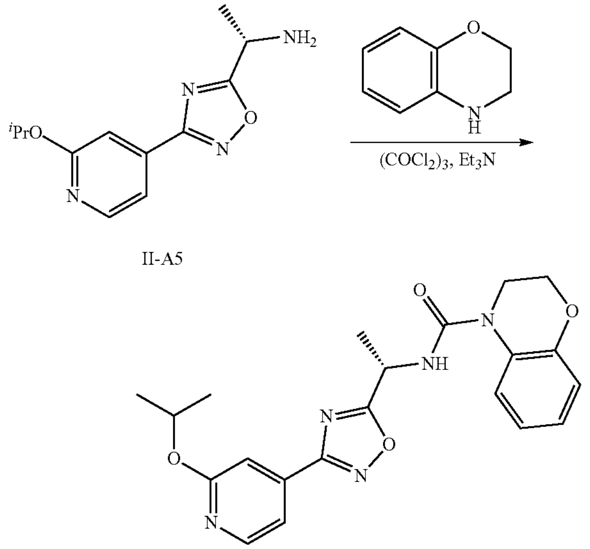

II-A5

II-4

To a stirred solution of (S)-1-(3-(2-isopropoxypyridin-4-yl)-1,2,4-oxadiazol-5-yl)ethan-1-amine (II-A5, 150 mg, 0.60 mmol) and 3,4-dihydro-2H-benzo[b][1,4]oxazine (80 mg, 0.60 mmol) in DCM (10.0 mL) was added $Et_3N$ (0.1 mL, 0.72 mmol) at 0° C. The reaction mixture was stirred for 10 min and triphosgene (59 mg, 0.20 mmol) was added. The reaction mixture was slowly warmed to room temperature and stirred for 1 h. The reaction mixture was treated with 10% $NaHCO_3$ solution (30 mL) and extracted with DCM (2×40 mL). The organic layer was washed with brine (30 mL), dried over anhydrous $Na_2SO_4$ and concentrated. The residue was purified by preparative HPLC to afford Compound II-4 (75 mg, 0.18 mmol, 30% yield) as a solid. Prep. HPLC method: Rt 7.9; Column: Atlantis C-18 (150×19 mm), 5.0 μm; Mobile phase: 0.1% TFA in water/acetonitrile; Flow Rate: 15.0 mL/min. HPLC: Rt 4.95 min, 97.6% Column: X-Bridge C8 (50×4.6) mm, 3.5 μm Mobile phase: A: 0.1% TFA in water, B: 0.1% TFA in ACN; Flow Rate: 2.0 mL/min. LCMS: 410.2 (M+H), Rt 2.61 min, Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1H$ NMR (400 MHz, $CD_3OD$): $\delta_H$=8.28 (d, 1H), 7.57 (d, 1H), 7.51 (d, 1H), 7.33 (s, 1H), 7.05-7.01 (m, 1H), 6.94-6.90 (m, 2H), 5.36-5.28 (m, 2H), 4.32-4.29 (m, 2H), 3.92-3.78 (m, 2H), 1.71 (d, 3H), 1.37 (d, 6H).

Example II-5. Synthesis of Compound II-5

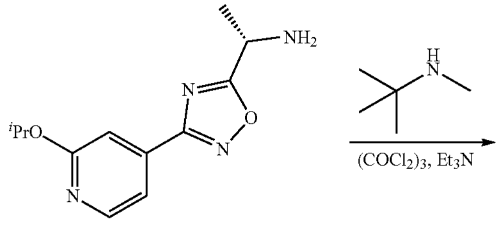

II-A5

-continued

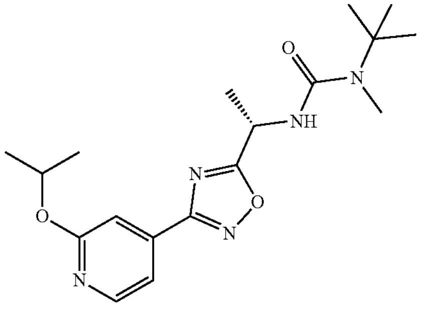

II-5

To a stirred solution of N,2-dimethylpropan-2-amine (52 mg, 0.60 mmol) in DCM (10.0 mL) was added $Et_3N$ (0.1 mL, 0.72 mmol) followed by triphosgene (59 mg, 0.20 mmol) at 0° C. The reaction mixture was stirred for 30 min and (S)-1-(3-(2-isopropoxypyridin-4-yl)-1,2,4-oxadiazol-5-yl)ethan-1-amine (II-A5, 150 mg, 0.60 mmol) in DCM (3.0 mL) was added at 0° C. The reaction mixture was warmed to room temperature and stirred for 3 h. The reaction mixture was treated with 10% $NaHCO_3$ solution (30 mL) and extracted with DCM (2×50 mL). The organic layer was washed with brine (25 mL), dried over anhydrous $Na_2SO_4$ and concentrated. The residue was purified by preparative HPLC to afford Compound II-5 (20 mg, 0.05 mmol, 9% yield) as a solid. Prep. HPLC method: Rt 10.1; Column: YMC-C18 (150×19 mm), 5.0 μm; Mobile phase: 10 mM $NH_4OAc$ in water/acetonitrile; Flow Rate: 15.0 mL/min. HPLC: Rt 4.92 min, 97.2% Column: X-Bridge C8 (50×4.6) mm, 3.5 μm Mobile phase: A: 0.1% HCOOH in water, B: ACN; Flow Rate: 2.0 mL/min. LCMS: 362.3 (M+H), Rt 2.55 min, Column: ZORBAX XDB C-18 (50×4.6 mm), 3.5 μm Mobile Phase: A: 0.1% HCOOH in water:ACN (95:5), B: ACN; Flow Rate:1.5 mL/min. $^1H$ NMR (400 MHz, $CD_3OD$): $\delta_H$=8.28 (dd, 1H), 7.51 (dd, 1H), 7.31 (d, 1H), 5.36-5.30 (m, 1H), 5.15 (q, 1H), 2.97 (s, 3H), 1.65 (d, 3H), 1.40 (s, 9H), 1.38 (d, 6H).

Example 6. Synthesis of Compound II-6

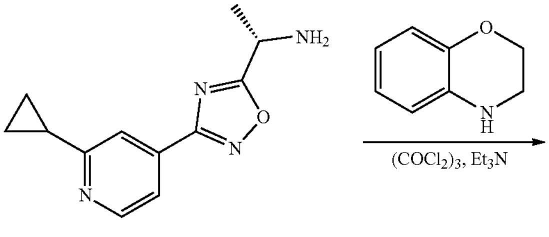

II-A6

-continued

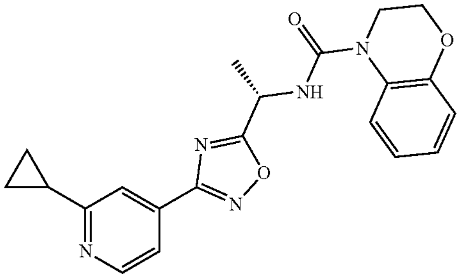

II-6

To a stirred solution of 3,4-dihydro-2H-benzo[b][1,4] oxazine (65 mg, 0.48 mmol) in DCM (8.0 mL) was added $Et_3N$ (0.18 mL, 1.3 mmol) followed by triphosgene (42 mg, 0.14 mmol) at 0° C. The reaction mixture was stirred for 30 min and (S)-1-(3-(2-cyclopropylpyridin-4-yl)-1,2,4-oxadiazol-5-yl)ethan-1-amine (II-A6, 100 mg, 0.43 mmol) in DCM (3.0 mL) was added at 0° C. The reaction mixture was warmed to room temperature and stirred for 16 h. The reaction mixture was treated with 10% $NaHCO_3$ solution (30 mL) and extracted with DCM (2×50 mL). The organic layer was washed with brine (25 mL), dried over anhydrous $Na_2SO_4$ and concentrated. The residue was purified by preparative HPLC to afford Compound II-6 (40 mg, 0.10 mmol, 23% yield) as a solid. Prep. HPLC method: Rt 9.6; Column: Atlantis C-18 (150×19 mm), 5.0 μm; Mobile phase: 0.1% TFA in water/acetonitrile; Flow Rate: 15.0 mL/min. HPLC: Rt 3.15 min, 99.5% Column: X-Bridge C8 (50×4.6) mm, 3.5 μm Mobile phase: A: 0.1% TFA in water, B: 0.1% TFA in ACN; Flow Rate: 2.0 mL/min. LCMS: 392.3 (M+H), Rt 2.13 min, Column: ZORBAX XDB C-18 (50×4.6 mm), 3.5 μm Mobile Phase: A: 0.1% HCOOH in water:ACN (95:5), B: ACN; Flow Rate:1.5 mL/min. $^1H$ NMR (400 MHz, $CD_3OD$): $\delta_H$=8.53 (d, 1H), 7.84 (d, 1H), 7.75 (dd, 1H), 7.56 (d, 1H), 7.01 (dd, 1H), 6.93-6.89 (m, 2H), 5.30 (q, 1H), 4.30-4.28 (m, 2H), 3.87-3.82 (m, 2H), 2.22-2.18 (m, 1H), 1.71 (d, 3H), 1.11-1.03 (m, 4H).

Example II-7. Synthesis of Compound II-7

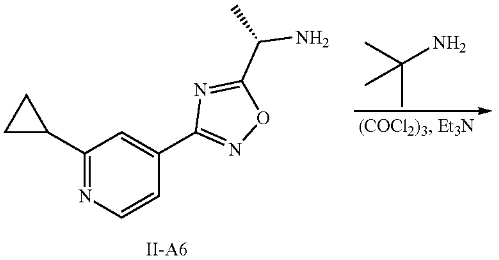

II-A6

-continued

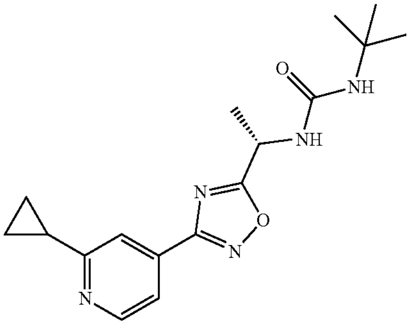

II-7

To a stirred solution of 2-methylpropan-2-amine (35 mg, 0.48 mmol) in DCM (8.0 mL) was added $Et_3N$ (0.18 mL, 1.3 mmol) followed by triphosgene (42 mg, 0.14 mmol) at 0° C. The reaction mixture was stirred for 30 min and (S)-1-(3-(2-cyclopropylpyridin-4-yl)-1,2,4-oxadiazol-5-yl)ethan-1-amine (II-A6, 100 mg, 0.43 mmol) in DCM (3.0 mL) was added at 0° C. The reaction mixture was warmed to room temperature and stirred for 2 h. The reaction mixture was treated with 10% $NaHCO_3$ solution (30 mL) and extracted with DCM (2×50 mL). The organic layer was washed with brine (25 mL), dried over anhydrous $Na_2SO_4$ and concentrated. The residue was purified by preparative HPLC to afford Compound II-7 (20 mg, 0.06 mmol, 14% yield) as a solid. Prep. HPLC method: Rt 11.3; Column: YMC-C18 (150×19 mm), 5.0 μm; Mobile phase: 10 mM $NH_4OAc$ in water/acetonitrile; Flow Rate: 15.0 mL/min. HPLC: Rt 2.67 min, 99.8% Column: X-Bridge C8 (50×4.6) mm, 3.5 μm Mobile phase: A: 0.1% TFA in water, B: 0.1% TFA in ACN; Flow Rate: 2.0 mL/min. LCMS: 330.2 (M+H), Rt 1.75 min, Column: ZORBAX XDB C-18 (50×4.6 mm), 3.5 μm Mobile Phase: A: 0.1% HCOOH in water:ACN (95:5), B: ACN; Flow Rate:1.5 mL/min. 1H NMR (400 MHz, $CD_3OD$): $\delta_H$=8.53 (d, 1H), 7.83 (s, 1H), 7.74 (dd, 1H), 5.14 (q, 1H), 2.22-2.17 (m, 1H), 1.59 (d, 3H), 1.32 (s, 9H), 1.11-1.04 (m, 4H).

Example II-8. Synthesis of Compound II-8

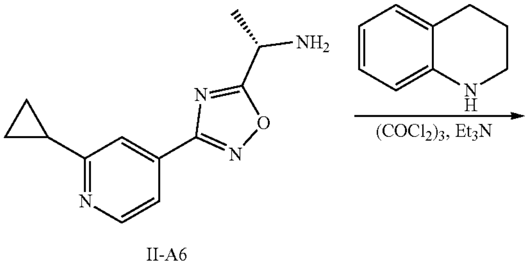

II-A6

-continued

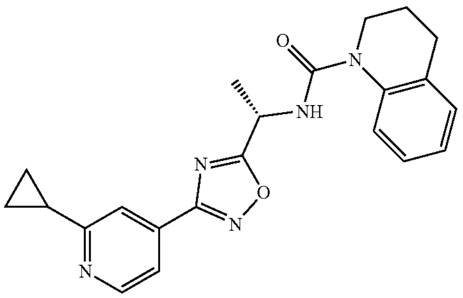

II-8

To a stirred solution of 1,2,3,4-tetrahydroquinoline (65 mg, 0.48 mmol) in DCM (8.0 mL) was added $Et_3N$ (0.18 mL, 1.3 mmol) followed by triphosgene (42 mg, 0.14 mmol) at 0° C. The reaction mixture was stirred for 30 min and (S)-1-(3-(2-cyclopropylpyridin-4-yl)-1,2,4-oxadiazol-5-yl) ethan-1-amine (II-A6, 100 mg, 0.43 mmol) in DCM (3.0 mL) was added at 0° C. The reaction mixture was warmed to room temperature and stirred for 16 h. The reaction mixture was treated with 10% $NaHCO_3$ solution (30 mL) and extracted with DCM (2×50 mL). The organic layer was washed with brine (25 mL), dried over anhydrous $Na_2SO_4$ and concentrated. The residue was purified by preparative HPLC to afford Compound II-8 (57 mg, 0.14 mmol, 33% yield) as a solid. Prep. HPLC method: Rt 6.6; Column: X-Bridge (150×19 mm), 5.0 µm; Mobile phase: 0.1% TFA in water/acetonitrile; Flow Rate: 15.0 mL/min. HPLC: Rt 3.53 min, 99.4% Column: X-Bridge C8 (50×4.6) mm, 3.5 µm Mobile phase: A: 0.1% TFA in water, B: 0.1% TFA in ACN; Flow Rate: 2.0 mL/min. LCMS: 390.2 (M+H), Rt 2.26 min, Column: ZORBAX XDB C-18 (50×4.6 mm), 3.5 µm Mobile Phase: A: 0.1% HCOOH in water:ACN (95:5), B: ACN; Flow Rate: 1.5 mL/min. $^1H$ NMR (400 MHz, $CD_3OD$): $\delta_H$=8.54 (d, 1H), 7.85 (s, 1H), 7.76 (dd, 1H), 7.50 (d, 1H), 7.22-7.18 (m, 2H), 7.06 (t, 1H), 5.30 (q, 1H), 3.78-3.70 (m, 2H), 2.80 (t, 2H), 2.23-2.19 (m, 1H), 2.02-1.98 (m, 2H), 1.70 (d, 3H), 1.12-1.04 (m, 4H).

Example II-9. Synthesis of Compound II-9

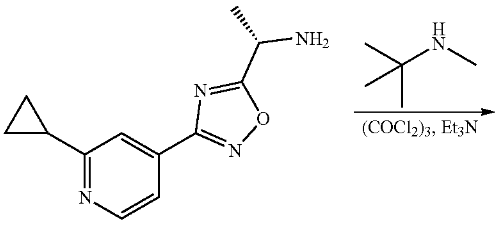

II-A6

-continued

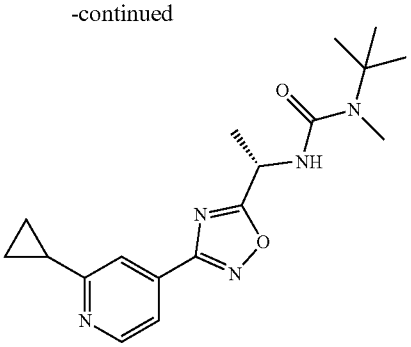

II-9

To a stirred solution of N,2-dimethylpropan-2-amine (57 mg, 0.65 mmol) in DCM (10.0 mL) was added $Et_3N$ (0.11 mL, 0.78 mmol) followed by triphosgene (64 mg, 0.21 mmol) at 0° C. The reaction mixture was stirred for 30 min and (S)-1-(3-(2-cyclopropylpyridin-4-yl)-1,2,4-oxadiazol-5-yl)ethan-1-amine (II-A6, 150 mg, 0.65 mmol) in DCM (3.0 mL) was added at 0° C. The reaction mixture was warmed to room temperature and stirred for 3 h. The reaction mixture was treated with 10% $NaHCO_3$ solution (30 mL) and extracted with DCM (2×50 mL). The organic layer was washed with brine (25 mL), dried over anhydrous $Na_2SO_4$ and concentrated. The residue was purified by preparative HPLC to afford Compound II-9 (6.5 mg, 0.02 mmol, 3% yield) as a liquid. Prep. HPLC method: Rt 7.4; Column: X-Bridge (150×19 mm), 5.0 µm; Mobile phase: 0.1% TFA in water/acetonitrile; Flow Rate: 15.0 mL/min. HPLC: Rt 2.86 min, 93.7% Column: X-Bridge C8 (50×4.6) mm, 3.5 µm Mobile phase: A: 0.1% TFA in water, B: 0.1% TFA in ACN; Flow Rate: 2.0 mL/min. LCMS: 344.3 (M+H), Rt 1.97 min, Column: ZORBAX XDB C-18 (50×4.6 mm), 3.5 µm Mobile Phase: A: 0.1% HCOOH in water:ACN (95:5), B: ACN; Flow Rate:1.5 mL/min. $^1H$ NMR (400 MHz, $CD_3OD$): $\delta_H$=8.54 (dd, 1H), 7.85 (dd, 1H), 7.76 (dd, 1H), 5.16 (q, 1H), 2.98 (s, 3H), 2.23-2.21 (m, 1H), 1.66 (d, 3H), 1.41 (s, 9H), 1.12-1.05 (m, 4H).

Example II-10. Synthesis of Compound II-10

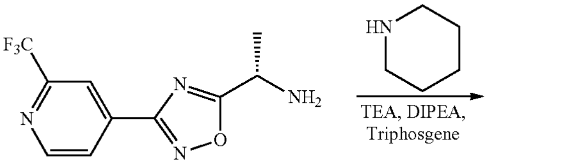

II-A7

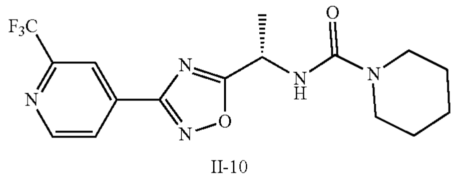

II-10

To a stirred solution of triphosgene (60.43 mg, 0.20 mmol) in DCM (10 mL) was added A7 (100 mg, 0.34 mmol), triethylamine (102.83 mg, 1.02 mmol) at 0° C. and stirred at RT for 2 h. The reaction was quenched using water (5 mL) and diluted with DCM (10 mL). Organic layer was washed with brine solution, dried over $MgSO_4$ and evaporated to obtain a residue. The residue was diluted with DCM (10 mL) and transferred into piperidine (34.68 mg, 0.41 mmol), DIPEA (0.18 mL, 1.02 mmol) in DCM (10 mL) at 0° C. and stirred at RT 12 h. The reaction mixture was diluted with water (5 mL) and DCM (10 mL). Combined organic layer washed, with saturated brine solution and dried over $MgSO_4$ then concentrated to afford a a residue. The a residue was purified by flash column chromatography eluting 50% EtOAc in hexane to afford desired Compound II-10 (4 mg, 0.10 mmol, 31% yield) as a solid. HPLC: Rt:6.93 min, 99.6% Column: X-Bridge C18 (4.6x150) mm, 5 μm Mobile phase: A: 0.1% $NH_3$ in water: B: ACN; Flow Rate: 1.0 mL/min. LCMS: 370.15 (M+H), Rt 1.87 min, Column: X-select CSH C18 (3*50) mm, 2.5 μm. $^1$H NMR (400 MHz, DMSO): $\delta_H$=9.01 (d, 1H), 8.26-8.25 (m, 2H), 7.21 (d, 1H), 5.12-5.09 (m, 1H), 1.57-1.55 (m, 5H), 1.46 (bs, 4H), (4 proton merged in solvent).

Example II-11. Synthesis of Compound II-11

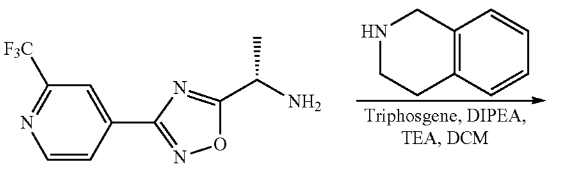

II-A7

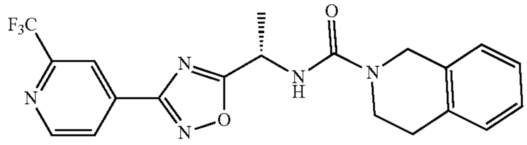

II-11

To a stirred solution of triphosgene (120 mg, 0.40 mmol) in DCM (10 mL) was added II-A7 (200 mg, 0.68 mmol), triethylamine (0.28 mL, 2.03 mmol) at 0° C. and stirred at RT for 2 h. The reaction was quenched using water (5 mL) and diluted with DCM (10 mL). The organic layer was separated, washed with brine solution, dried over $MgSO_4$ and evaporated to obtain The residue. The residue was diluted with DCM (10 mL) and transferred into 1,2,3,4-tetrahydroisoquinoline (140 mg, 1.01 mmol), DIPEA (0.35 mL, 2.03 mmol) in DCM (10 mL) at 0° C. and stirred at RT 12 h. The reaction mixture was diluted with water (5 mL) and DCM (10 mL). The combined organic layer washed with saturated brine solution, dried over $MgSO_4$ and evaporated to afford a a residue. The a residue was purified by flash column chromatography eluting 50% EtOAc in hexane to afford desired Compound II-11 (75 mg, 0.17 mmol, 26% yield) as a solid. HPLC: Rt 8.71 min, 99.9% Column: X-Select CSH C18 (4.6x150) mm, 3.5 μm Mobile phase: A: 0.1% Formic acid in water:ACN (95:05), B: ACN; Flow Rate: 1.0 mL/min. LCMS: 418.20 (M+H), Rt 2.01 min, Column: X-select CSH C18 (3*50) mm, 2.5 μm. $^1$H NMR (400 MHz, DMSO): $\delta_H$=9.00 (d, 1H), 8.26-8.25 (m, 2H), 7.41 (d, 1H), 7.17-7.13 (m, 4H), 5.20-5.17 (m, 1H), 4.53 (s, 2H), 3.59 (bs, 2H), 2.81-2.79 (m, 2H), 1.60 (d, 3H).

Example II-12. Synthesis of Compound II-12

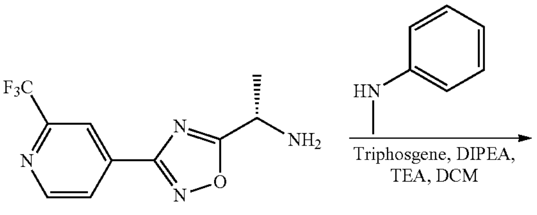

II-A7

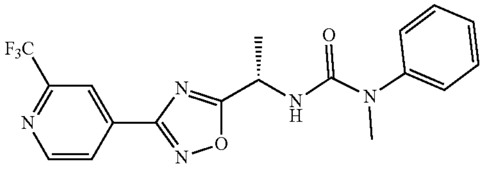

II-12

To a stirred solution of triphosgene (120 mg, 0.41 mmol) in DCM (10 mL) was added II-A7 (200 mg, 0.68 mmol) and triethylamine (210 mg, 2.04 mmol) at 0° C. and stirred at RT for 2 h. The reaction was quenched using water (5 mL) and diluted with DCM (10 mL). The organic layer was washed with brine solution, dried over $MgSO_4$ and evaporated to obtain The residue. The The residue was diluted with DCM (10 mL) and poured into N-methylaniline (110 mg, 1.02 mmol), DIPEA (0.35 mL, 2.04 mmol) in DCM (10 mL) at 0° C. and stirred at RT 12 h. The reaction mass was diluted with water (5 mL) and DCM (10 mL). Combined organic layer washed with saturated brine solution and dried over ($MgSO_4$) then evaporated to afford a a residue. The a residue was purified by flash column chromatography eluting 50% EtOAc in hexane to afford desired Compound II-12 (115 mg, 0.29 mmol, 43% yield) as a solid. HPLC: Rt 8.51 min, 99.4% Column: X-Select CSH C18 (4.6x150) mm, 5 μm Mobile phase: A: 0.1% Formic acid in water:ACN (95:05), B: ACN; Flow Rate: 1.0 mL/min. LCMS: 392.20 (M+H), Rt 1.98 min, Column: X-select CSH C18 (3*50) mm, 2.5 μm. $^1$H NMR (400 MHz, DMSO): $\delta_H$=9.02 (d, 1H), 8.28 (bs, 2H), 7.42-7.22 (m, 5H), 6.94 (d, 1H), 5.21-5.14 (m, 1H), 3.19 (s, 3H), 1.57 (d, 3H).

Example II-13. Synthesis of II-A6 (tert-butyl (S)-(1-(3-(2-cyclopropylpyridin-4-yl)-1,2,4-oxadiazol-5-yl)ethyl)carbamate)

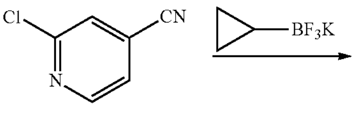

II-A1

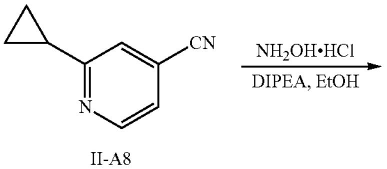

II-A8

-continued

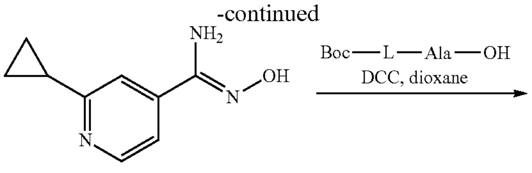

II-A9

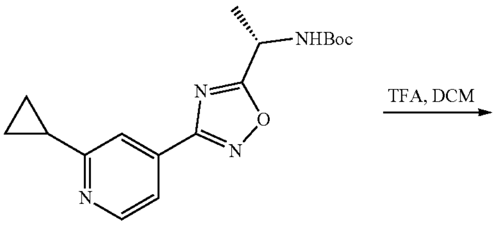

II-A10

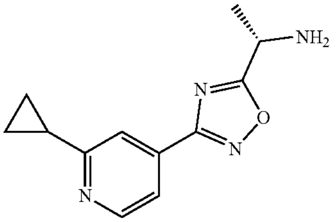

II-A6

II-A8: To a solution of II-A1 (2-chloropyridine-4-carbonitrile) (2.0 g, 14.4 mmol) in 1,4-dioxane (25 mL) was added potassium cyclopropyltrifluoroborate (6.41 g, 43.3 mmol) followed by $K_2CO_3$ (7.98 g, 57.7 mmol) and RuPhos (1.35 g, 2.89 mmol). The resulting mixture was degassed with $N_2$ gas for 10 min and $Pd(OAc)_2$ (324 mg, 1.44 mmol) was added. The mixture was stirred at 100° C. for 1 h. The reaction mixture was cooled to room temperature and filtered through celite. The filtrate was concentrated under reduced pressure and the residue was purified by column chromatography on silica gel with 15% EtOAc/PE to afford II-A8 (1.1 g, 7.6 mmol, 50% yield) as a solid. LCMS: 145.1 (M+H), Rt 1.87 min Column: ZORBAX XDB C-18 (50×4.6 mm), 3.5 μm Mobile Phase: A: 0.1% TFA in water:ACN (95:5), B: 0.1% TFA in ACN; Flow Rate:1.5 mL/min.

II-A9: To a solution of II-A8 (450 mg, 3.1 mmol) in ethanol (15.0 mL) was added hydroxylamine hydrochloride (312 mg, 4.4 mmol) followed by DIPEA (1.49 mL, 8.99 mmol) at room temperature. The reaction mixture was heated at 80° C. for 5 h. The reaction mixture was cooled to room temperature and concentrated under reduced pressure. The residue was treated with water (30 mL) followed by saturated sodium bicarbonate solution (20 mL) and extracted with ethyl acetate (2×25 mL). The organic layer was washed with brine (10 mL), dried over $Na_2SO_4$ and concentrated to afford II-A9 (420 mg) as a solid. It was used for the next step without further purification.

II-A10: To a solution of (2S)-2-(tert-butoxycarbonylamino)propanoic acid (0.44 g, 2.31 mmol) in 1,4-dioxane (10.0 mL) was added II-A9 (0.41 g, 2.31 mmol) followed by DCC (0.52 g, 2.55 mmol). The resulting mixture was stirred at 100° C. for 16 h. The reaction mixture was cooled to room temperature and concentrated under reduced pressure. The mixture was treated with water (30 mL) and extracted with ethyl acetate (2×25 mL). The organic layer was washed with brine (20 mL), dried over $Na_2SO_4$ and concentrated. The residue was purified by column chromatography on silica gel with 15% ethyl acetate/PE to afford II-A10 (570 mg, 1.72 mmol, 74% yield) as a solid. LCMS: 331.3 (M+H), Rt 2.22 min Column: ZORBAX XDB C-18 (50×4.6 mm), 3.5 μm Mobile Phase: A: 0.1% TFA in water:ACN (95:5), B: 0.1% TFA in ACN; Flow Rate:1.5 mL/min.

II-A6: To a solution of tert-butyl II-A10 (410 mg, 1.24 mmol) in DCM (5.0 mL) was added TFA (1.36 mL) at 0° C. The reaction mixture was slowly warmed to room temperature and stirred for 3 h. The mixture was concentrated under reduced pressure and treated with ice water (20 mL). The mixture was treated with 10% aqueous $NaHCO_3$ solution (5 mL) and extracted with EtOAc (2×25 mL). The organic layer was washed with brine (20 mL), dried over anhydrous $Na_2SO_4$ and concentrated to afford II-A6 (240 mg).

Example II-A. Synthesis of II-A7 ((1S)-1-[3-[2-(trifluoromethyl)-4-pyridyl]-1,2,4-oxadiazol-5-yl]ethanamine)

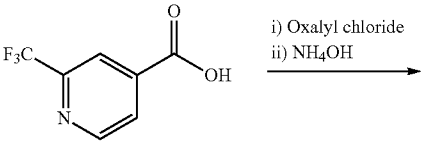

II-A11

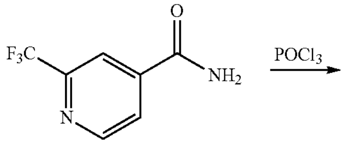

II-A12

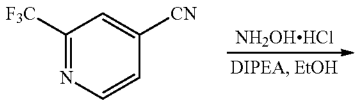

II-A13

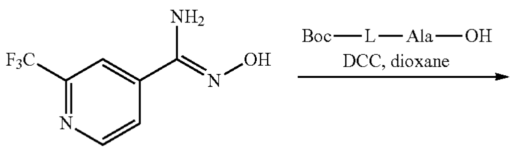

II-A14

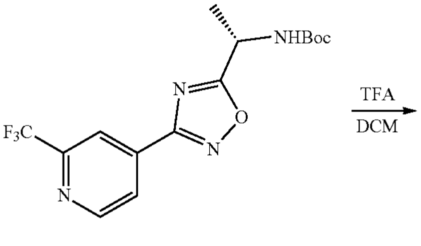

II-A15

-continued

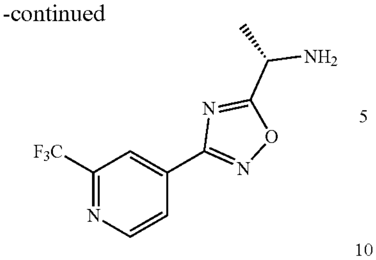

II-A7

II-A12: To a stirred solution of 2-(trifluoromethyl)pyridine-4-carboxylic acid (2.0 g, 10.47 mmol) in DCM (20.0 mL) was added oxalyl chloride (1.39 g, 10.99 mmol) and catalytic amount of DMF (0.05 mL) at 0° C. The reaction mixture was warmed to room temperature and stirred for 2 h. The reaction mixture was concentrated under reduced pressure and aqueous $NH_4OH$ (2.0 mL) was added at 0° C. dropwise followed by MeCN (10.0 mL). The reaction mixture was stirred at room temperature for 30 min and diluted with ethylacetate (100 mL). The organic layer was washed with water (2×50 mL), washed with brine (20 mL), dried over $Na_2SO_4$ and concentrated to afford II-A12 (1.3 g). The compound was used for the next step without further purification.

II-A13: $POCl_3$ (3.04 mL, 32.61 mmol) was added dropwise to the II-A12 (1.3 g, 6.84 mmol) at 0° C. The reaction mixture heated at 100° C. for 3 h. The reaction mixture was cooled to room temperature and treated with 50% NaOH solution (10 mL). The reaction mixture was diluted with water (50 mL) and extracted with ethyl acetate (2×70 mL). The organic layer was washed with brine (40 mL), dried over $Na_2SO_4$ and concentrated. The residue was purified by column chromatography on silica gel with 8% ethyl acetate/PE to afford II-A13 (520 mg, 3.0 mmol, 44% yield). LCMS: 173.1 (M+H), Rt 1.84 min Column: ZORBAX XDB C-18 (50×4.6 mm), 3.5 μm Mobile Phase: A: 0.1% HCOOH in water:ACN (95:5), B: ACN; Flow Rate:1.5 mL/min.

II-A14: To a stirred solution of II-A13 (520 mg, 3.02 mmol) in ethanol (10.0 mL) was added hydroxylamine hydrochloride (314 mg, 4.53 mmol) and DIPEA (1.58 mL, 9.05 mmol) at room temperature under nitrogen atmosphere. The reaction mixture was heated at 80° C. for 2 h. The reaction mixture was cooled to room temperature and concentrated under reduced pressure. The residue was treated with water (15 mL) followed by saturated sodium bicarbonate solution (10 mL) and extracted with ethyl acetate (2×30 mL). The organic layer was washed with brine (20 mL), dried over $Na_2SO_4$ and concentrated to afford II-A14 (580 mg). It was used for the next step without further purification.

II-A15: To a stirred solution of II-A14 (580 mg, 2.83 mmol) in 1,4-dioxane (20.0 mL) was added (2S)-2-(tert-butoxycarbonylamino)propanoic acid (534 mg, 2.83 mmol) and DCC (640 mg, 3.11 mmol). The reaction mixture was stirred at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The residue was purified by column chromatography on silica gel with 12% ethyl acetate/PE to afford II-A15 (840 mg, 2.34 mmol, 82% yield). LCMS: 359.2 (M+H), Rt 2.42 min Column: ZORBAX XDB C-18 (50×4.6 mm), 3.5 μm Mobile Phase: A: 0.1% HCOOH in water:ACN (95:5), B: ACN; Flow Rate:1.5 mL/min.

II-A7: To a stirred solution of II-A15 (400 mg, 1.12 mmol) in DCM (8.0 mL) was added TFA (1.5 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford II-A7 (260 mg).

Example III-1: (S)-2-(dimethylamino)-N-(1-(3-(2-(trifluoromethyl)pyridin-4-yl)-1,2,4-oxadiazol-5-yl)ethyl)acetamide (III-1)

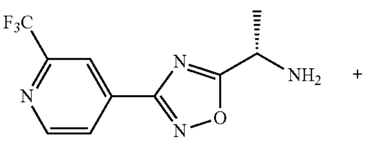

III-A1 •HCl

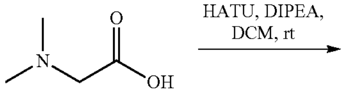

III-A2

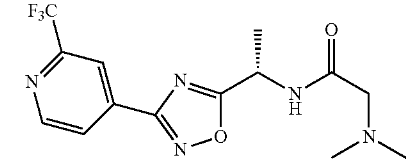

III-1

To a stirred solution of III-A2 (42 mg, 0.41 mmol) and III-A1 (0.1 g, 0.34 mmol) in DCM (2 mL) were added DIPEA (0.18 mL, 1.02 mmol) and HATU (193.6 mg, 0.51 mmol) at RT and stirred at RT for 2 h. The reaction mixture was quenched using water (6 mL) and diluted with DCM. The organic layer was dried over sodium sulphate and evaporated to obtain a residue which was purified by prep HPLC to give III-1 (60 mg, 0.17 mmol, 51% yield) as a solid. HPLC: Rt 8.16 min, 99.5%; Column: X-Select CSH C18 (4.6×150) mm, 5 μm; Mobile phase: A: 10 mM Ammonium Bicarbonate in water, B: ACN; Int Volume:5 μL; Flow Rate: 1.0 mL/min. LCMS: 343.9 (M+H), Rt 1.33 min, Column: X-select CSH C18 (3×50) mm, 2.5 μm. $^1$H NMR (400 MHz, DMSO-d6) $\delta_H$=9.02 (d, 1H), 8.66 (d, 1H), 8.28-8.24 (m, 2H), 5.32 (p, 1H), 3.0-2.9 (m, 2H), 2.25 (s, 6H), 1.61 (d, 3H). Chiral method: Rt 9.15 min, 97.6%; column: DIACEL CHIRALPAK-IG (250×4.6 mm, 5 um), Mobile Phase: A) n-Hexane+0.1% Isopropylamine B) DCM:MeOH (1:1), Isocratic:20% B; Wavelength: 225 nm, Flow Rate: 1.0 mL/min.

Example III-2: (S)-3,3,3-trifluoro-N-(1-(3-(2-(trifluoromethyl)pyridin-4-yl)-1,2,4-oxadiazol-5-yl)ethyl)propenamide (III-2)

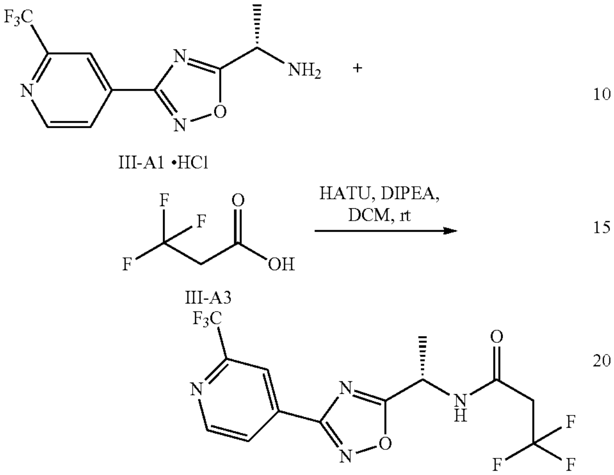

III-A1 •HCl

III-A3

III-2

To a stirred solution of III-A3 (52.1 mg, 0.41 mmol) and III-A1 (0.1 g, 0.34 mmol) in DCM (2 mL) were added DIPEA (0.18 mL, 1.02 mmol) and HATU (193.6 mg, 0.51 mmol) at RT and stirred at RT for 2 h. The reaction mixture was quenched using water (6 mL) and diluted with DCM. The organic layer was dried over sodium sulphate and evaporated to obtain the a residue which was purified by prep HPLC to give III-2 (55 mg, 0.15 mmol, 44% yield) as a solid. HPLC: Rt 8.22 min, 99%; Column: X-Select CSH C18 (4.6×150) mm, 3.5 μm; Mobile phase: A: 0.1% FA in water:ACN (95:05), B: ACN; Flow Rate: 1.0 mL/min. LCMS: 368.9 (M+H), Rt 1.95 min, Column: X-select CSH C18 (3×50) mm, 2.5 μm. $^1$H NMR (400 MHz, DMSO-d6) $\delta_H$=9.21 (d, 1H), 9.01 (d, 1H), 8.28-8.25 (m, 2H), 5.35-5.30 (m, 1H), 1.58 (d, 3H), 2H merged in solvent peak. Chiral method: Rt 7.45 min, 100%; column: DIACEL CHIRALPAK-IG (250×4.6 mm, 5 um), Mobile Phase: A) n-Hexane+0.1% Isopropylamine B) DCM:MeOH (1:1), Isocratic:20% B; Wavelength: 225 nm, Flow Rate: 1.0 mL/min.

Example III-3: (S)-3,3-dimethyl-N-(1-(3-(2-(trifluoromethyl)pyridin-4-yl)-1,2,4-oxadiazol-5-yl)ethyl)butanamide (III-3)

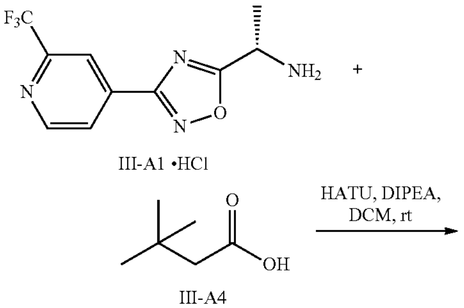

III-A1 •HCl

III-A4

-continued

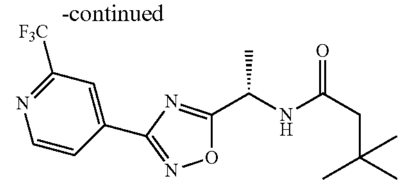

III-3

To a stirred solution of III-A4 (47.3 mg, 0.41 mmol) and III-A1 (0.1 g, 0.38 mmol) in DCM (2 mL) was added DIPEA (0.18 mL, 1.02 mmol) and HATU (193.6 mg, 0.51 mmol) at RT and stirred at RT for 2 h. The reaction mixture was quenched with water (2 mL×3) and diluted with DCM. The organic layer was dried over sodium sulphate and evaporated to give the a residue which was purified by column chromatography using 50% ethyl acetate in hexane to give III-3 (30 mg, 0.084 mmol, 25% yield) as a solid. HPLC: Rt 8.56 min, 99.7%; Column: X-Select CSH C18 (4.6×150) mm, 3.5 μm; Mobile phase: A: 0.1% FA in water:ACN (95:05), B: ACN; Flow Rate: 1.0 mL/min. LCMS: 357.4 (M+H), Rt 2.07 min, Column: X-select CSH C18 (3×50) mm, 2.5 μm. $^1$H NMR (400 MHz, DMSO-d6) $\delta_H$=9.02 (d, 1H), 8.67 (d, 1H), 8.28-8.24 (m, 2H), 5.25-5.20 (m, 1H), 2.10-2.00 (m, 2H), 1.56 (d, 3H), 0.98 (s, 9H). Chiral method: Rt 7.7 min, 100%; column: DIACEL CHIRALPAK-IG (250×4.6 mm, 5 um), Mobile Phase: A) n-Hexane+0.1% Isopropylamine B) DCM: MeOH (1:1), Isocratic:20% B; Wavelength: 225 nm, Flow Rate: 1.0 mL/min.

Example III-4: (S)-2-(methyl(phenyl)amino)-N-(1-(3-(2-(trifluoromethyl)pyridin-4-yl)-1,2,4-oxadiazol-5-yl)ethyl)acetamide (11I-4)

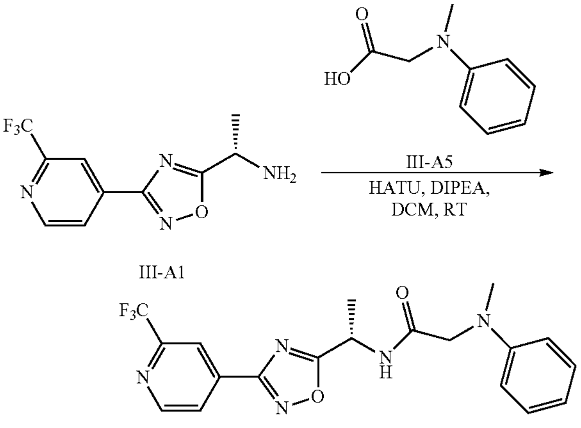

III-A1

III-4

To a stirred solution of III-A5 (67.27 mg, 0.41 mmol) in DCM (2 mL) was added DIPEA (0.18 mL, 1.02 mmol) and HATU (193.56 mg, 0.51 mmol) at RT and stirred for 10 min. To this solution was added III-A1 (100 mg, 0.34 mmol) and stirred at RT for 2 h. The reaction mixture was diluted with DCM (10 mL×2) and washed with water (10 mL). The organic layer was dried over anhydrous sodium sulphate, filtered and evaporated to give the a residue. The The residue was purified by prep. HPLC to give III-4 (75 mg, 0.181 mmol, 53% yield) as a solid. HPLC: Rt 8.950 min, 98%; Column: X-Select CSH C18 (4.6×150) mm, 5 μm; Mobile phase: A: 0.1% Formic acid in water:ACN (95:05), B: ACN; Flow Rate: 1.0 mL/min. LCMS: 406.4 (M+H), Rt 2.105 min, Column: X-select CSH C18 (3×50) mm, 2.5 μm. $^1$H NMR (400 MHz, DMSO-d6) $\delta_H$=9.03 (d, 1H), 8.87 (d, 1H), 8.28-8.24 (m, 2H), 7.18-7.12 (m, 2H), 6.67-6.61 (m, 3H), 5.32-5.26 (m, 1H), 3.99 (s, 2H), 2.99 (s, 3H), 1.58 (d, 3H). Chiral method: Rt 7.974 min, 94.9%; column: DIACEL CHIRALPAK-IG (250×4.6 mm, 5 um), –Mobile Phase: A) n-Hexane+0.1% Iso-propyl amine, B) Iso-propyl alcohol, Isocratic:50% B; Wavelength: 240 nm, Flow Rate: 1.0 mL/min.

Example III-5: Synthesis of (tert-butyl (S)-(1-(3-(2-cyclopropylpyridin-4-yl)-1,2,4-oxadiazol-5-yl)ethyl) carbamate (III-5)

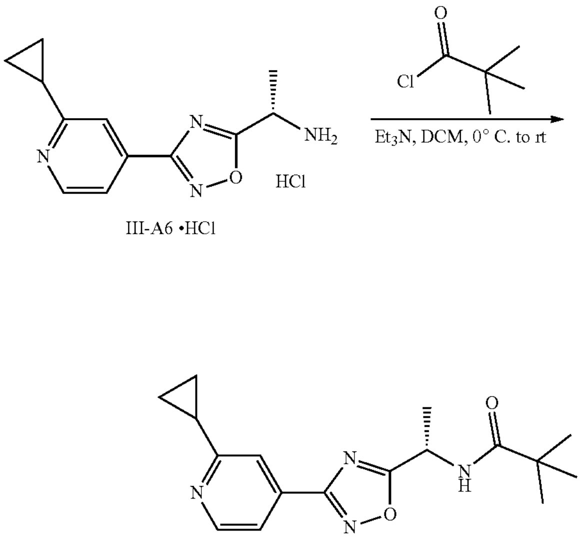

III-A6 •HCl

III-5

To a stirred solution of III-A6 (200 mg, 0.87 mmol) in DCM (3 mL) was added TEA (17.578 mg, 0.1737 mmol) dropwise, followed by pivaloyl chloride (104 mg, 0.8625 mmol) at 0° C. The reaction mixture was allowed to warm room temperature and continued stirring for 16 hrs. After completion of reaction (monitored by TLC and LCMS), the reaction mixture was quenched with water and extracted with DCM, washed with water followed by brine, dried over anhydrous $Na_2SO_4$, filtered and concentrated under reduced pressure. The The residue was purified by flash column chromatography eluting with 0-40% ethyl acetate in n-hexane to afford III-5 (18 mg, 0.0572 mmol, 7%) as a solid. HPLC: $R_t$=6.071 min, 99.91%. Column: XSELECT CSH C18 (150×4.6 mm, 3.5); Mobile Phase-A:0.05% TFA: ACETONITRILE (95:05); Mobile Phase-B:ACETONITRILE:0.05% TFA (95:05); Programme:T/B %: 0.01/10, 12/90, 16/90; Flow: 1.0 mL/min; Diluent:ACN:WATER. LCMS: 315.2 (M+H), $R_t$=1.945 min, 99.79%. Column:X-Bridge BEH C-18(3.0×50 mm, 2.5 m). CHIRAL HPLC: $R_t$=6.929 min, 98.67%. $^1$H NMR (400 MHz, DMSO-d6) $\delta_H$=8.60 (d, 1H), 8.24 (d, 1H), 8.83 (s, 1H), 7.69-7.57 (m, 1H), 5.27-5.18 (m, 1H), 2.30-2.22 (m, 1H), 1.58 (d, 3H), 1.14 (s, 9H), 1.07-0.91 (m, 4H).

Example III-A. Synthesis of Intermediates

Synthesis of III-A1

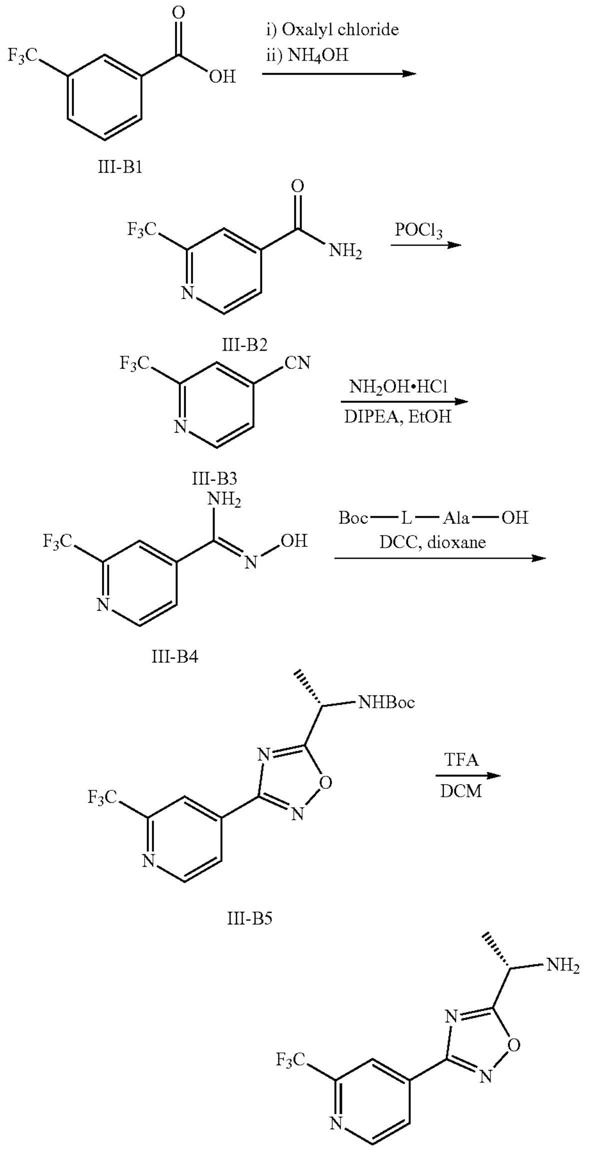

III-B1

III-B2

III-B3

III-B4

III-B5

III-A1

III-B2: 2-(trifluoromethyl)isonicotinamide

To a stirred solution of 2-(trifluoromethyl)pyridine-4-carboxylic acid (III-B1, 2.0 g, 10.47 mmol) in DCM (20.0 mL) was added oxalyl chloride (1.39 g, 10.99 mmol) and a catalytic amount of DMF (0.05 mL) at 0° C. The reaction mixture was warmed to room temperature and stirred for 2 h. The reaction mixture was concentrated under reduced pressure and aqueous $NH_4OH$ (2 mL) was added at 0° C. dropwise followed by MeCN (10 mL). The reaction mixture was stirred at room temperature for 30 min and diluted with ethyl acetate (100 mL). The organic layer was washed with water (2×50 mL), washed with brine (20 mL), dried over $Na_2SO_4$ and concentrated to afford III-B2 (1.3 g).

III-B3: 2-(trifluoromethyl)pyridine-4-carbonitrile $POCl_3$ (3.04 mL, 32.61 mmol) was added dropwise to III-B2 (1.3 g, 6.84 mmol) at 0° C. The reaction mixture was heated at 100° C. for 3 h. The reaction mixture was cooled to room temperature and treated with 50% NaOH solution (10 mL). The reaction mixture was diluted with water (50 mL) and extracted with ethyl acetate (2×70 mL). The organic layer was washed with brine (40 mL), dried over $Na_2SO_4$ and concentrated. The residue was purified by column chromatography on silica gel with 8% ethyl acetate/PE to afford III-B3 (520 mg, 3.0 mmol, 44% yield). LCMS: 173.1 (M+H), Rt 1.84 min; Column: ZORBAX XDB C-18 (50×4.6 mm), 3.5 μm; Mobile Phase: A: 0.1% HCOOH in water:ACN (95:5), B: ACN; Flow Rate:1.5 mL/min.

III-B4: N'-hydroxy-2-(trifluoromethyl)pyridine-4-carboxamidine

To a stirred solution of III-B3 (520 mg, 3.02 mmol) in ethanol (10.0 mL) was added hydroxylamine hydrochloride (314 mg, 4.53 mmol) and DIPEA (1.58 mL, 9.05 mmol) at room temperature under nitrogen atmosphere. The reaction mixture was heated at 80° C. for 2 h. The reaction mixture was cooled to room temperature and concentrated under reduced pressure. The residue was treated with water (15 mL) followed by saturated sodium bicarbonate solution (10 mL) and extracted with ethyl acetate (2×30 mL). The organic layer was washed with brine (20 mL), dried over $Na_2SO_4$ and concentrated to afford III-B4 (580 mg).

III-B5: tert-butyl (S)-(1-(3-(2-(trifluoromethyl)pyridin-4-yl)-1,2,4-oxadiazol-5-yl)ethyl)carbamate To a stirred solution of III-B4 (580 mg, 2.83 mmol) in 1,4-dioxane (20.0 mL) was added (2S)-2-(tert-butoxycarbonylamino)propanoic acid (534 mg, 2.83 mmol) and DCC (640 mg, 3.11 mmol). The reaction mixture was stirred at 100° C. for 16 h. The reaction mixture was cooled to room temperature and concentrated under reduced pressure. The mixture was treated with water (30 mL) and extracted with ethyl acetate (2×30 mL). The organic layer was washed with brine (20 mL), dried over $Na_2SO_4$ and concentrated. The residue was purified by column chromatography on silica gel with 12% ethyl acetate/PE to afford III-B5 (840 mg, 2.34 mmol, 82% yield). LCMS: 359.2 (M+H), Rt 2.42 min; Column: ZORBAX XDB C-18 (50×4.6 mm), 3.5 μm; Mobile Phase: A: 0.1% HCOOH in water:ACN (95:5), B: ACN; Flow Rate:1.5 mL/min.

III-A1: (1S)-1-[3-[2-(trifluoromethyl)-4-pyridyl]-1,2,4-oxadiazol-5-yl]ethanamine To a stirred solution of III-B5 (400 mg, 1.12 mmol) in DCM (8.0 mL) was added TFA (1.5 mL) at 0° C. The reaction mixture was slowly warmed to room temperature and stirred for 2 h. The mixture was concentrated under reduced pressure and treated with ice water (20 mL). The mixture was treated with saturated $NaHCO_3$ solution (10 mL) and extracted with EtOAc (2×25 mL). The organic layer was washed with brine (20 mL), dried over anhydrous $Na_2SO_4$ and concentrated to afford III-A1 (260 mg).

Synthesis of III-A6

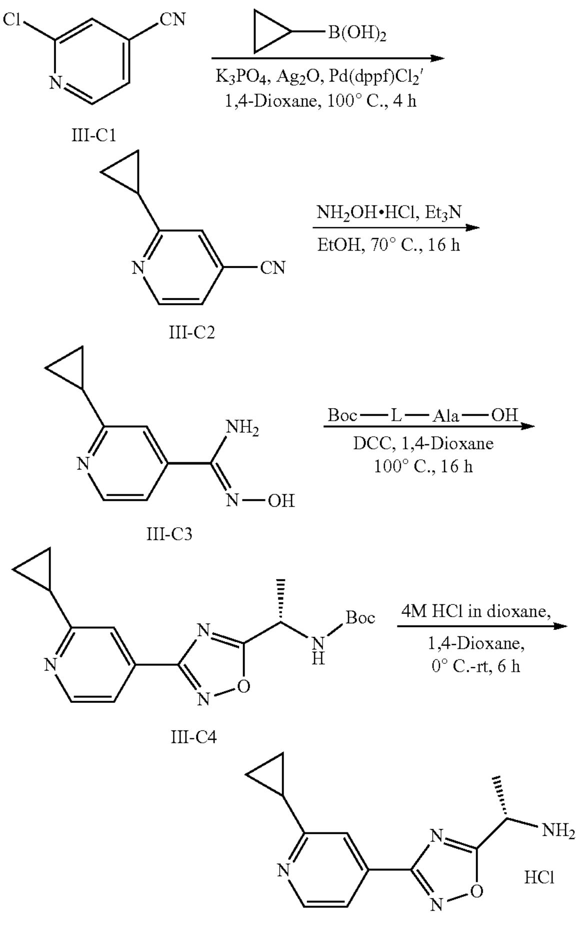

III-A6•HCl

III-C2: (2-cyclopropylisonicotinonitrile)

To a stirred solution of compound III-C1 (10.0 g, 72.18 mmol) in 1,4-dioxane (100 mL) was added $K_3PO_4$ (38.3 g, 180.44 mmol) and cyclopropylboronic acid (12.4 g, 144.35 mmol) at room temperature and purged with argon for 20 min. To the resulting solution was added silver oxide (3.35 g, 14.44 mmol) and $Pd(dppf)Cl_2$ (5.28 g, 7.22 mmol) at room temperature. The reaction mixture was further heated at 100° C. for 4 h. After completion of reaction, the reaction mixture was cooled to room temperature and filtered through pad of Celite and washed with ethyl acetate (100 mL). The filtrate collected was washed with water (3×100 mL). Organic layer was separated, dried over anhydrous $Na_2SO_4$, filtered and concentrated under reduced pressure resulting in the The residue. The The residue was purified by 100-200 mesh size silica gel column chromatography eluting with 5-10% f ethyl acetate in n-hexane to afford III-C2 (5.50 g, 38.19 mmol, 53% yield) as a solid.

III-C3: ((Z)-2-cyclopropyl-N'-hydroxyisonicotinimidamide)

To a stirred solution of III-C2 (5.50 g, 38.15 mmol) in ethanol (50 mL) was added triethyl amine (10.6 mL, 76.38 mmol) and hydroxylamine hydrochloride (4.00 g, 57.23 mmol) at room temperature. The reaction mixture was further heated at 70° C. for 16 h. After completion of reaction, the reaction mixture was cooled to room temperature and concentrated under reduced pressure. The residue was diluted with water (50 mL) and extracted with DCM (3×50 mL). The organic layer was separated, dried over anhydrous $Na_2SO_4$, filtered and concentrated under reduced pressure to afford III-C3 (6.00 g 33.86 mmol, 89% yield) as a solid which was used in the next step without further purification.

III-C4: (tert-butyl (S)-(1-(3-(2-cyclopropylpyridin-4-yl)-1,2,4-oxadiazol-5-yl)ethyl)carbamate)

To a stirred solution of compound III-C3 (6.00 g, 33.86 mmol) in 1,4-Dioxane (60 mL) was added Boc-L-Ala-OH (7.05 g, 37.25 mmol) and DCC (7.67 g, 37.25 mmol) at room temperature. The reaction mixture was further heated at 100° C. for 16 h. The reaction mixture was cooled to room temperature and concentrated under reduced pressure. The residue was diluted with ethyl acetate (50 mL) and washed with water (2×20 mL). The organic layer was separated, washed with water (2×20 mL) followed by saturated brine solution (1×20 mL). The organic layer was separated, dried over anhydrous $MgSO_4$, filtered and concentrated under reduced pressure resulting in the The residue. The The residue was purified by 100-200 mesh size silica column chromatography eluting with 5-10% of ethyl acetate in n-hexane to afford compound III-C4 (8.00 g, 24.25 mmol, 71% yield) as a liquid.

III-A6: (tert-butyl (S)-(1-(3-(2-cyclopropylpyridin-4-yl)-1,2,4-oxadiazol-5-yl)ethyl)carbamate)

To a stirred solution of compound III-C4 (8.00 g, 24.21 mmol) in 1,4-Dioxane (20 mL) at 0° C. was added 4M HCl in dioxane (20 mL). The reaction mixture was allowed to warm to room temperature and stirred for 6 h. The reaction mixture was concentrated under reduced pressure to afford compound III-A6 (6.00 g, 22.95 mmol) as a solid which was used in the next step without further purification.

Efficacy of Exemplary Compounds in the Inhibition of KCNT1

KCNT1-WT-Basal—Patch Clamp Assay

Inhibition of KCNT1 (KNa1.1, Slack) was evaluated using a tetracycline inducible cell line (HEK-TREX). Currents were recorded using the SyncroPatch 384PE automated, patch clamp system. Pulse generation and data collection were performed with PatchController384 V1.3.0 and DataController384 V1.2.1 (Nanion Technologies). The access resistance and apparent membrane capacitance were estimated using built-in protocols. Current were recorded in perforated patch mode (10 μM escin) from a population of cells. The cells were lifted, triturated, and resuspended at 800,000 cells/ml. The cells were allowed to recover in the cell hotel prior to experimentation. Currents were recorded at room temperature. The external solution contained the following (in mM): NaCl 105, NMDG 40, KCl 4, $MgCl_2$ 1, $CaCl_2$ 5 and HEPES 10 (pH=7.4, Osmolarity ~300 mOsm). The extracellular solution was used as the wash, reference and compound delivery solution. The internal solution contained the following (in mM): NaCl 70, KF 70, KCl 10, EGTA 5, HEPES 5 and Escin 0.01 (pH=7.2, Osmolarity ~295 mOsm). Escin is made at a 5 mM stock in water, aliquoted, and stored at −20° C. The compound plate was created at 2× concentrated in the extracellular solution. The compound was diluted to 1:2 when added to the recording well. The amount of DMSO in the extracellular solution was held constant at the level used for the highest tested concentration. A holding potential of −80 mV with a 100 ms step to 0 mV was used. Mean current was measured during the step to 0 mV. 100 μM Bepridil was used to completely inhibit KCNT1 current to allow for offline subtraction of non-KCNT1 current. The average mean current from 3 sweeps was calculated and the % inhibition of each compound was calculated. The % Inhibition as a function of the compound concentration was fit with a Hill equation to derive $IC_{50}$, slope, min and max parameters. If KCNT1 inhibition was less than 50% at the highest tested concentration or if an $IC_{50}$ could not be calculated, then a percent inhibition was reported in place of the $IC_{50}$.

Results from this assay are summarized in Table 1 below. In this table, “A” indicates $IC_{50}$ of less than or equal to 1 μM; “B” indicates inhibition of between 1 μM to 20 μM; and “C” indicates inhibition of greater than or equal to 20 μM.

TABLE 1

| Compound No. | KCNT1 WT $IC_{50}$ (μM) |
|---|---|
| I-1 | B |
| I-2 | B |
| I-3 | A |
| I-4 | C |
| I-5 | A |
| I-6 | C |
| I-7 | C |
| I-8 | A |
| I-9 | A |
| I-10 | A |
| I-11 | B |
| I-12 | C |
| I-13 | B |
| I-14 | A |
| I-15 | A |
| I-16 | A |
| I-17 | A |
| I-18 | A |
| I-19 | A |
| I-20 | A |
| I-21 | B |
| I-22 | B |
| I-23 | C |
| I-24 | C |
| I-25 | A |
| I-26 | A |
| I-29 | A |
| I-30 | B |
| I-32 | C |
| I-33 | B |
| I-34 | C |
| I-35 | C |
| I-36 | A |
| I-37 | B |
| I-38 | C |
| I-39 | B |
| I-40 | B |
| I-41 | A |
| I-42 | A |
| I-43 | A |
| I-44 | A |
| I-45 | A |
| I-46 | A |
| I-47 | B |
| I-48 | C |
| I-49 | C |
| I-50 | C |

TABLE 1-continued

| Compound No. | KCNT1 WT $IC_{50}$ (μM) |
|---|---|
| I-51 | B |
| I-52 | C |
| I-53 | A |
| I-54 | C |
| I-56 | A |
| I-57 | A |
| I-58 | A |
| I-59 | A |
| I-60 | A |
| I-61 | A |
| I-62 | A |
| I-63 | A |
| I-64 | A |
| I-65 | C |
| I-66 | C |
| I-67 | A |
| I-68 | C |
| I-69 | B |
| I-70 | A |
| I-71 | A |
| I-72 | B |
| I-73 | C |
| I-74 | A |
| I-75 | A |
| I-76 | A |
| I-77 | C |
| I-78 | C |
| I-79 | A |
| I-80 | A |
| I-81 | A |
| I-82 | A |
| I-83 | A |
| I-84 | A |
| I-85 | C |
| I-86 | C |
| I-87 | A |
| I-88 | A |
| I-89 | A |
| I-90 | B |
| I-91 | B |
| I-92 | A |
| I-93 | A |
| I-94 | A |
| I-95 | A |
| I-96 | A |
| I-97 | A |
| I-98 | A |
| I-99 | A |
| I-100 | A |
| I-101 | A |
| I-102 | A |
| I-103 | A |
| I-104 | B |
| I-105 | A |
| II-1 | A |
| II-2 | A |
| II-3 | A |
| II-4 | A |
| II-5 | A |
| II-6 | A |
| II-7 | A |
| II-8 | A |
| II-9 | A |
| II-10 | B |
| II-11 | A |
| II-12 | A |
| III-1 | C |
| III-2 | B |
| III-3 | B |
| III-4 | A |
| III-5 | A |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A pharmaceutical composition comprising a compound of Formula I-I:

(I-I)

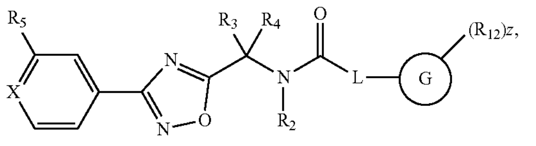

or a pharmaceutically acceptable salt thereof, wherein

L is a bond or $C_{1-6}$alkyl;

X is CH or N, wherein, if X is CH, the hydrogen of CH may be substituted by $R_5$;

G is selected from the group consisting of phenyl, $C_{3-10}$cycloalkyl, 5-10 membered heterocyclyl, and 5-10 membered heteroaryl, wherein G is not pyrazolyl;

$R_2$ is hydrogen;

$R_3$ is $C_{1-6}$alkyl optionally substituted with $C_{1-6}$alkoxy;

$R_4$ is hydrogen;

$R_5$ is each independently selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —$C(O)C_{1-6}$alkyl, —$C(O)N(R_6)_2$, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4;

and a pharmaceutically acceptable excipient.

2. The pharmaceutical composition of claim 1, wherein the compound of Formula I-I is a compound of Formula I-I-I:

(I-I-I)

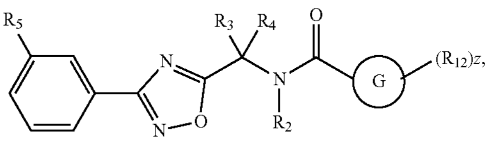

or a pharmaceutically acceptable salt thereof, wherein

G is selected from the group consisting of phenyl, 5-10 membered heterocyclyl comprising at least one unsaturated bond in the heterocyclyl ring, and 5-10 membered heteroaryl; and $R_{12}$ is each independently selected from the group consisting of halogen, cyano, oxo, —$S(O)_2(C_{1-6}$alkyl), $C_{1-6}$alkyl, $C_{1-6}$haloalkyl, $C_{1-6}$alkoxy, $C_{1-6}$haloalkoxy, $C_{3-10}$cycloalkyl and phenyl.

3. The pharmaceutical composition of claim 1, wherein the compound of Formula I-I is a compound of Formula I-I-I2:

(I-I-I2)

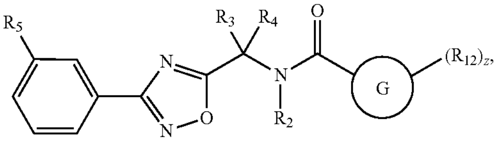

or a pharmaceutically acceptable salt thereof, wherein

G is selected from the group consisting of phenyl, 5-10 membered heterocyclyl comprising at least one unsaturated bond in the heterocyclyl ring, and 5-10 membered heteroaryl; and $R_5$ is halogen.

4. The pharmaceutical composition of claim 1, wherein the compound is a compound of Formula I—I-Ia or Formula I—I-Ib:

(I-I-Ia)

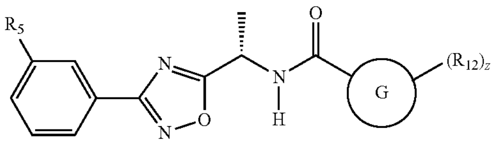

(I-I-Ib)

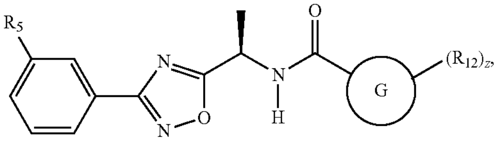

or a pharmaceutically acceptable salt thereof.

5. The pharmaceutical composition of claim 1, wherein the compound of Formula I-I is a compound of Formula I—I-II:

(I-I-II)

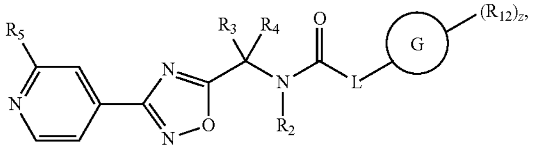

or a pharmaceutically acceptable salt thereof.

6. The pharmaceutical composition of claim 1, wherein the compound is a compound of Formula I—I-IIa, Formula I—I-IIb, Formula I—I-IIc, Formula I—I-IId, Formula I—I-Ile, or Formula I—I-IIf:

(I-I-IIa)

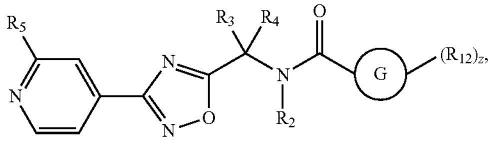

-continued (I-I-IIb)

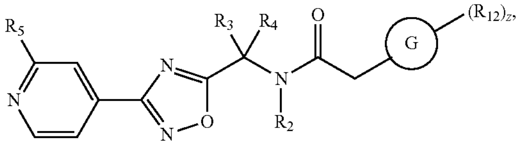

(I-I-IIc)

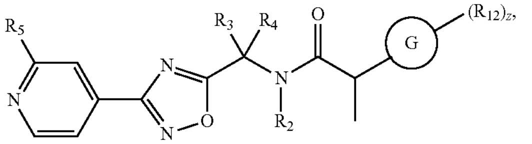

(I-I-IId)

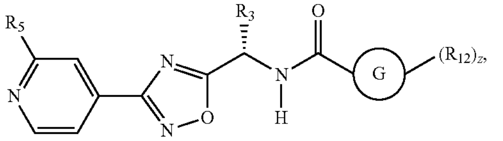

(I-I-IIe)

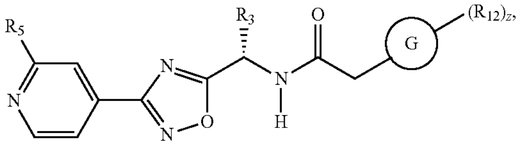

(I-I-IIf)

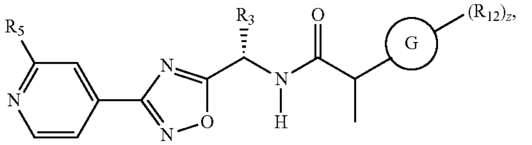

or a pharmaceutically acceptable salt thereof.

7. The pharmaceutical composition of claim 1, wherein G is selected from the group consisting of phenyl, cyclopropyl, cyclobutyl, cyclopentyl, cyclohexyl, imidazolyl, thiazolyl, pyridyl, tetrahydropyranyl, thiophenyl, isoxazolyl, isothiazolyl, pyridazinyl, piperidinyl, pyrrolidinyl, triazolyl, benzothiophenyl, pyrimidinyl, bicyclo[2.2.2]octanyl, cyclo[1.1.1]pentanyl, spiro[2.4]heptanyl, spiro[3.3]heptanyl,

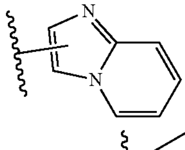,

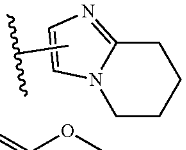, and

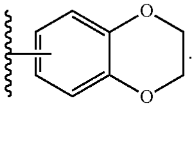

8. The pharmaceutical composition of claim 1, wherein the compound is selected from the group consisting of:

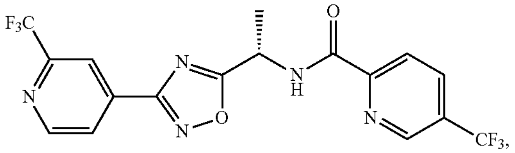

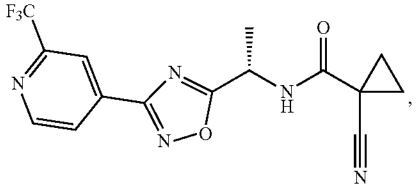

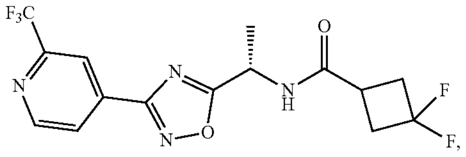

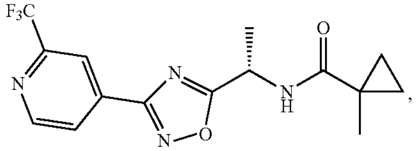

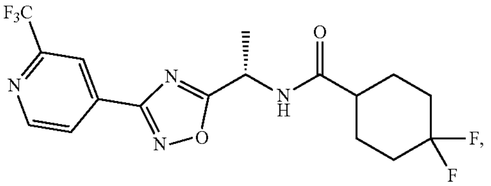

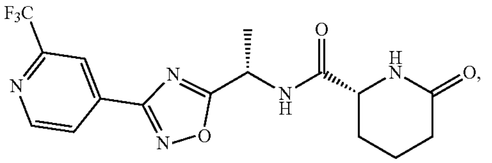

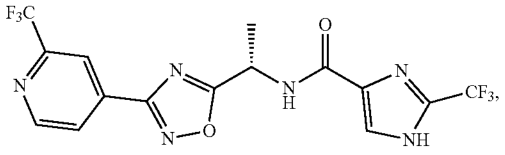

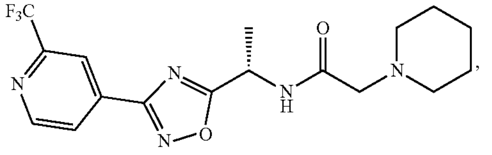

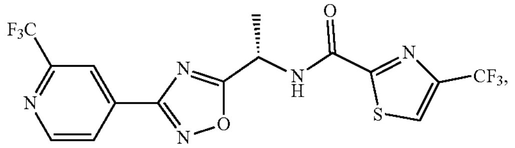

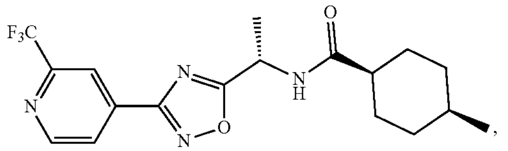

-continued
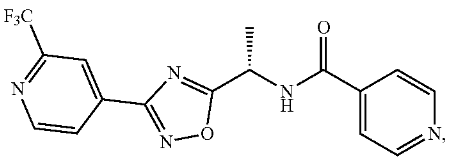
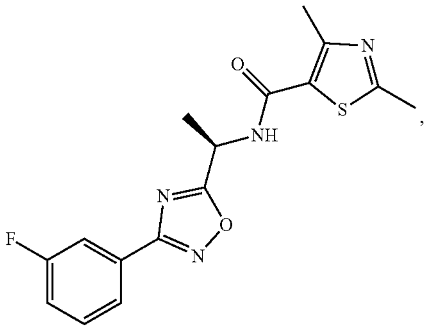
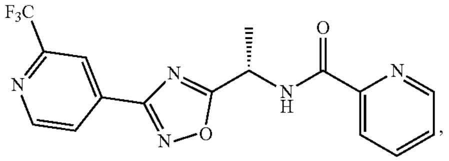
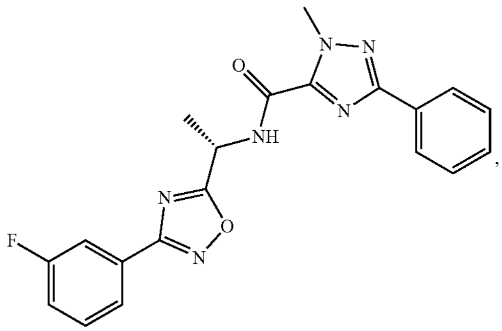
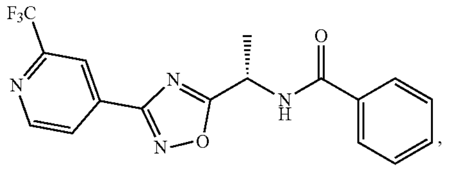
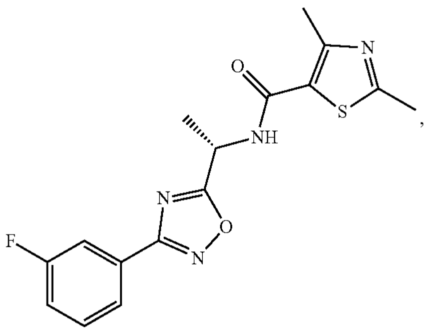
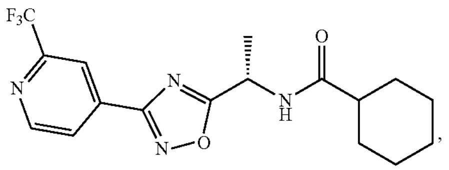
-continued
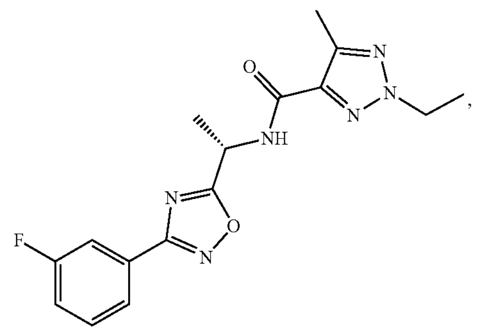
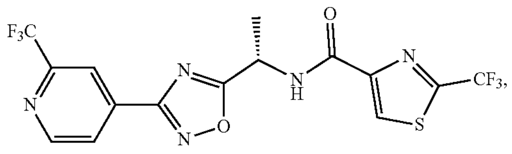
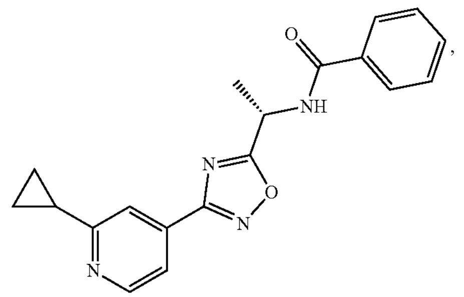
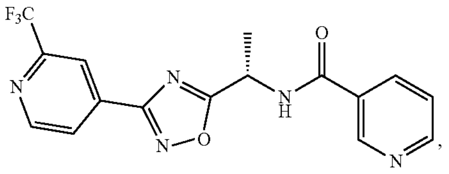
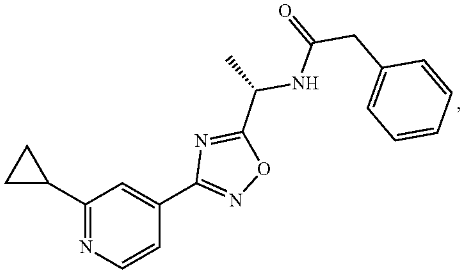
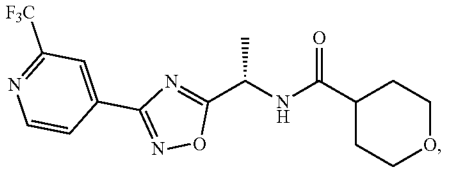
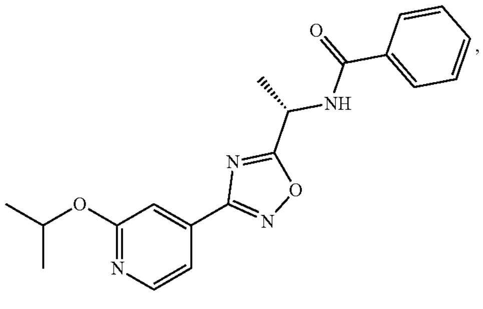

-continued
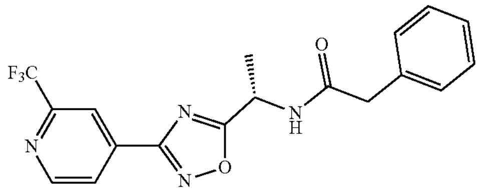
,
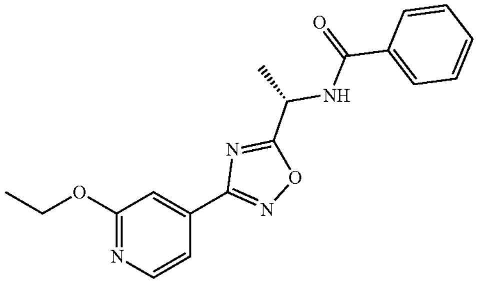
,
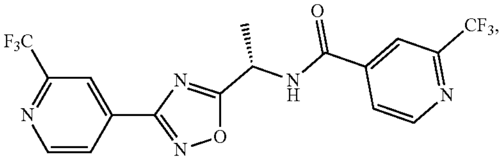
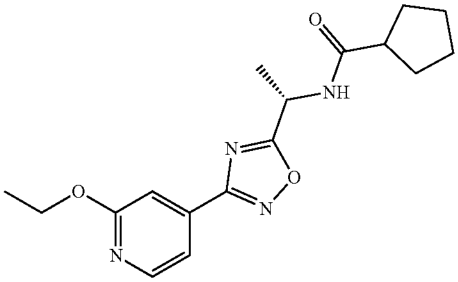
,
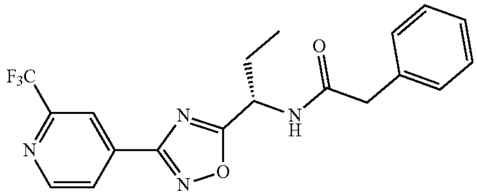
,
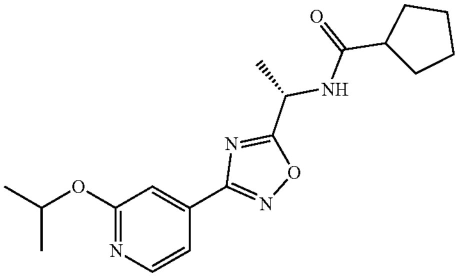
,
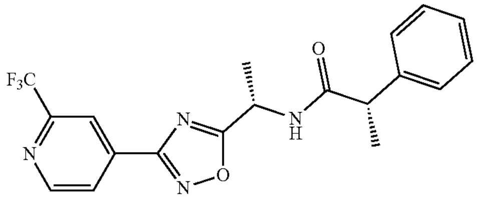
,
-continued
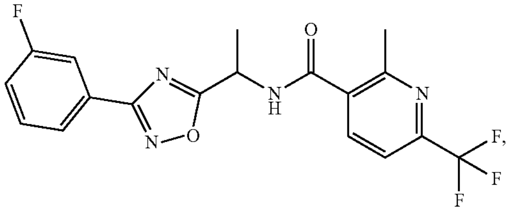
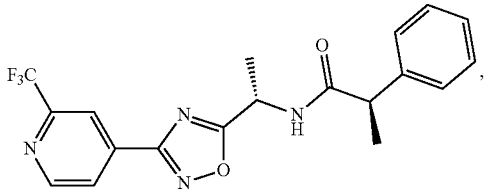
,
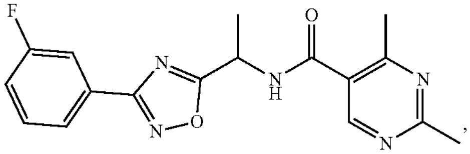
,
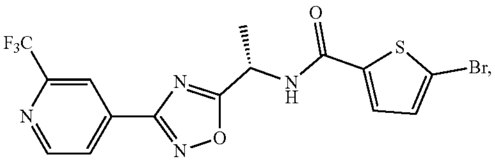
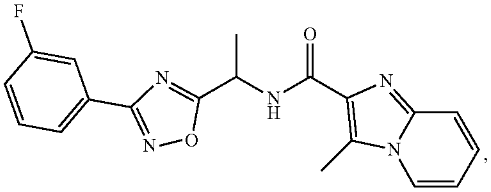
,
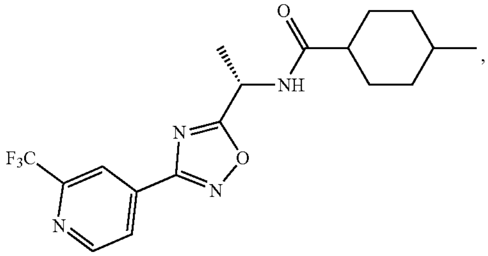
,
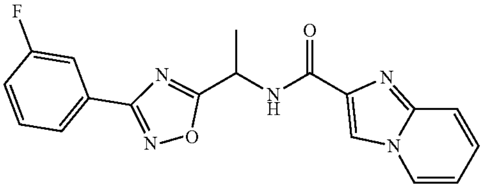
,
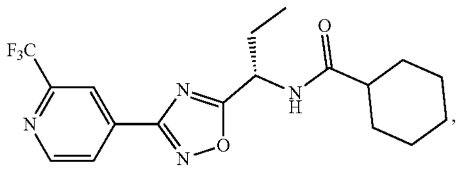
,
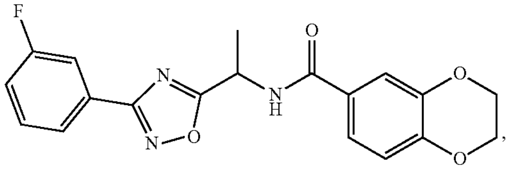
, -continued
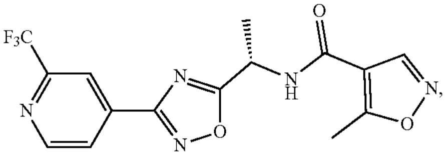,
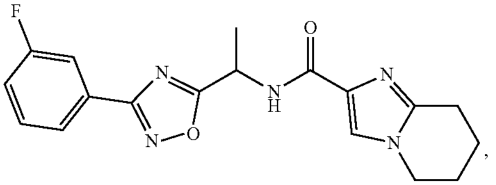,
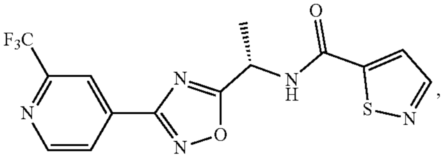,
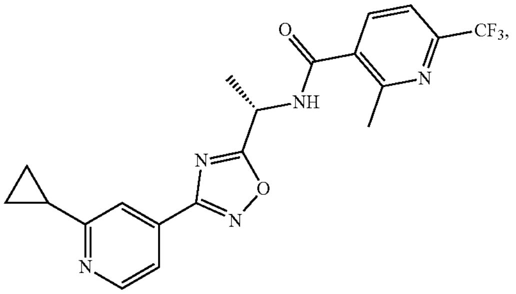,
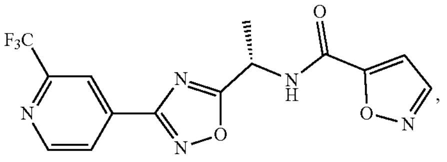,
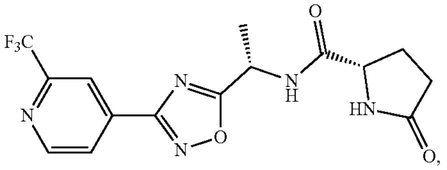,
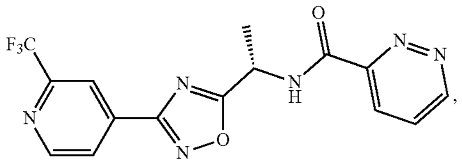,
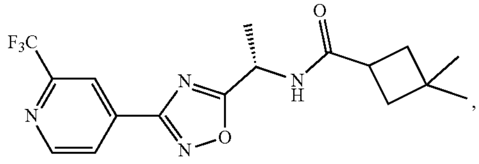,
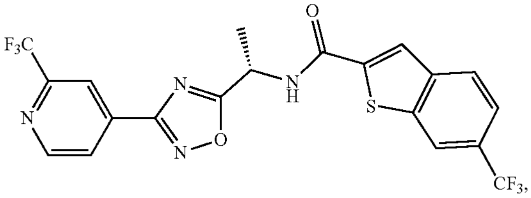,
-continued
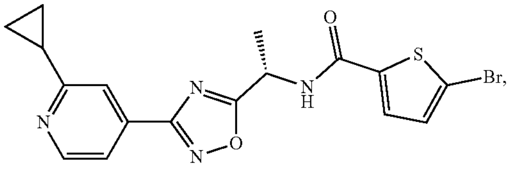,
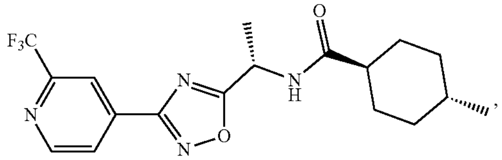,
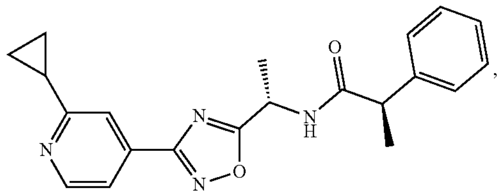,
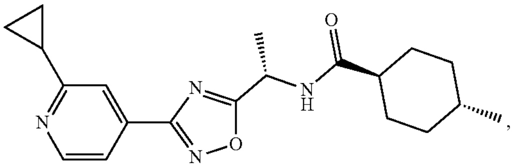,
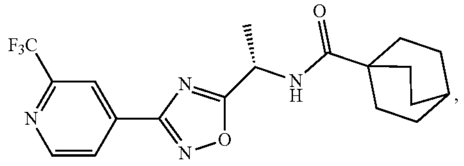,
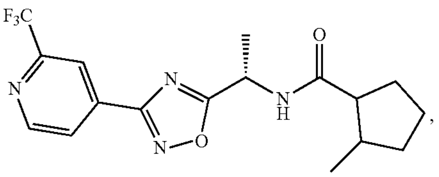,
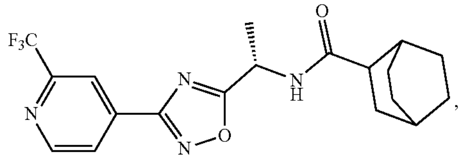,
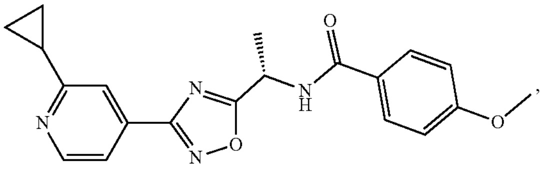,
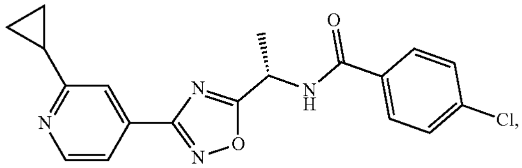,
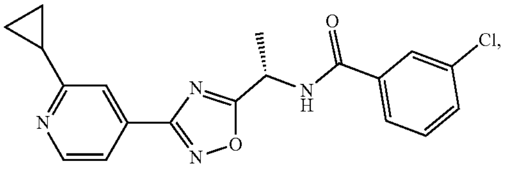, -continued
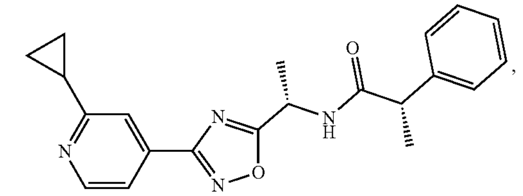
,
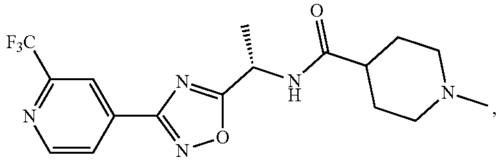
,
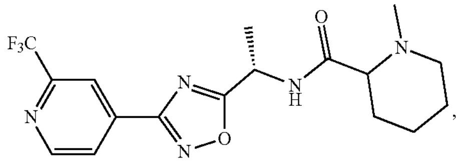
,
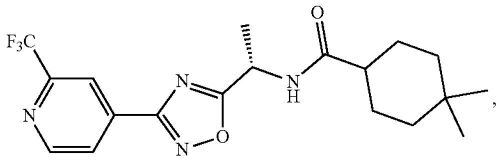
,
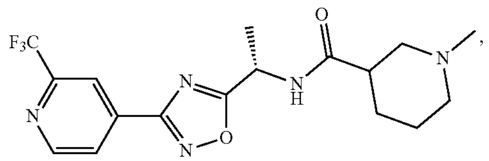
,
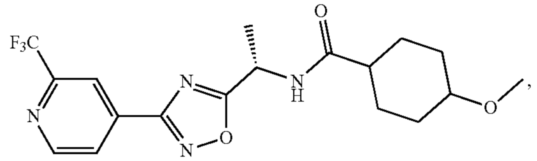
,
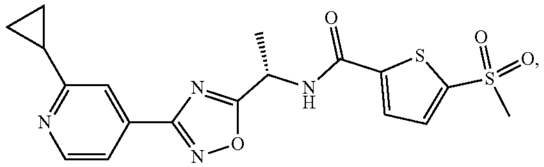
,
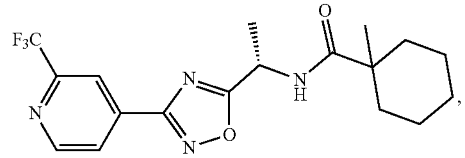
,
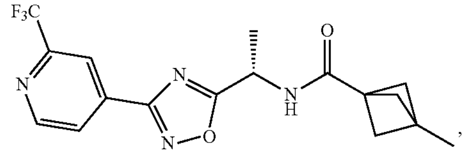
,
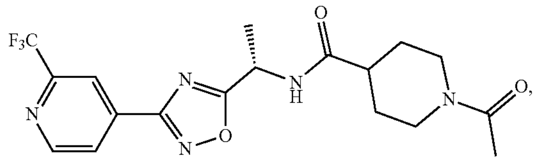
,
-continued
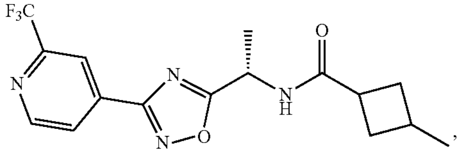
,
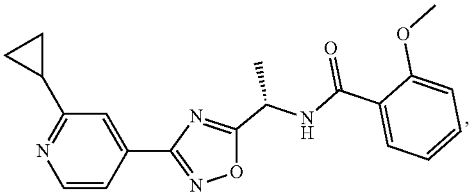
,
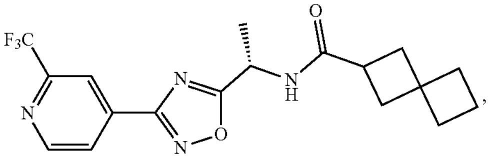
,
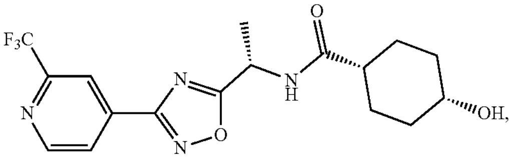
,
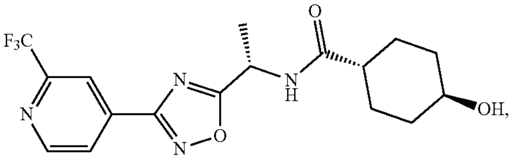
,
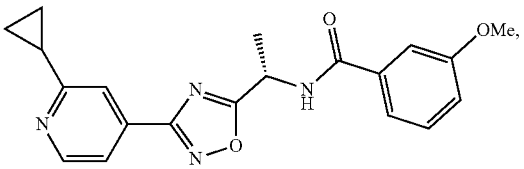
,
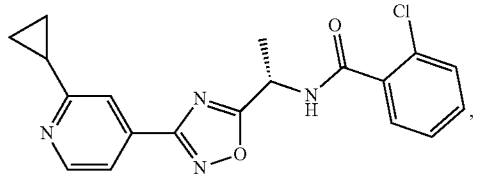
,
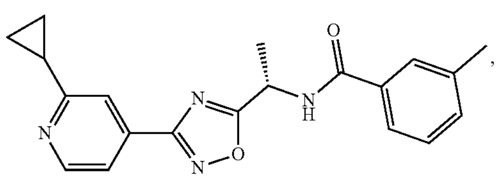
,
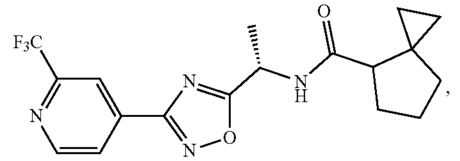
,
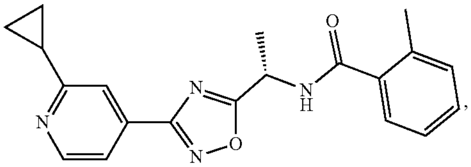
, -continued
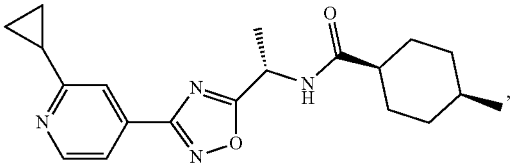
,
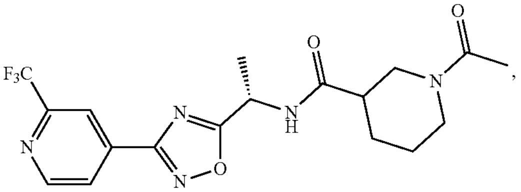
,
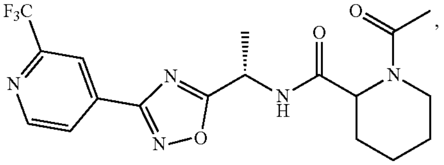
,
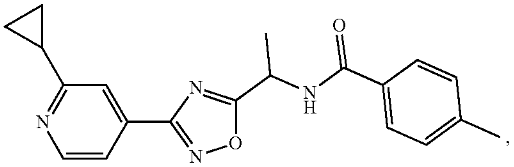
,
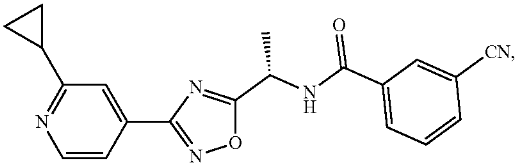
,
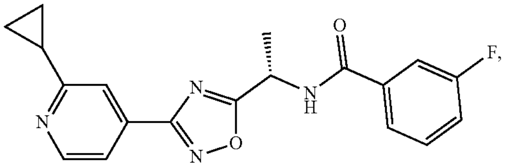
,
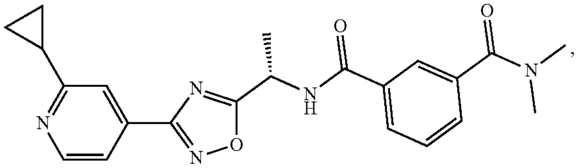
,
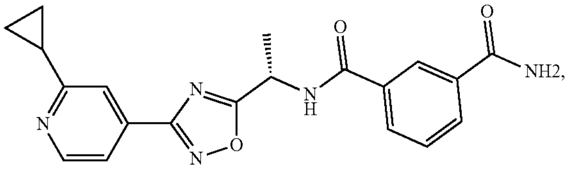
,
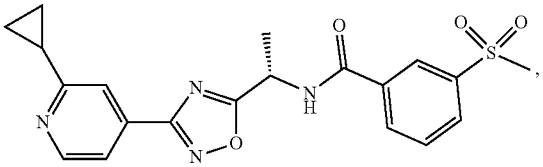
,
-continued
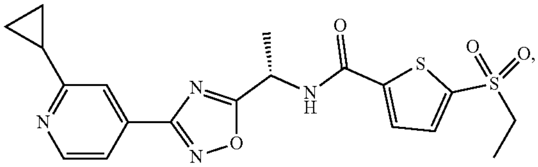
,
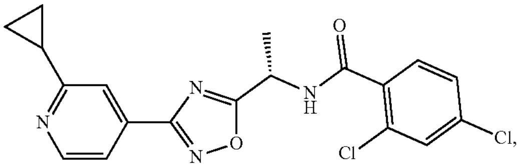
,
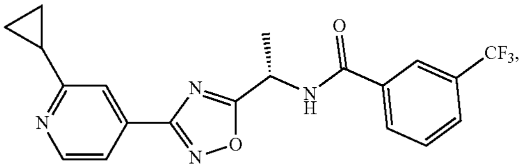
,
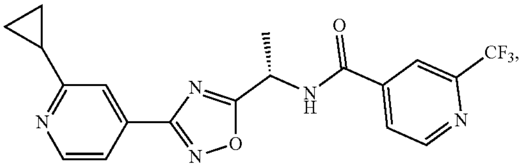
,
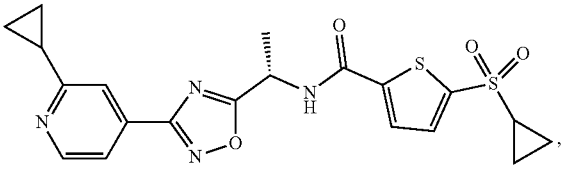
,
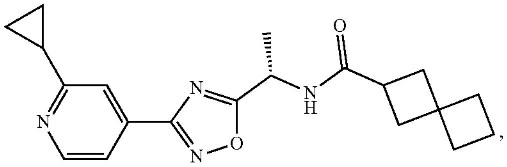
,
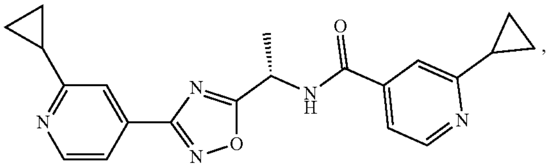
,
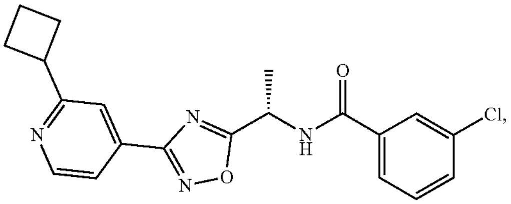
,
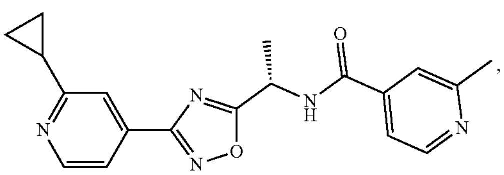
, -continued

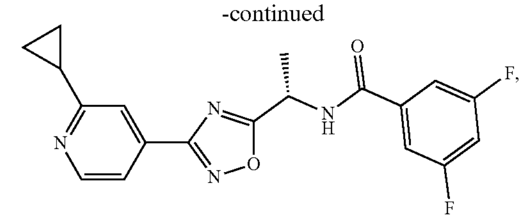

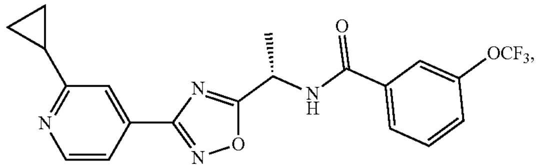

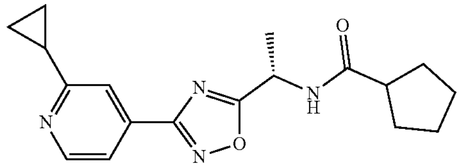

, and

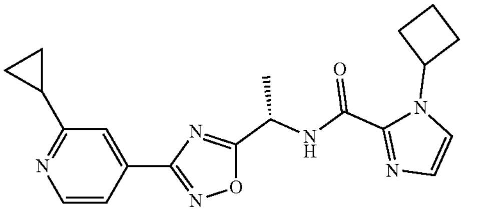

or a pharmaceutically acceptable salt thereof.

9. A method of treating a neurological disease or disorder, a disease or condition associated with excessive neuronal excitability, or a disease or condition associated with a gain-of-function mutation of a gene, wherein the method comprises administering to a subject in need thereof an effective amount of a pharmaceutical composition of claim 1.

10. The method of claim 9, wherein the neurological disease or disorder, the disease or condition associated with excessive neuronal excitability, or the disease or condition associated with a gain-of-function mutation of a gene is epilepsy, an epilepsy syndrome, an encephalopathy, a genetic or pediatric epilepsy, a genetic or pediatric epilepsy syndrome, a cardiac dysfunction, cardiac arrhythmia, sudden unexpected death in epilepsy (SUDEP), Brugada syndrome, myocardial infarction, pain and related conditions, a muscle disorder, itch and pruritis, ataxia and cerebellar ataxias, psychiatric disorders, learning disorders, Fragile X, neuronal plasticity, or autism spectrum disorders.

11. The method of claim 9, wherein the neurological disease or disorder, the disease or condition associated with excessive neuronal excitability, or the disease or condition associated with a gain-of-function mutation of a gene is selected from the group consisting of epilepsy of infancy with migrating focal seizures (MMFSI, EIMFS), autosomal dominant nocturnal frontal lobe epilepsy (ADNFLE), West syndrome, infantile spasms, epileptic encephalopathy, focal epilepsy, Ohtahara syndrome, developmental and epileptic encephalopathy, Lennox Gastaut syndrome, seizures, leukodystrophy, leukoencephalopathy, intellectual disability, Multifocal Epilepsy, Drug resistant epilepsy, Temporal lobe epilepsy, or cerebellar ataxia.

12. The method of claim 9, wherein the neurological disease or disorder, the disease or condition associated with excessive neuronal excitability, or the disease or condition associated with a gain-of-function mutation of a gene is selected from the group consisting of epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy (SUDEP), Rasmussen encephalitis, malignant migrating partial seizures of infancy, autosomal dominant nocturnal frontal lobe epilepsy, KCNQ2 epileptic encephalopathy, and KCNT1 epileptic encephalopathy.

13. A compound of Formula I-I:

(I-I)

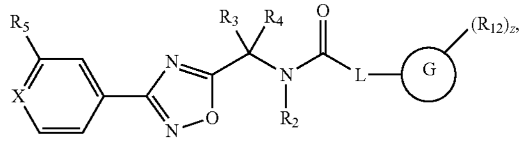

or a pharmaceutically acceptable salt thereof, wherein

L is a bond or $C_{1-6}$alkyl;

X is CH or N, wherein, if X is CH, the hydrogen of CH may be substituted by $R_5$;

G is selected from the group consisting of phenyl, $C_{3-10}$cycloalkyl, 5-10 membered heterocyclyl, and 5-10 membered heteroaryl, wherein G is not pyrazolyl;

$R_2$ is hydrogen;

$R_3$ is $C_{1-6}$alkyl optionally substituted with $C_{1-6}$alkoxy;

$R_4$ is hydrogen;

$R_5$ is each independently selected from the group consisting of halogen, $C_{1-6}$alkyl, $C_{1-6}$haloalkyl, $C_{1-6}$alkoxy, $C_{1-6}$haloalkoxy, and $C_{3-10}$cycloalkyl;

$R_6$ is each independently selected from hydrogen or $C_{1-6}$alkyl;

$R_{12}$ is each independently selected from the group consisting of halogen, cyano, hydroxyl, oxo, —$S(O)_2(C_{1-6}$ alkyl), —$S(O)_2(C_{3-6}$cycloalkyl), —C(O) $C_{1-6}$alkyl, —C(O) $N(R_6)$ 2, $C_{1-6}$alkyl, $C_{1-6}$haloalkyl, $C_{1-6}$alkoxy, $C_{1-6}$haloalkoxy, $C_{3-10}$cycloalkyl and phenyl; and z is 0, 1, 2, 3, or 4.

14. The compound of claim 13, wherein the compound is selected from the group consisting of:

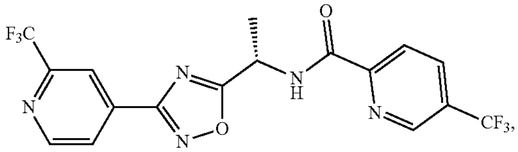

,

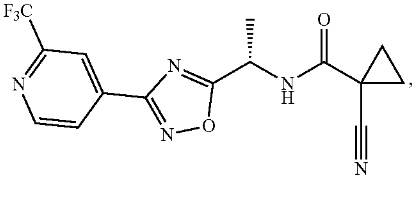

,

-continued
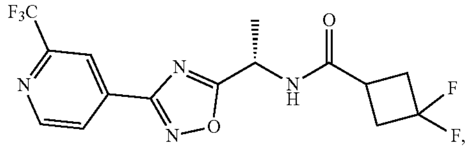
,
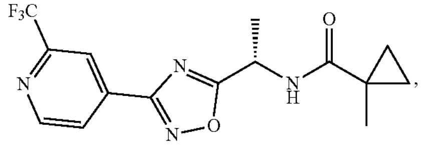
,
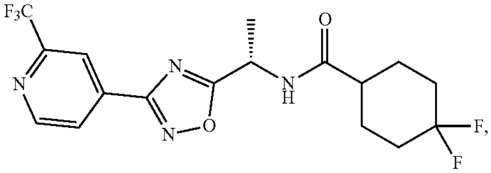
,
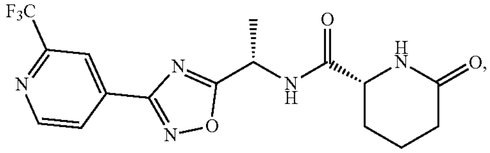
,
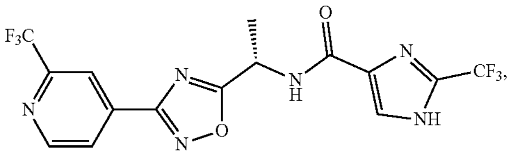
,
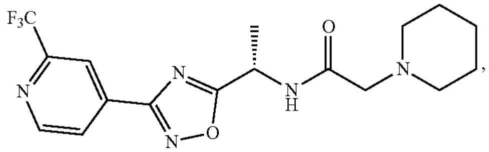
,
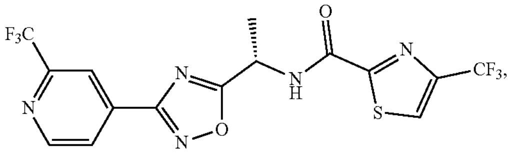
,
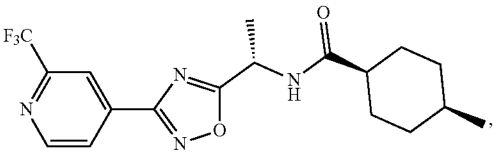
,
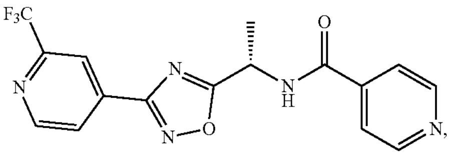
,
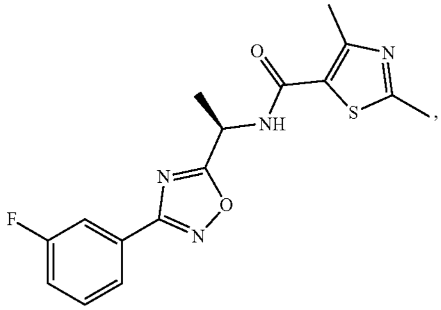
,
-continued
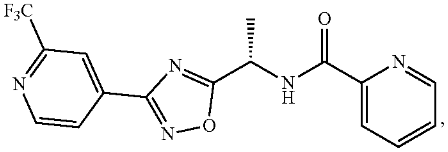
,
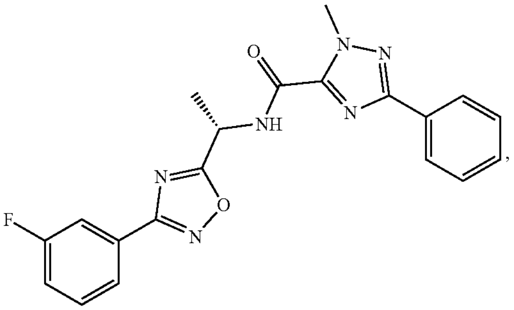
,
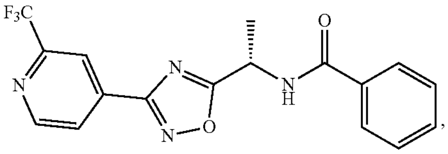
,
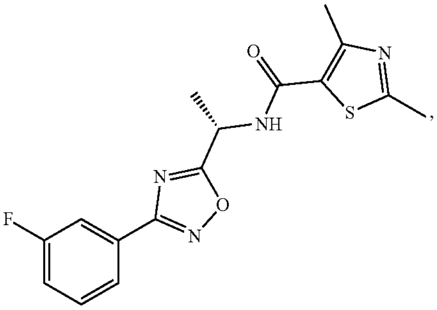
,
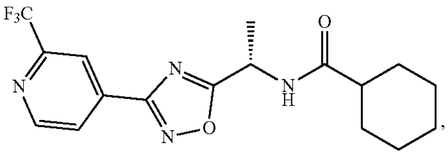
,
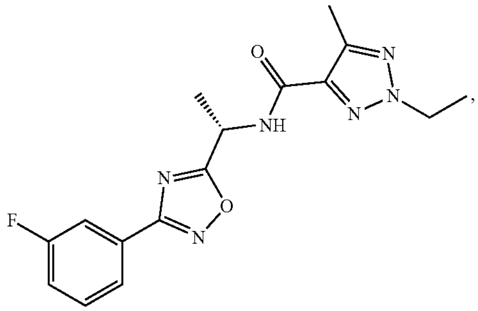
,
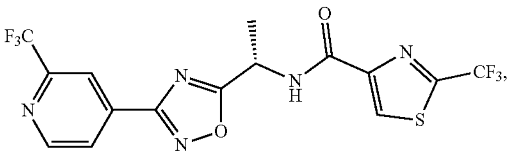
, -continued
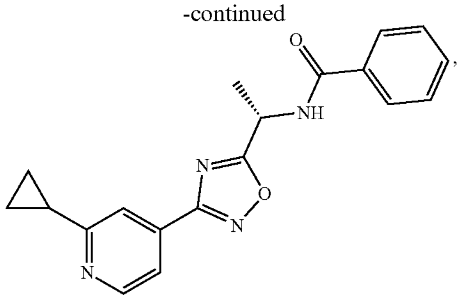,
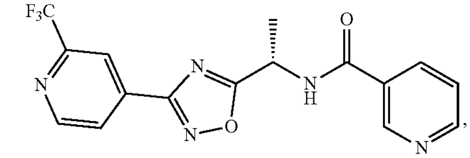,
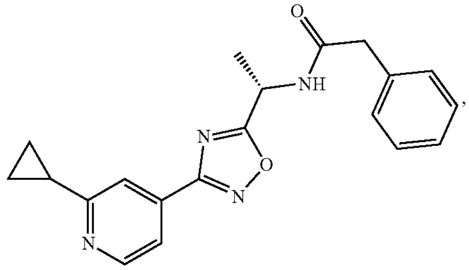,
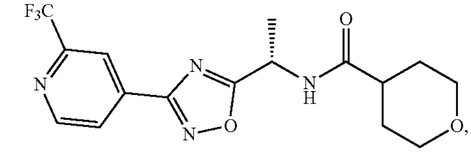,
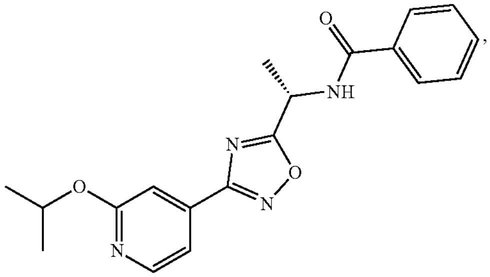,
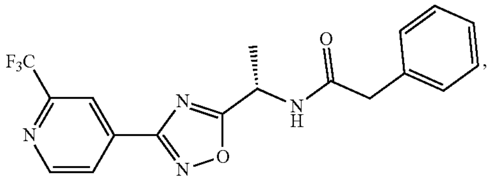,
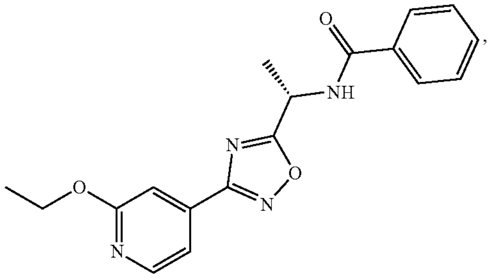,
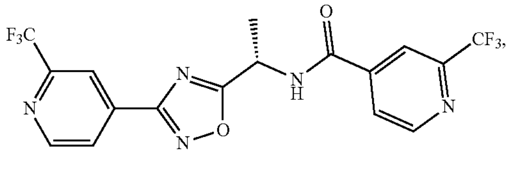,
-continued
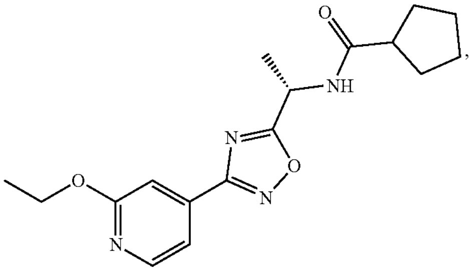,
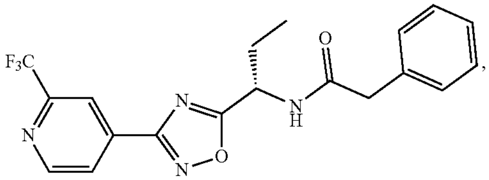,
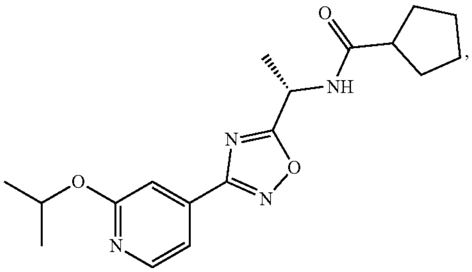,
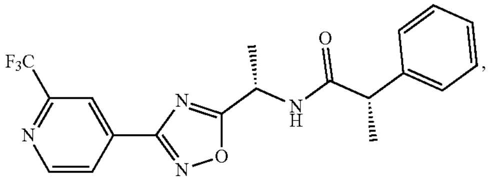,
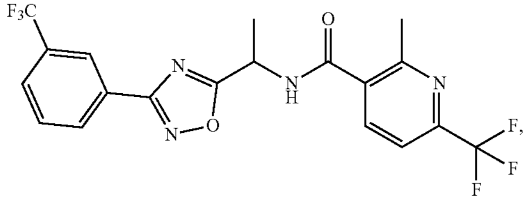,
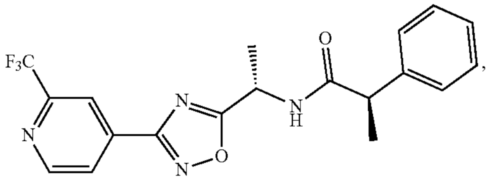,
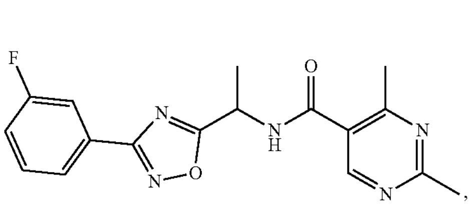,
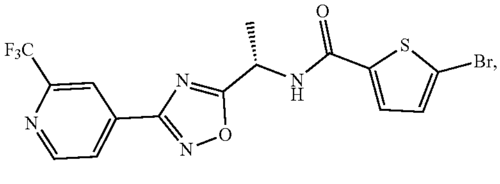, -continued
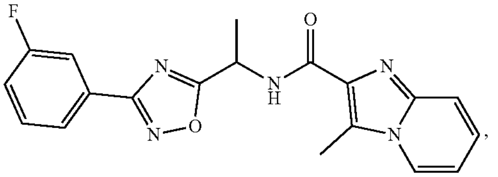
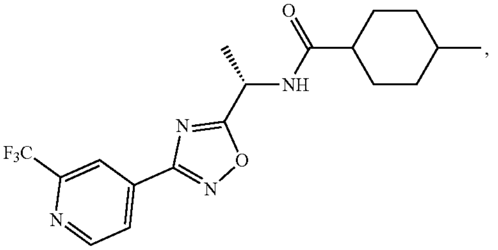
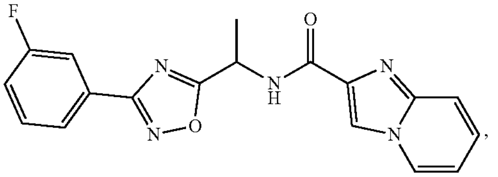
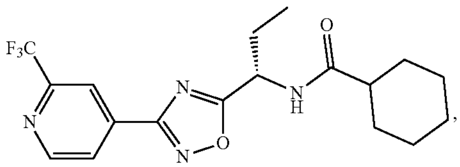
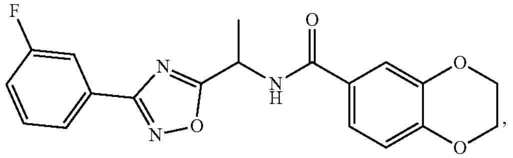
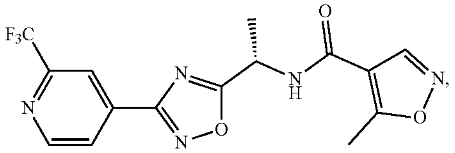
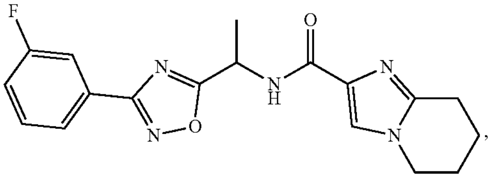
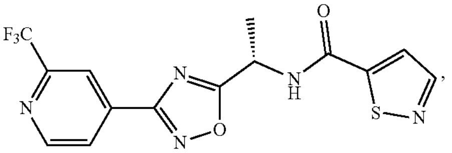
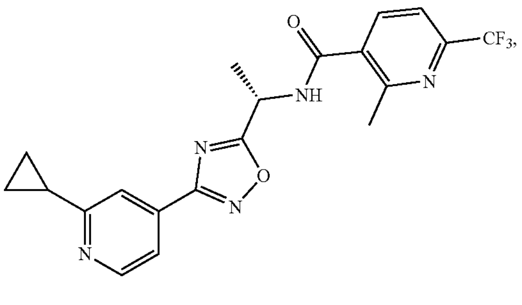
-continued
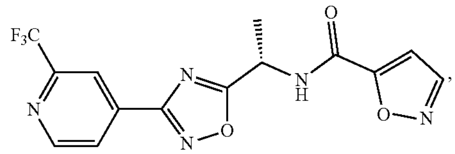
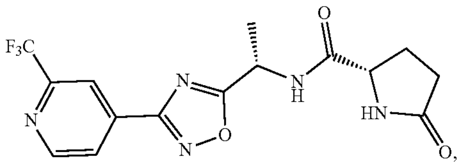
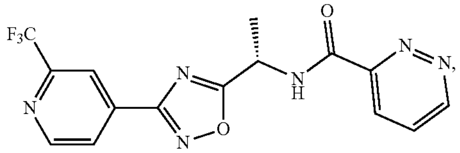
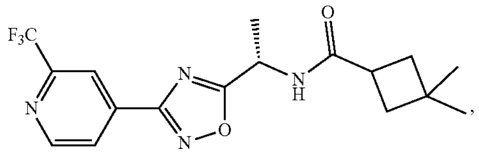
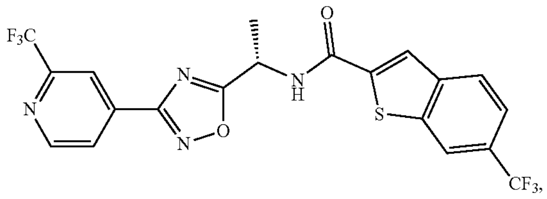
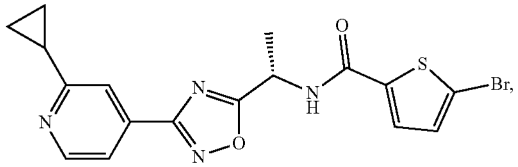
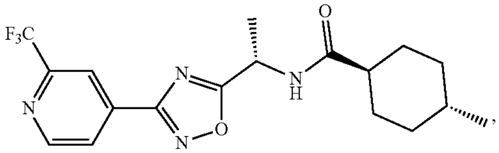
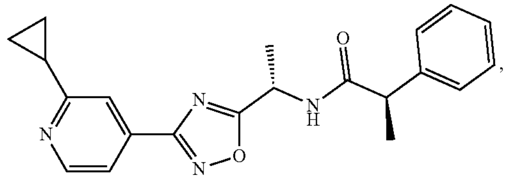
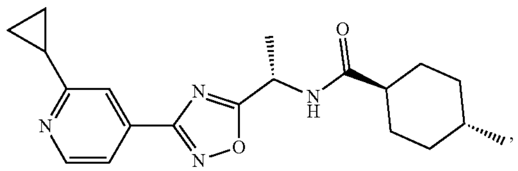
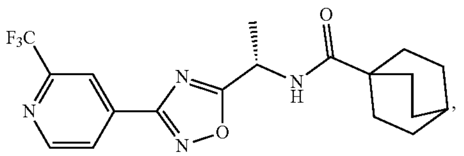

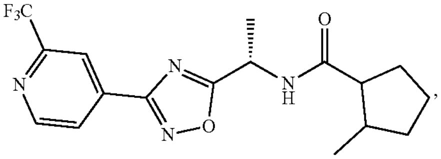
,
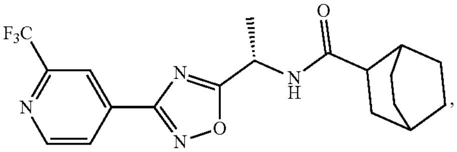
,
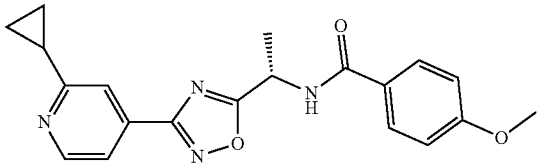
,
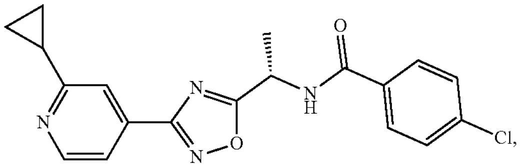
,
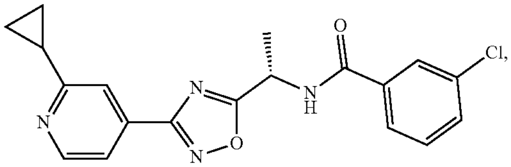
,
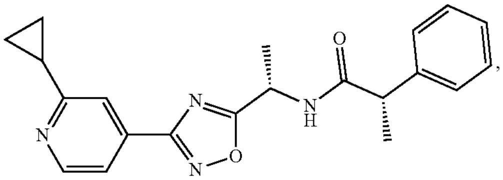
,
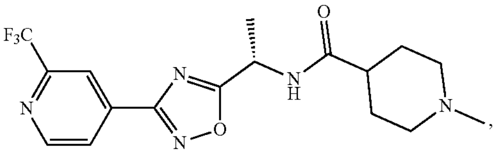
,
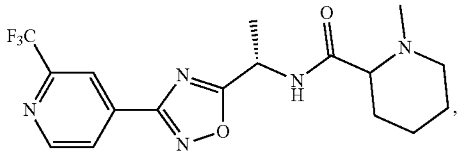
,
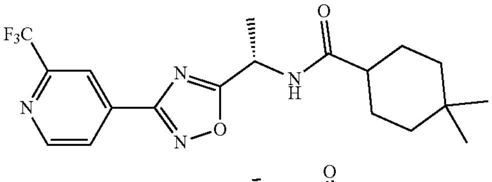
,
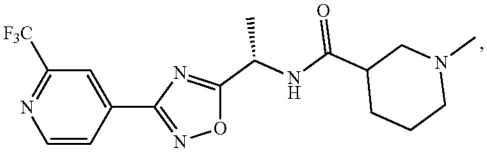
,
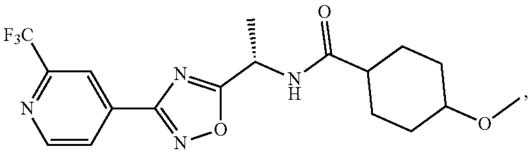
,
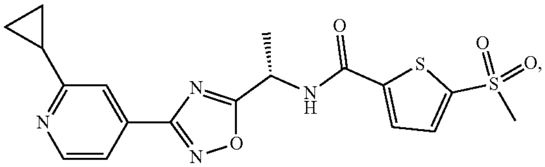
,
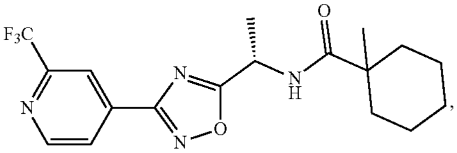
,
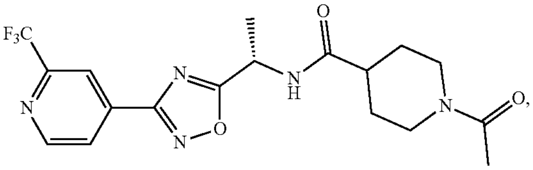
,
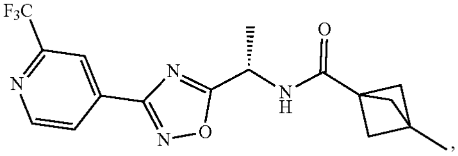
,
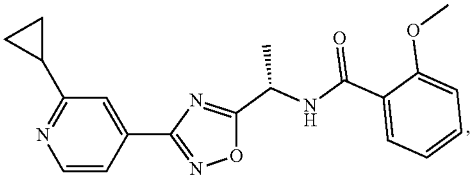
,
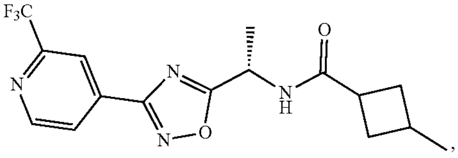
,
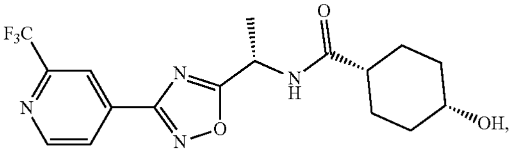
,
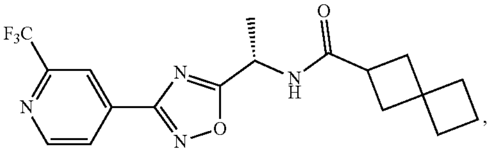
,
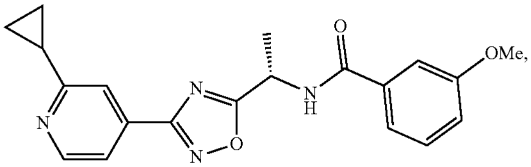
, -continued
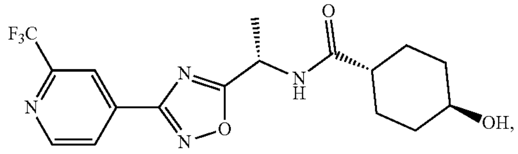
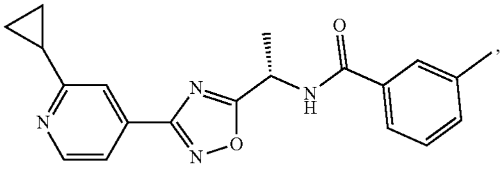
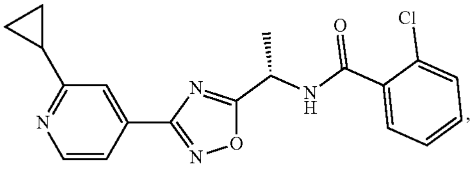
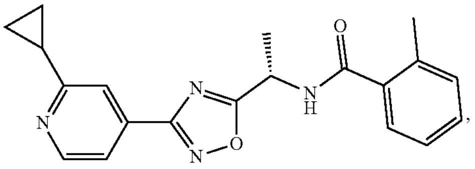
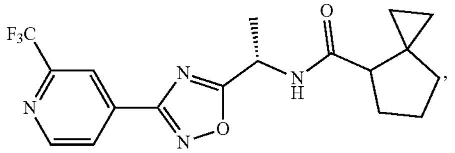
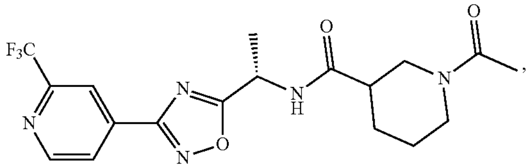
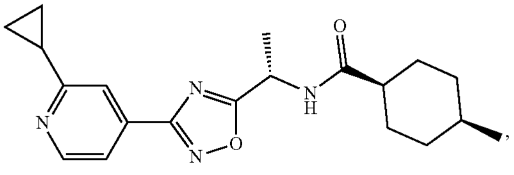
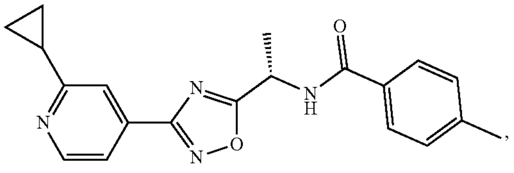
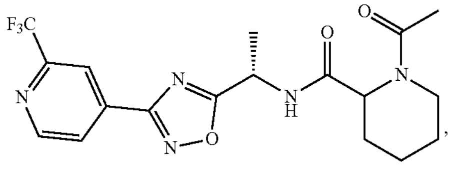
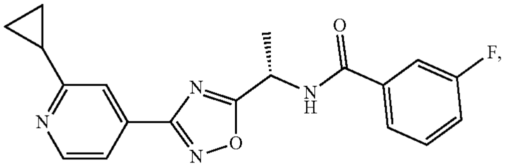
-continued
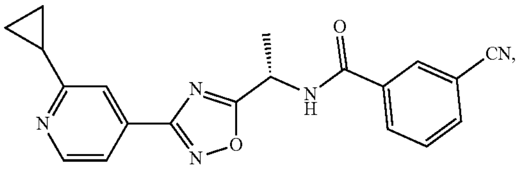
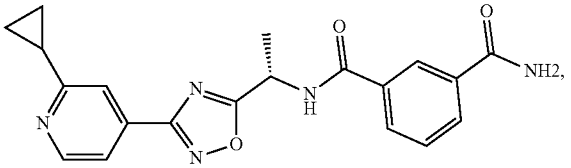
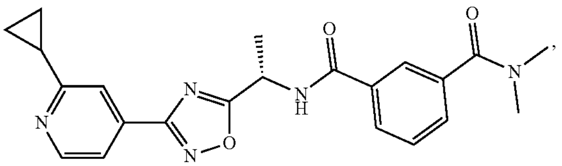
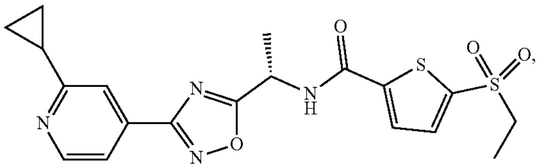
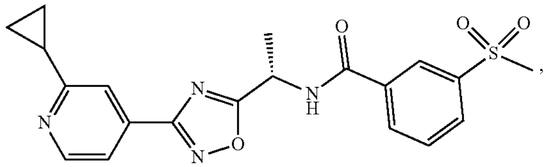
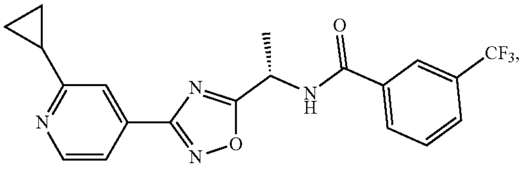
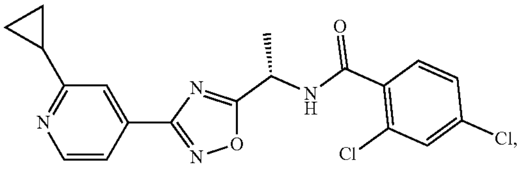
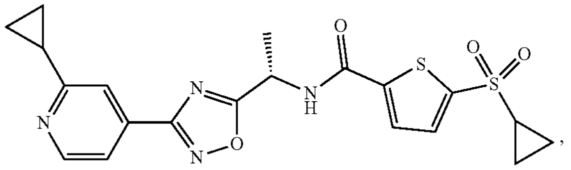
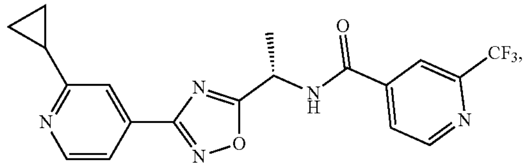

-continued
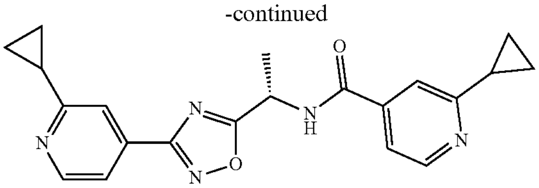
,
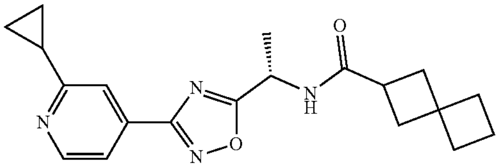
,
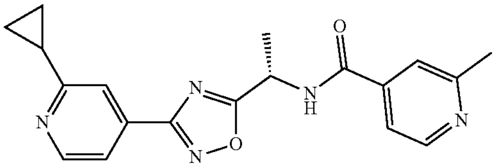
,
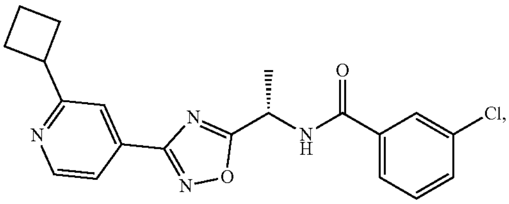
,
-continued
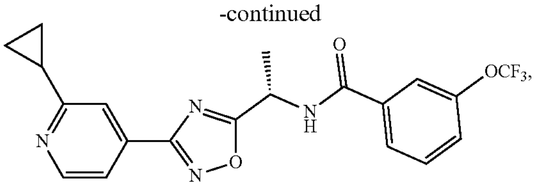
,
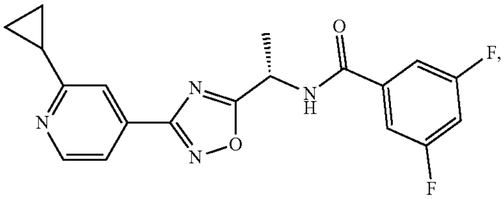
,
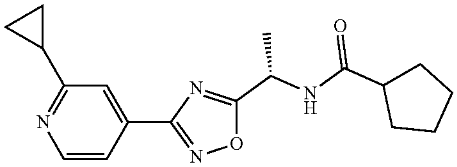
, and
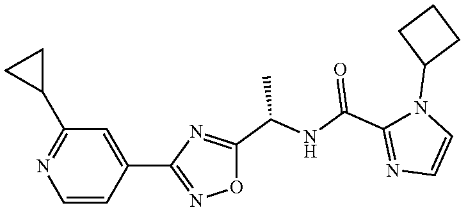
or a pharmaceutically acceptable salt thereof.
* * * * *